(12) United States Patent
Chae et al.

(10) Patent No.: US 11,691,966 B2
(45) Date of Patent: Jul. 4, 2023

(54) COMPOUND FOR ORGANIC ELECTRONIC ELEMENT, ORGANIC ELECTRONIC ELEMENT USING THE SAME, AND AN ELECTRONIC DEVICE THEREOF

(71) Applicant: DUK SAN NEOLUX CO., LTD., Cheonan-si (KR)

(72) Inventors: Mi Young Chae, Cheonan-si (KR); Moo Jin Park, Cheonan-si (KR); Jae Taek Kwon, Cheonan-si (KR); Jin Bae Jeon, Cheonan-si (KR); Sun Hee Lee, Cheonan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 516 days.

(21) Appl. No.: 16/652,369

(22) PCT Filed: Aug. 8, 2018

(86) PCT No.: PCT/KR2018/009014
§ 371 (c)(1),
(2) Date: Mar. 30, 2020

(87) PCT Pub. No.: WO2019/066242
PCT Pub. Date: Apr. 4, 2019

(65) Prior Publication Data
US 2020/0231581 A1    Jul. 23, 2020

(30) Foreign Application Priority Data

Sep. 29, 2017  (KR) .................. 10-2017-0127656
Feb. 13, 2018  (KR) .................. 10-2018-0017403

(51) Int. Cl.
*C07D 409/14*   (2006.01)
*C07D 405/14*   (2006.01)
(Continued)

(52) U.S. Cl.
CPC ......... *C07D 409/14* (2013.01); *C07D 405/14* (2013.01); *H10K 85/615* (2023.02);
(Continued)

(58) Field of Classification Search
CPC .............. C07D 405/14; H01L 51/0052; H01L 51/0054; H01L 51/0067; H01L 51/0072; H01L 51/0073; H01L 51/0074
See application file for complete search history.

(56) References Cited

U.S. PATENT DOCUMENTS

2017/0207397 A1*  7/2017  Lee .................. H01L 51/0052
2018/0337348 A1*  11/2018  Jung ................... C07F 7/0812

FOREIGN PATENT DOCUMENTS

KR    10-2016-0085206 A    7/2016
KR    10-2017-0057797 A    5/2017
(Continued)

OTHER PUBLICATIONS

The Notice of Allowance issued in corresponding KR Patent Application No. 10-2018-0017403, dated Jul. 1, 2022, two pages.
(Continued)

*Primary Examiner* — Vu A Nguyen
(74) *Attorney, Agent, or Firm* — Vorys, Sater, Seymour and Pease LLP; Mih Suhn Koh

(57) ABSTRACT

The present invention provides the compound represented by Formula 1, an organic electric element comprising a first electrode, a second electrode, and an organic material layer formed between the first electrode and the second electrode, and electronic device thereof, and by comprising the compound represented by Formula 1 in the organic material layer, the driving voltage of the organic electronic device can be lowered, and the luminous efficiency and life time of the organic electronic device can be improved.

21 Claims, 2 Drawing Sheets

(51) Int. Cl.
| | |
|---|---|
| *H01L 51/00* | (2006.01) |
| *H01L 51/50* | (2006.01) |
| *H10K 85/60* | (2023.01) |
| *H10K 50/11* | (2023.01) |
| *H10K 50/15* | (2023.01) |
| *H10K 50/16* | (2023.01) |
| *H10K 50/17* | (2023.01) |
| *H10K 101/10* | (2023.01) |
| *H10K 101/00* | (2023.01) |

(52) U.S. Cl.
CPC ......... *H10K 85/622* (2023.02); *H10K 85/654* (2023.02); *H10K 85/6572* (2023.02); *H10K 85/6574* (2023.02); *H10K 85/6576* (2023.02); *H10K 50/11* (2023.02); *H10K 50/15* (2023.02); *H10K 50/16* (2023.02); *H10K 50/171* (2023.02); *H10K 2101/10* (2023.02); *H10K 2101/90* (2023.02)

(56) References Cited

FOREIGN PATENT DOCUMENTS

| | | | |
|---|---|---|---|
| KR | 10-2017-0086397 A | | 7/2017 |
| KR | 20170086397 A | * | 7/2017 |
| KR | 10-2017-0089599 A | | 8/2017 |
| KR | 10-2017-0093061 A | | 8/2017 |
| KR | 20170113320 A | * | 10/2017 |
| KR | 10-2018-0002353 A | | 1/2018 |
| KR | 10-2018-0010130 A | | 1/2018 |
| KR | 10-2018-0012693 A | | 2/2018 |
| KR | 10-1857703 B1 | | 5/2018 |
| KR | 10-2018-0076358 A | | 7/2018 |
| KR | 10-2019-0009721 A | | 1/2019 |
| KR | 10-2019-0010474 A | | 1/2019 |
| KR | 10-2019-0010475 A | | 1/2019 |
| KR | 10-2019-0031718 A | | 3/2019 |
| KR | 10-1959821 B1 | | 3/2019 |
| WO | WO-2018016742 A1 | * | 1/2018 ........... C07D 307/91 |

OTHER PUBLICATIONS

The Notice of Preliminary Examination for corresponding KR Patent Application No. 10-2018-0017403, 11 pages, dated Jan. 10, 2022.

* cited by examiner

COMPOUND FOR ORGANIC ELECTRONIC ELEMENT, ORGANIC ELECTRONIC ELEMENT USING THE SAME, AND AN ELECTRONIC DEVICE THEREOF

CROSS-REFERENCE TO RELATED APPLICATION

This patent application claims priority from and the benefit under 35 U.S.C. § 119 to § 121, and § 365 of Korean Patent Application No. 10-2017-0127656, filed on Sep. 29, 2017, Korean Patent Application No. 10-2018-0017403, filed on Feb. 13, 2018, which is hereby incorporated by reference for all purposes as if fully set forth herein. Further, this application claims the benefit of priority in countries other than U.S., which is hereby incorporated by reference herein.

BACKGROUND

Technical Field

The present invention relates to compounds for organic electric elements, organic electric elements comprising the same, and electronic devices thereof.

Background Art

In general, an organic light emitting phenomenon refers to a phenomenon in which electric energy is converted into light energy of an organic material. An organic electric element utilizing the organic light emitting phenomenon usually has a structure including an anode, a cathode, and an organic material layer interposed therebetween. In many cases, the organic material layer has a multi-layered structure having respectively different materials in order to improve efficiency and stability of an organic electric element, and for example, may include a hole injection layer, a hole transport layer, a light emitting layer, an electron transport layer, an electron injection layer, or the like.

Materials used as an organic material layer in an organic electric element may be classified into a light emitting material and a charge transport material, for example, a hole injection material, a hole transport material, an electron transport material, an electron injection material, and the like according to its function.

Further, the light emitting material may be divided into a high molecular weight type and a low molecular weight type according to its molecular weight, and may also be divided into a fluorescent material derived from excited singlet states of electron and a phosphorescent material derived from excited triplet states of electron according to its light emitting mechanism. Further, the light emitting material may be divided into blue, green, and red light emitting material and yellow and orange light emitting material required for better natural color reproduction according to its light emitting color.

Meanwhile, when only one material is used as a light emitting material, there occur problems of shift of a maximum luminescence wavelength to a longer wavelength due to intermolecular interactions and lowering of the efficiency of a corresponding element due to a deterioration in color purity or a reduction in luminous efficiency. On account of this, a host/dopant system may be used as the light emitting material in order to enhance the color purity and increase the luminous efficiency through energy transfer. This is based on the principle that if a small amount of dopant having a smaller energy band gap than a host forming a light emitting layer is mixed in the light emitting layer, then excitons generated in the light emitting layer are transported to the dopant, thus emitting light with high efficiency. With regard to this, since the wavelength of the host is shifted to the wavelength band of the dopant, light having a desired wavelength can be obtained according the type of the dopant.

Currently, the power consumption is required more than more as size of display becomes larger and larger in the portable display market. Therefore, the power consumption is a very important factor in the portable display with a limited power source of the battery, and efficiency and life span issue also is solved.

Efficiency, life span, driving voltage, and the like are correlated with each other. For example, if efficiency is increased, then driving voltage is relatively lowered, and the crystallization of an organic material due to Joule heating generated during operation is reduced as driving voltage is lowered, as a result of which life span shows a tendency to increase. However, efficiency cannot be maximized only by simply improving the organic material layer. This is because long life span and high efficiency can be simultaneously achieved when an optimal combination of energy levels and $T_1$ values, inherent material properties (mobility, interfacial properties, etc.), and the like among the respective layers included in the organic material layer is given.

Therefore, it is required to develop a light emitting material that has high thermal stability and can achieve efficiently a charge balance in the light-emitting layer. That is, in order to allow an organic electric element to fully exhibit excellent features, it should be prerequisite to support a material constituting an organic material layer in the element, for example, a hole injection material, a hole transport material, a light emitting material, an electron transport material, an electron injection material, or the like, by a stable and efficient material. However, the stable and efficient material of organic material layer for an organic electronic element has not been fully developed yet, and it the development of organic material layer materials for organic electric devices has not been sufficiently achieved.

Object, Technical Solution and Effects of the Invention

The present invention is to provide a compound lowering a driving voltage, improving luminous efficiency, color purity, stability and lifetime of the element, an organic electric element comprising the same, and an electronic device thereof.

In an aspect of the present invention, the present invention provides the compound represented by the following formula.

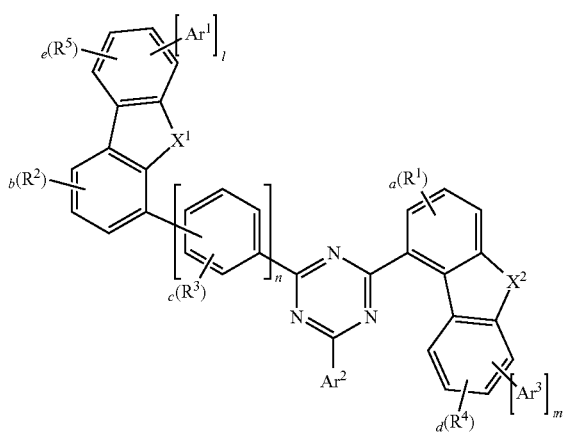

In another aspect of the present invention, the present invention provides an organic electric element using the compound represented by formula above and an electric device thereof.

By using the compound according to embodiments of the present invention, a driving voltage can be lowered and the luminous efficiency, color purity, stability and lifetime of the element can be largely improved.

DETAILED DESCRIPTION

In the present description, a 'group name' corresponding to an aryl group, an arylene group, a heterocyclic group, and the like exemplified for each symbol and its substituent may be written in the name of functional group reflecting the valence, and may also be described under the name of a parent compound. For example, in the case of phenanthrene which is a kind of aryl group, it may be described by distinguishing valence such as 'phenanthryl (group)' when it is 'monovalent group', and as 'phenanthrylene (group)' when it is 'divalent group', and it may also be described as a parent compound name, 'phenanthrene', regardless of its valence. Similarly, in the case of pyrimidine, it may be described as 'pyrimidine' regardless of its valence, and it may also be described as the name of corresponding functional group such as pyrimidinyl (group) when it is 'monovalent group', and as 'pyrimidylene (group)' when it is 'divalent group'.

Unless otherwise stated, the term "fluorenyl group" or "fluorenylene group" as used herein means univalent or bivalent functional group in which R, R' and R" are all hydrogen in the following structure, "substituted fluorenyl group" or "substituted fluorenylene group" means that at least any one of R, R' and R" is a substituent other than hydrogen, and it comprises spiro compound formed by linking R and R' together with the carbon bonded to them.

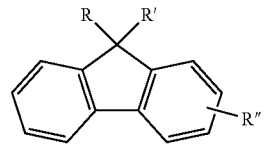

Unless otherwise stated, the term "spiro compound" as used herein has, a spiro union which means union having one atom as the only common member of two rings. The common atom is designated as 'spiro atom'. The compounds are defined as 'monospiro', 'dispiro-' or 'trispiro-' depending on the number of spiro atoms in one compound.

The term "heterocyclic group" as used herein means a ring comprising a heteroatom like N, O, S, P, Si or the like, it comprises a non-aromatic ring as well as an aromatic ring like "heteroaryl group" or "heteroarylene group" and the compound comprising heteroatom group like $SO_2$, $P=O$ or the like instead of carbon consisting of a ring such as the following compound.

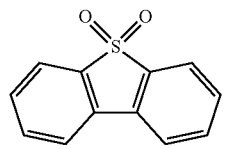 [SMILES: O=S1(=O)c2ccccc2-c2ccccc21]

Otherwise specified, the formulas used in the present invention are as defined in the index definition of the substituent of the following formula:

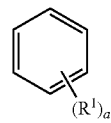

Wherein, the substituent $R^1$ is absent when a is an integer of zero, the sole $R^1$ is bonded to any one of the carbon atoms constituting the benzene ring when a is an integer of 1, when a is an integer of 2 or 3, the substituent $R^1$s may be bonded as follows and the substituents $R^1$s may be the same or different each other, and the substituent $R^1$s may be bonded to the carbon of the benzene ring in a similar manner when a is an integer of 4 to 6. Herein, the indication of the hydrogen bonded to the carbon which forms the benzene ring is omitted.

(a=2)

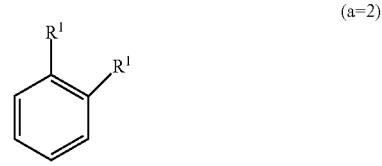

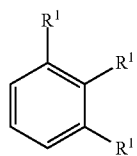
(a=3)

Figure 1:
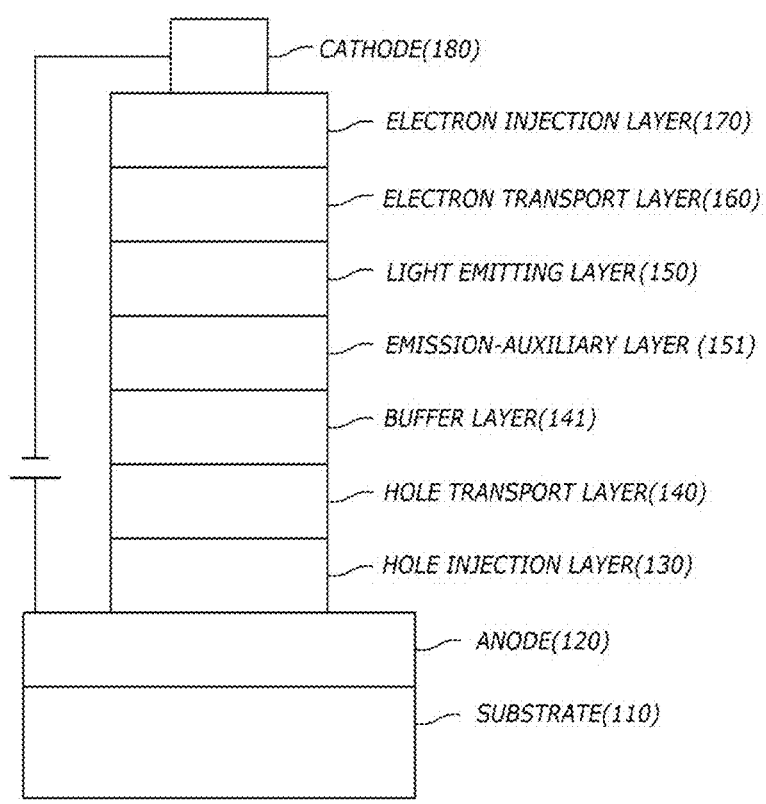
FIG. 1 illustrate an example of an organic electroluminescent element according to the present invention: 100 is organic electric element, 110 is substrate, 120 is first electrode, 130 is hole injection layer, 140 is hole transport layer, 141 is buffer layer, 150 is light emitting layer, 151 is emission-auxiliary layer, 160 is electron transport layer, 170 is electron injection layer, and 180 is second electrode.

The FIG. 1 illustrates an organic electric element according to an embodiment of the present invention.

Referring to the FIG. 1, an organic electric element 100 according to an embodiment of the present invention includes a first electrode 120 formed on a substrate 110, a second electrode 180, and an organic material layer formed between the first electrode 120 and the second electrode 180 and comprising the compound of the present invention. Here, the first electrode 120 may be an anode (positive electrode), and the second electrode 180 may be a cathode (negative electrode). In the case of an inverted organic electric element, the first electrode may be a cathode, and the second electrode may be an anode.

The organic material layer may include a hole injection layer 130, a hole transport layer 140, a light emitting layer 150, an electron transport layer 160, and an electron injection layer 170 formed in sequence on the first electrode 120. Here, at least one layer of the organic material layer may be omitted, or the organic material layer may further include a hole blocking layer, an electron blocking layer, an emission-auxiliary layer 151, an electron transport auxiliary layer, a buffer layer 141, etc., and the electron transport layer 160 or the like may serve as the hole blocking layer.

Although not shown, the organic electric element according to an embodiment of the present invention may further include a protective layer or a layer for improving luminous efficiency formed on at least one side of sides of the first electrode and the second electrode, wherein at least one side is not facing the organic material layer.

The inventive compound employed in the organic material layer may be used as a material of a hole injection layer 130, a hole transport layer 140, an emission-auxiliary layer 151, an electron transport auxiliary layer, an electron transport layer 160, an electron injection layer 170 and the like, as a host or a dopant material of a light emitting layer 150, or as a material of a layer for improving luminous efficiency. For example, the inventive compound may be used as material of the light emitting layer 150, preferably, as host material of the light emitting layer 150.

On the other hand, even if the core is the same core, the band gap, the electrical characteristics, the interface characteristics, and the like may be different depending on which substituent is bonded at which position. Therefore, it is necessary to study the selection of the core and the combination of the core and the sub-substituent bonded to the core. Specially, long life span and high efficiency can be simultaneously achieved when the optimal combination of energy levels and $T_1$ values, inherent material properties (mobility, interfacial properties, etc.), and the like among the respective layers of an organic material layer is achieved.

Therefore, according to the present invention, energy level and $T_1$ value between the respective layers of the organic material layer, inherent material properties (mobility, interfacial properties, etc.) and the like can be optimized by using as a host material of a light emitting layer a single compound represented by the Formula 1 or a mixture of the compound represented by the Formula 1 and the compound represented by the Formula 15, and thus it is possible to simultaneously improve the life span and efficiency of the organic electric element.

The organic electric element according to an embodiment of the present invention may be manufactured using various deposition methods. The organic electric element according to an embodiment of the present invention may be manufactured using a PVD (physical vapor deposition) method or CVD (chemical vapor deposition) method. For example, the organic electric element may be manufactured by depositing a metal, a conductive metal oxide, or a mixture thereof on the substrate to form the anode 120, forming the organic material layer including the hole injection layer 130, the hole transport layer 140, the light emitting layer 150, the electron transport layer 160, and the electron injection layer 170 thereon, and then depositing a material, which can be used as the cathode 180, thereon. Also, an emitting auxiliary layer 151 may be formed between a hole transport layer 140 and a light emitting layer 150, and an electron transport auxiliary layer may be formed between a light emitting layer 150 and an electron transport layer 160.

Also, the organic material layer may be manufactured in such a manner that a smaller number of layers are formed using various polymer materials by a soluble process or solvent process, for example, spin coating, nozzle printing, inkjet printing, slot coating, dip coating, roll-to-roll, doctor blading, screen printing, or thermal transfer, instead of deposition. Since the organic material layer according to the present invention may be formed in various ways, the scope of protection of the present invention is not limited by a method of forming the organic material layer.

Also, the organic electric element according to an embodiment of the present invention may be any one of an organic light emitting diode, an organic solar cell, an organic photo conductor, an organic transistor, and an element for monochromatic or white illumination.

Another embodiment of the present invention provides an electronic device including a display device which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, the compound according to an aspect of the present invention will be described.

The compound according to an aspect of the present invention is represented by formula 1 below.

[Formula 1]

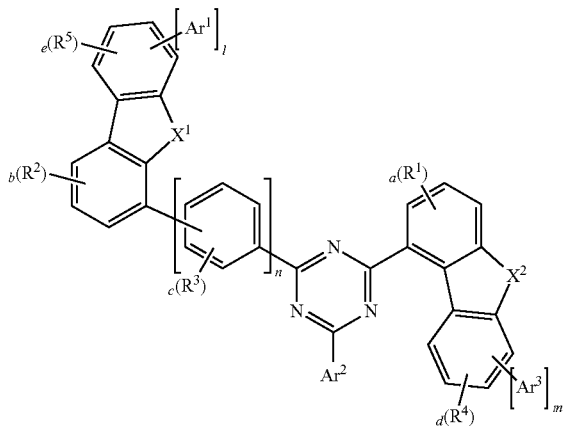

In the formula 1, each of symbols may be defined as follows.

In Formula 1, $X^1$ and $X^2$ are each independently O or S. For example, both $X^1$ and $X^2$ are O or S, is O and $X^2$ is S, or $X^1$ is S and $X^2$ is O. Preferably, $X^1$ is S and $X^2$ is O.

$Ar^1$ to $Ar^3$ are each independently a $C_6$-$C_{60}$ aryl group, preferably, a $C_6$-$C_{30}$ or a $C_6$-$C_{20}$ aryl group, more preferably a $C_6$-$C_{18}$ aryl group, for example, phenyl, naphthyl, biphenyl, terphenyl, phenanthryl, triphenylene, pyrene or the like.

$R^1$ to $R^5$ are each independently selected from the group consisting of hydrogen, deuterium, halogen, a $C_6$-$C_{60}$ aryl group, a fluorenyl group, a $C_2$-$C_{60}$ heterocyclic group containing at least one heteroatom selected from the group consisting of O, N, S, Si, and P, a $C_3$-$C_{60}$ aliphatic ring, a fused ring group formed by a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -L'-N($R_a$)($R_b$).

In addition, adjacent $R^1$ groups to adjacent $R^5$ groups may be optionally linked to each other to form a ring. Here, the ring is selected from the group consisting of a $C_6$-$C_{60}$ aromatic ring, a $C_2$-$C_{60}$ heterocyclic group, a $C_3$-$C_{60}$ aliphatic ring, and a fused ring group formed by a $C_3$-$C_{60}$ aliphatic ring with a $C_6$-$C_{60}$ aromatic ring.

Here, "adjacent groups connected to each other" means that adjacent $R^1$s, adjacent $R^2$s, adjacent $R^3$s, adjacent $R^4$s, or adjacent $R^4$s are respectively connected to each other.

a and b are each an integer of 0 to 3, c, d, e, l and m are each an integer of 0 to 4, and n is an integer of 0 to 5, provided that e+l and d+m are integers of 4 or less, respectively. When each of these is an integer of 2 or more, each of $R^1$s, each of $R^2$s, each of $R^3$s, each of $R^4$s, each of $R^5$s, each of $Ar^1$s, each of $Ar^3$s is the same or different from each other.

When $R^1$ to $R^5$ are each an aryl group, $R^1$ to $R^5$ may be preferably a $C_6$-$C_{30}$ or a $C_6$-$C_{20}$ aryl group, more preferably a $C_6$-$C_{18}$ aryl group, for example, phenyl, biphenyl, naphthyl, terphenyl or the like.

When adjacent $R^1$s, adjacent $R^2$s, adjacent $R^3$, adjacent $R^4$, or adjacent $R^5$ are linked to each other to form a ring, preferably a $C_6$-$C_{20}$ aromatic ring group may be formed, for example, benzene rings, naphthalene, phenanthrene or the like may be formed.

L' is selected from the group consisting of a single bond, a $C_6$-$C_{60}$ arylene group, a fluorenylene group, a $C_2$-$C_{60}$ heterocyclic group containing at least one heteroatom selected from the group consisting of O, N, S, Si, and P, a $C_3$-$C_{60}$ aliphatic ring and a fused ring group formed by a $C_3$-$C_{60}$ aliphatic ring with a $C_6$-$C_{60}$ aromatic ring.

$R_a$ and $R_b$ are each independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a $C_3$-$C_{60}$ aliphatic ring and a fused ring group formed by a $C_3$-$C_{60}$ aliphatic ring with a $C_6$-$C_{60}$ aromatic ring.

$Ar^1$ to $Ar^3$, $R^1$ to $R^5$, L', $R_a$, $R_b$, and a ring formed by bonding neighboring groups of $R^1$ to $R^5$ to each other may be each further substituted with one or more substituents selected from the group consisting of deuterium, halogen, a silane group unsubstituted or substituted with a $C_1$-$C_{20}$ alkyl group or a $C_6$-$C_{20}$ aryl group, a siloxane group, a boron group, a germanium group, a cyano group, a nitro group, a phosphine oxide group unsubstituted or substituted with a $C_1$-$C_{20}$ alkyl group or a $C_6$-$C_{20}$ aryl group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a fused ring group formed by a $C_3$-$C_{60}$ aliphatic ring with a $C_6$-$C_{60}$ aromatic ring, a $C_7$-$C_{20}$ arylalkyl group, and a $C_8$-$C_{20}$ arylalkenyl group.

That is, when $Ar^1$ to $Ar^3$, $R^1$ to $R^5$, L', $R_a$, $R_b$, and a ring formed by bonding neighboring groups of $R^1$ to $R^5$ to each other are each an aryl group, an arylene group, an aromatic hydrocarbon, a fluorenyl group, a fluorenylene group, a heterocyclic group, an aliphatic ring (group), a fused ring (group), an alkyl group, an alkenyl group, an alkynyl group, an alkoxy group, an aryloxy group and the like, each of these may be further substituted with one or more substituents selected from the group above.

For example, when $Ar^1$ to $Ar^3$, $R^1$ to $R^5$, L', $R_a$, $R_b$, and a ring formed by bonding neighboring groups of $R^1$ to $R^5$ to each other may be further substituted with an aryl group, preferably a $C_6$-$C_{20}$ aryl group, more preferably, a $C_6$-$C_{18}$ aryl group, for example, phenyl, naphthyl, biphenyl, terphenyl, and the like.

Also, when $Ar^1$ to $Ar^3$, $R^1$ to $R^5$, L', $R_a$, $R_b$, and a ring formed by bonding neighboring groups of $R^1$ to $R^5$ to each other are further substituted with deuterium or F.

Formula 1 may be represented by one of the following Formula 2 to Formula 5.

<Formula 2>

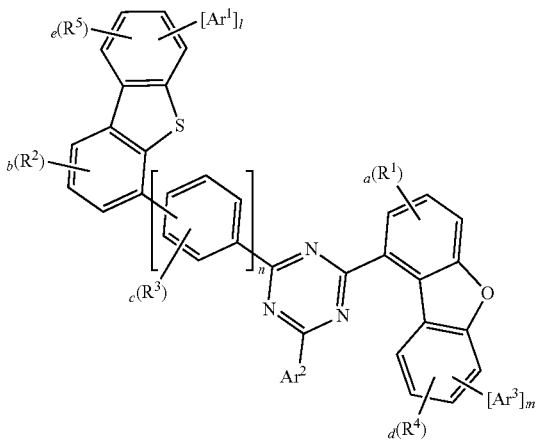

<Formula 3>

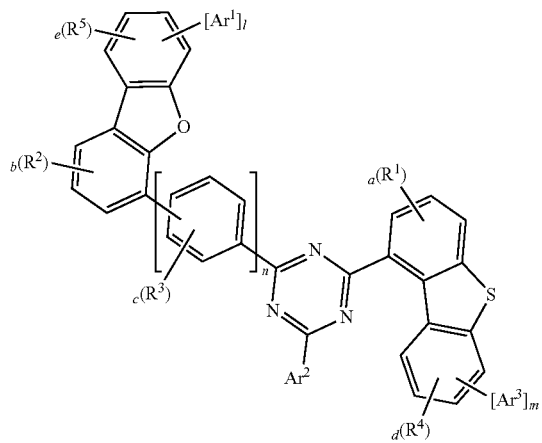

<Formula 4>

<Formula 5>

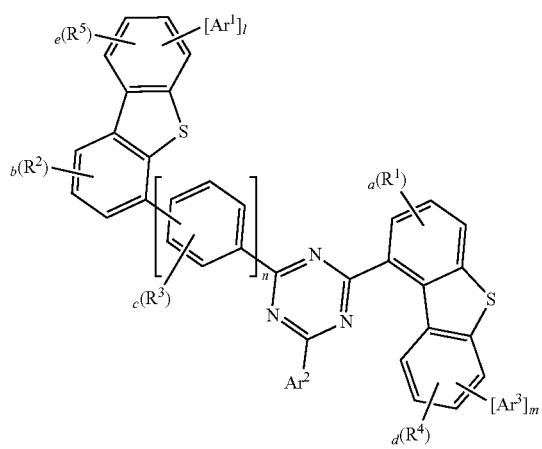

<Formula 6>

<Formula 7>

<Formula 8>

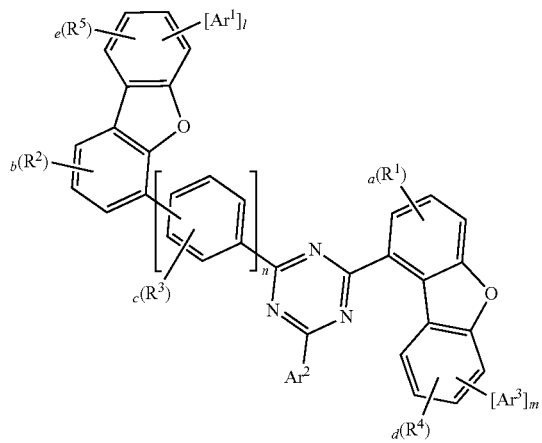

In Formulas 2 to 5, $Ar^1$ to $Ar^3$, $R^1$ to $R^5$, a, b, c, d, e, l, m and n are the same as defined in Formula 1.

In addition, Formula 1 may be represented by one of Formula 6 to Formula 8.

In Formulas 6 to 8, $X^1$, $X^2$, $Ar^1$ to $Ar^3$, $R^1$ to $R^5$, a, b, c, d, e, l and m are the same as defined in Formula 1.

In addition, Formula 1 may be represented the following Formula 9 or Formula 10.

<Formula 9>

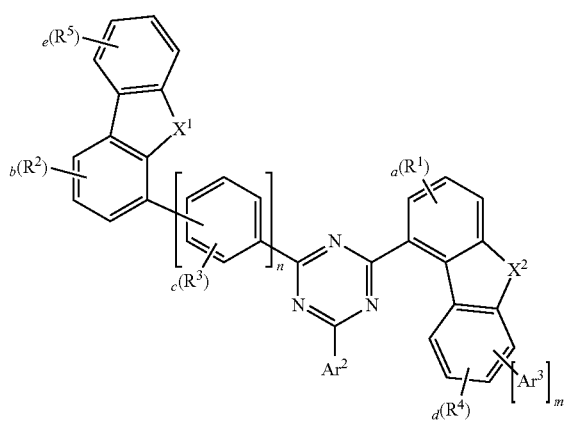

<Formula 10>

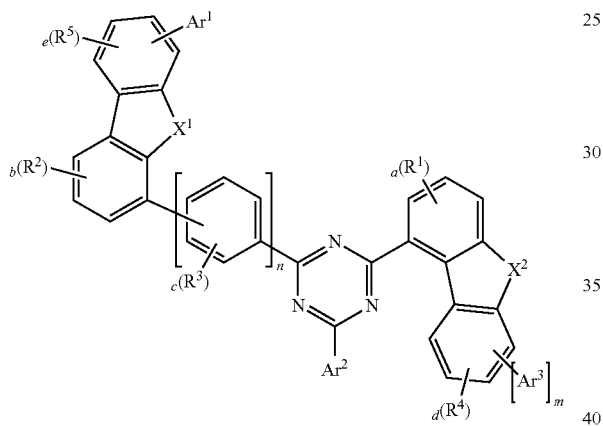

In Formula 9 and 10, $X^1$, $X^2$, $Ar^1$ to $Ar^3$, $R^1$ to $R^5$, a, b, c, d, e, m and n are the same as defined in Formula 1.

In addition, Formula 1 may be represented by one of Formula 11 to Formula 13.

<Formula 11>

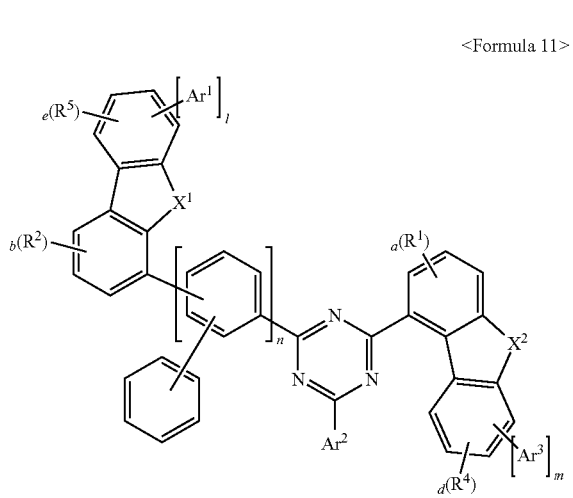

<Formula 12>

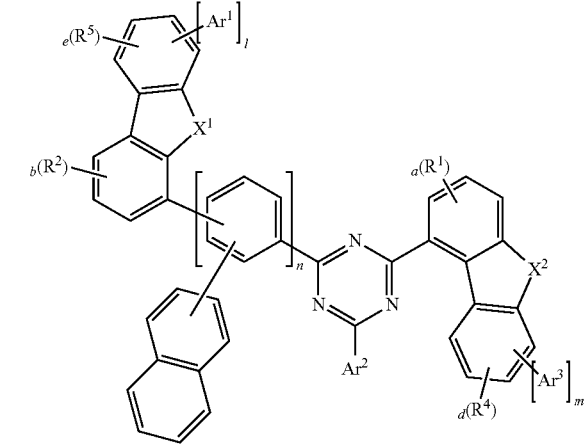

<Formula 13>

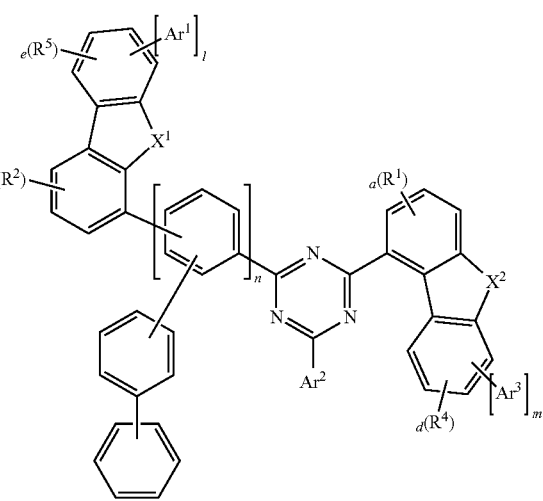

In Formulas 11 to 13, $X^1$, $X^2$, $Ar^1$ to $Ar^3$, $R^1$, $R^2$, $R^4$, $R^5$, a, b, d, e, l, m and n are the same as defined in Formula 1.

In addition, Formula 1 may be represented by Formula 14:

<Formula 14>

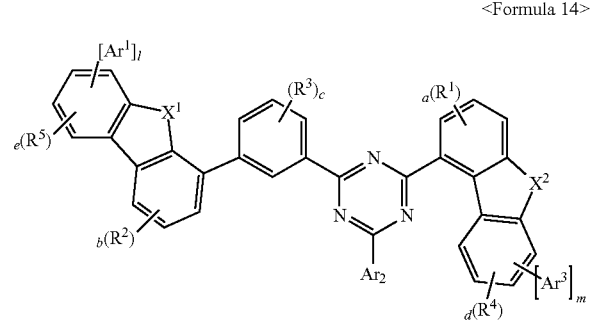

In Formula 14, $X^1$, $X^2$, $Ar^1$ to $Ar^3$, $R^1$ to $R^5$, a, b, c, d, e, l and m are the same as defined in Formula 1.

Preferably, in Formula 1, at least one of $Ar^1$, $Ar^3$ and $R^3$ is a $C_6$-$C_{24}$ aryl group, more preferably, $Ar^1$ or $Ar^3$ is a $C_6$-$C_{24}$ aryl group, and more preferably, $R^3$ is a $C_6$-$C_{24}$ aryl group.

Specifically, the compound represented by formula 1 may be one of the following compounds, but it is not limited thereto.
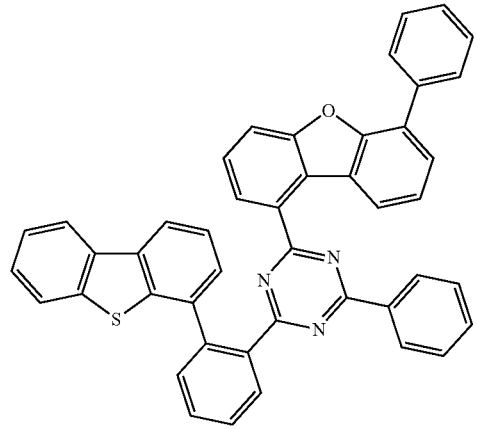
1-1
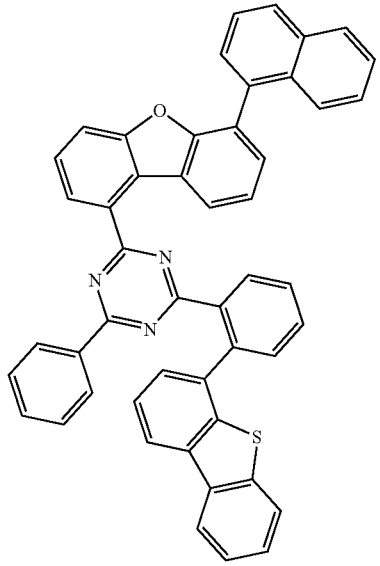
1-2
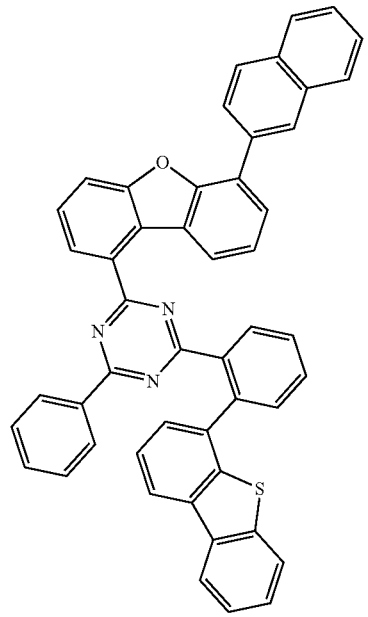
1-3
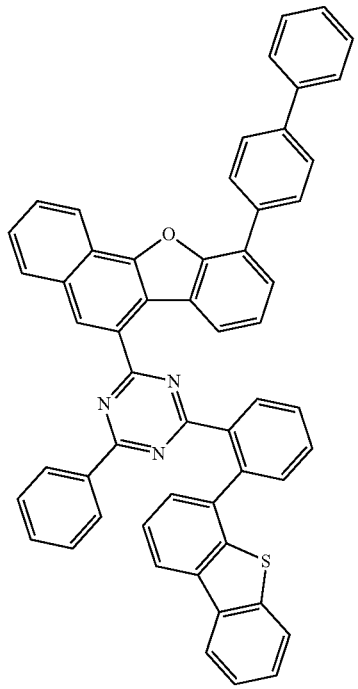
1-4
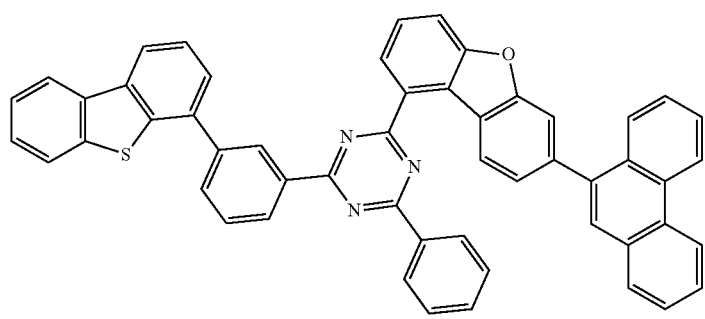
1-5

-continued
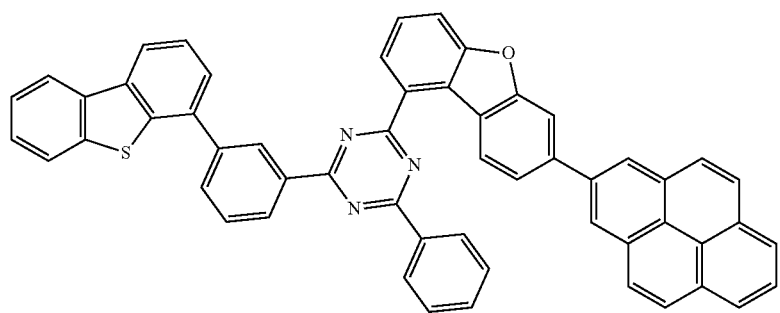
1-6
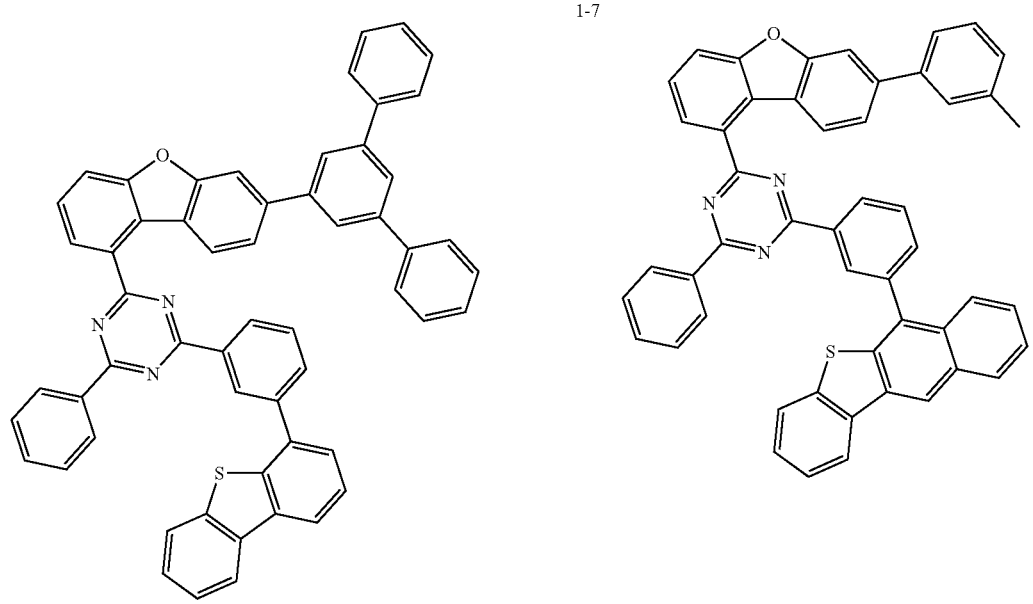
1-7
1-8
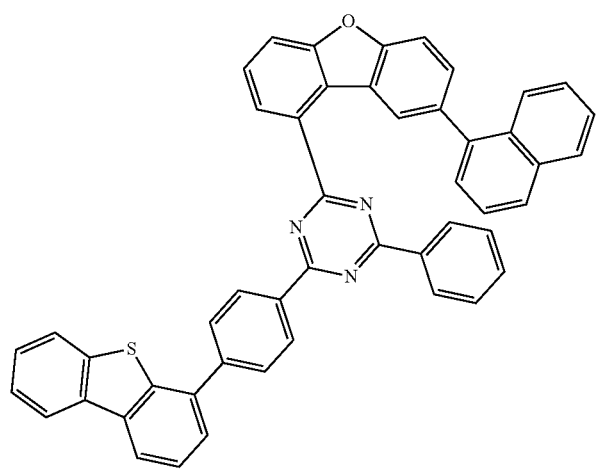
1-9

1-10
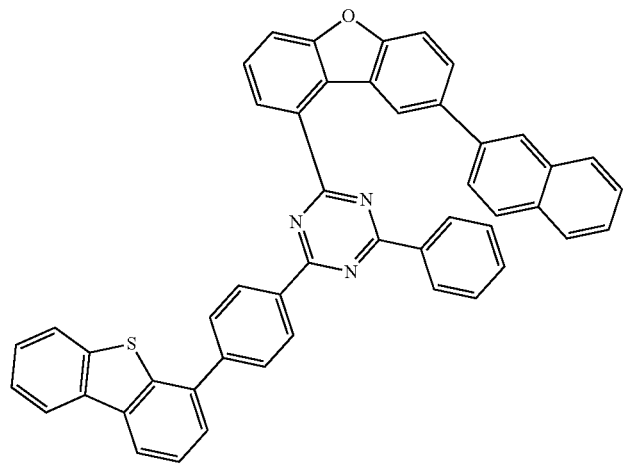
1-11
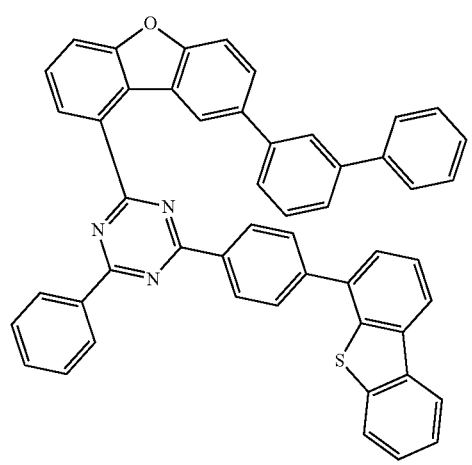
1-12
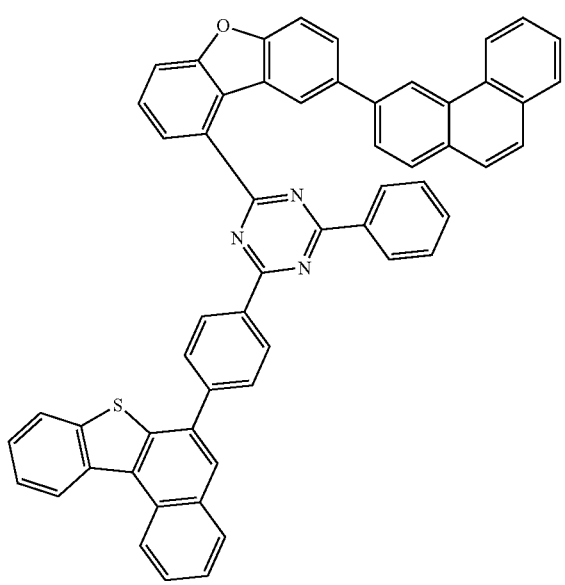
1-13
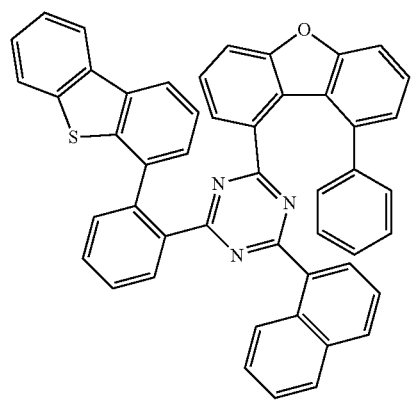
1-14
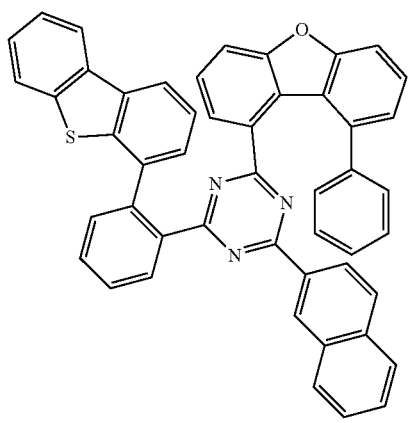

1-15
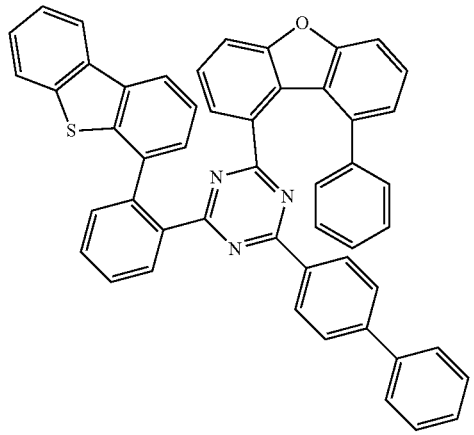
1-16
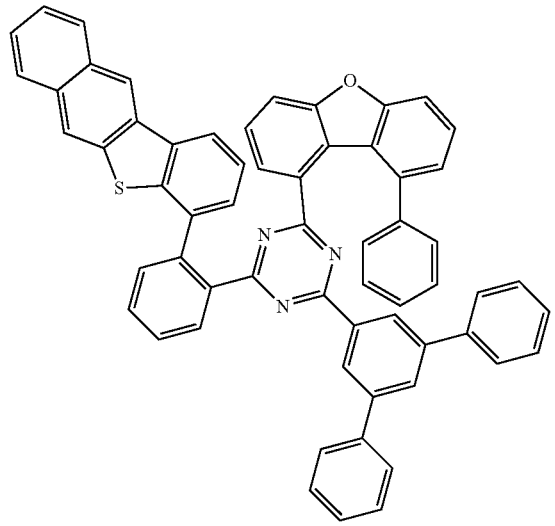
1-17
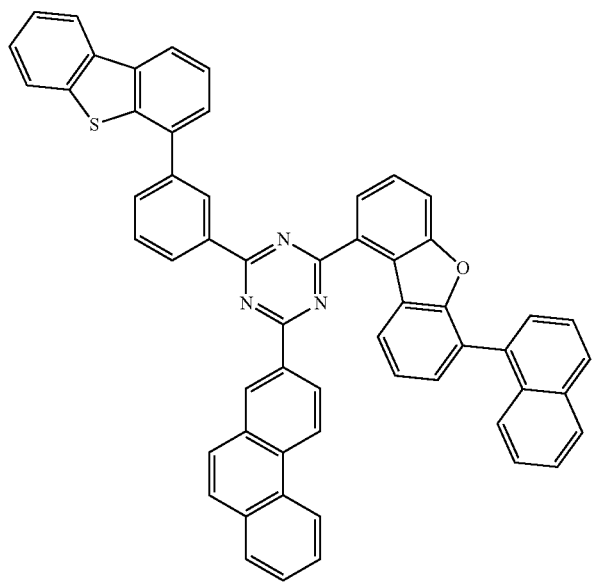
1-18
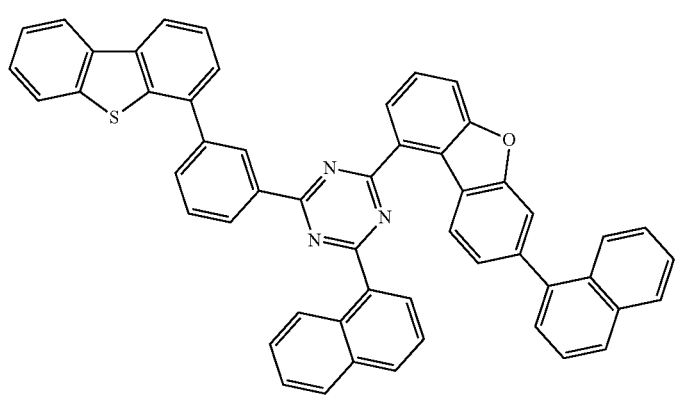

1-19
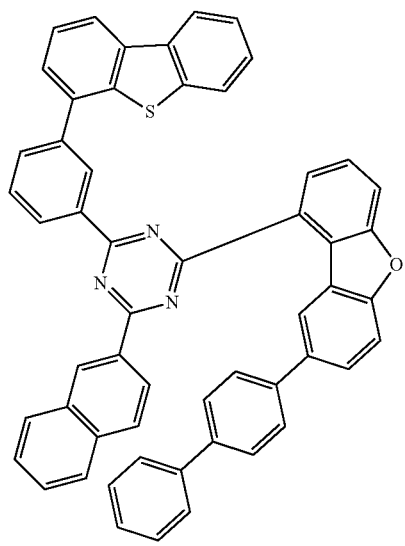
1-20
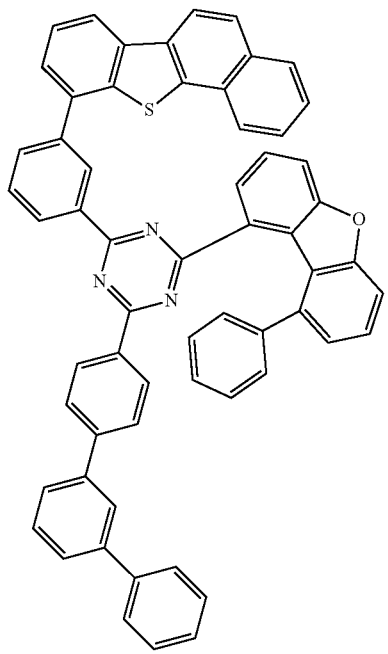
1-21
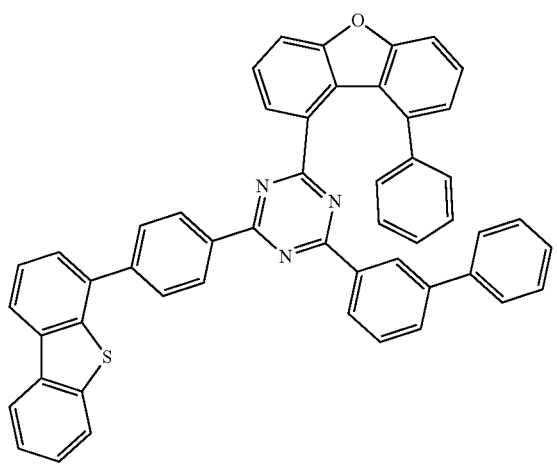
1-22
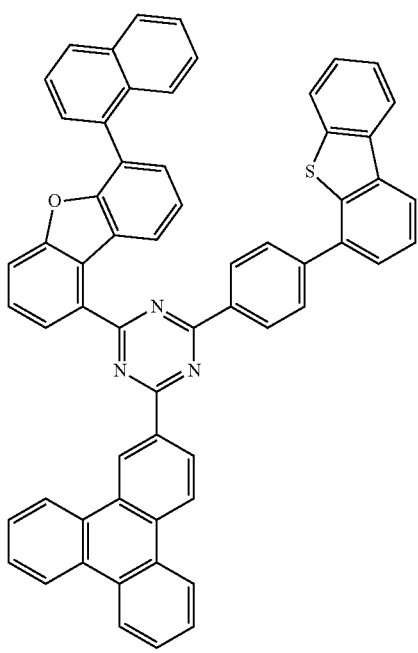

-continued
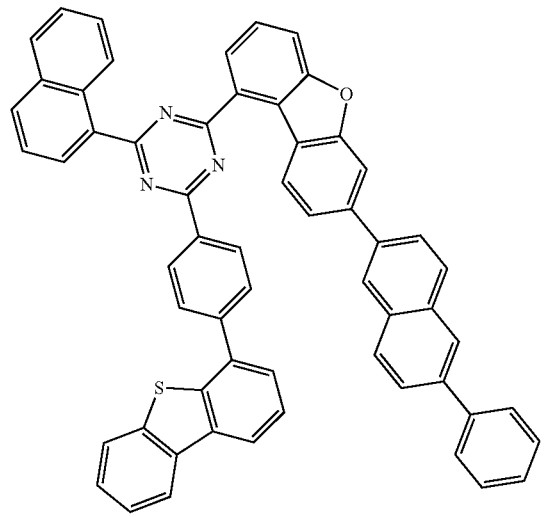
1-23
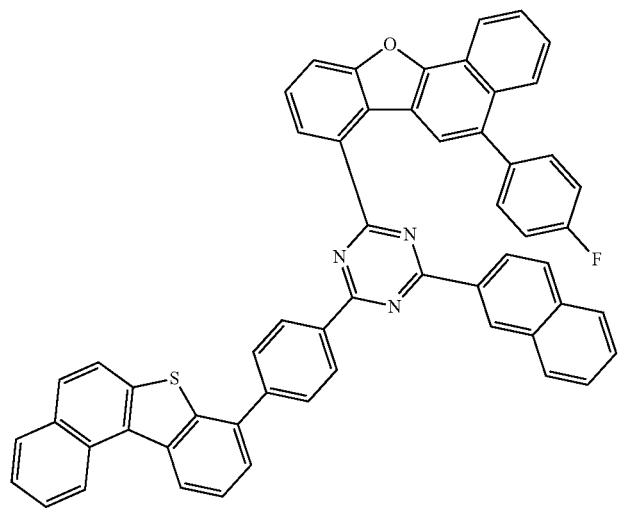
1-24
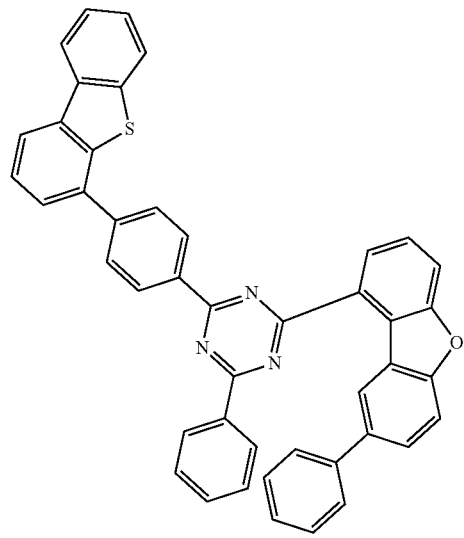
1-25
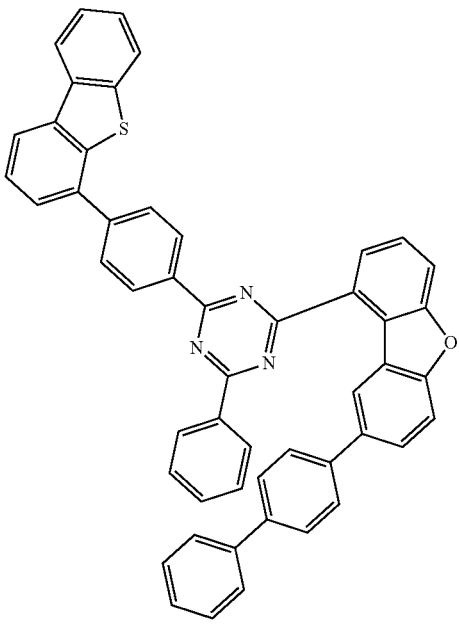
1-26

1-27
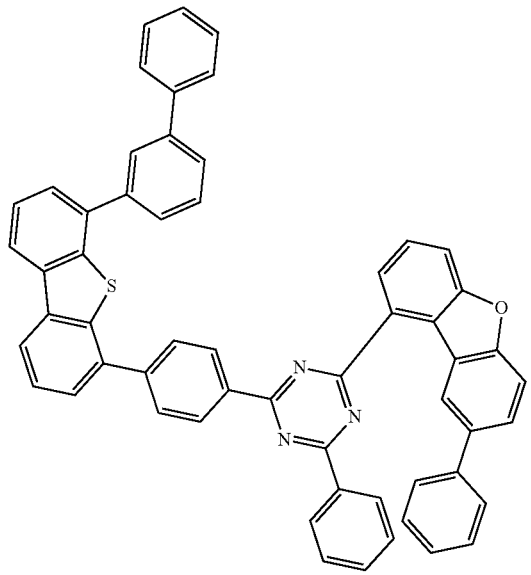
1-28
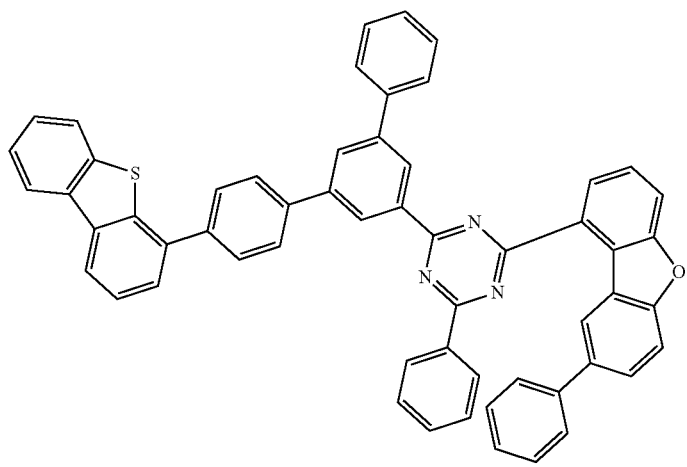
1-29
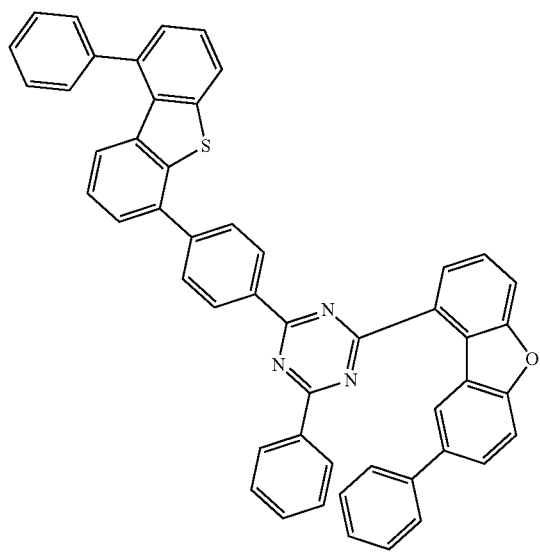
1-30
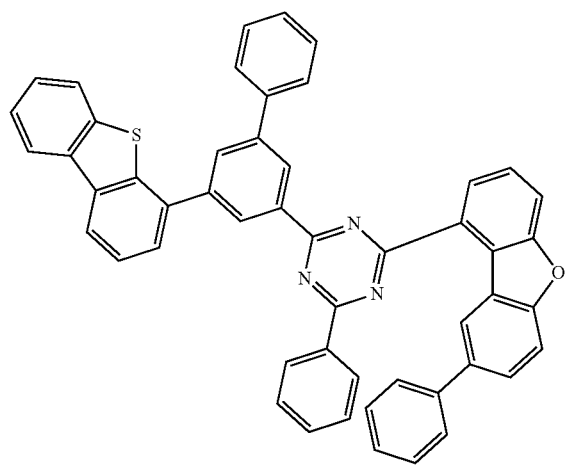

1-31 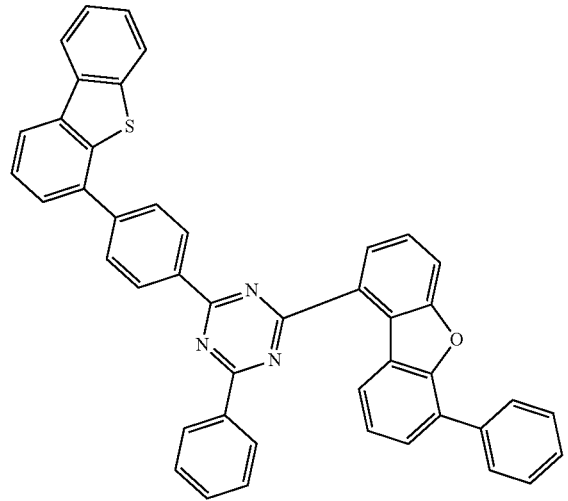
1-32 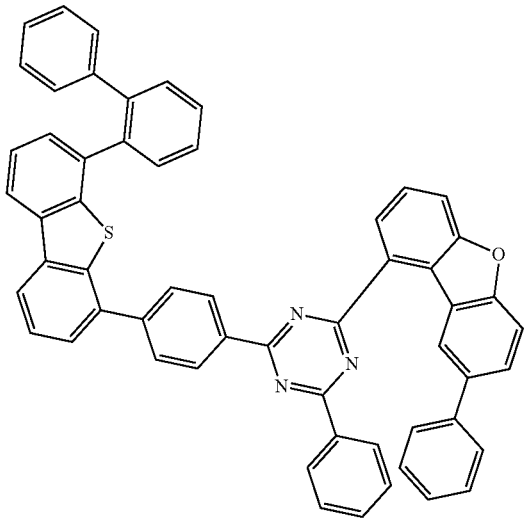
1-33 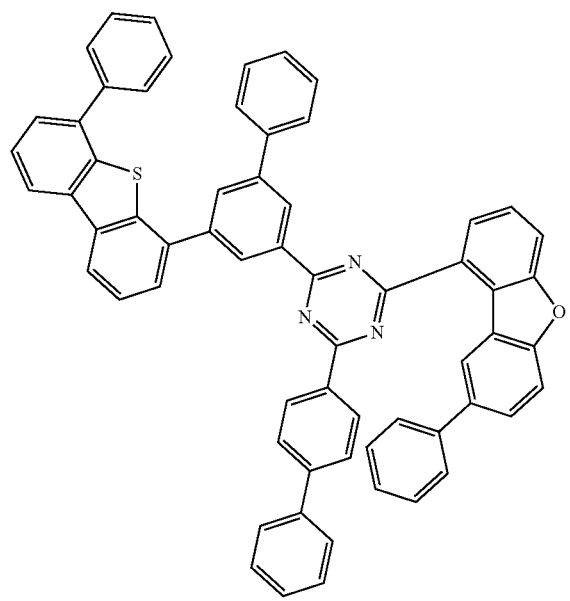
1-34 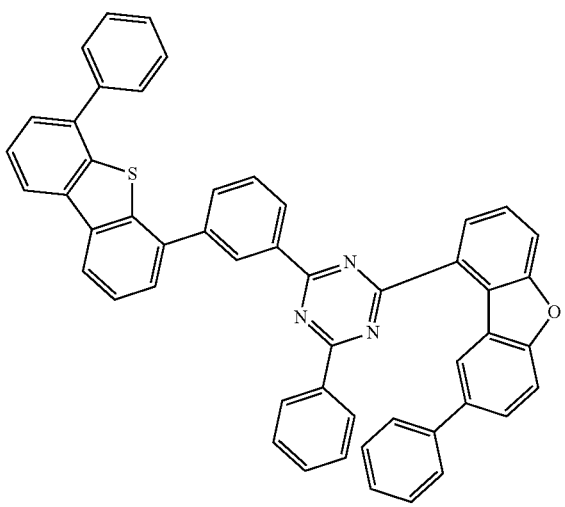

-continued
1-35
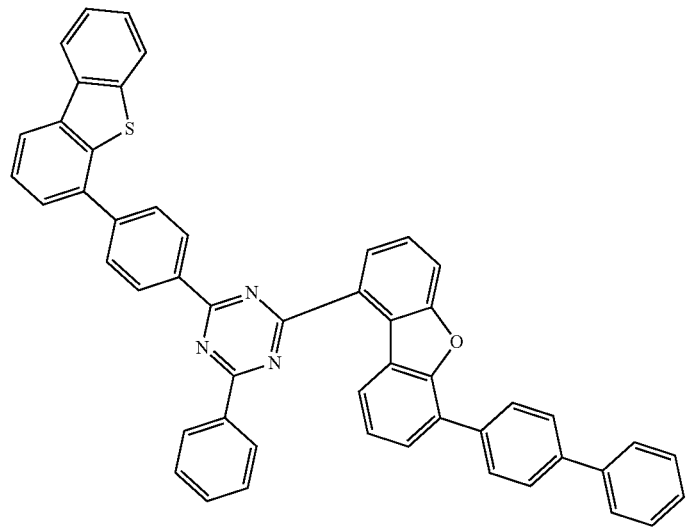
1-36 1-37
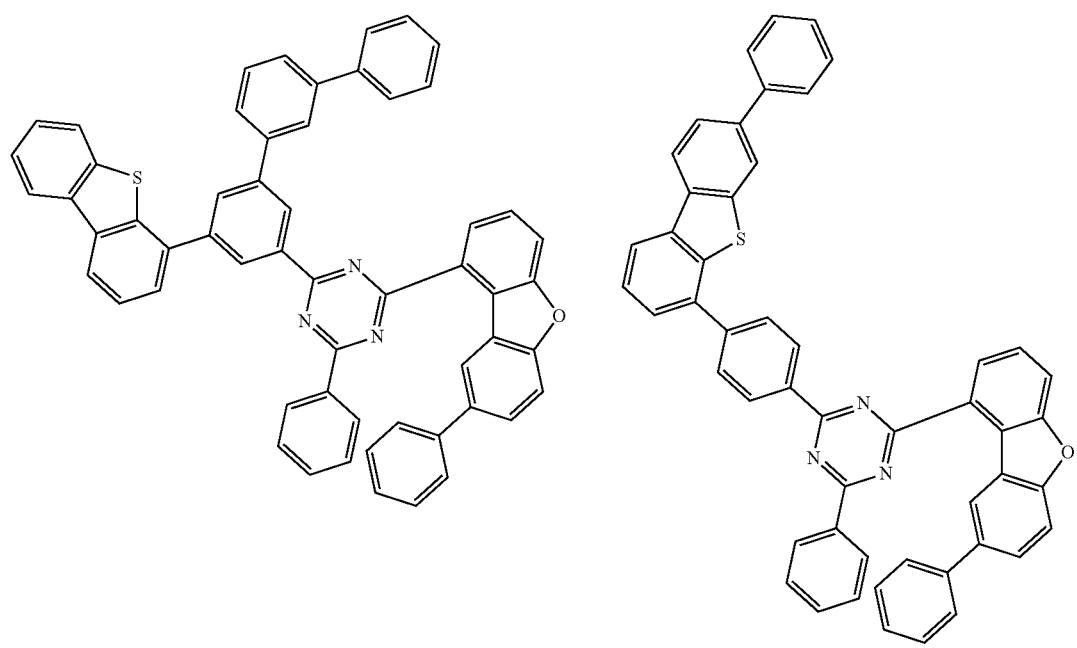
1-38
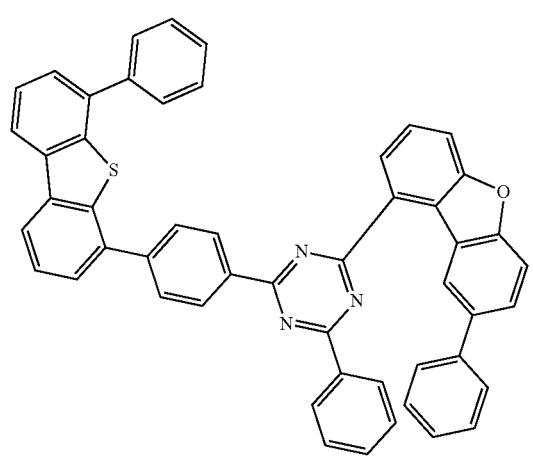

-continued
1-39
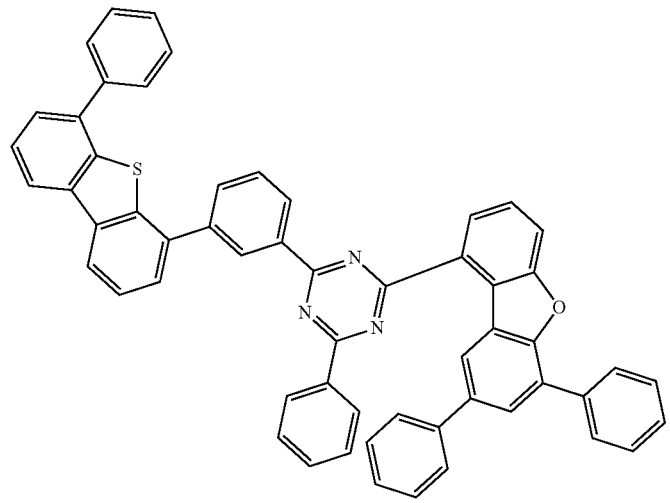
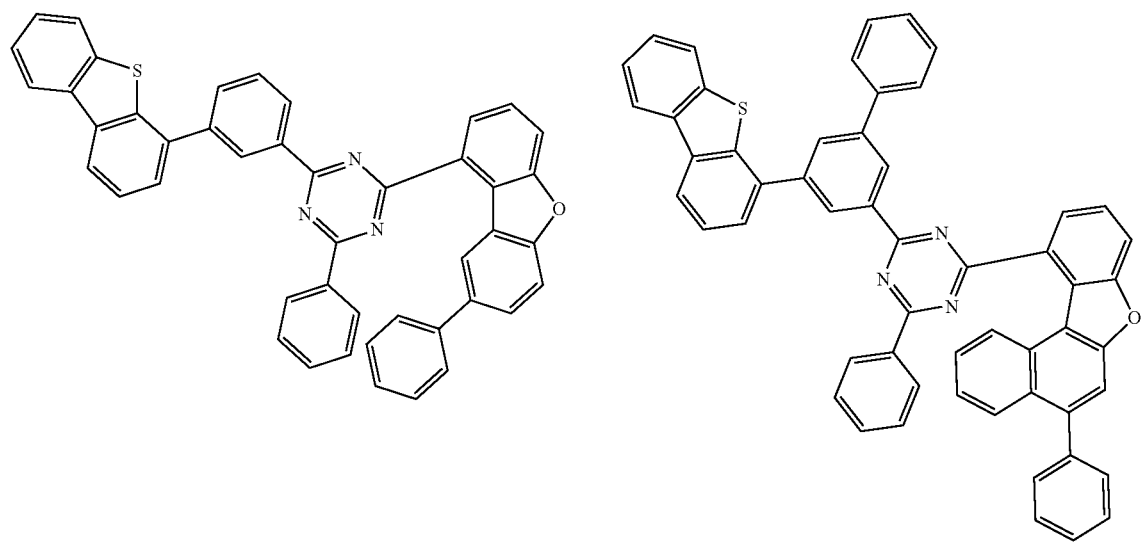

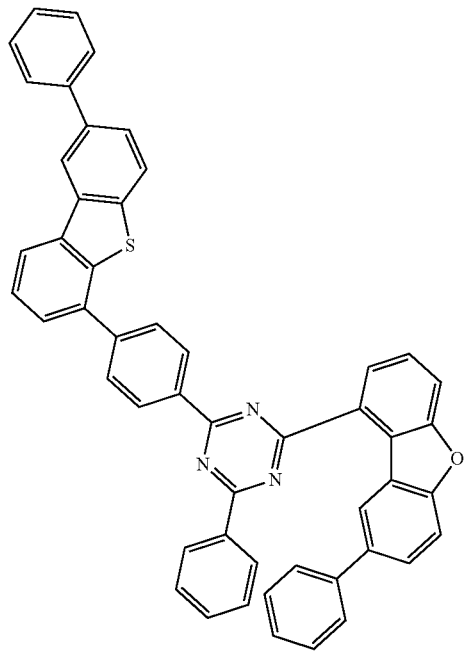
1-42
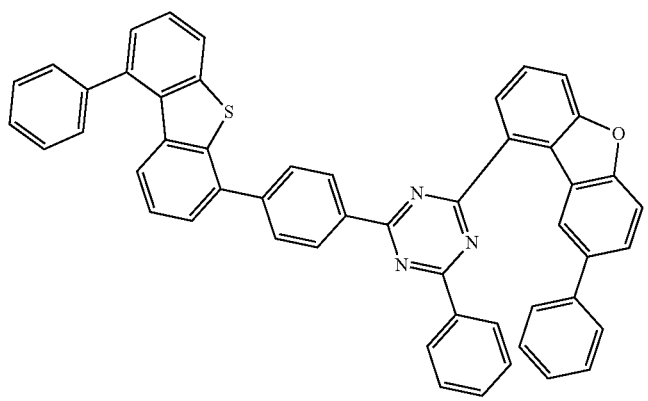
1-43
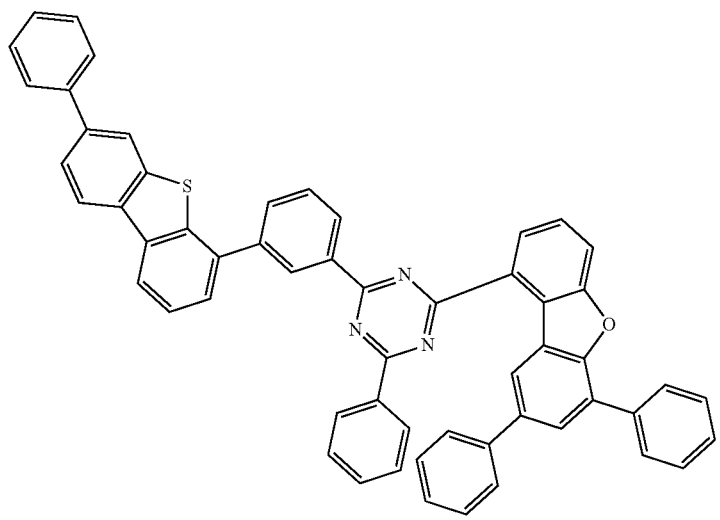
1-44

-continued
1-45
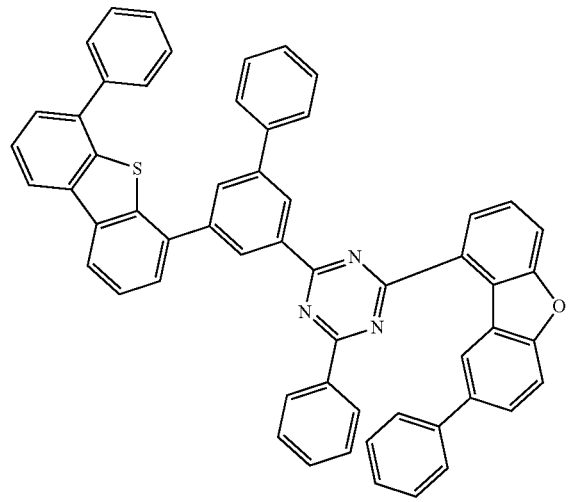
1-46
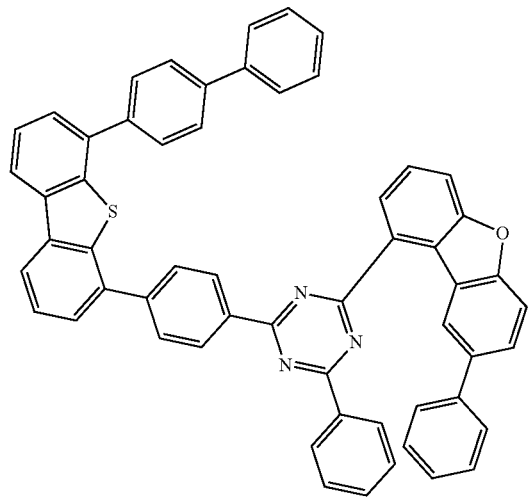
1-47
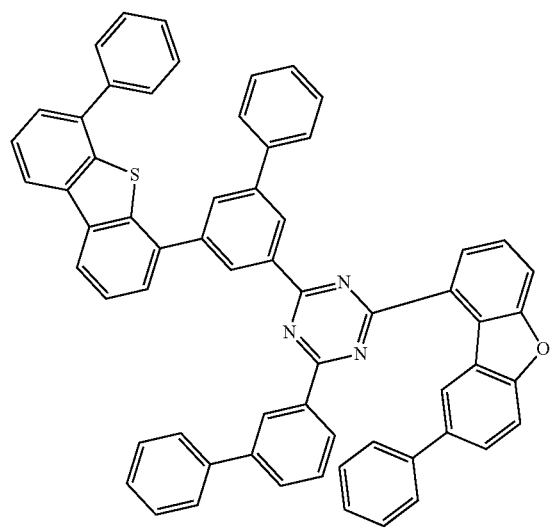
1-48
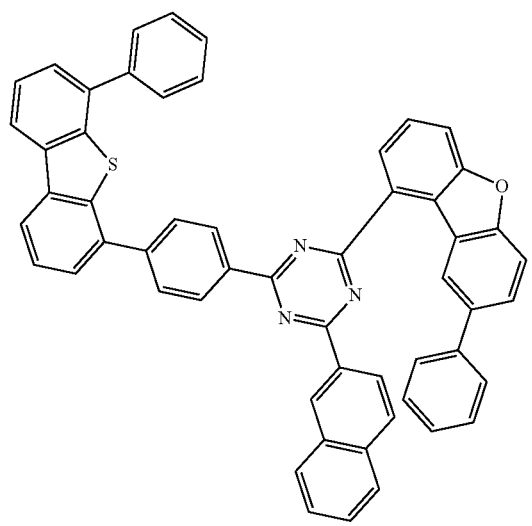
1-49
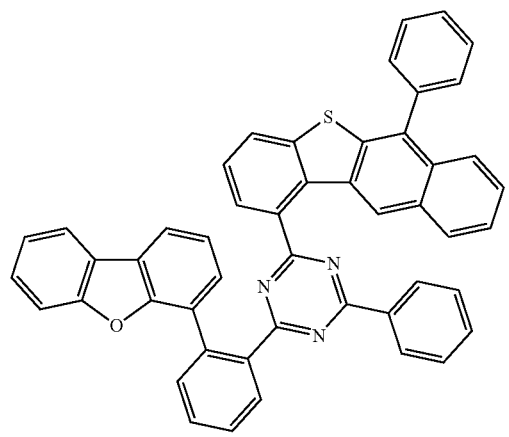
1-50
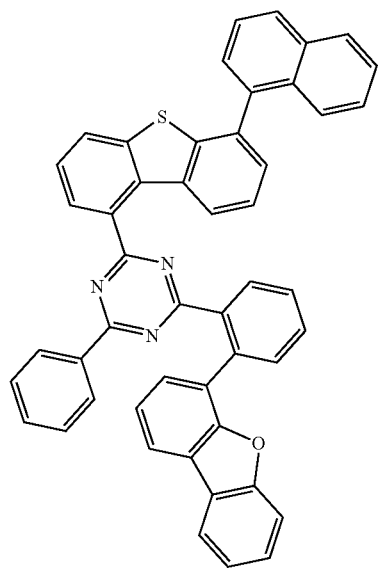

1-51
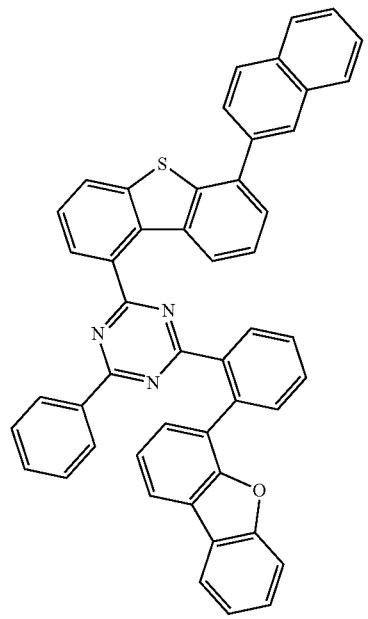
1-52
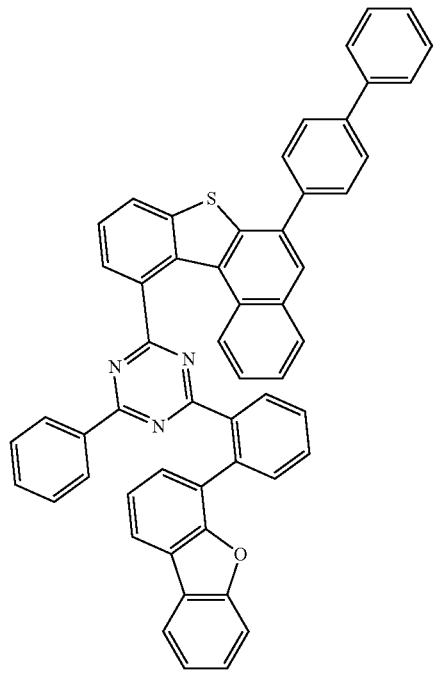
1-53
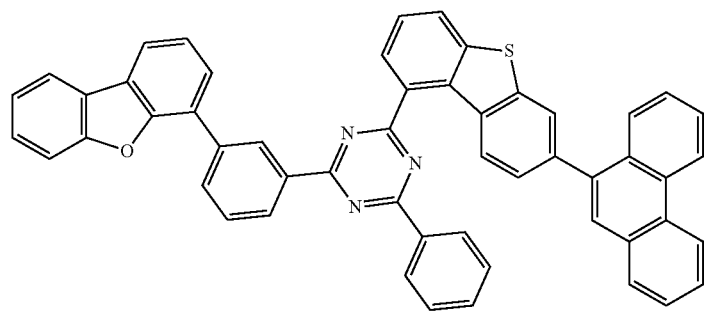
1-54
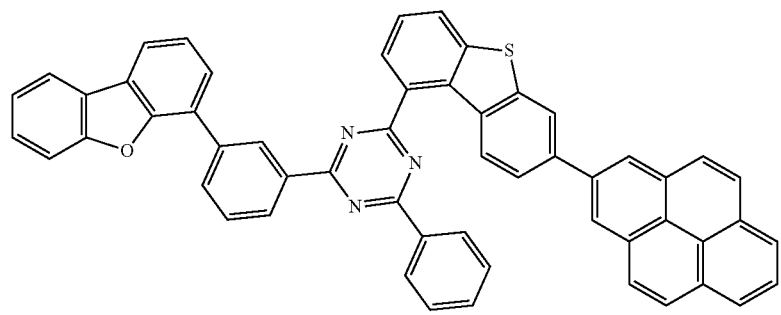

1-55
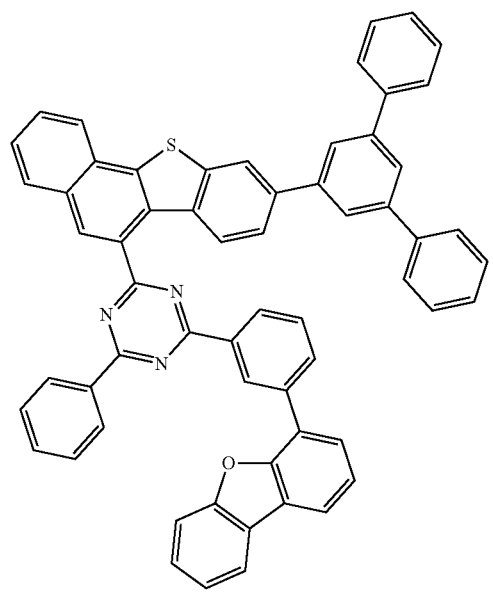
1-56
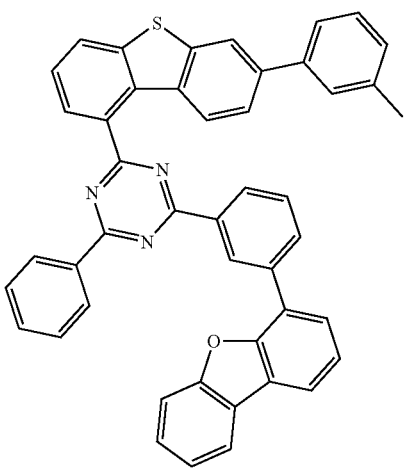
1-57
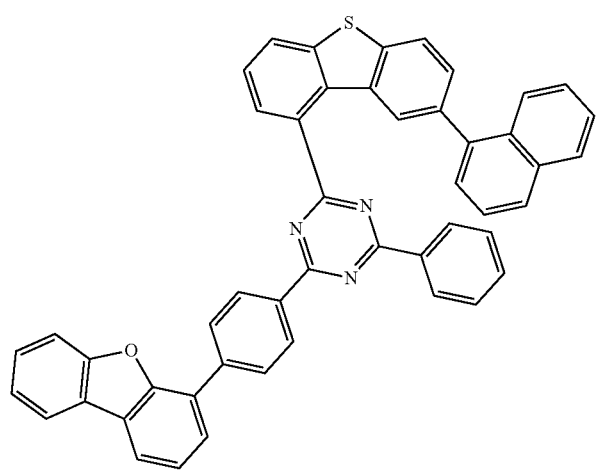
1-58
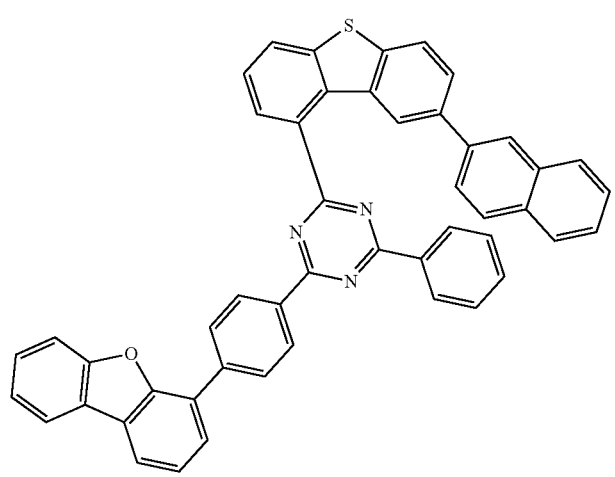

-continued
1-59
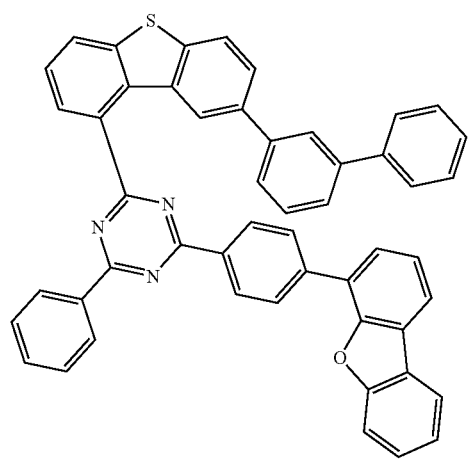
1-60
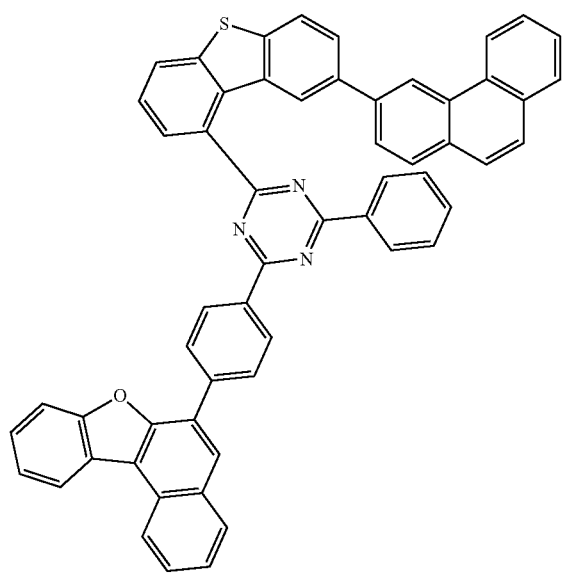
1-61
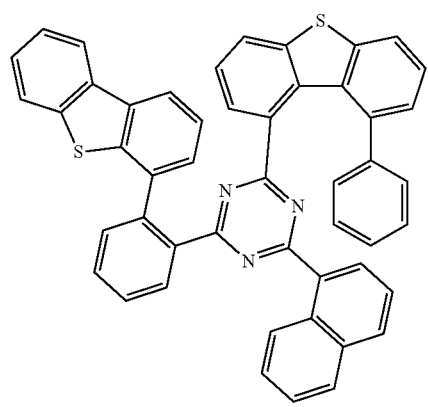
1-62
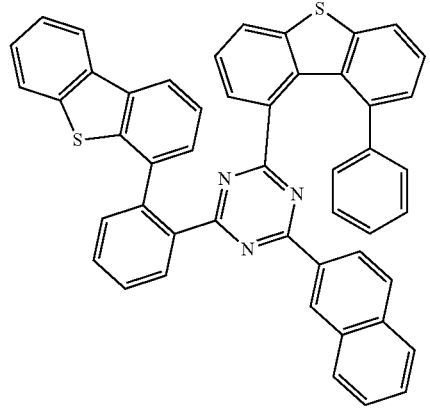
1-63
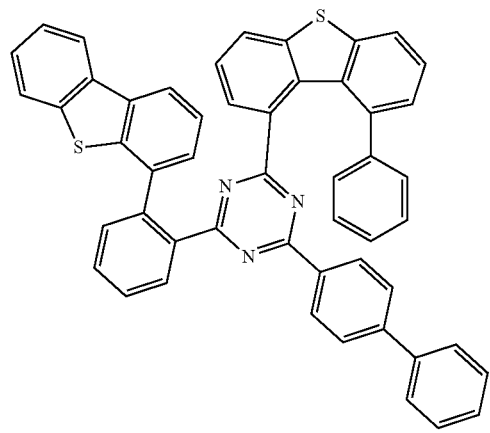
1-64
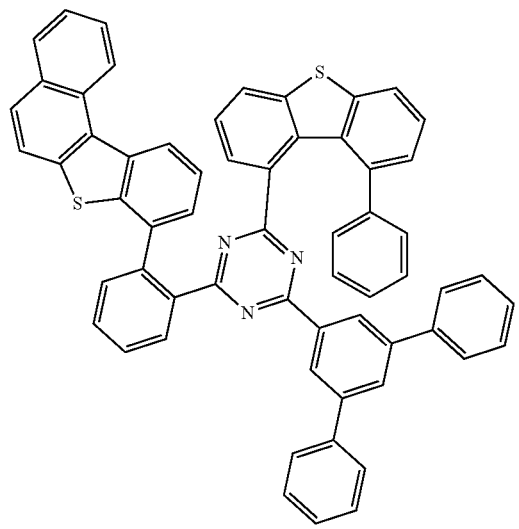

1-65
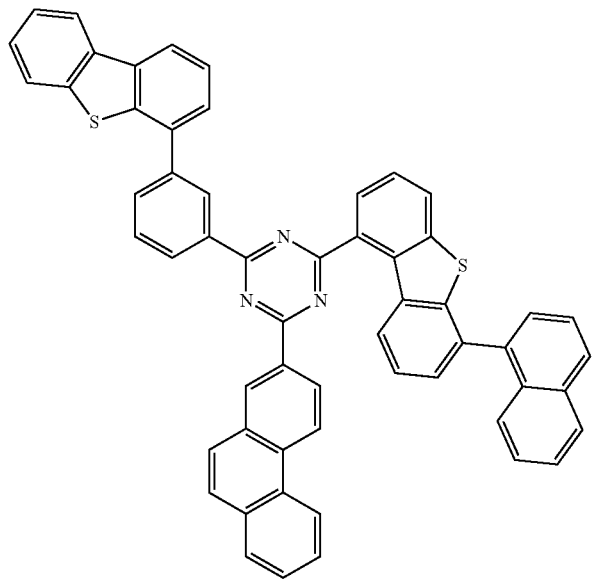
1-66
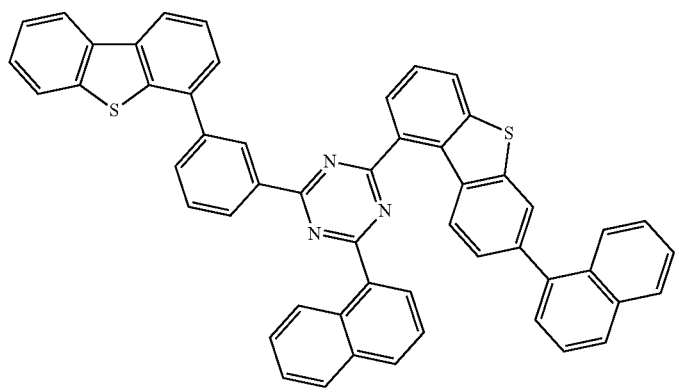
1-67
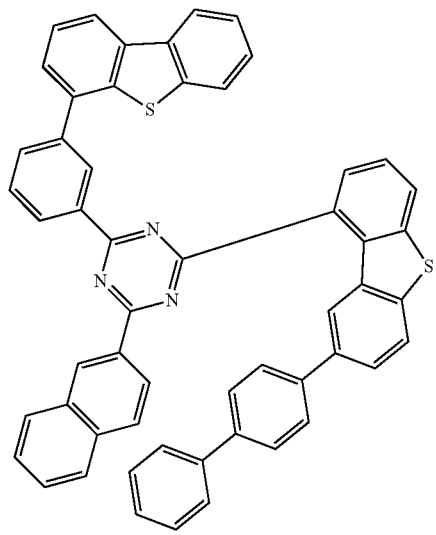
1-68
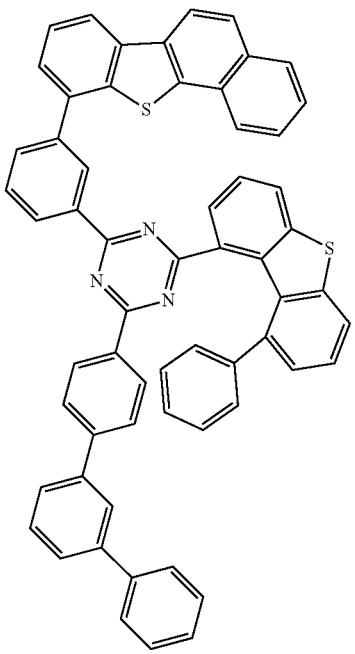

-continued
1-69
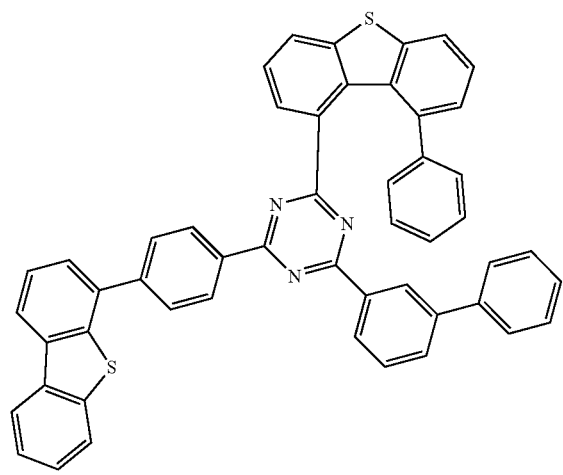
1-70
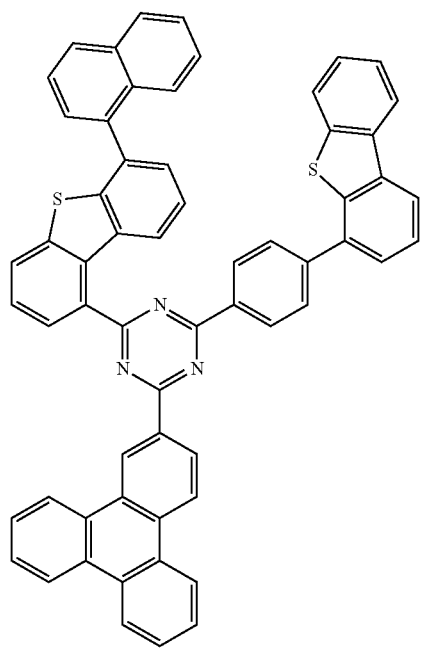
1-71
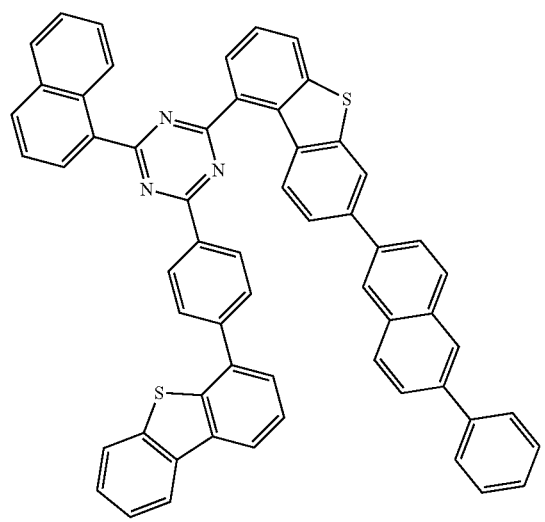
1-72
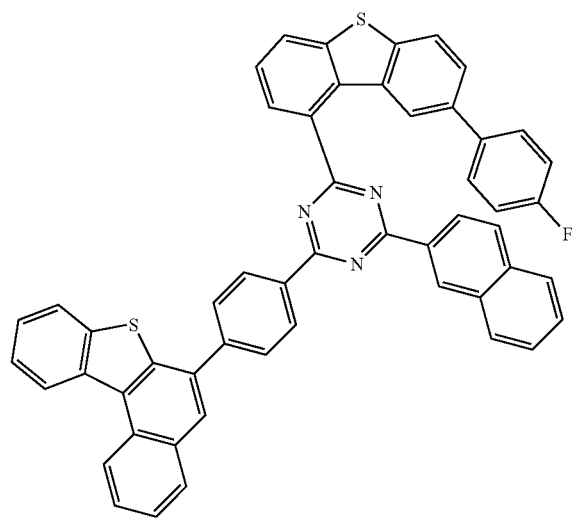

-continued
1-73
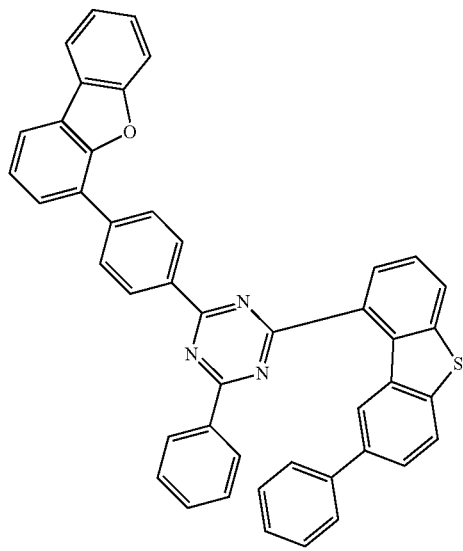
1-74
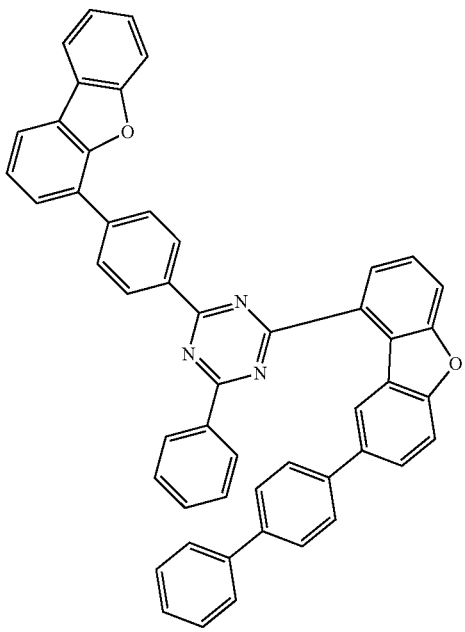
1-75
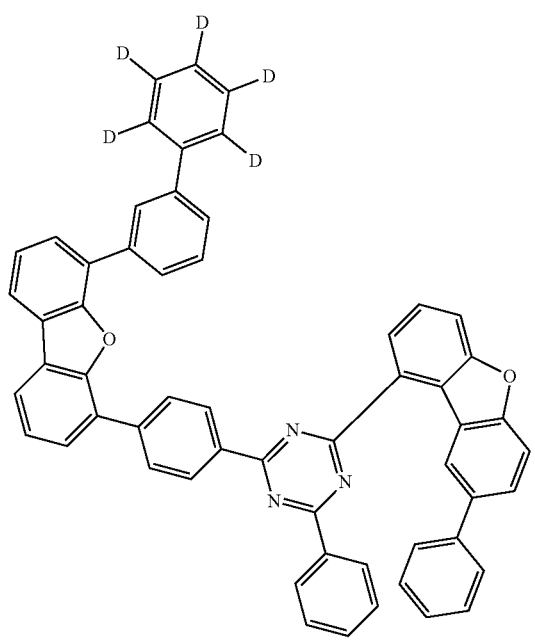

1-76
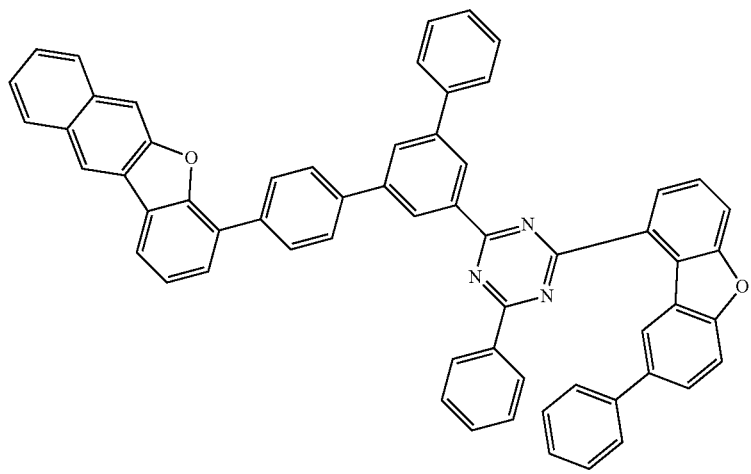
1-77
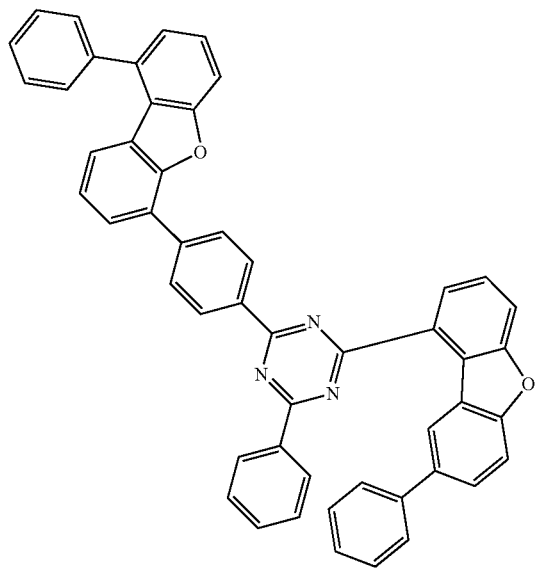
1-78
1-79
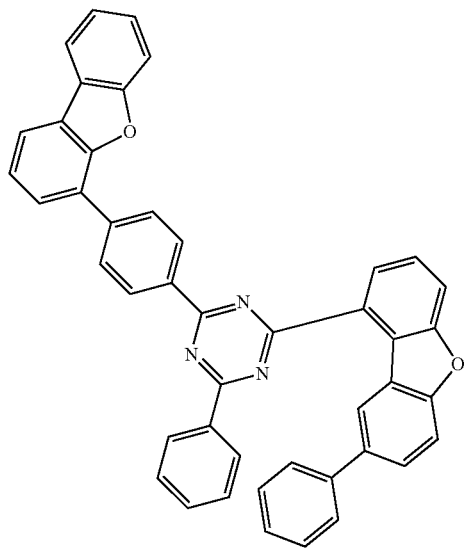
1-80
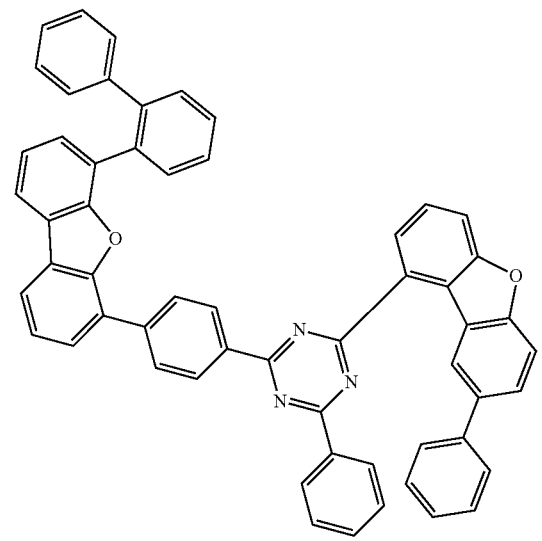

1-81
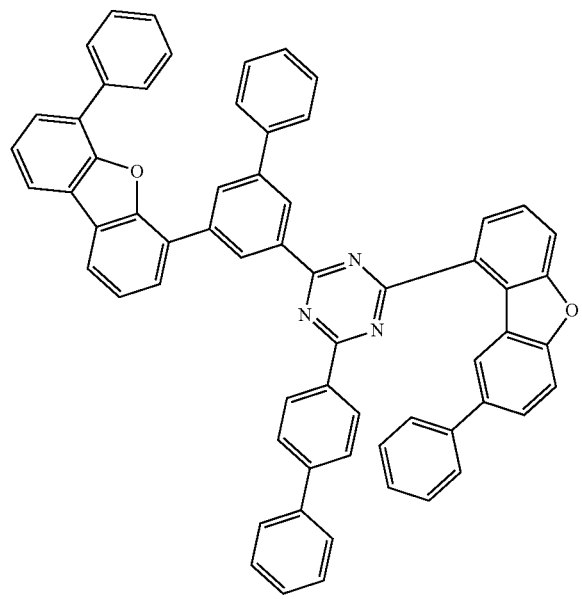
1-82
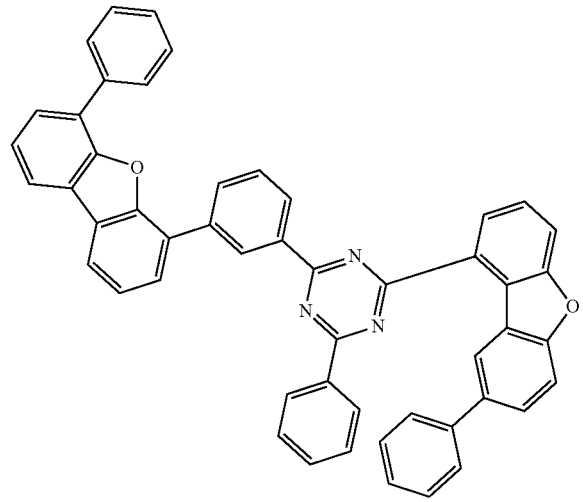
1-83
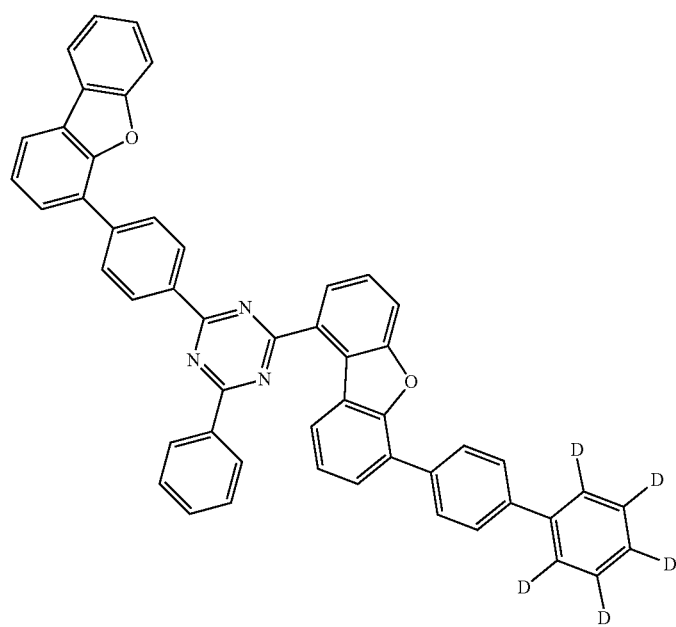

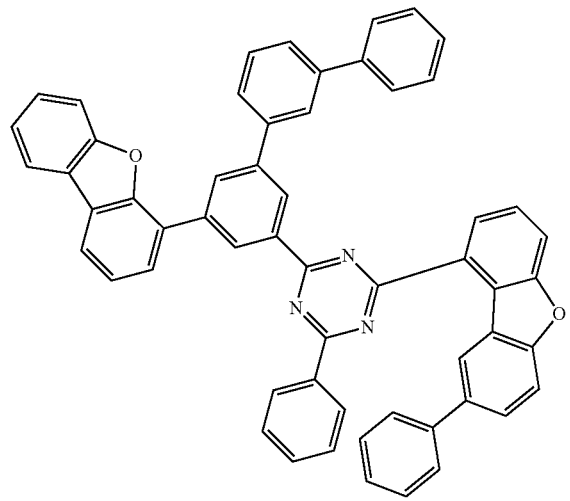
1-84
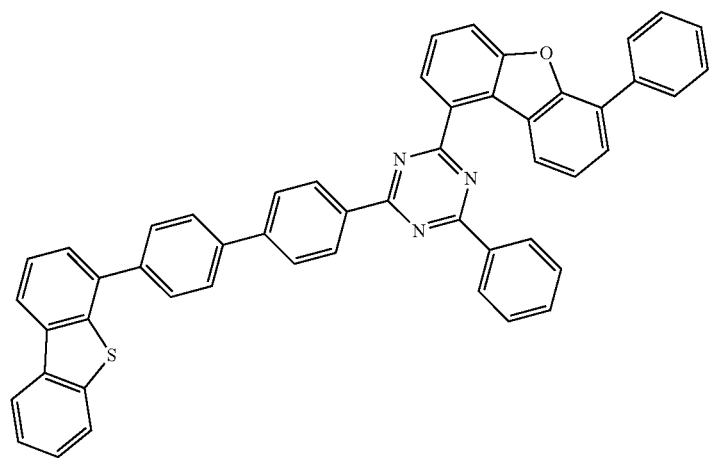
2-1
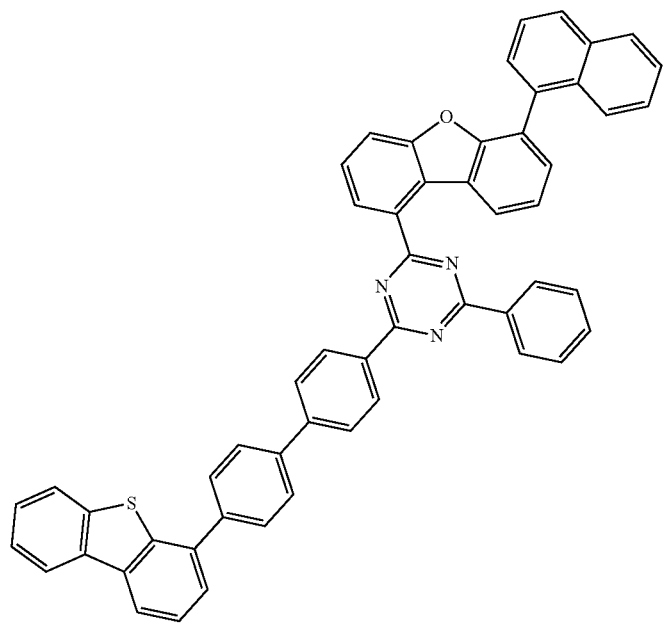
2-2

2-3
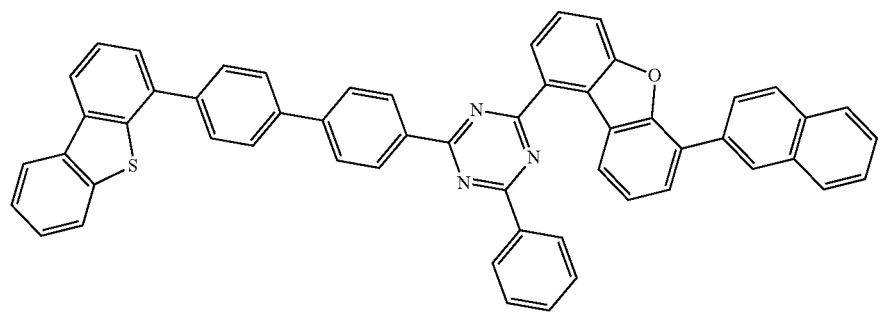
2-4
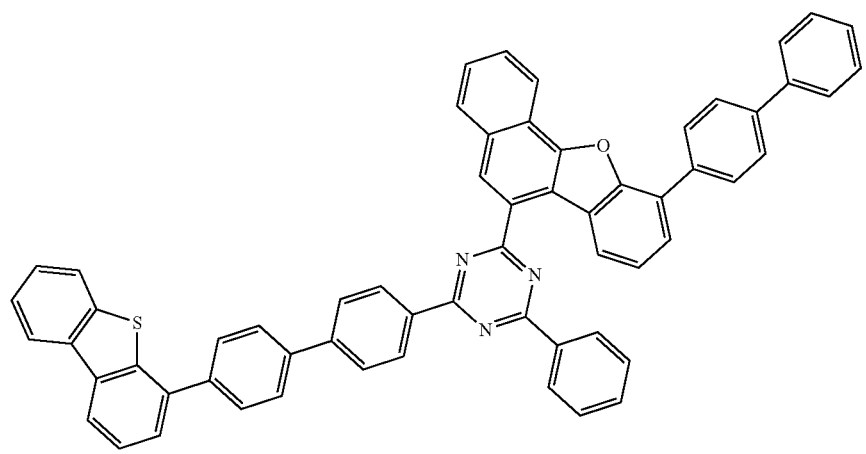
2-5
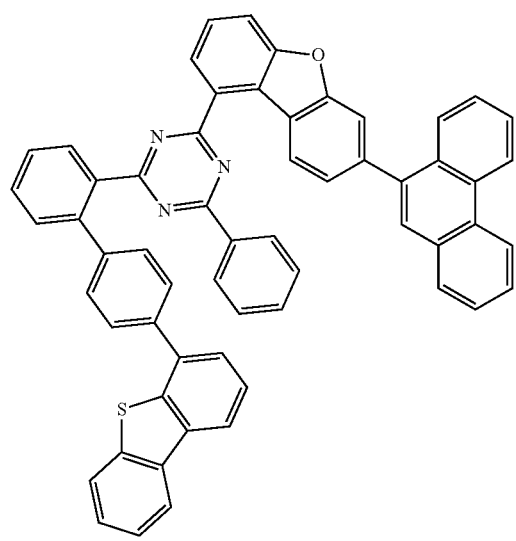
2-6
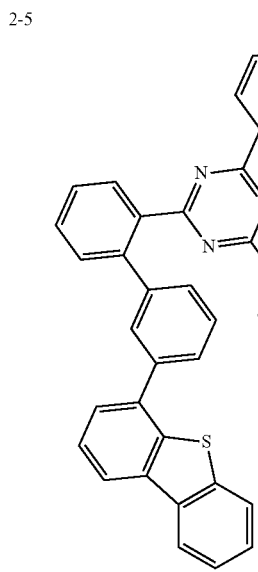

2-7
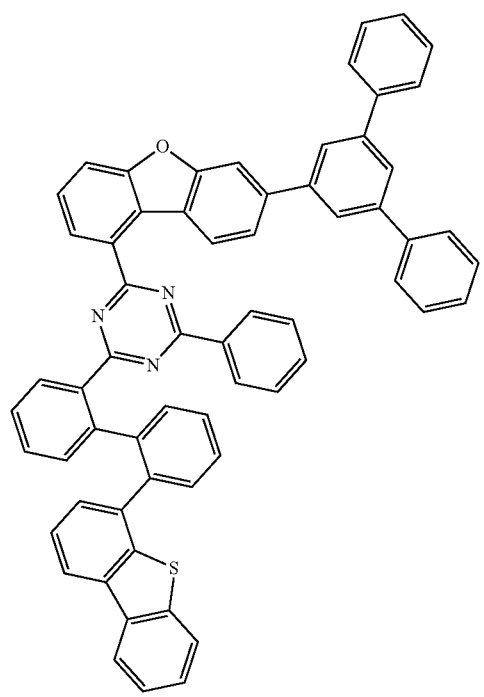
2-8
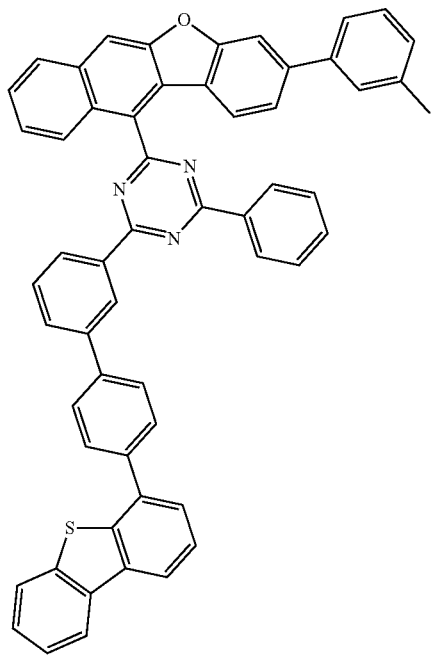
2-9
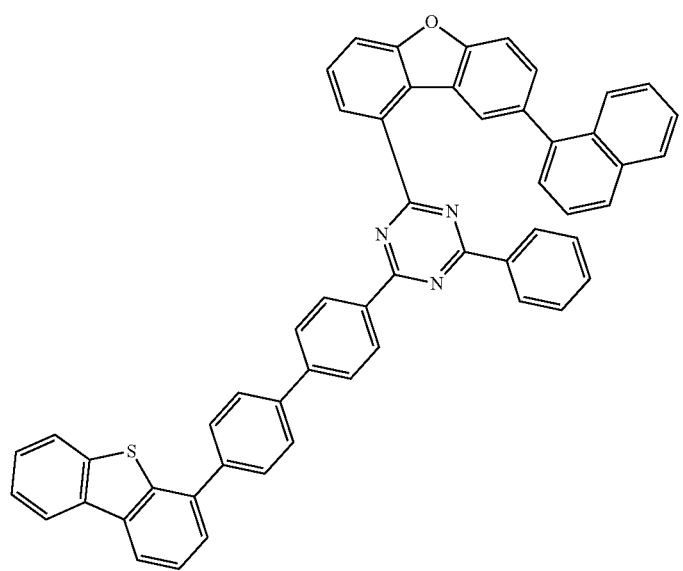

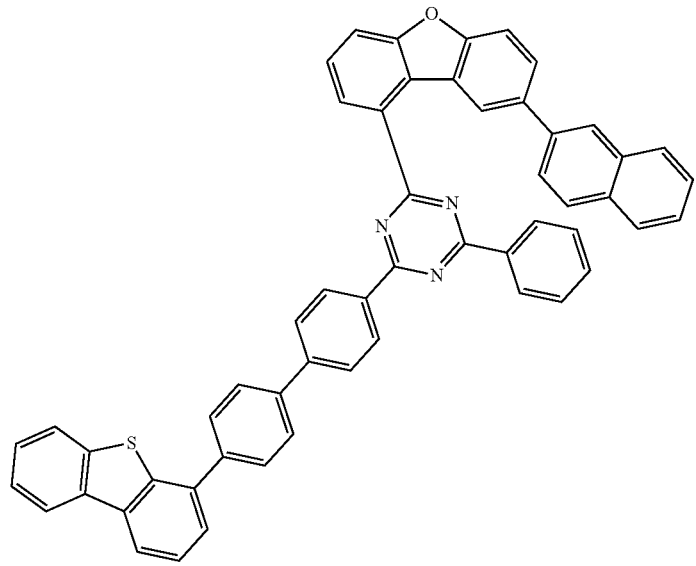
2-10
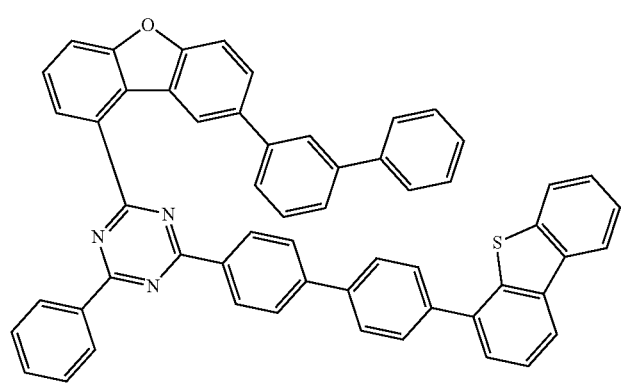
2-11
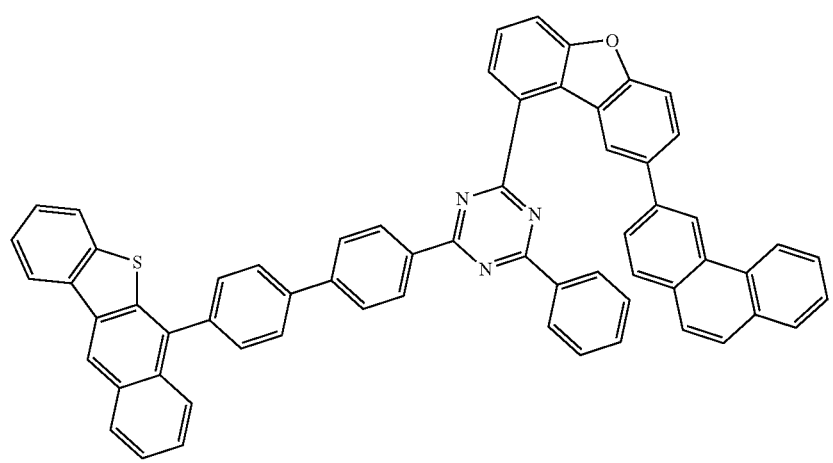
2-12

-continued
2-13
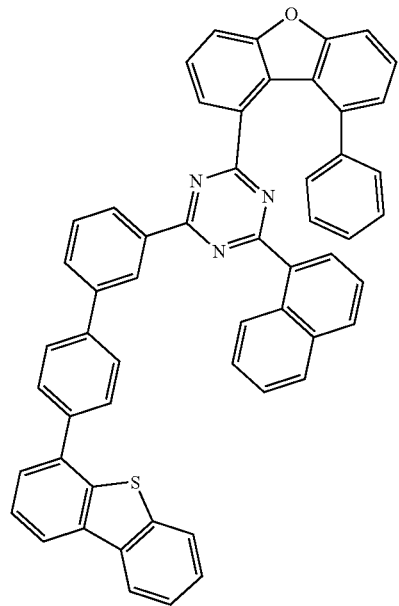
2-14
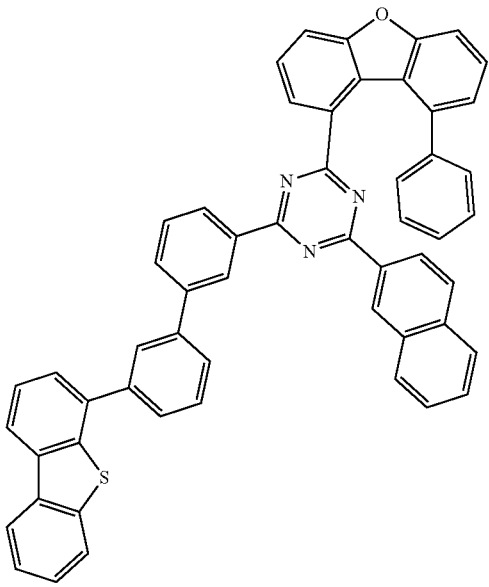
2-15
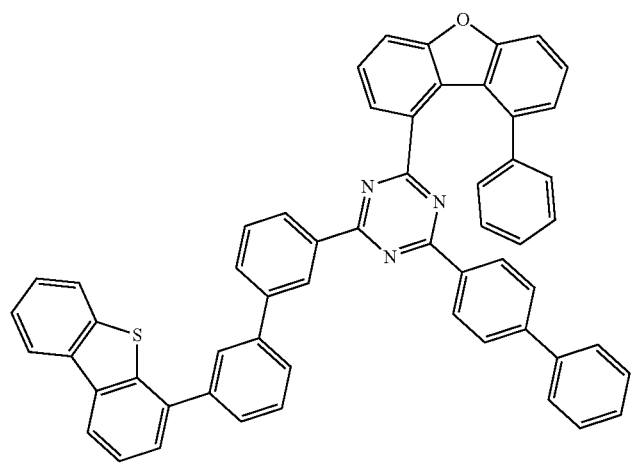

2-16
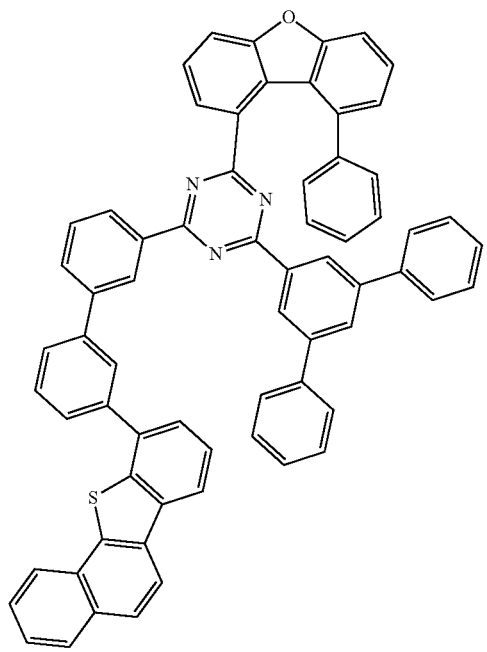
2-17
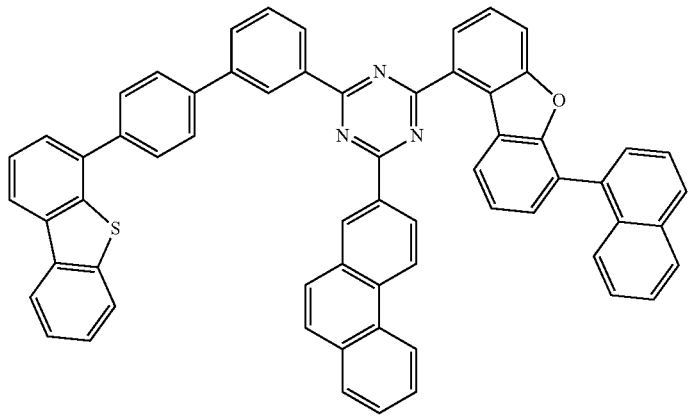
2-18
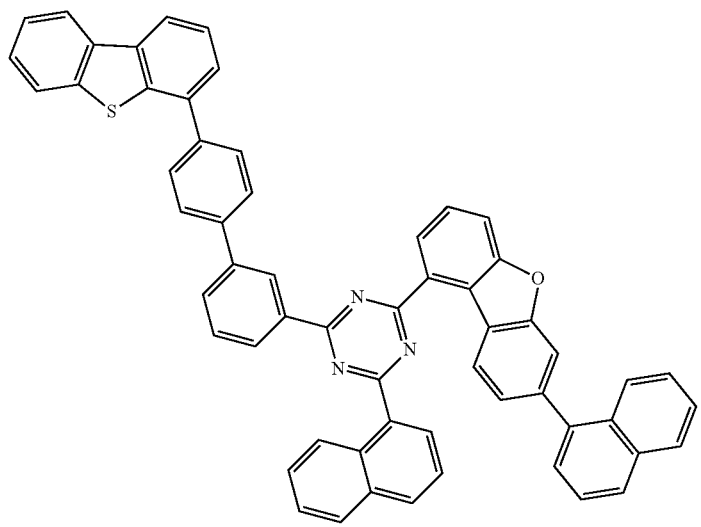

2-19
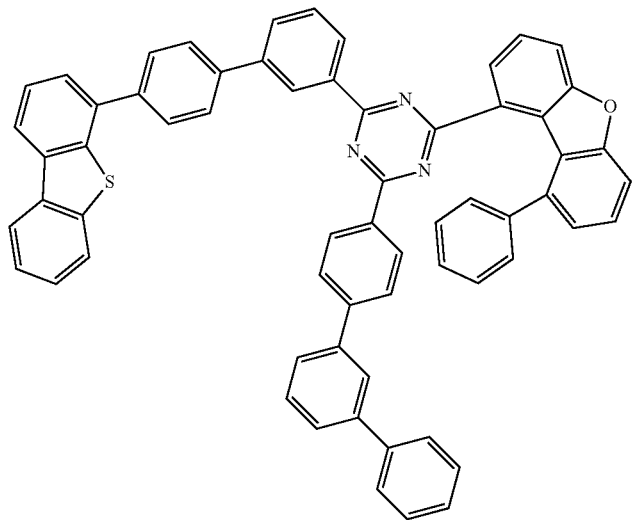
2-20
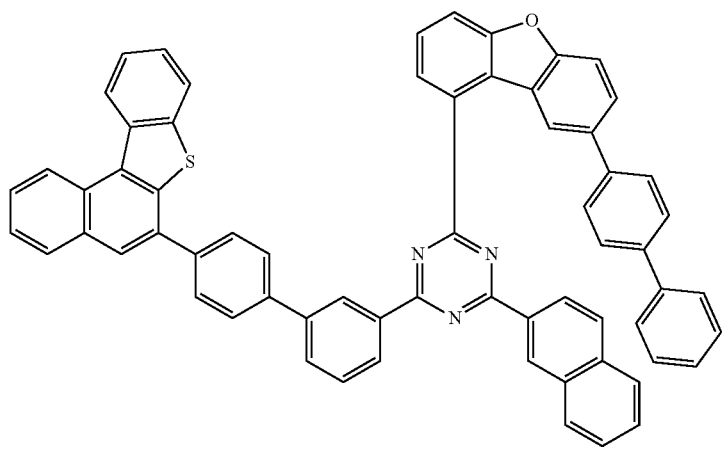
2-21
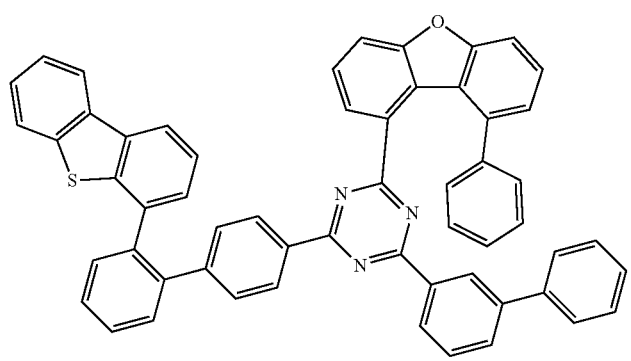

2-22
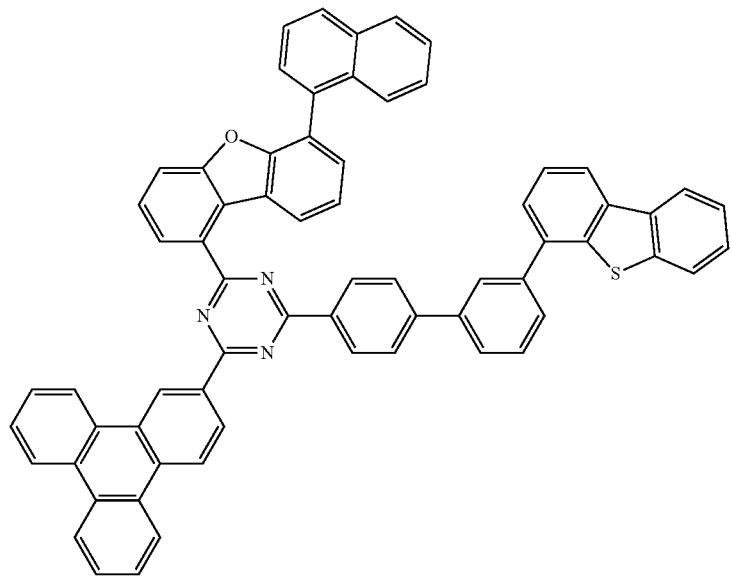
2-23
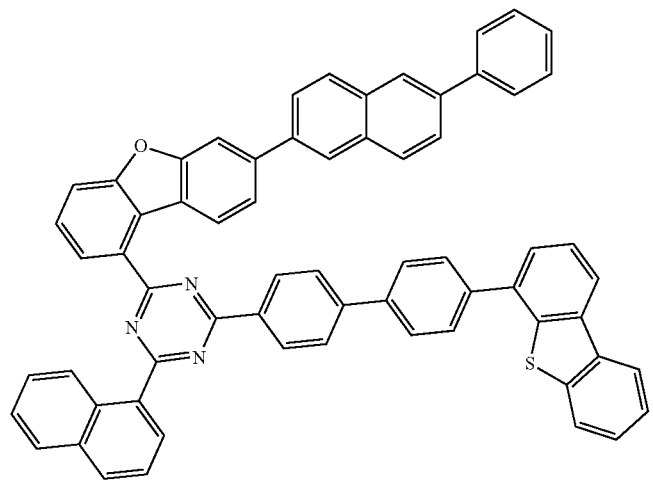
2-24
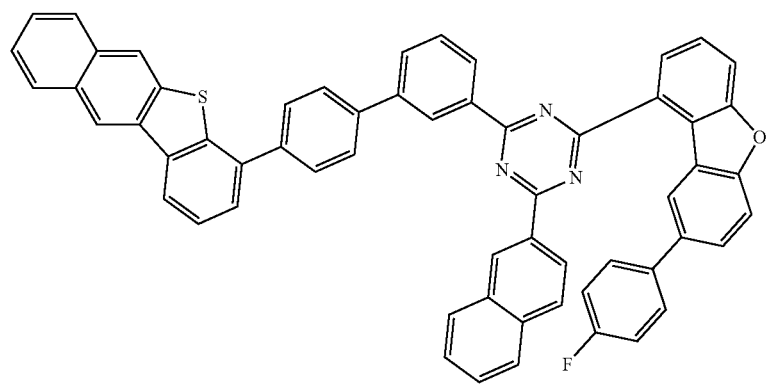

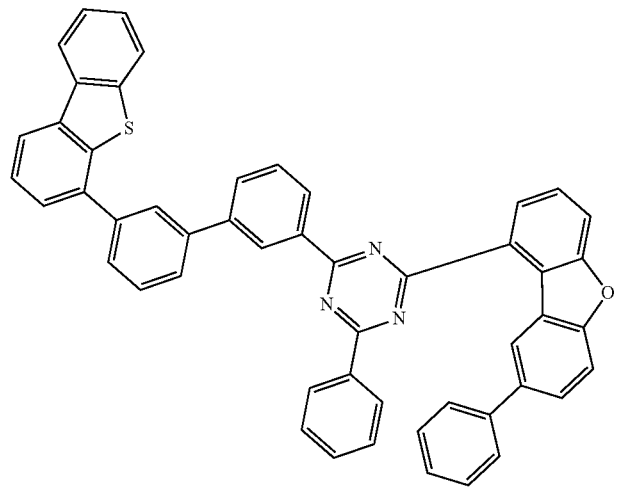
2-25
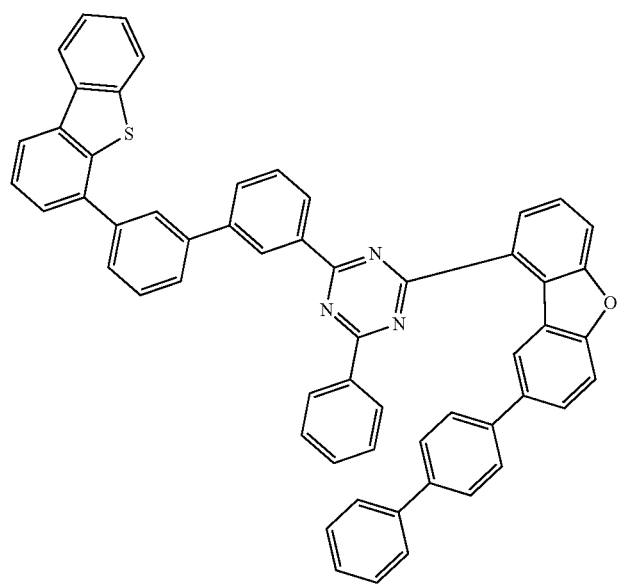
2-26
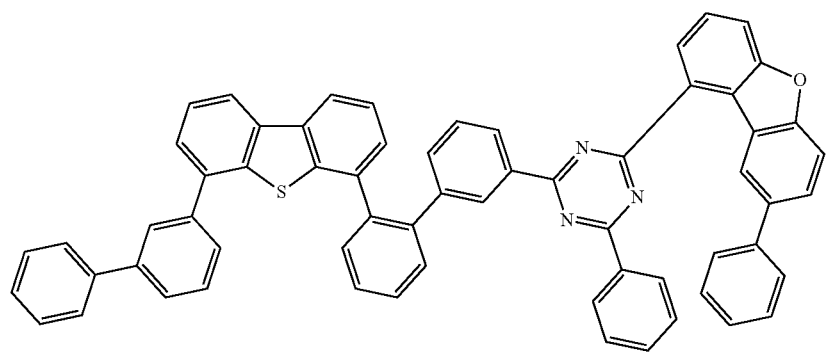
2-27

2-28
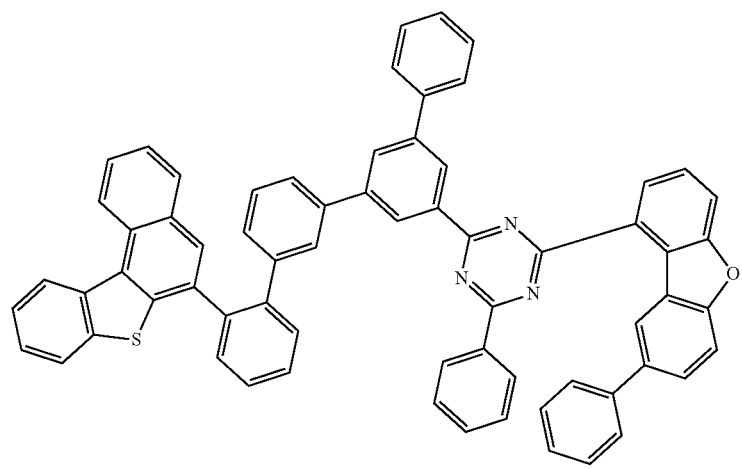
2-29 2-30
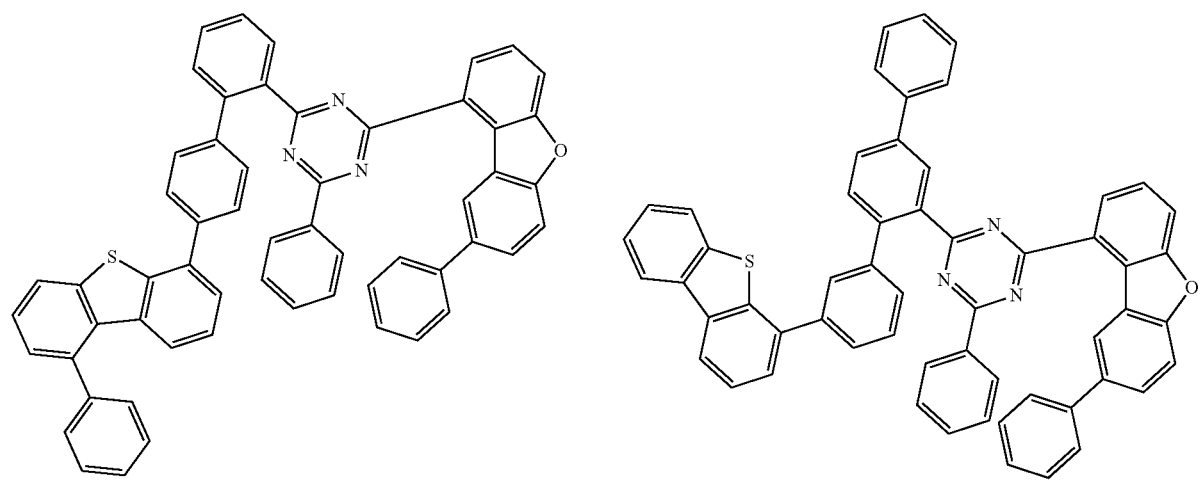
2-31
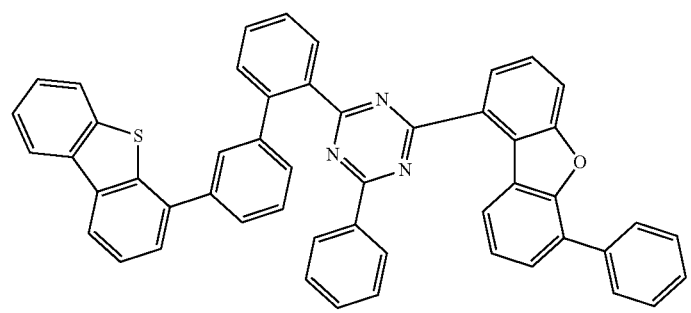

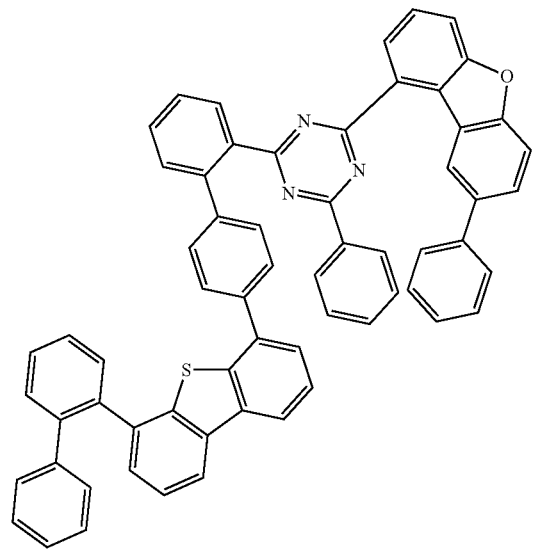
2-32
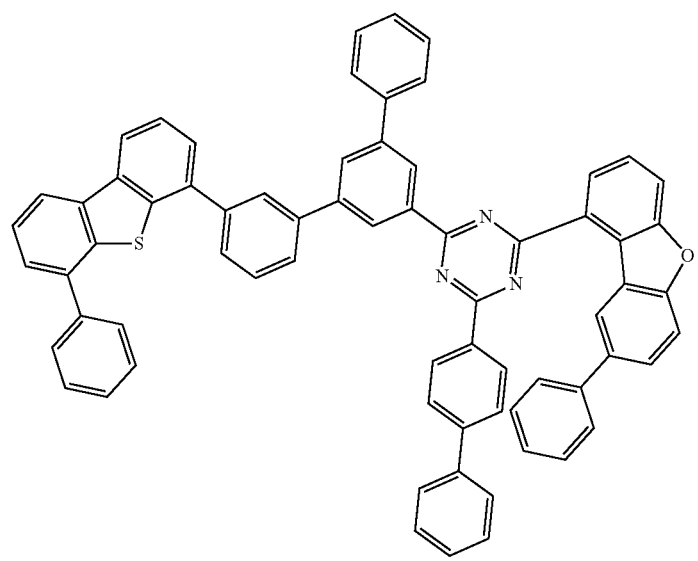
2-33
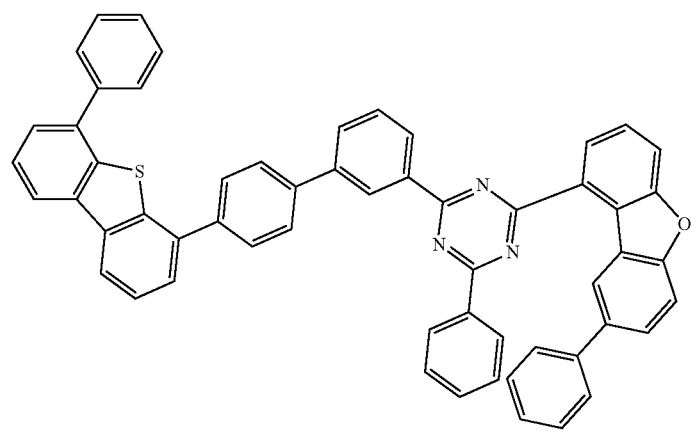
2-34

2-35
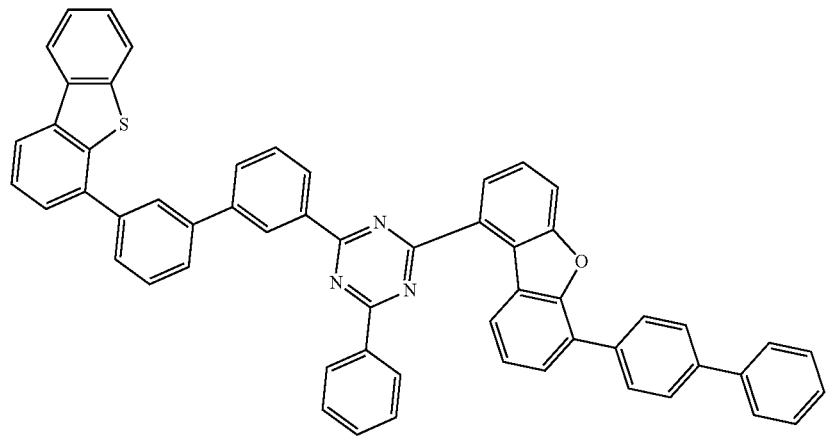
2-36
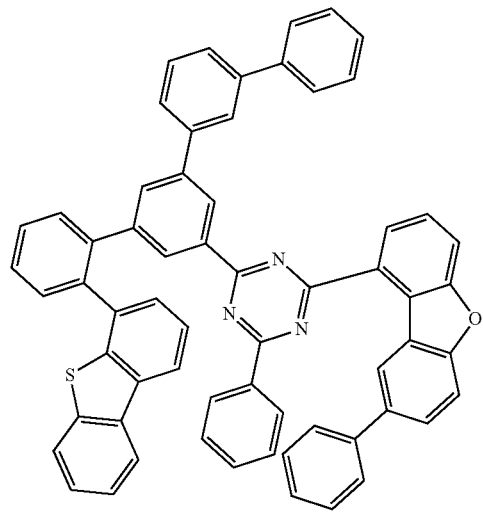
2-37
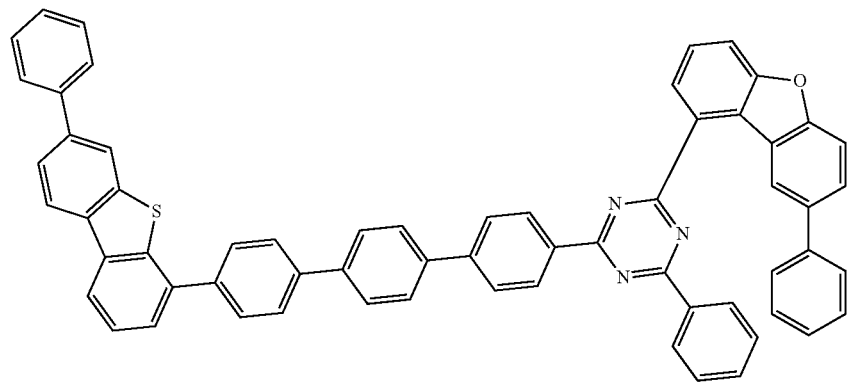

2-38
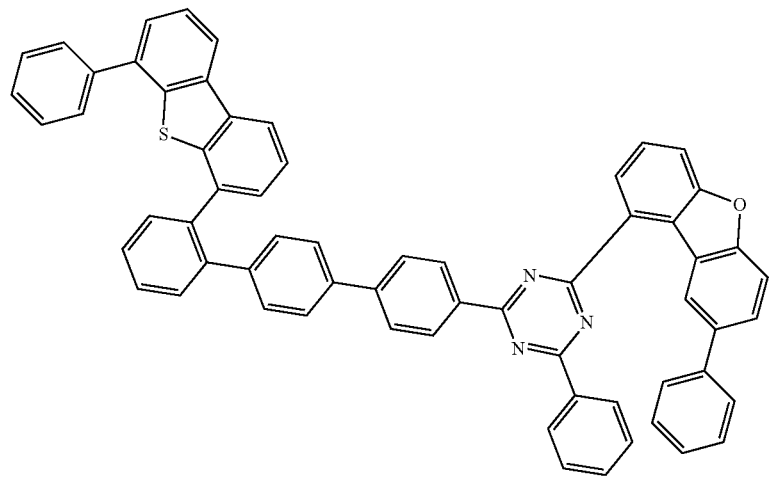
2-39
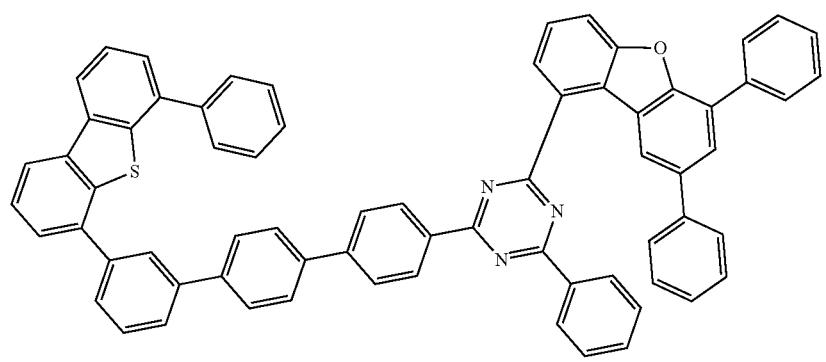
2-40
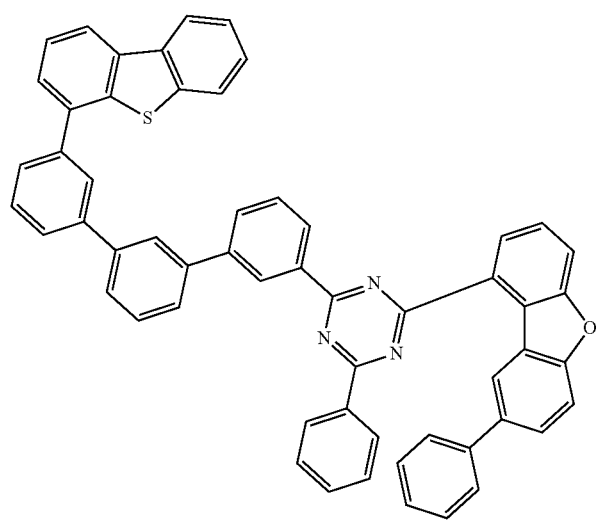

2-41
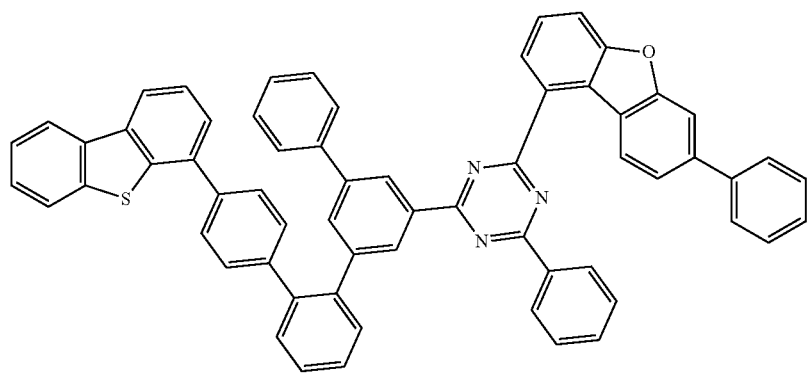
2-42
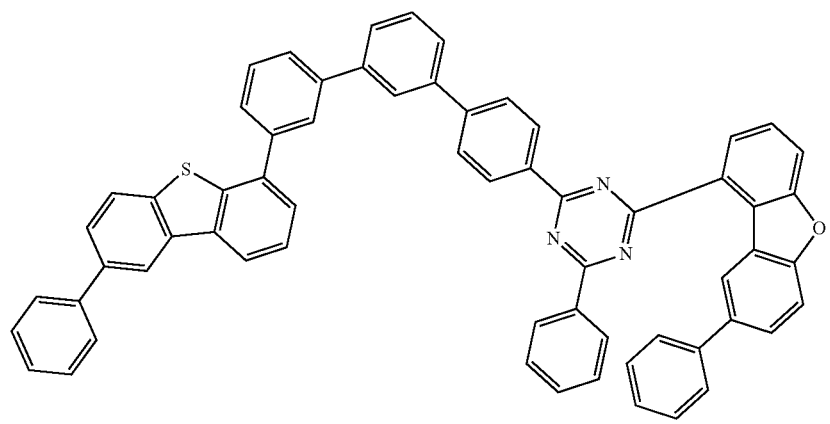
2-43
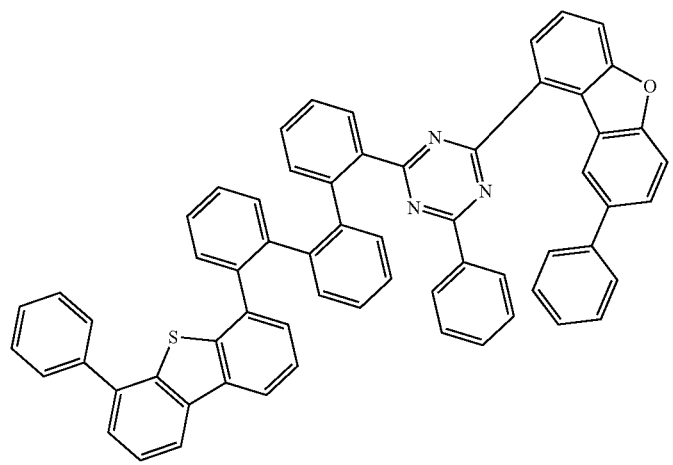
2-44
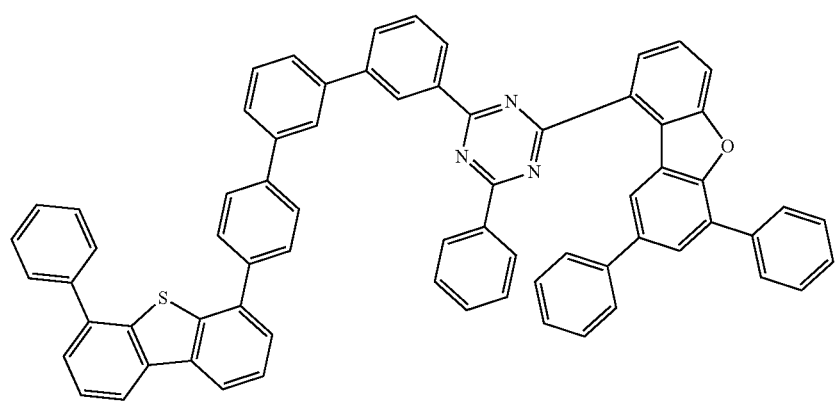

2-45
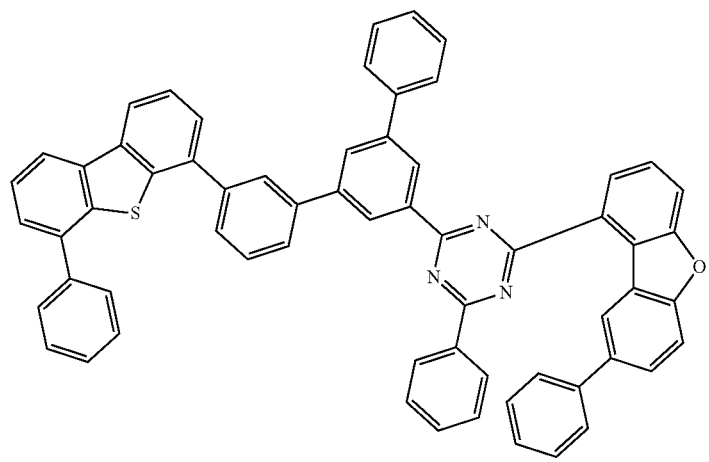
2-46
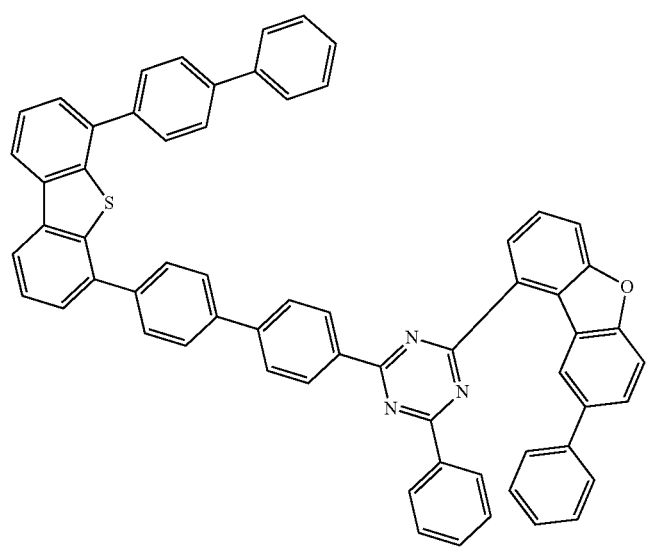
2-47
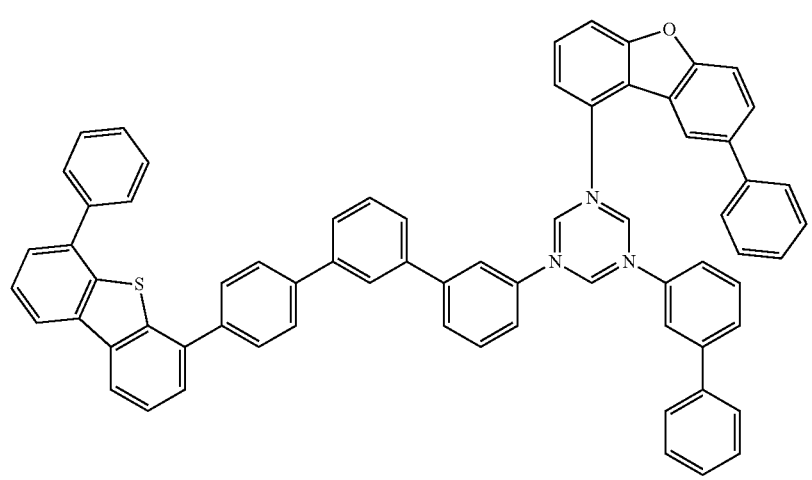

-continued
2-48
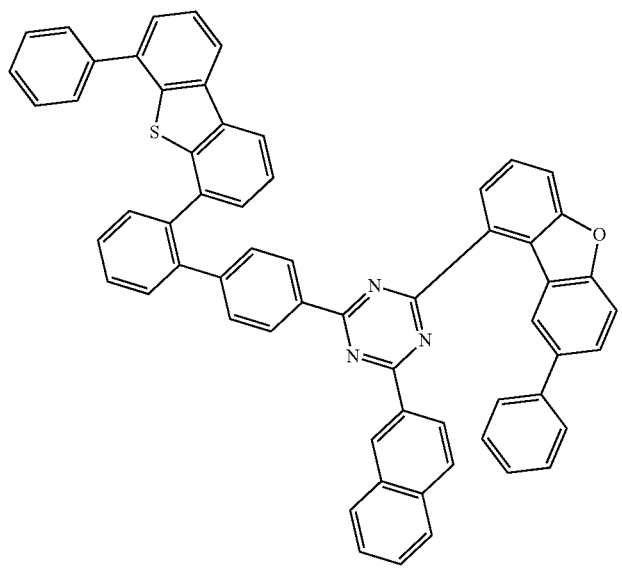
2-49
2-50
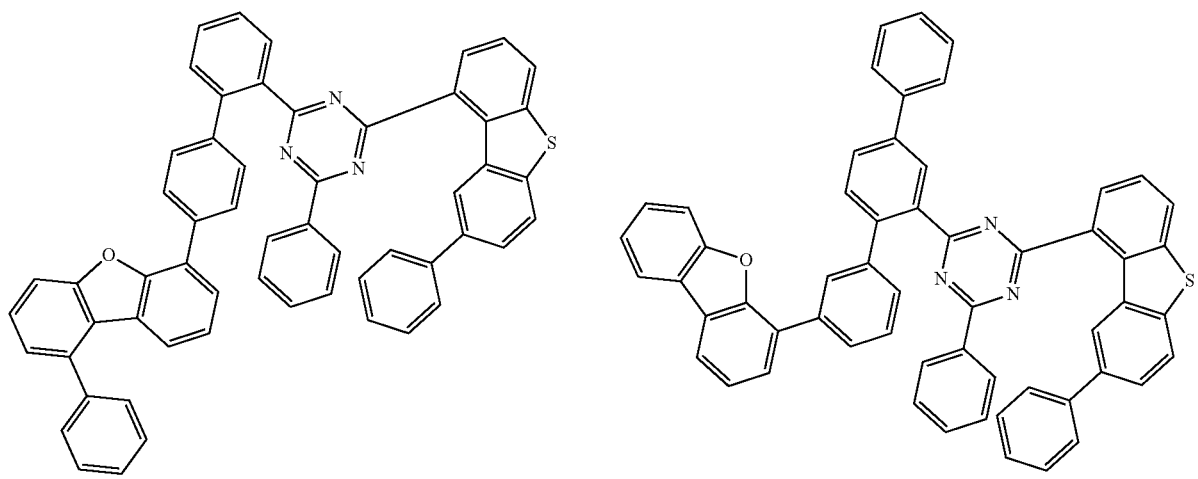
2-51
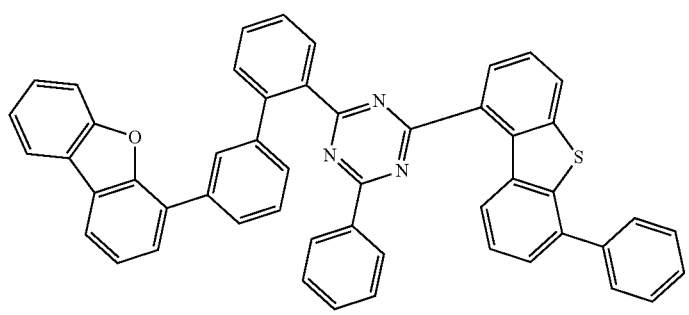

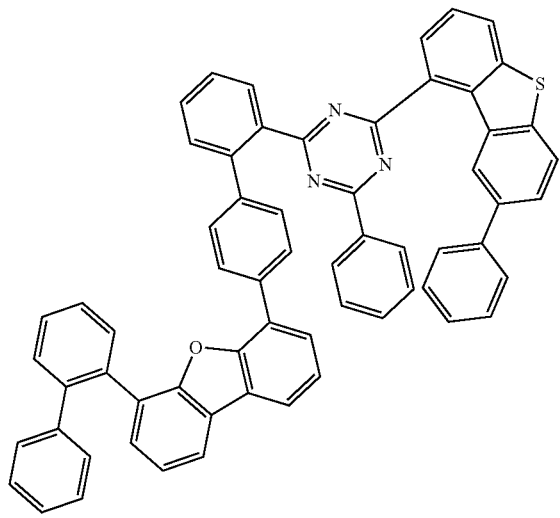
2-52
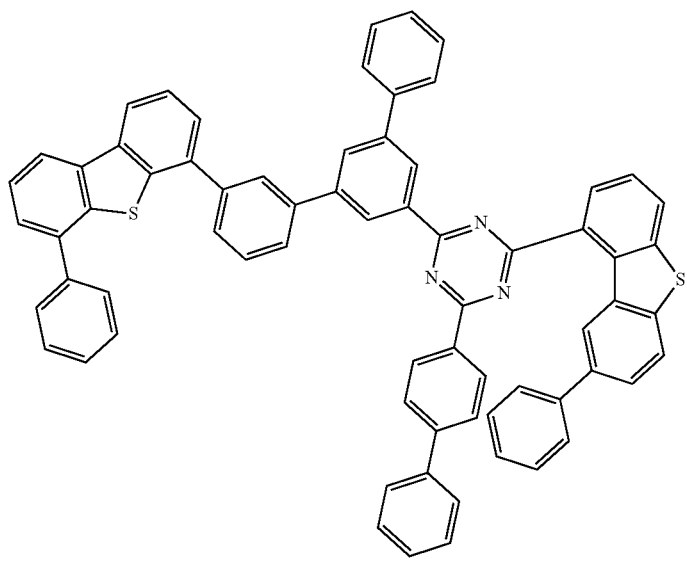
2-53
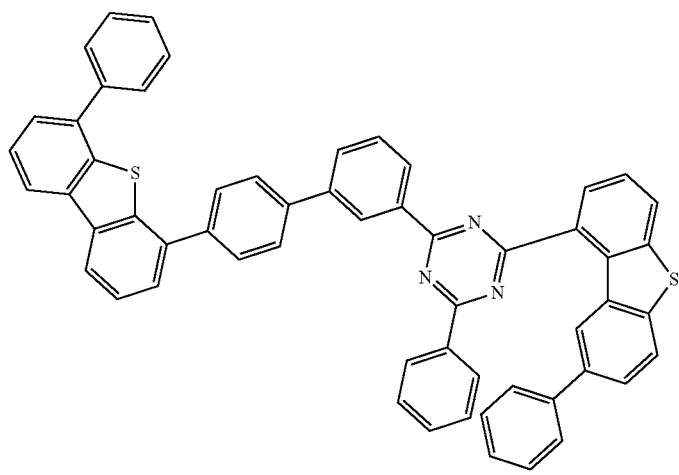
2-54

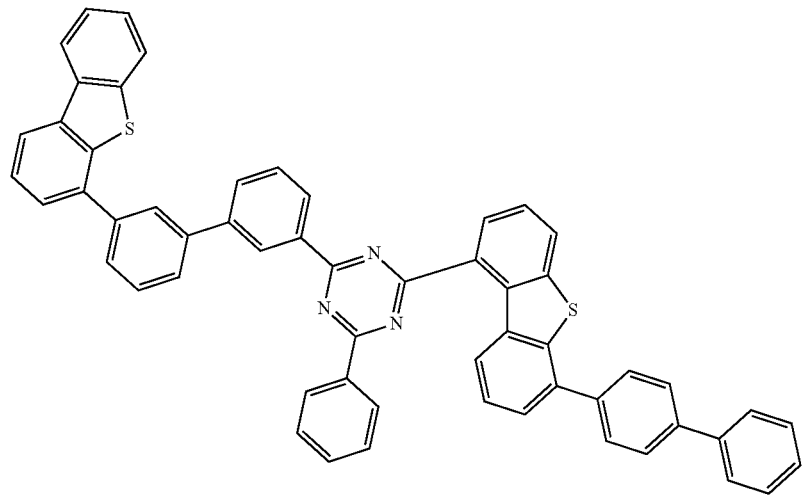
2-55
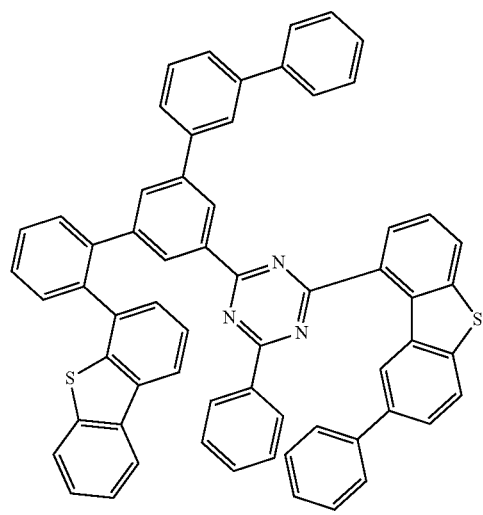
2-56
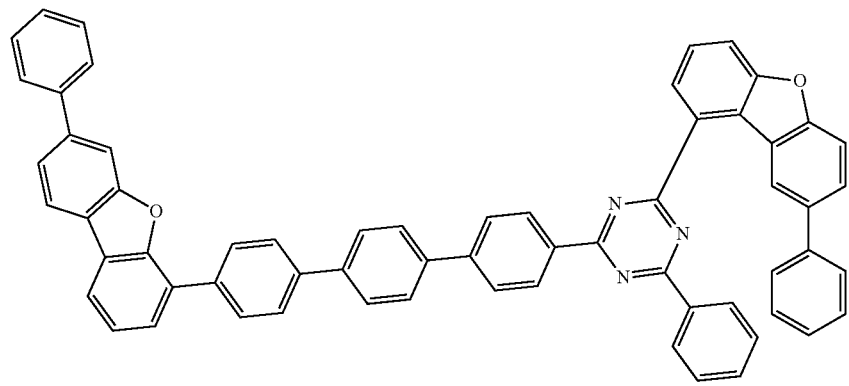
2-57

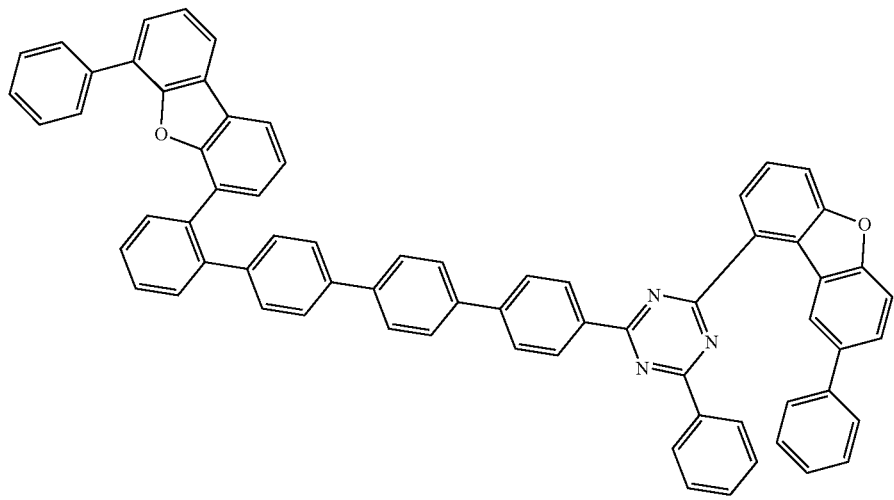
2-58
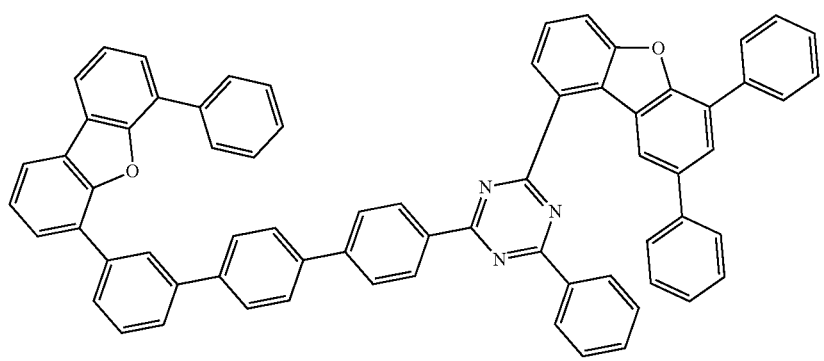
2-59
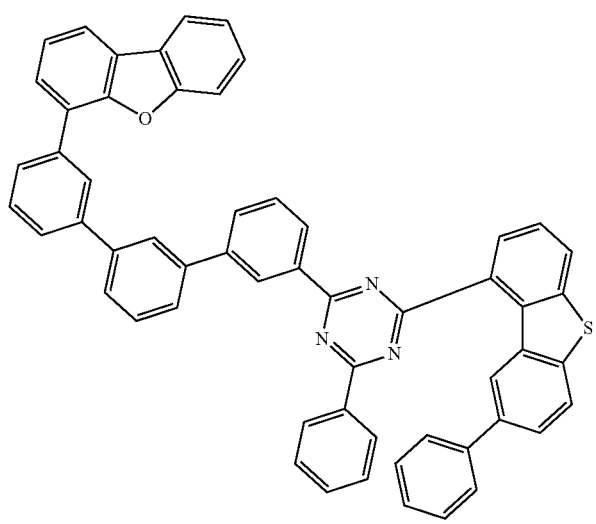
2-60

-continued
3-1
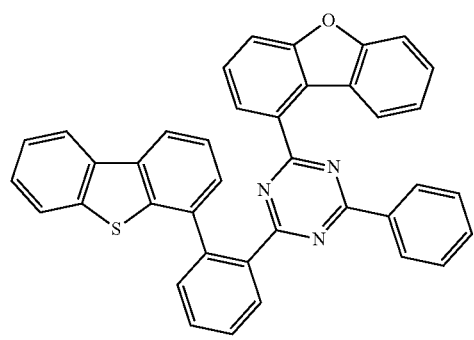
3-2
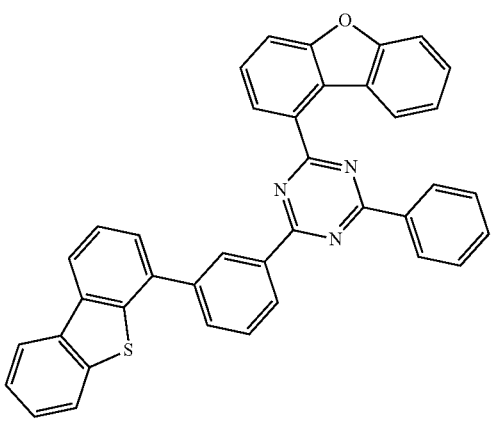
3-3
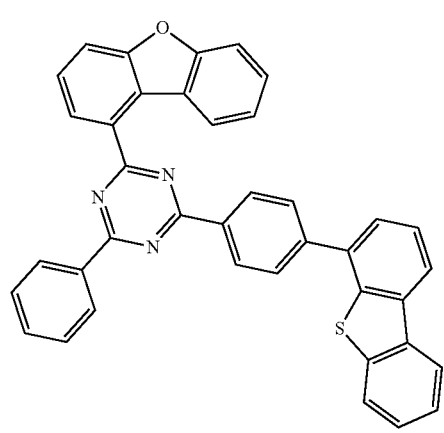
3-4
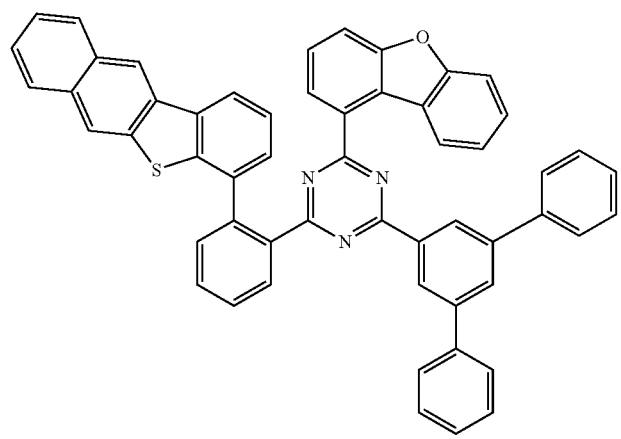

-continued
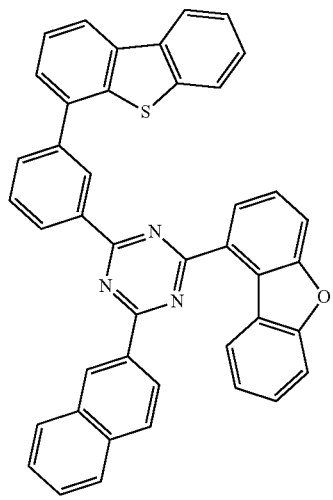
3-5
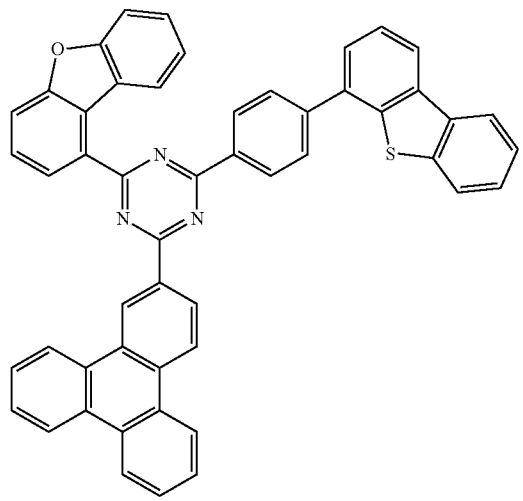
3-6
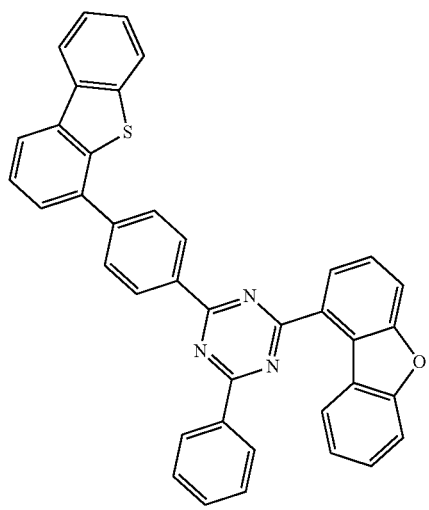
3-7
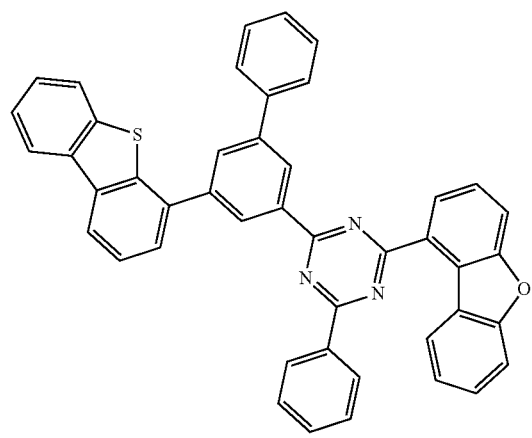
3-8
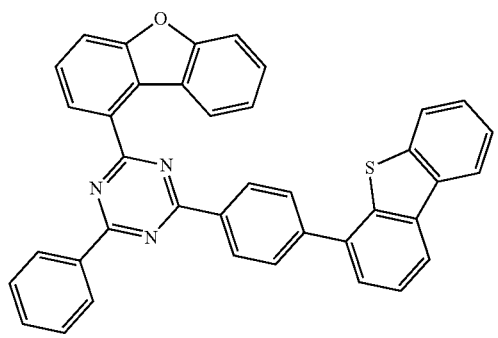
3-9
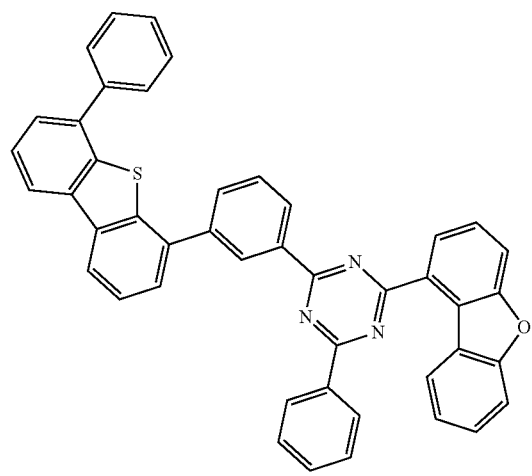
3-10

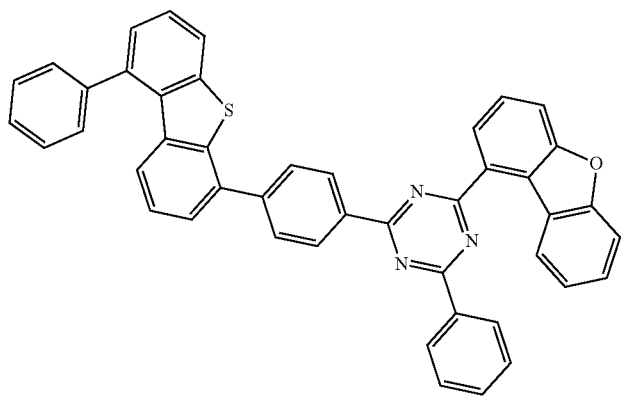
3-11
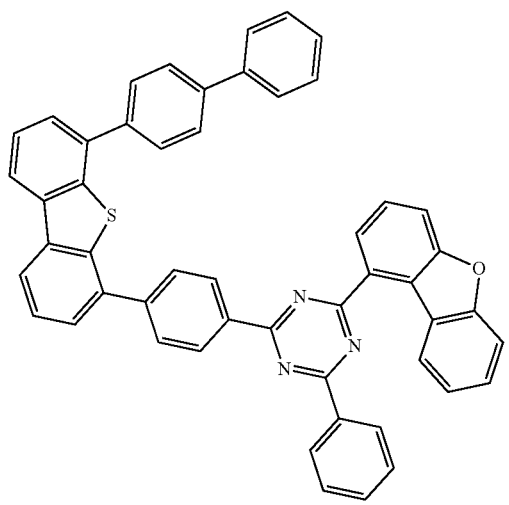
3-12
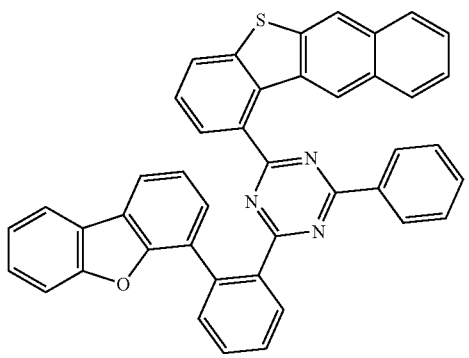
3-13
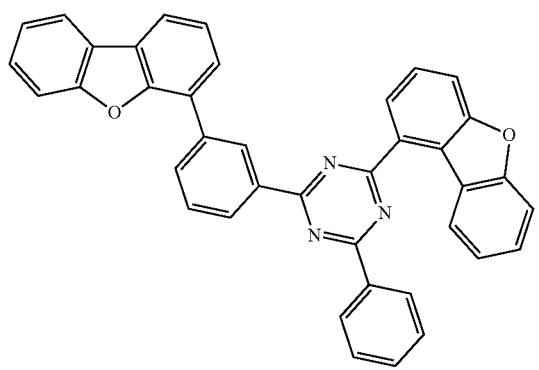
3-14
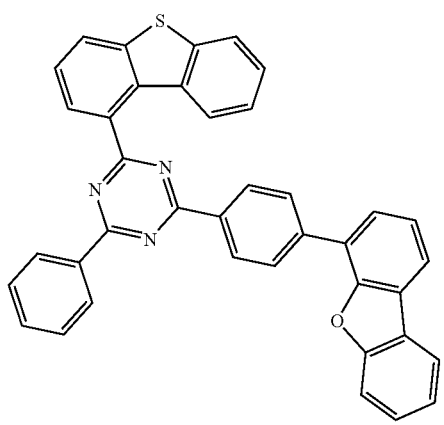
3-15

-continued
3-16
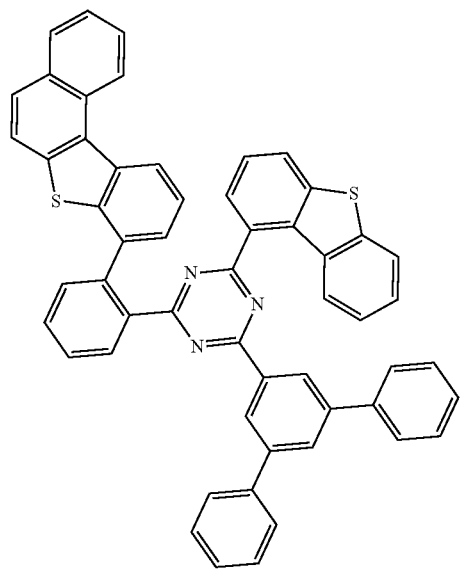
3-17
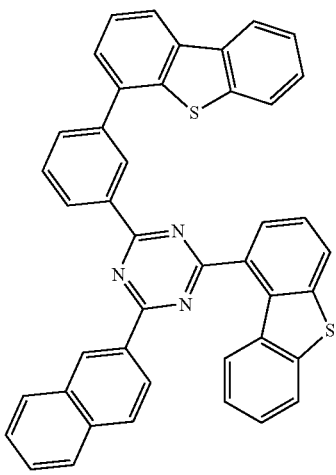
3-18
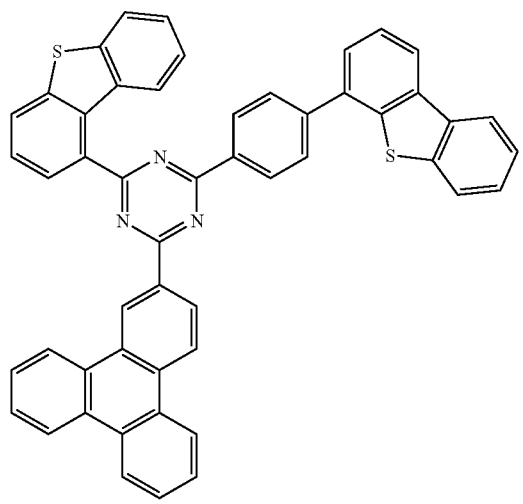
3-19
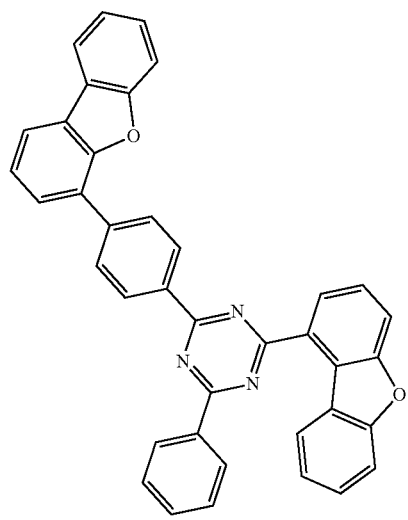
3-20
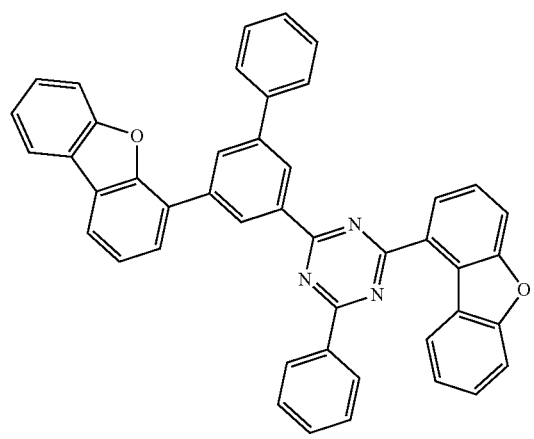
3-21
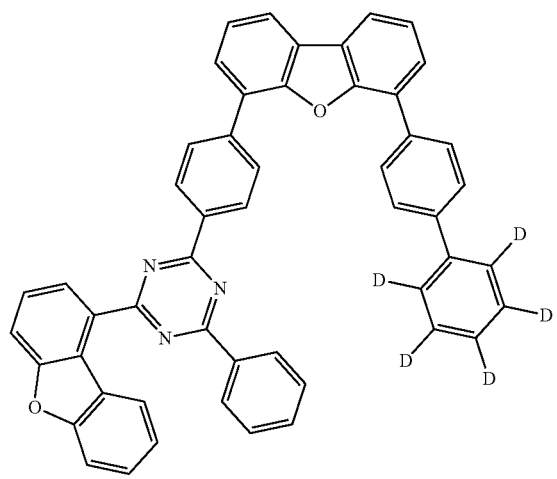

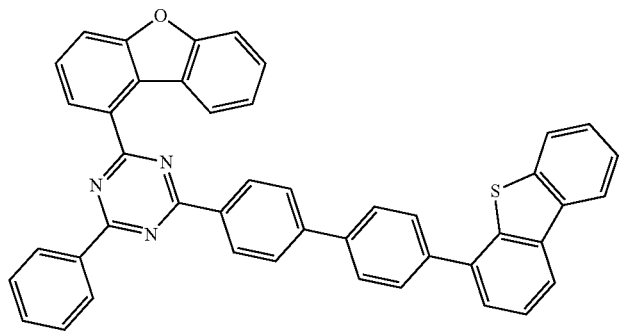
3-22
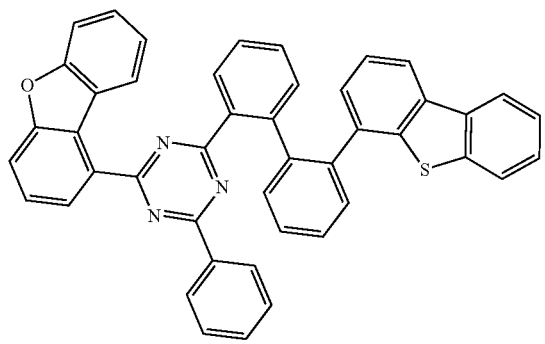
3-23
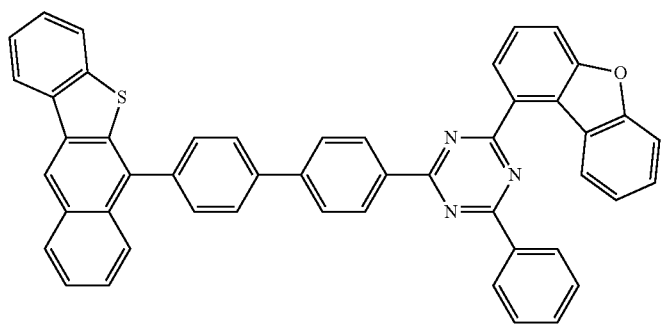
3-24
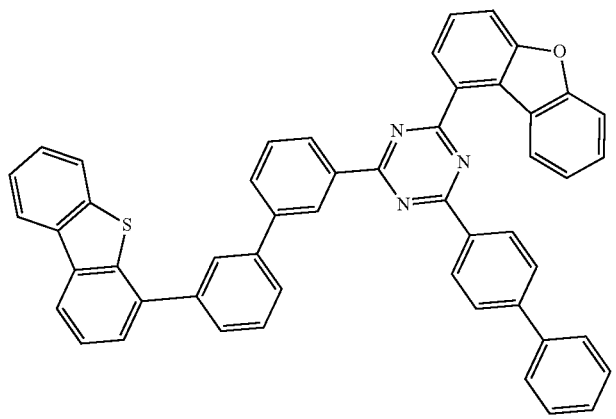
3-25

-continued
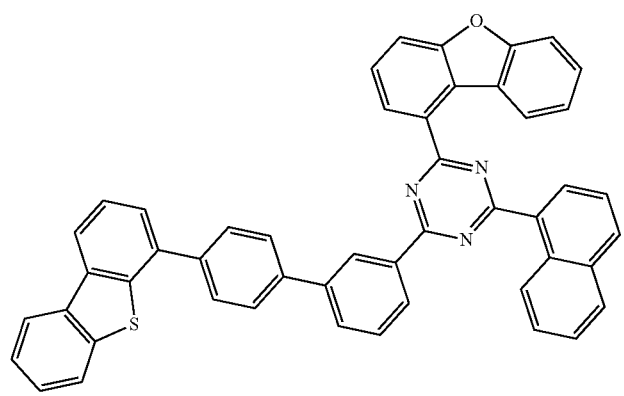
3-26
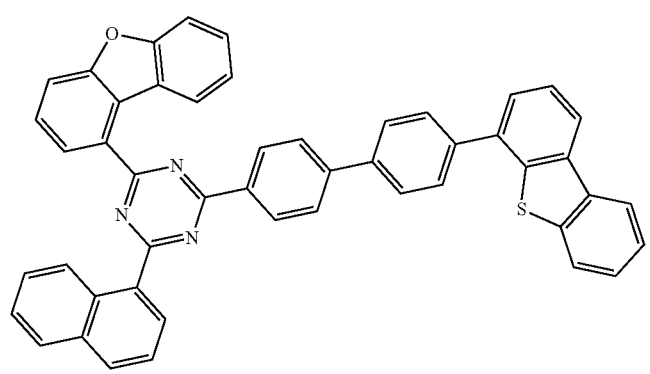
3-27
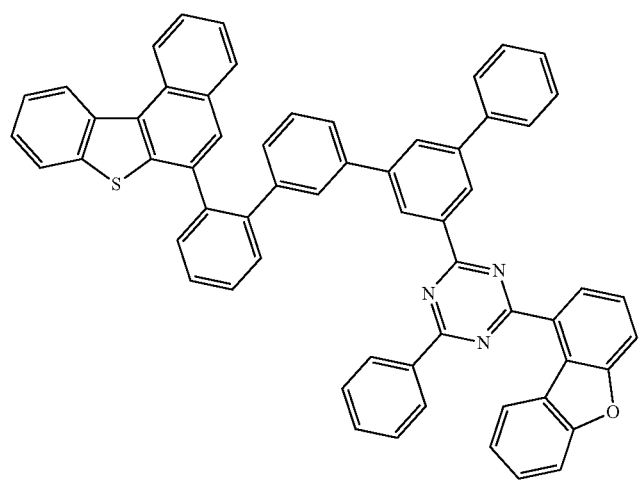
3-28

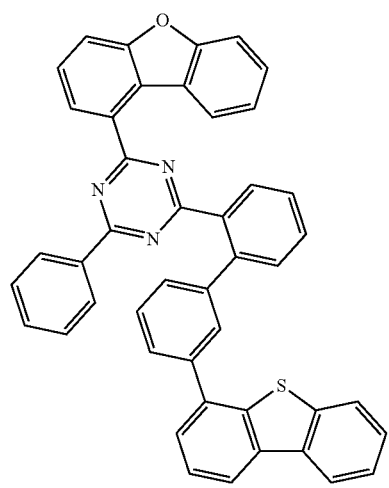
3-29
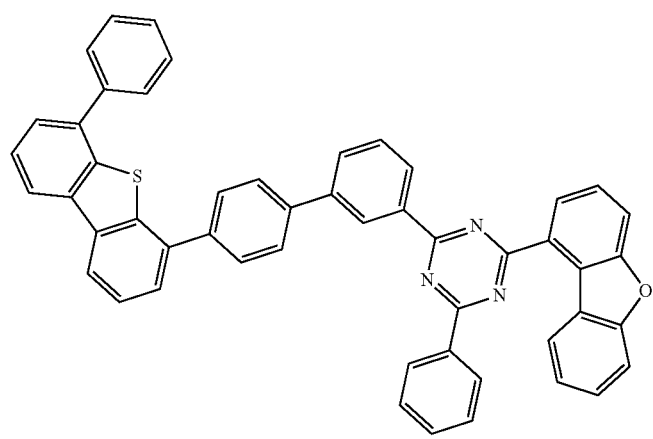
3-30
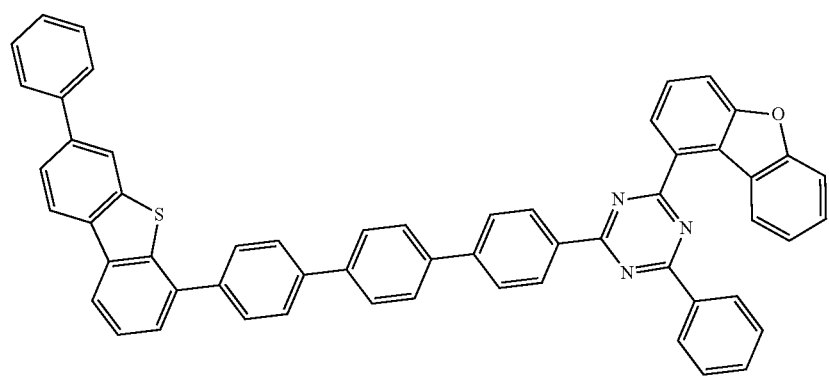
3-31

3-32
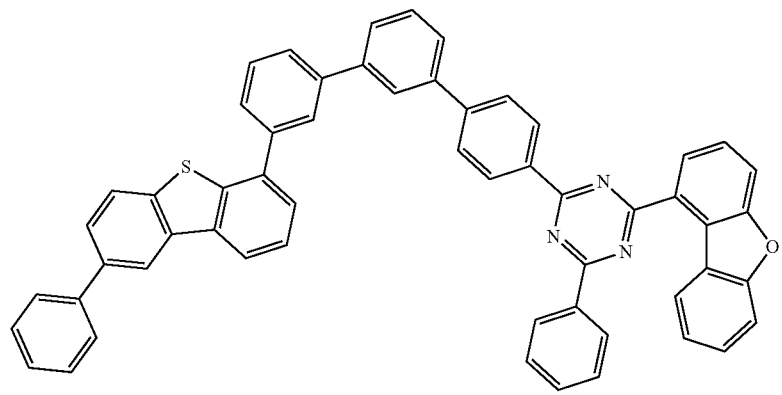
3-33
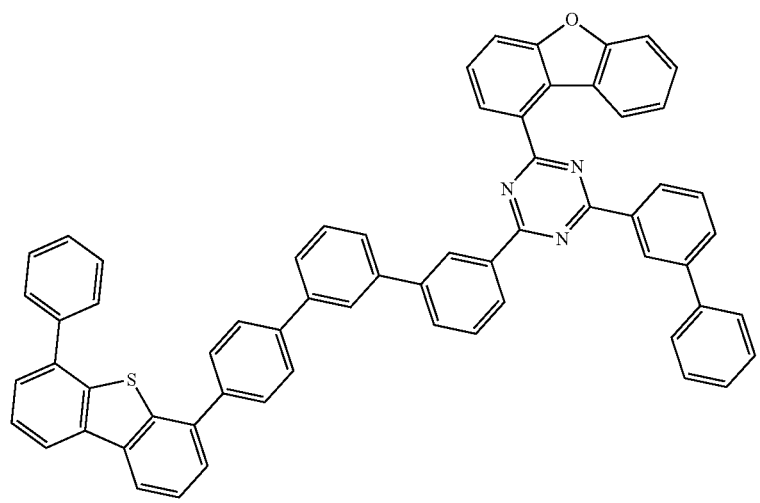
3-34 3-35
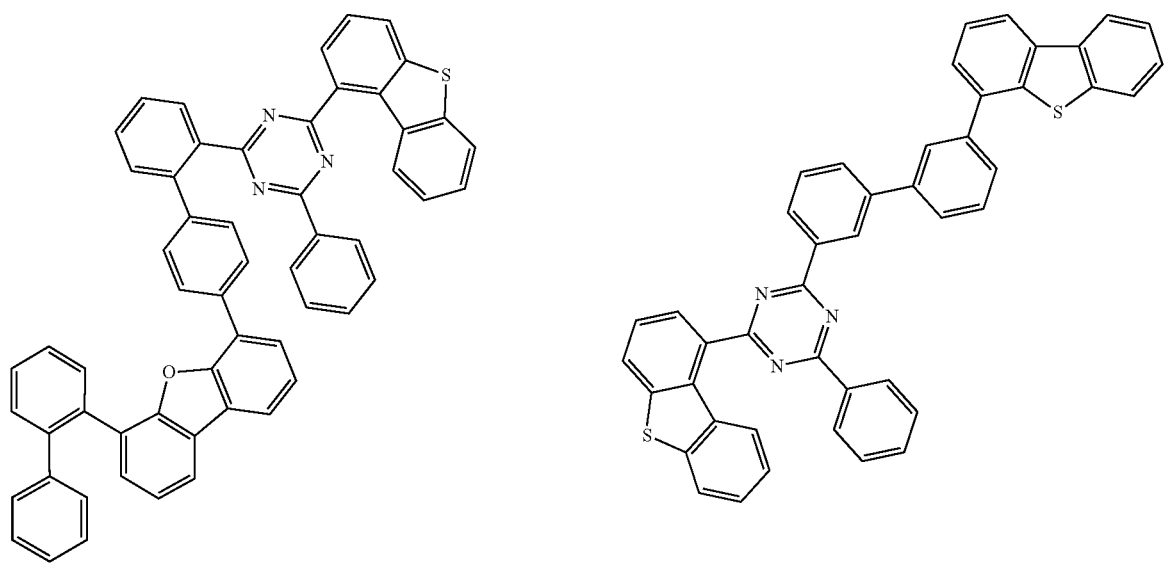

-continued 3-36

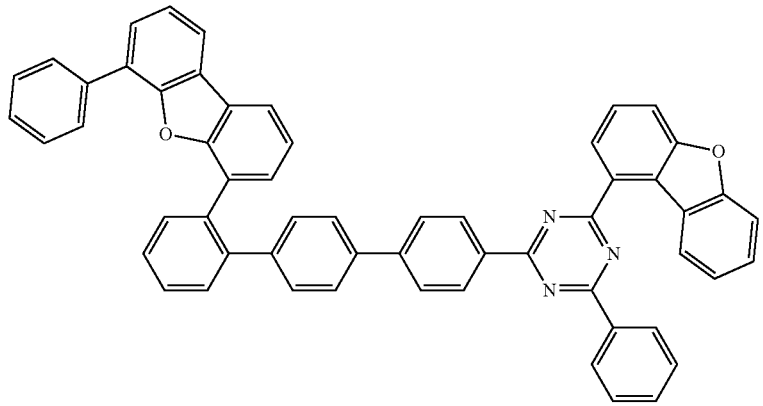

In another aspect of the present invention, the present invention provides an organic electric element comprising a first electrode, a second electrode, and an organic material layer formed between the first electrode and the second electrode, wherein the organic material layer comprises compound represented by Formula 1. The organic material layer comprises at least one layer of a hole injection layer, a hole transport layer, an emission-auxiliary layer, a light emitting layer, an electron transport auxiliary layer, an electron transport layer and an electron injection layer, at least one layer of the organic material layers comprises a single compound or a mixture of two or more kinds represented by Formula 1.

Preferably, the compound represented by Formula 1 is comprised in the light emitting layer.

Also, preferably, the light emitting layer may be further comprise compound represented by Formula 15.

<Formula 15>

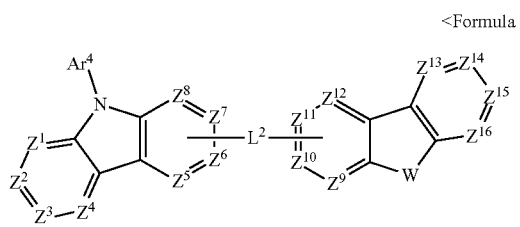

In Formula 15, each of symbols may be defined as follows.

$Z^1$ to $Z^4$, $Z^{13}$ to $Z^{16}$ are independently C(R) or N, $Z^5$ to $Z^{12}$ are independently C, C(R) or N.

$L^2$ is selected from the group consisting of a single bond, a $C_6$-$C_{60}$ arylene group, a fluorenylene group, a $C_2$-$C_{60}$ heterocyclic group containing at least one heteroatom selected from the group consisting of O, N, S, Si, and P, a $C_3$-$C_{60}$ aliphatic ring and a fused ring group formed by a $C_3$-$C_{60}$ aliphatic ring with a $C_6$-$C_{60}$ aromatic ring.

When $L^2$ is an arylene group, $L^2$ may be preferably a $C_6$-$C_{30}$ or $C_6$-$C_{20}$ arylene group, more preferably a $C_6$-$C_{18}$ arylene group, for example, phenylene, naphthalene, biphenyl, terphenyl or the like. When $L^2$ is a heterocyclic group, $L^2$ may be preferably a $C_2$-$C_{30}$ or $C_2$-$C_{20}$ heterocyclic group, more preferably a $C_2$-$C_{18}$ heterocyclic group, for example, carbazole, phenylcarbazole or the like.

W is N(Ar⁵), O, S or C(R')(R").

$Ar^4$ and $Ar^5$ are each independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a $C_3$-$C_{60}$ aliphatic ring, a fused ring group formed by a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group, -L'-N($R_a$)($R_b$) and a combination thereof. Here, the term "combination of these" means, for example, a combination of an aryl group and a heterocyclic group, a combination of an aryl group and an aliphatic ring, a combination of a heterocyclic group and an aliphatic ring group, and the like.

When $Ar^4$ and $Ar^5$ are each an aryl group, $Ar^4$ and $Ar^5$ may be preferably a $C_6$-$C_{30}$ or $C_6$-$C_{20}$ aryl group, more preferably a $C_6$-$C_{18}$ aryl group, for example, phenyl, naphthyl, biphenyl, terphenyl or the like. When $Ar^4$ and $Ar^5$ are each a heterocyclic group, $Ar^4$ and $Ar^5$ may be preferably a $C_2$-$C_{30}$ or a $C_2$-$C_{20}$ heterocyclic group, more preferably a $C_2$-$C_{18}$ heterocyclic group, for example, triazine, pyrimidine, pyridine, quinazoline, carbazole, phenylcarbazole, dibenzothiophene, dibenzofuran or the like.

R, R' and R" are each independently selected from the group consisting of hydrogen, deuterium, halogen, a $C_6$-$C_{60}$ aryl group, a fluorenyl group, a $C_2$-$C_{60}$ heterocyclic group containing at least one heteroatom selected from the group consisting of O, N, S, Si, and P, a $C_3$-$C_{60}$ aliphatic ring, a fused ring group formed by a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -L'-N($R_a$)($R_b$).

In addition, adjacent R groups may be optionally linked to each other to form a ring, and R' and R" may be optionally linked to each other to form a ring. The ring formed by linking between adjacent $R^1$ groups, between R' and R" may be a $C_6$-$C_{60}$ aromatic ring, a $C_2$-$C_{60}$ heterocyclic group, a $C_3$-$C_{60}$ aliphatic ring, or a fused ring group formed by a $C_3$-$C_{60}$ aliphatic ring with a $C_6$-$C_{60}$ aromatic ring, preferably, a $C_6$-$C_{20}$ aromatic ring group, or a $C_2$-$C_{20}$ heterocyclic group containing at least one heteroatom selected from the group consisting of O, N, S, Si, and P, more preferably, a $C_6$-$C_{10}$ aromatic ring group, or a $C_2$-$C_{10}$ heterocyclic group containing at least one heteroatom selected from the group consisting of O, N, S, Si, and P, for example, benzene ring, naphthalene, phenanthrene, thiophene, benzothiophene, pyridine and the like.

L', $R_a$ and $R_b$ are the same as defined in Formula 1.

$L^2$, $Ar^4$, $Ar^5$, R, R', R", a ring formed by linking between adjacent R groups, and a ring formed by linking between R' and R" may be each further substituted with one or more substituents selected from the group consisting of deuterium, halogen, a silane group unsubstituted or substituted with a $C_1$-$C_{20}$ alkyl group or a $C_6$-$C_{20}$ aryl group, a siloxane group, a boron group, a germanium group, a cyano group, a nitro group, a phosphine oxide group unsubstituted or substituted with a $C_1$-$C_{20}$ alkyl group or a $C_6$-$C_{20}$ aryl group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a fused ring group formed by a $C_3$-$C_{60}$ aliphatic ring with a $C_6$-$C_{60}$ aromatic ring, a $C_7$-$C_{20}$ arylalkyl group, and a $C_8$-$C_{20}$ arylalkenyl group.

Formula 15 may be represented by one of Formulas 16 to 19.

<Formula 16>

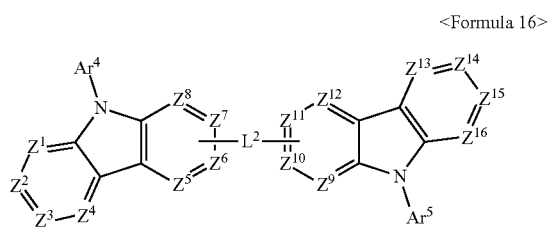

<Formula 17>

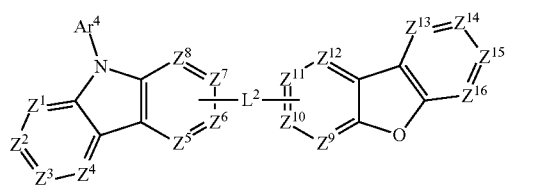

<Formula 18>

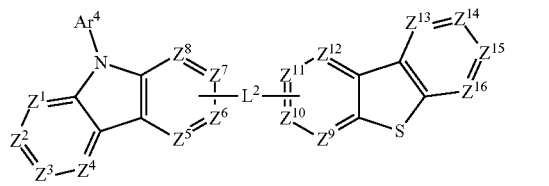

<Formula 19>

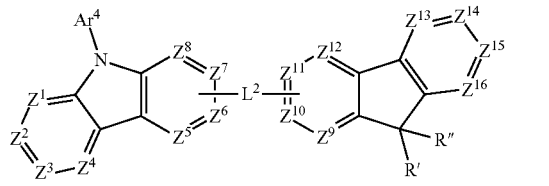

In Formulas 16 to 19, $Ar^4$, $Ar^5$, $Z^1$ to $Z^{16}$, $L^2$, R' and R" are the same as defined in Formula 11.

Preferably, in Formulas 16 to 19, at least one of $Ar^4$ and $Ar^5$ is a substituted or unsubstituted $C_6$-$C_{30}$ aryl group aryl group, more preferably, both $Ar^4$ and $Ar^5$ are a $C_6$-$C_{30}$ aryl group.

Preferably, Formula 15 may be represented by Formula 20.

<Formula 20>

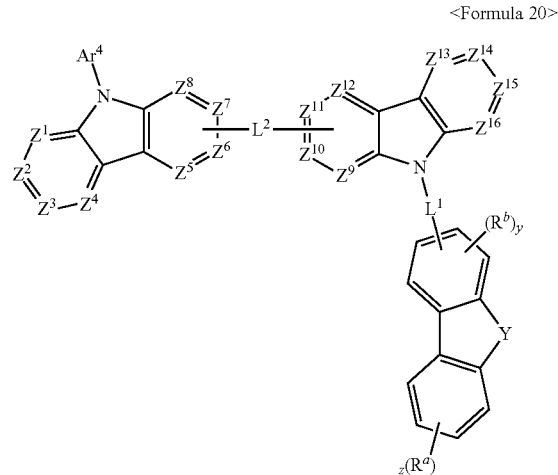

In Formula 20, each of symbols may be defined as follows.

$Ar^4$, $Z^1$ to $Z^{16}$, and $L^2$ are the same as defined in Formula 11.

$L^1$ is selected from the group consisting of a single bond, a $C_6$-$C_{60}$ arylene group, a fluorenylene group, a $C_2$-$C_{60}$ heterocyclic group containing at least one heteroatom selected from the group consisting of O, N, S, Si, and P, a $C_3$-$C_{60}$ aliphatic ring and a fused ring group formed by a $C_3$-$C_{60}$ aliphatic ring with a $C_6$-$C_{60}$ aromatic ring.

When L' is an arylene group, L' may be preferably a $C_6$-$C_{30}$ or $C_6$-$C_{20}$ arylene group, more preferably a $C_6$-$C_{18}$ arylene group, for example, phenylene, naphthalene, biphenyl or the like.

Y is O, S or $N(R^c)$.

$R^a$ and $R^b$ are each independently selected from the group consisting of hydrogen, deuterium, halogen, a $C_6$-$C_{20}$ aryl group, a fluorenyl group, a $C_6$-$C_{20}$ aryl group substituted with deuterium, a $C_2$-$C_{20}$ heterocyclic group containing at least one heteroatom selected from the group consisting of O, N, S, Si, and P, a $C_3$-$C_{20}$ cycloalkyl group, a fused ring group formed by a $C_3$-$C_{60}$ aliphatic ring with a $C_6$-$C_{60}$ aromatic ring, a $C_7$-$C_{20}$ arylalkyl group and a $C_8$-$C_{20}$ arylalkenyl group.

In addition, adjacent $R^a$ groups or adjacent $R^a$ groups may be optionally linked to each other to form a ring, wherein the ring is selected from the group consisting of a $C_6$-$C_{60}$ aromatic ring, a $C_2$-$C_{60}$ heterocyclic group, a $C_3$-$C_{60}$ aliphatic ring, and a fused ring group formed by a $C_3$-$C_{60}$ aliphatic ring with a $C_6$-$C_{60}$ aromatic ring.

$R^c$ is selected from the group consisting of a $C_6$-$C_{20}$ aryl group, a fluorenyl group, a $C_6$-$C_{20}$ aryl group substituted with deuterium, a $C_2$-$C_{20}$ heterocyclic group containing at least one heteroatom selected from the group consisting of O, N, S, Si, and P, a $C_3$-$C_{20}$ cycloalkyl group, a fused ring group formed by a $C_3$-$C_{60}$ aliphatic ring with a $C_6$-$C_{60}$ aromatic ring and a combination thereof.

y is an integer of 0 to 3, z is an integer of 0 to 4, where each of these is an integer of 2 or more, each of $R^a$s, each of $R^b$s is the same or different from each other.

Specifically, the compound represented by formula 15 may be one of the following compounds, but it is not limited thereto.

4-1
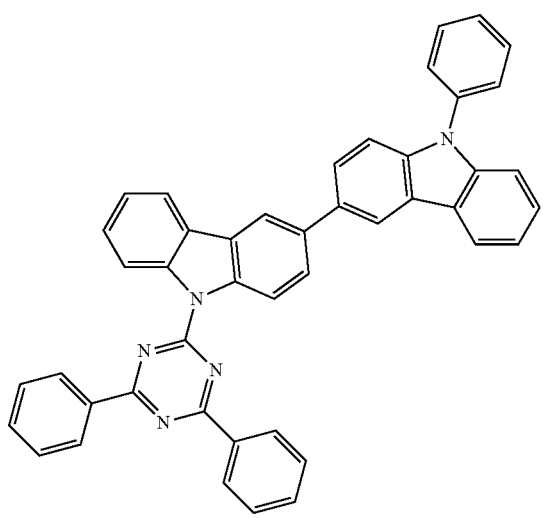
4-2
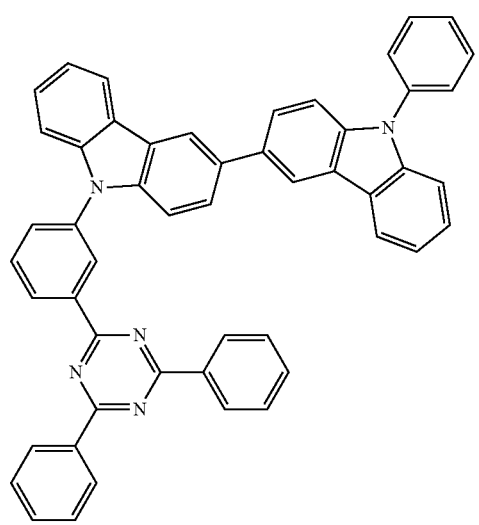
4-3
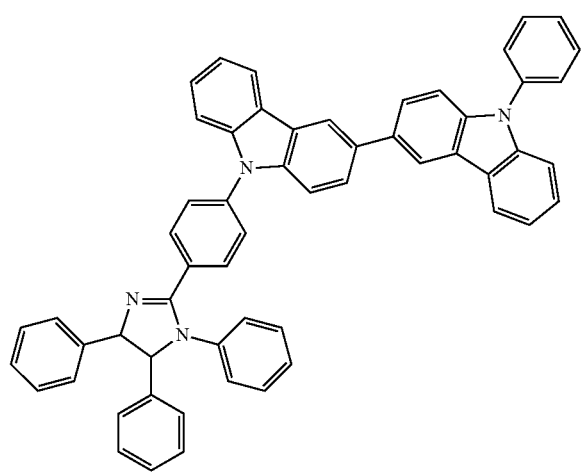
4-4
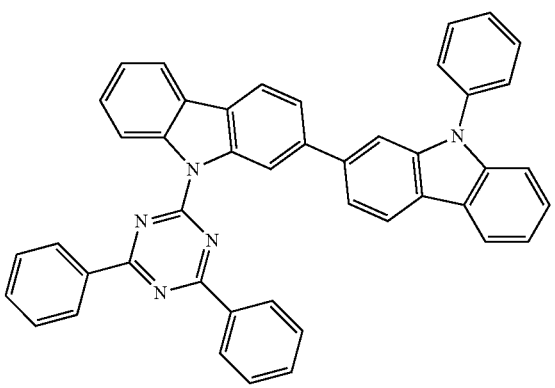
4-5
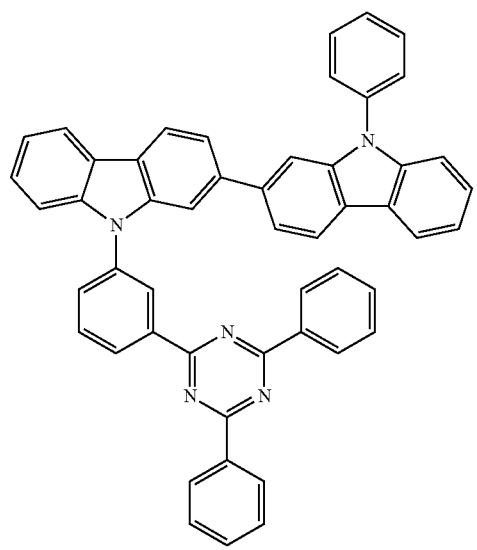
4-6
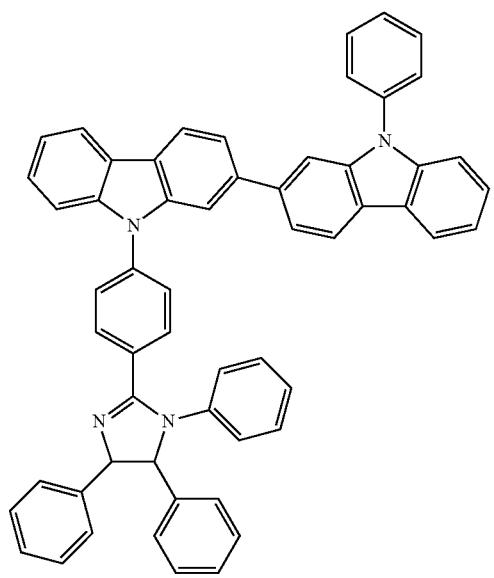

-continued
4-7
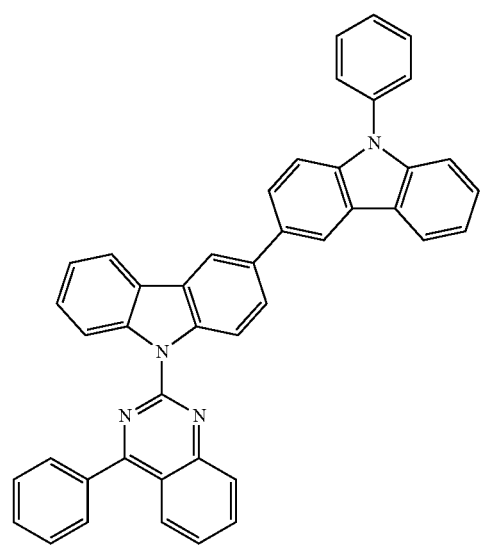
4-8
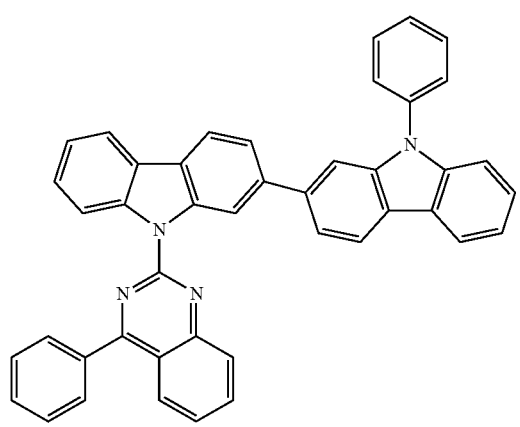
4-9
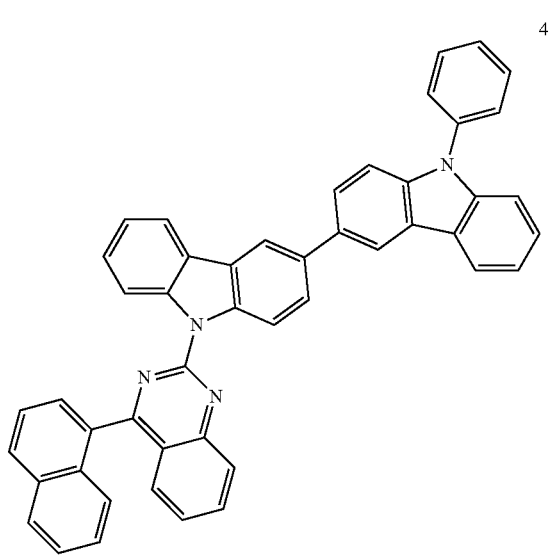
-continued
4-10
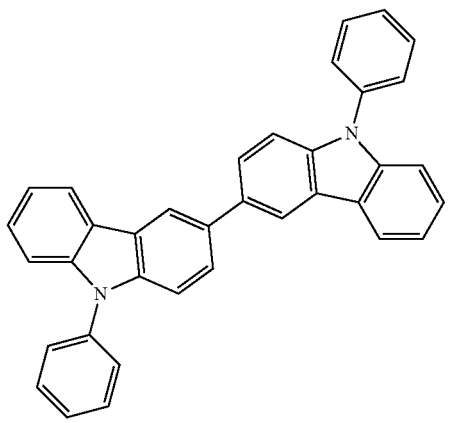
4-11
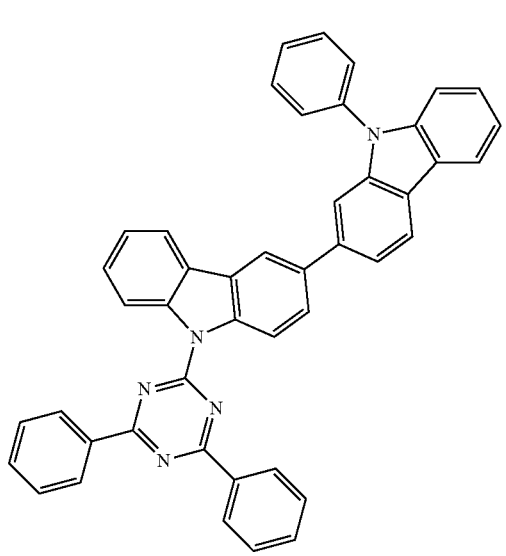
4-12
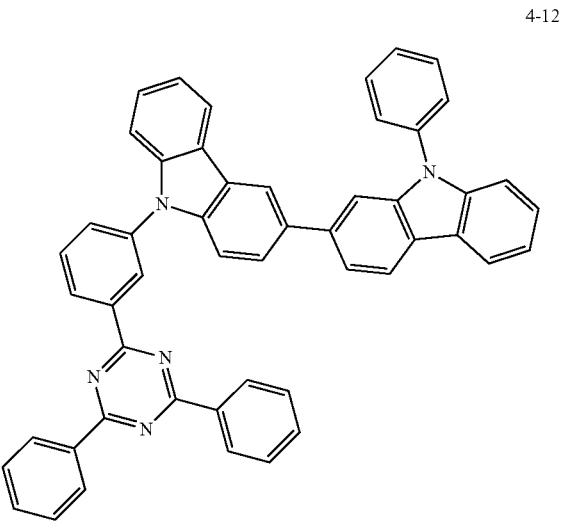

4-13
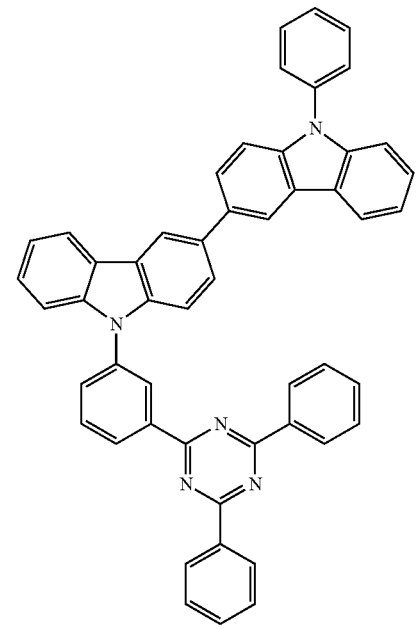
4-14
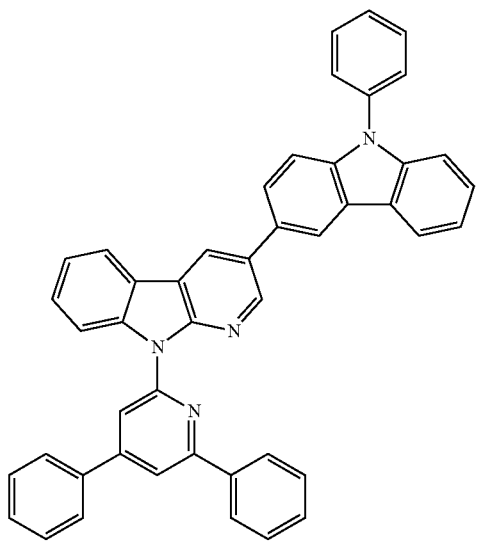
4-15
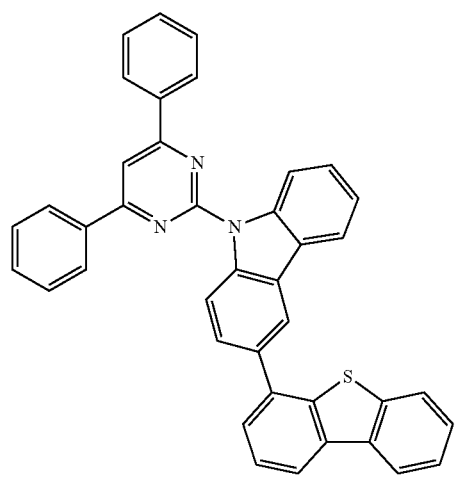
4-16
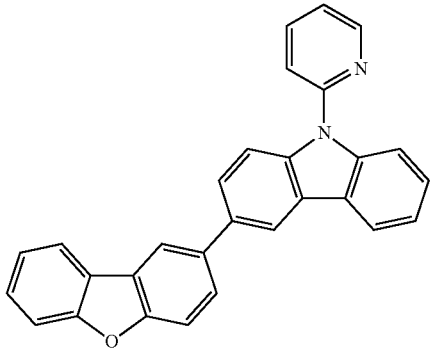
4-17
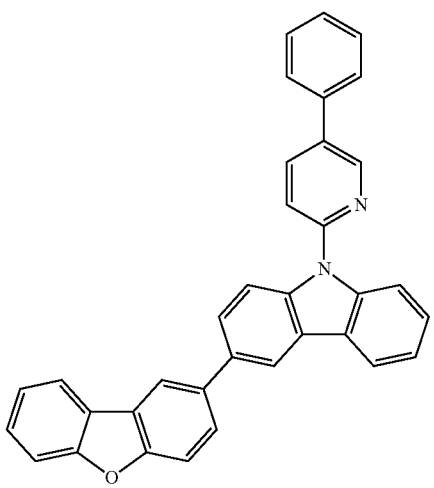
4-18
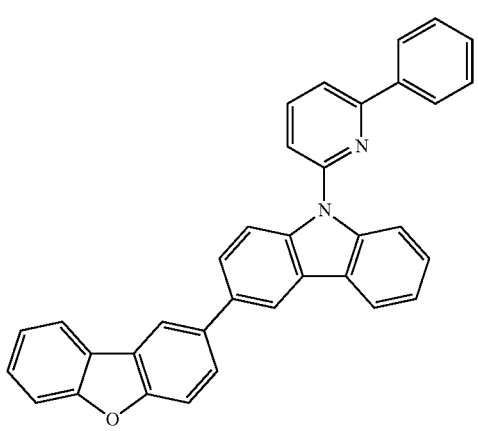

4-19
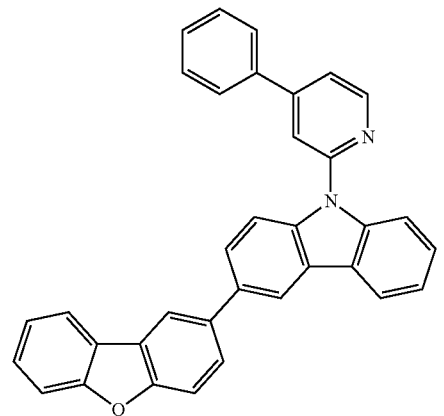
4-20
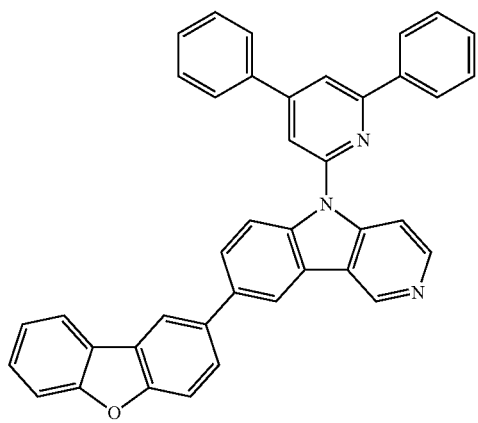
4-21
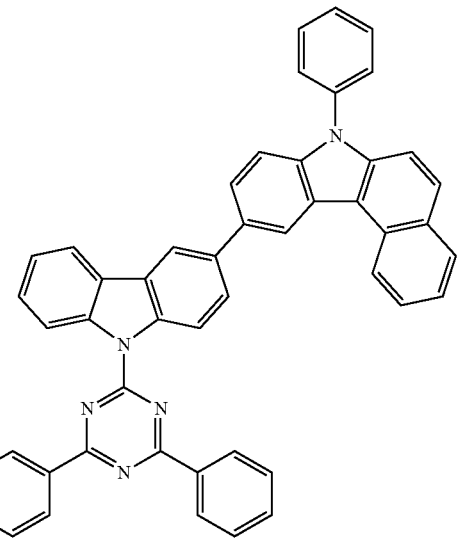
4-22
4-23
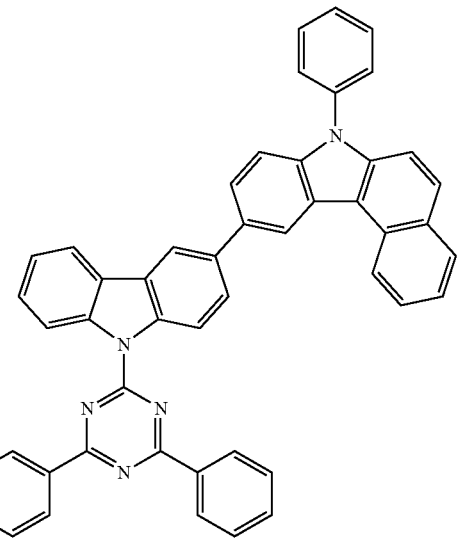
4-24
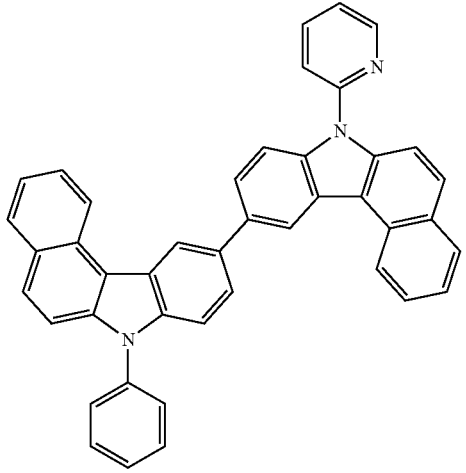
4-25
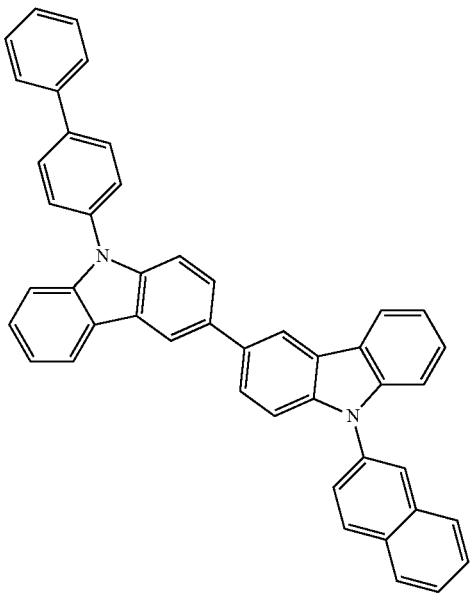

119
-continued
4-26
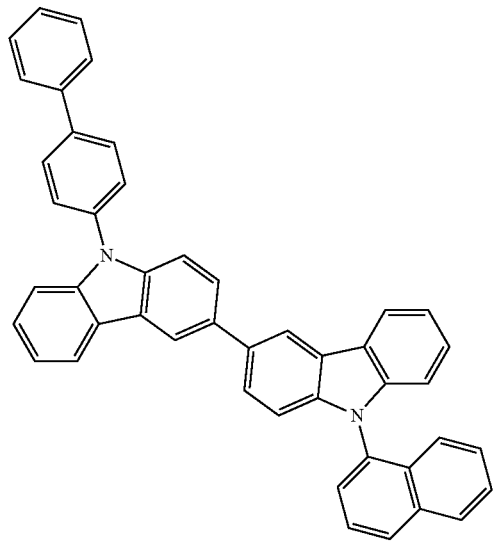
4-27
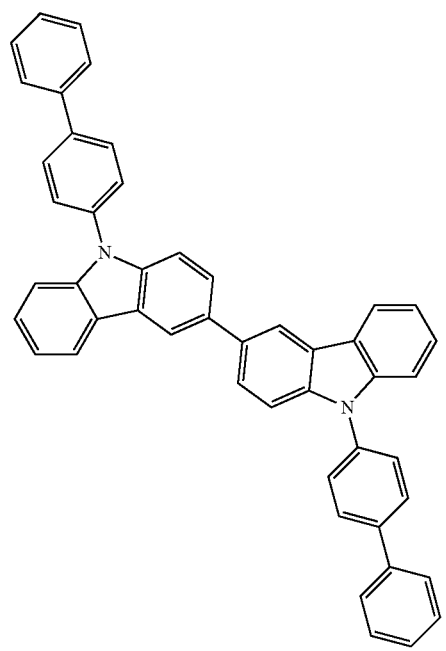
120
-continued
4-28
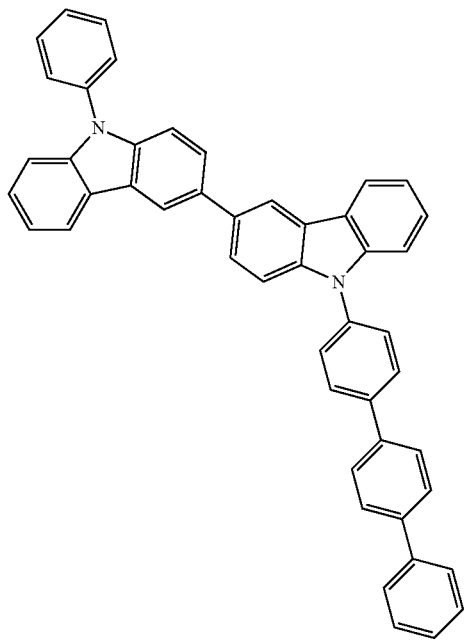
4-29
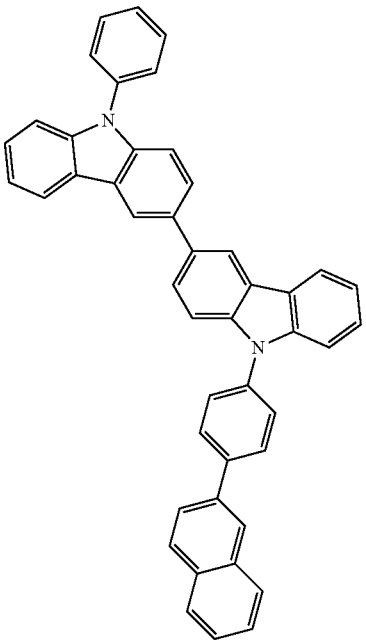

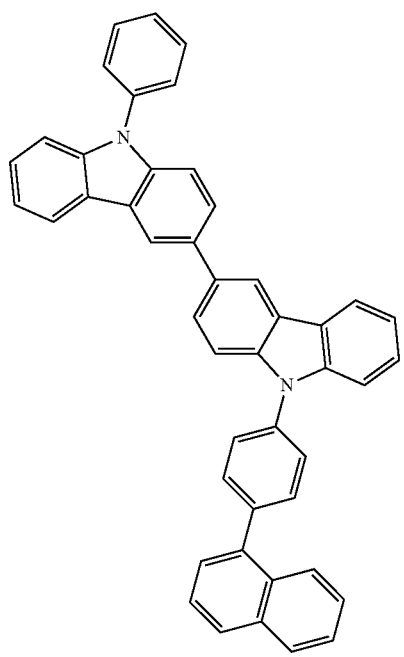
4-30
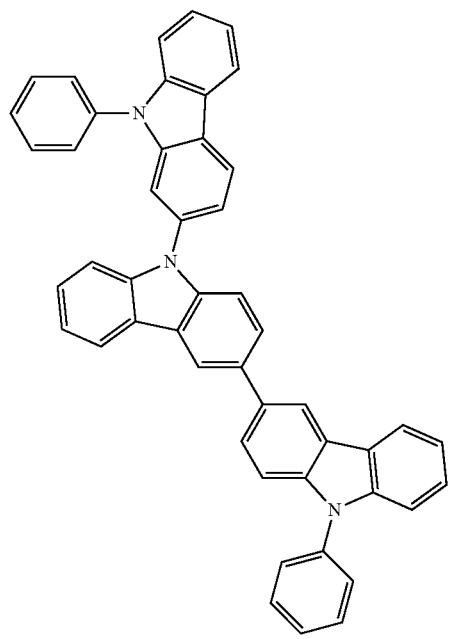
4-31
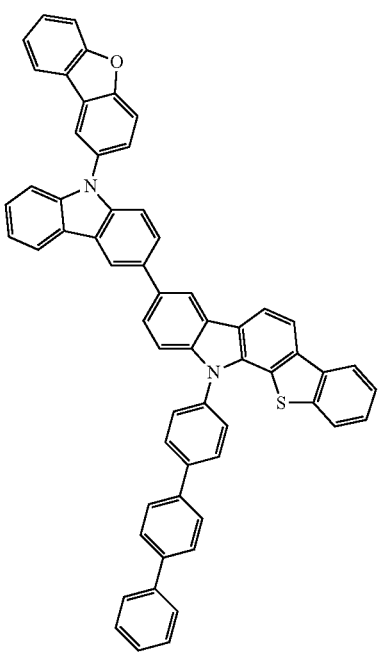
4-32
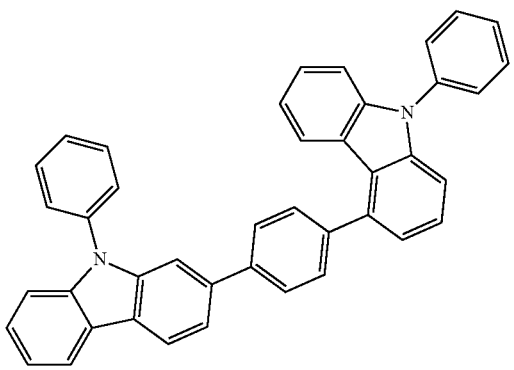
4-33
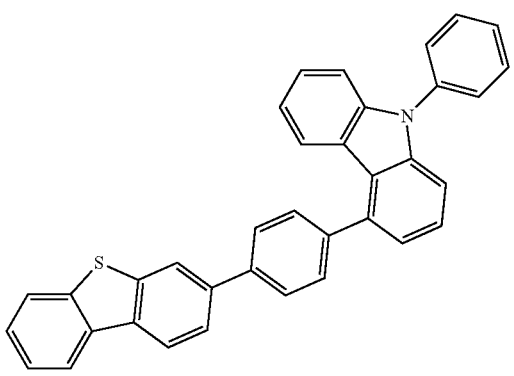
4-34

4-35
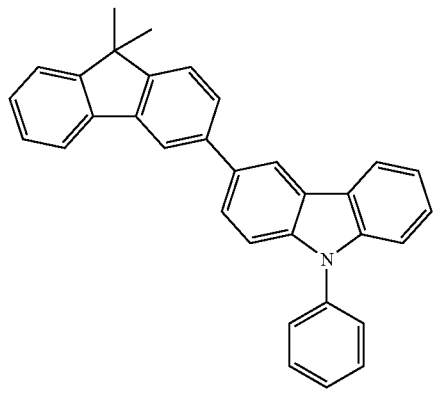
4-36
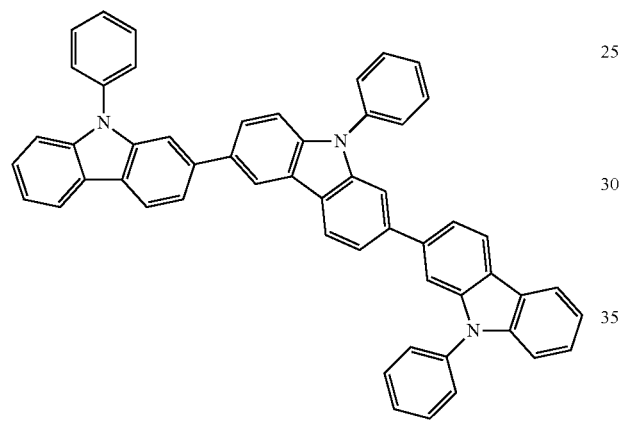
4-37
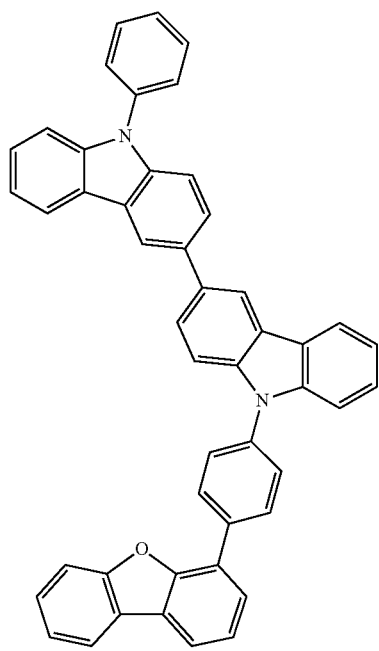
4-38
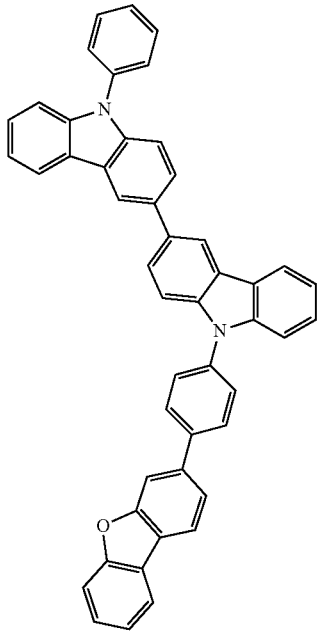
4-39
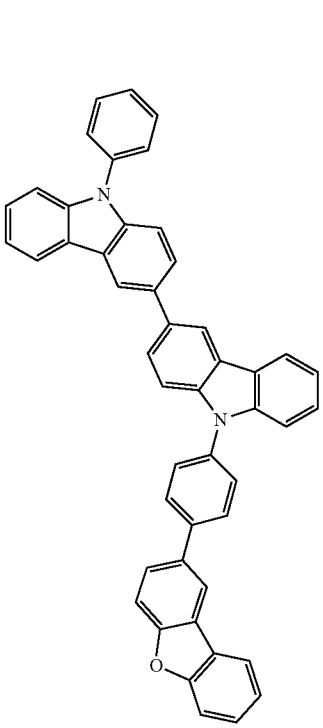

4-40
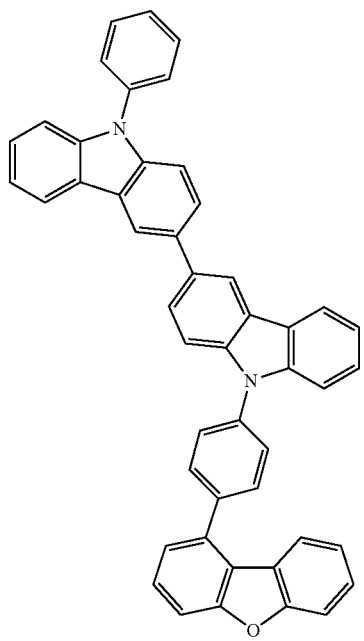
4-42
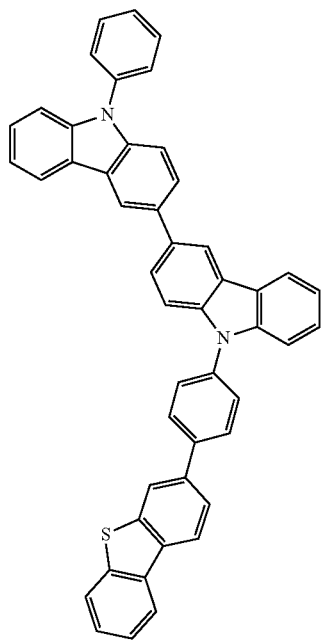
4-41
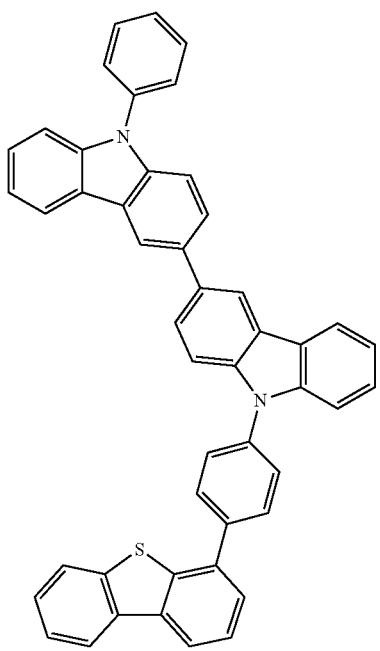
4-43
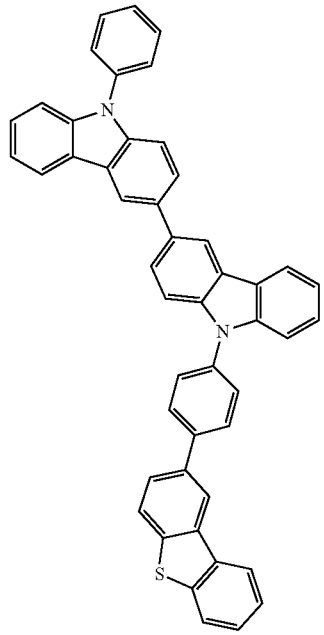

-continued
4-44
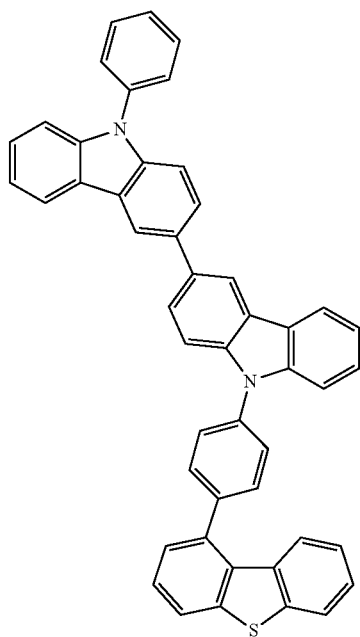
4-45
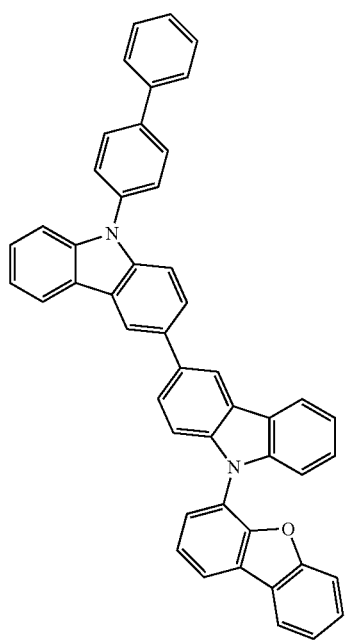
4-46
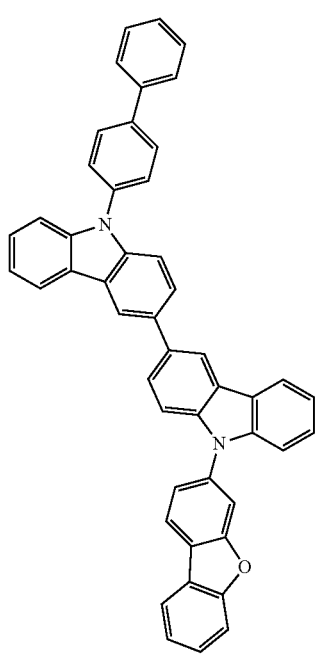
4-47
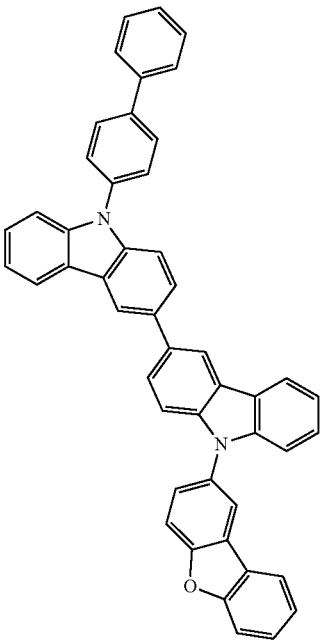

4-48
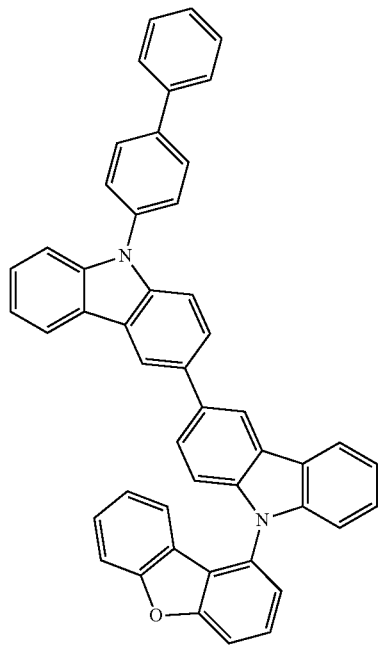
4-49
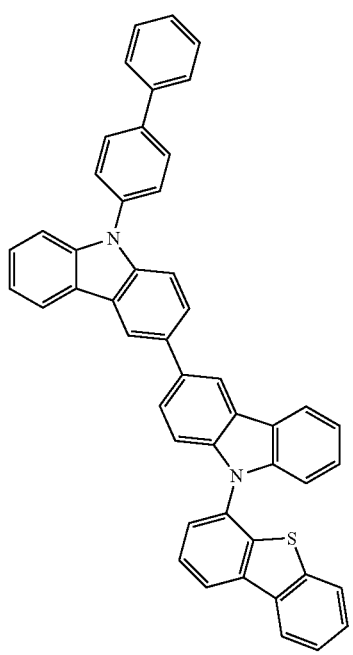
4-50
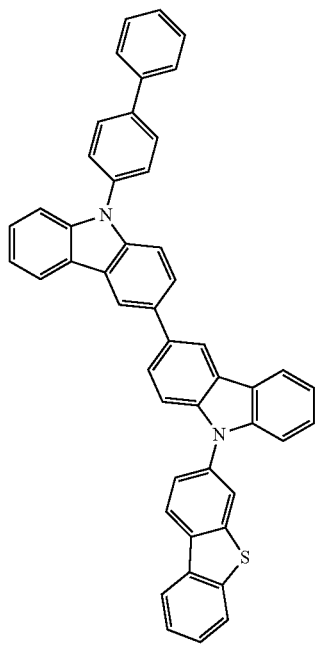
4-51
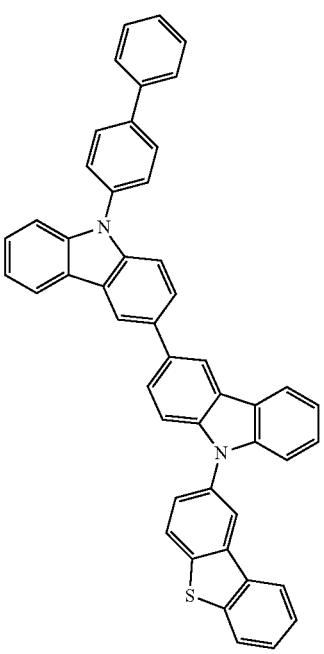

4-52

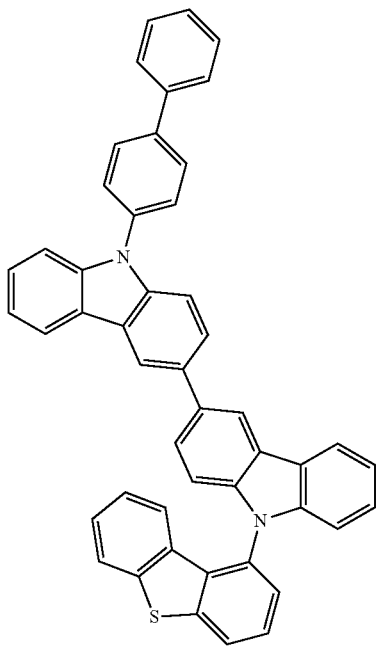

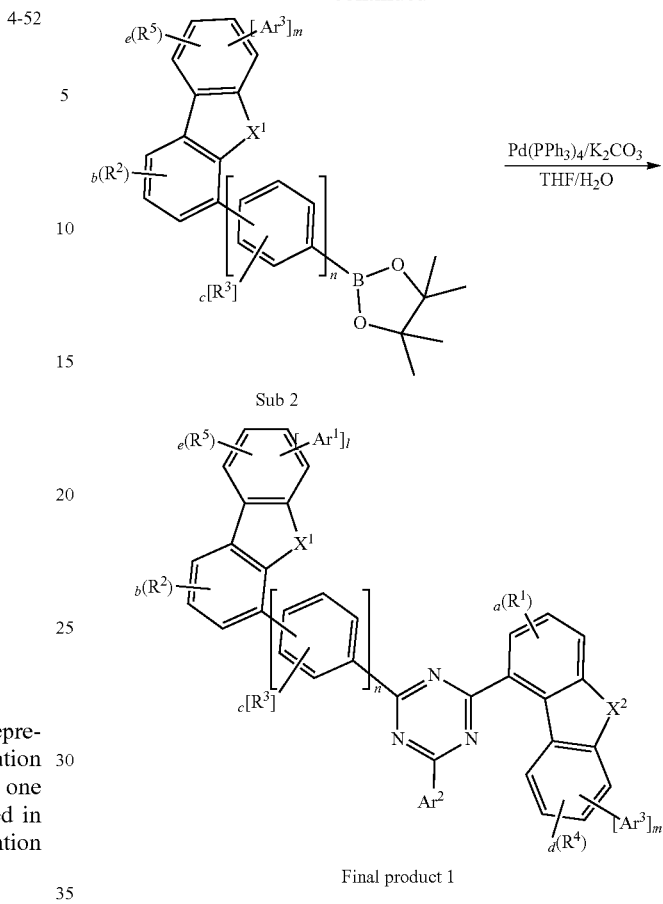

Sub 2

Final product 1

Hereinafter, synthesis examples of the compounds represented by Formulas 1 and 12, respectively, and preparation method of an organic electric element according to one embodiment of the present invention will be described in detail by way of examples. However, the present invention is not limited to the following examples.

Synthesis Example

Synthesis Example of Formula 1

As shown in Reaction Scheme 1 below, the compound (final product) represented by Formula 1 according to the present invention can be synthesized by reacting Sub 1 with Sub 2, but there is no limitation thereto.

Synthesis Example of Sub 1

Sub 1 of the Reaction Scheme 1 can be synthesized according to the reaction route of the following Reaction Scheme 2, but there is no limitation thereto.

<Reaction Scheme 2>

<Reaction Scheme 1>

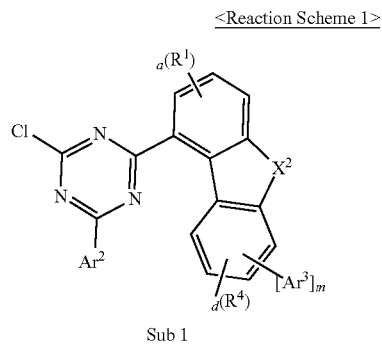

Sub 1

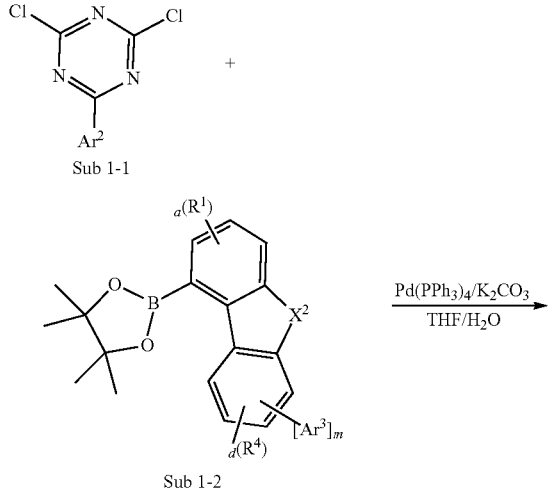

Sub 1-1

Sub 1-2

-continued

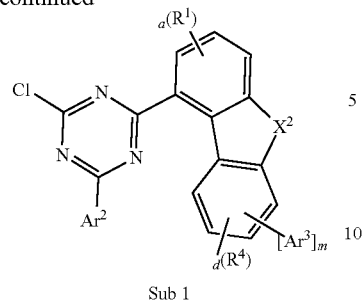

Sub 1

Synthesis Example of Sub 1(1)

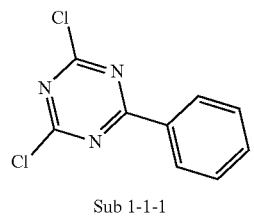

Sub 1-1-1

+

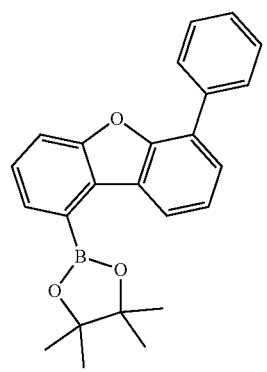

Sub 1-2-1

$\xrightarrow{\text{Pd(PPh}_3)_4/\text{K}_2\text{CO}_3}{\text{THF/H}_2\text{O}}$

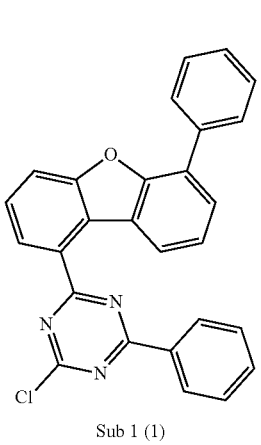

Sub 1 (1)

Sub 1-1-1 (18.1 g, 80 mmol), Sub 1-2-1 (29.6 g, 80 mmol), K$_2$CO$_3$ (19.3 g, 140 mmol) and Pd(PPh$_3$)$_4$ (2.8 g, 2.4 mmol) in a round bottom flask were dissolved in THF and water. The solution was refluxed at 80□ for 12 hours. When the reaction was completed, the reaction product was cooled to room temperature, extracted with CH$_2$Cl$_2$ and washed with water. The organic layer was dried with MgSO$_4$ and concentrated. Thereafter, the concentrate was applied to silica gel column to obtain 23.6 g (yield: 68%) of the product.

Synthesis Example of Sub 1(16)

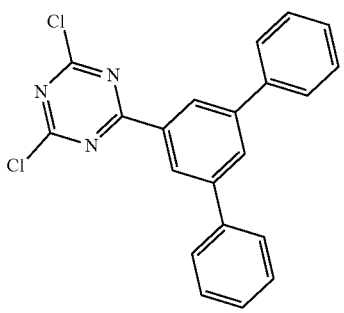

Sub 1-1-2

+

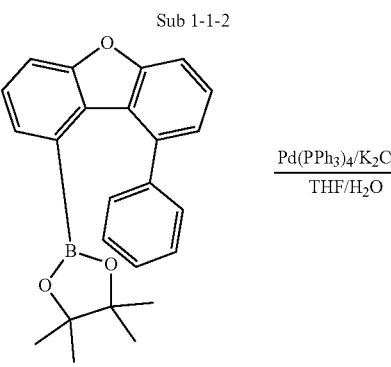

Sub 1-2-2

$\xrightarrow{\text{Pd(PPh}_3)_4/\text{K}_2\text{CO}_3}{\text{THF/H}_2\text{O}}$

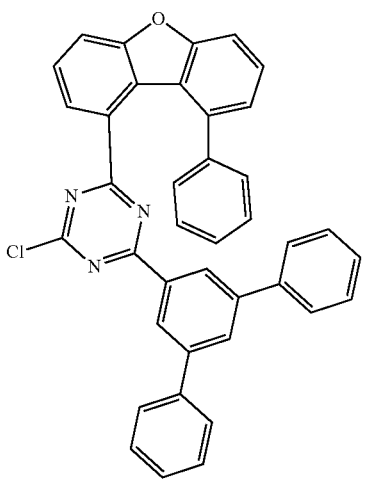

Sub 1 (16)

Sub 1-1-2 (30.3 g, 80 mmol) and Sub 1-2-2 (29.6 g, 80 mmol) were reacted in the same manner as in the synthesis method of Sub 1(1), as a result, 30.5 g (yield: 65%) of the product was obtained.

Synthesis Example of Sub 1(19)

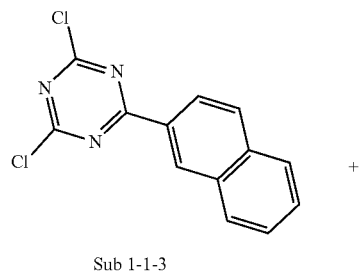

Sub 1-1-3

+

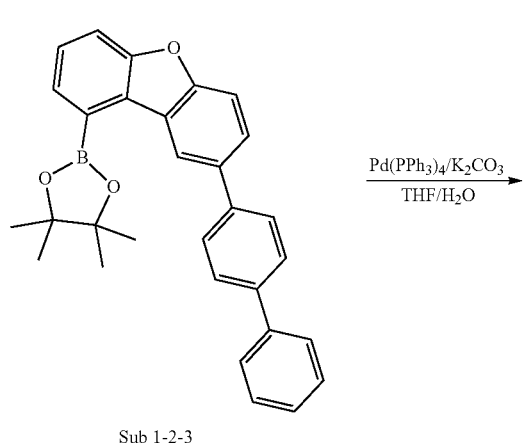

Sub 1-2-3

Pd(PPh₃)₄/K₂CO₃
THF/H₂O
→

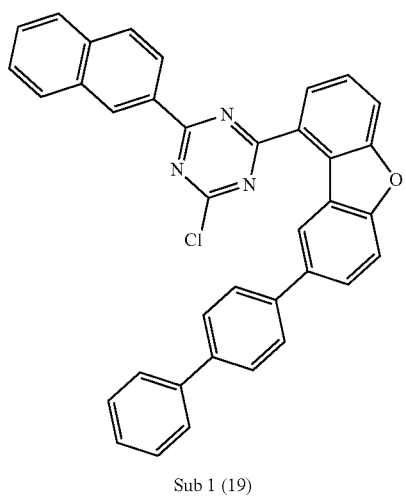

Sub 1 (19)

Sub 1-1-3 (22.1 g, 80 mmol) and Sub 1-2-3 (35.7 g, 80 mmol) were reacted in the same manner as in the synthesis method of Sub 1(1), as a result, 30.9 g (69%) of the product was obtained.

Synthesis Example of Sub 1(28)

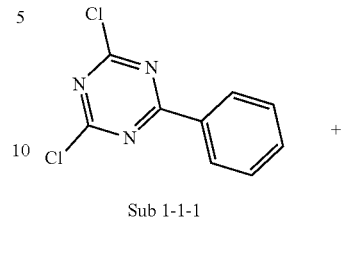

Sub 1-1-1

+

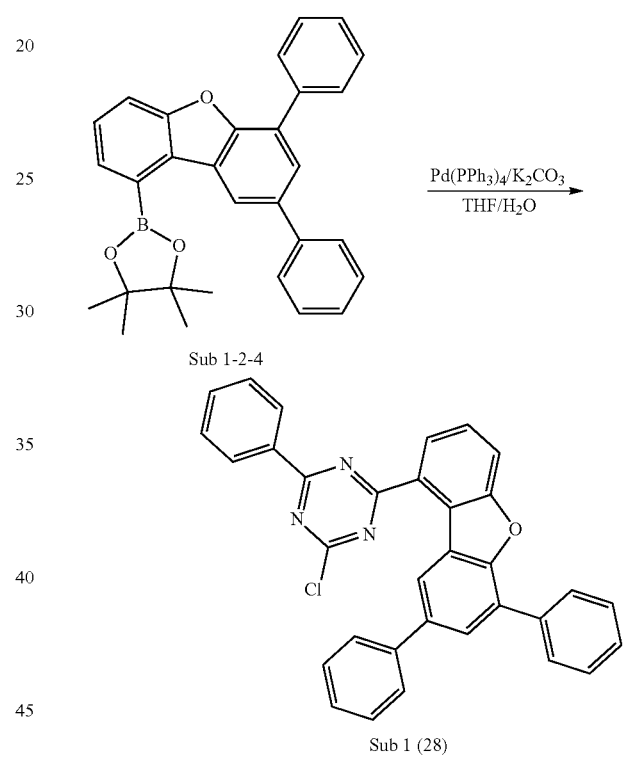

Sub 1-2-4

Pd(PPh₃)₄/K₂CO₃
THF/H₂O
→

Sub 1 (28)

Sub 1-1-1 (18.1 g, 80 mmol) and Sub 1-2-4 (35.7 g, 80 mmol) were reacted in the same manner as in the synthesis method of Sub 1(1), as a result, 28.6 g (70%) of the product was obtained.

Synthesis Example of Sub 1(29)

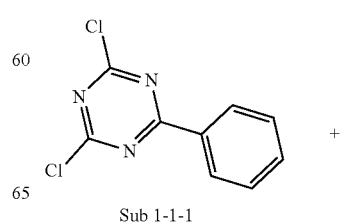

Sub 1-1-1

+

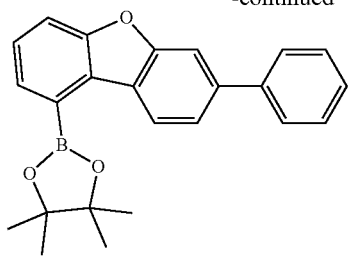
Sub 1-2-5

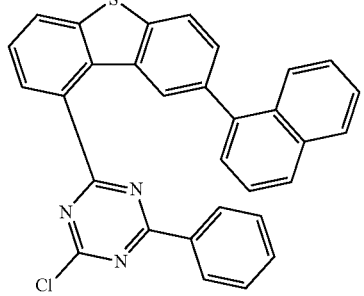
Sub 1 (35)

Sub 1-1-1 (18.1 g, 80 mmol) and Sub 1-2-6 (34.9 g, 80 mmol) were reacted in the same manner as in the synthesis method of Sub 1(1), as a result, 27.6 g (69%) of the product was obtained.

Synthesis Example of Sub 1(37)

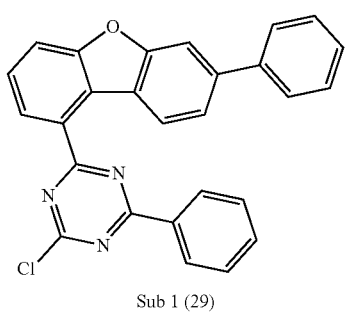
Sub 1 (29)

Sub 1-1-1 (18.1 g, 80 mmol) and Sub 1-2-5 (29.6 g, 80 mmol) were reacted in the same manner as in the synthesis method of Sub 1(1), as a result, 23.3 g (67%) of the product was obtained.

Synthesis Example of Sub 1(35)

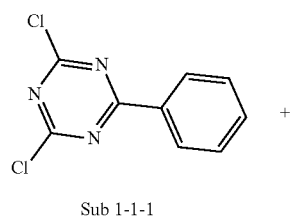
Sub 1-1-1

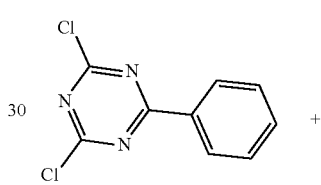
Sub 1-1-1

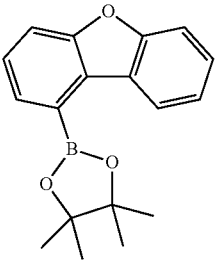
Sub 1-2-1'

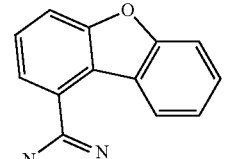
Sub 1 (37)

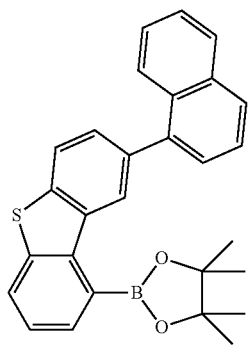
Sub 1-2-6

Sub 1-1-1 (18.1 g, 80 mmol) and Sub 1-2-1' (23.5 g, 80 mmol) were reacted in the same manner as in the synthesis method of Sub 1(1), as a result, 20.0 g (70%) of the product was obtained.

The example of the compound belonging to Sub 1 may be, but not limited to, the following compounds, and Table 1 shows FD-MS values of the following compounds.

Sub 1 (1)
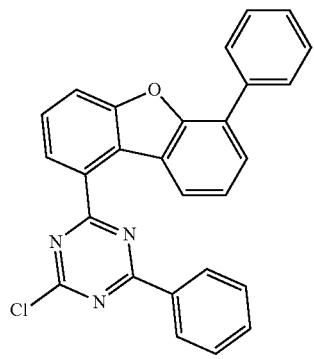
Sub 1 (2)
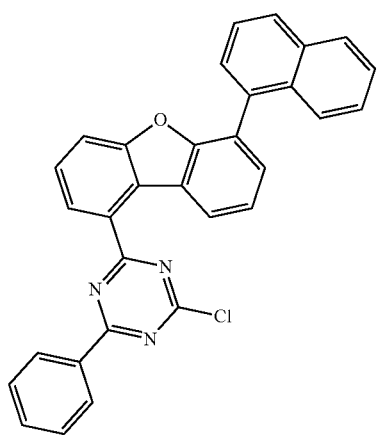
Sub 1 (3)
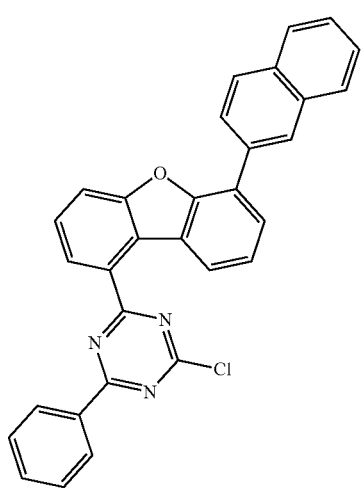
Sub 1 (4)
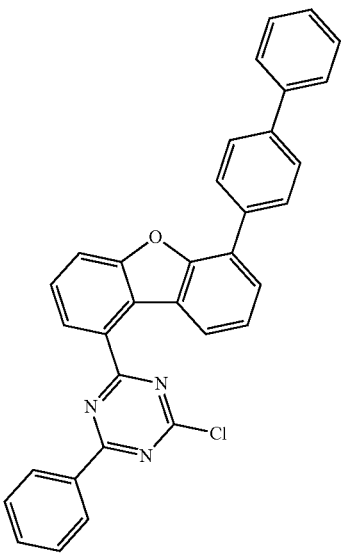
Sub 1 (5)
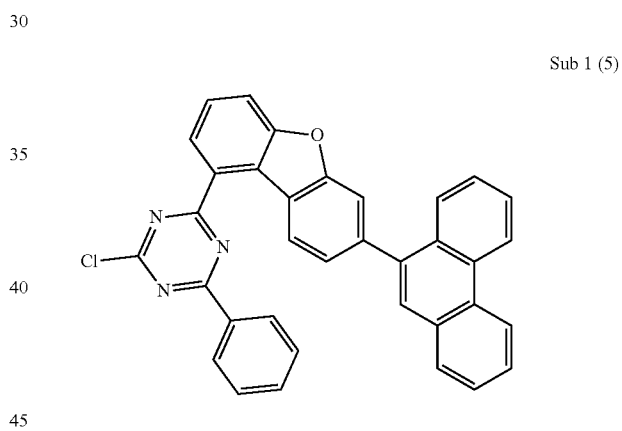
Sub 1 (6)
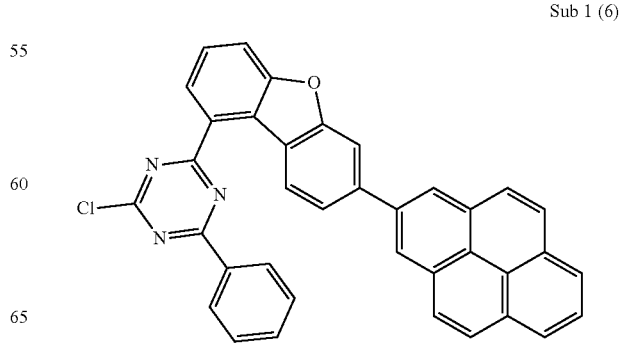

Sub 1 (7)
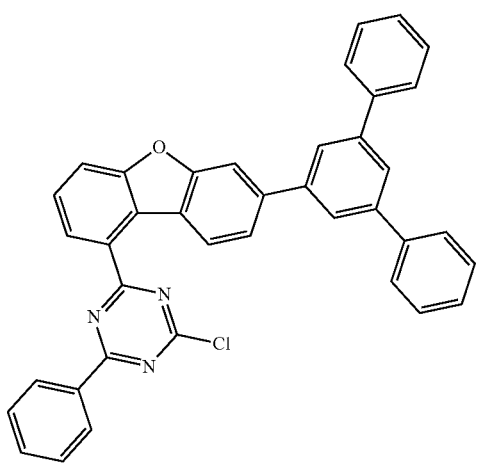
Sub 1 (11)
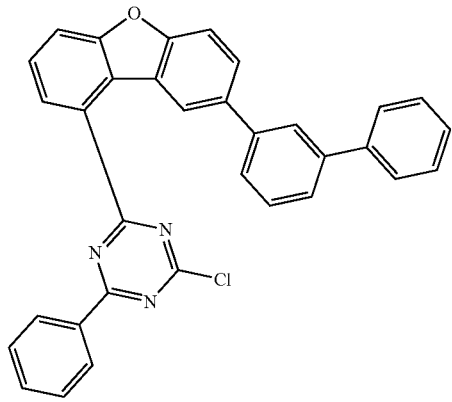
Sub 1 (8)
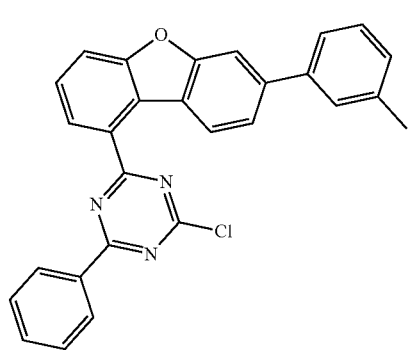
Sub 1 (12)
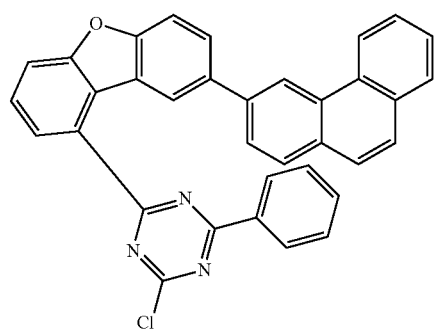
Sub 1 (9)
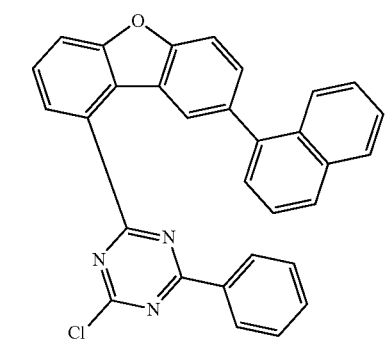
Sub 1 (13)
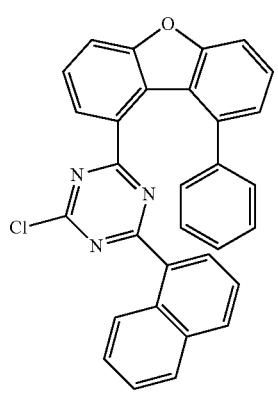
Sub 1 (10)
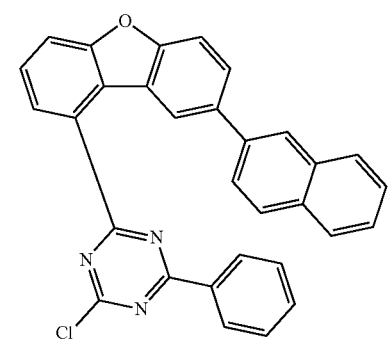
Sub 1 (14)
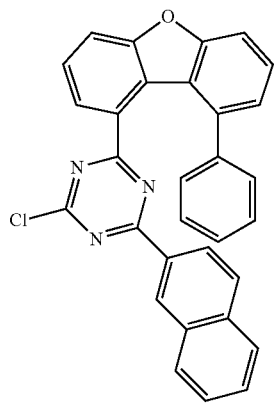

Sub 1 (15)
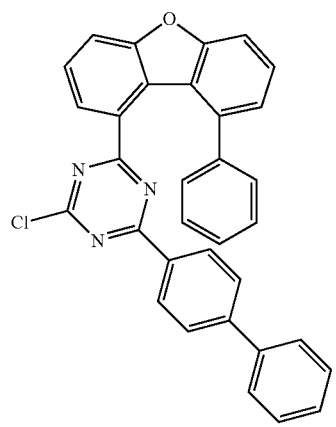
Sub 1 (16)
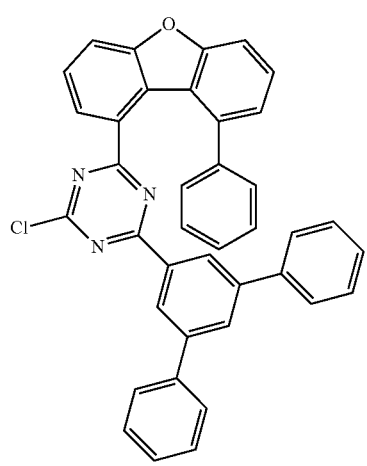
Sub 1 (17)
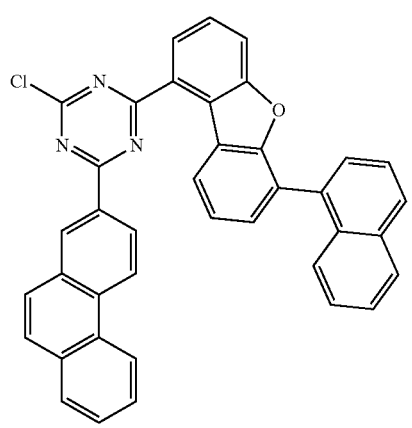
Sub 1 (18)
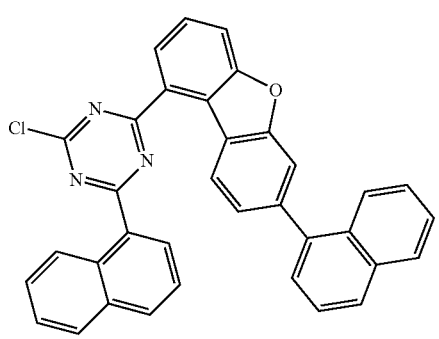
Sub 1 (19)
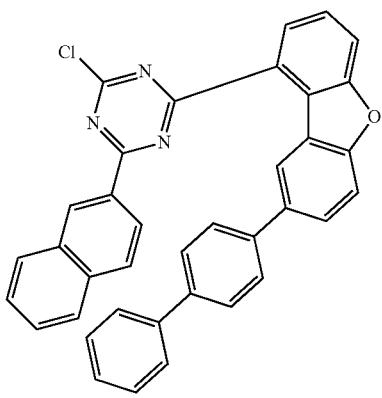
Sub 1 (20)
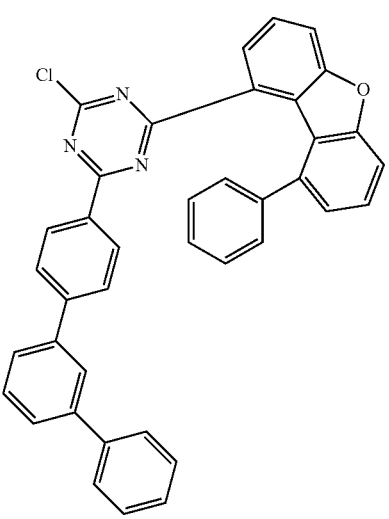
Sub 1 (21)
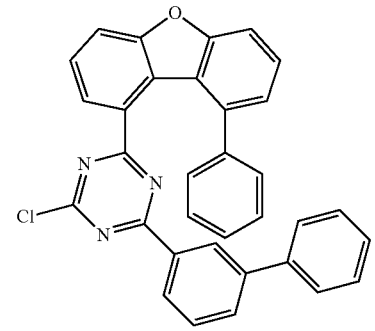
Sub 1 (22)
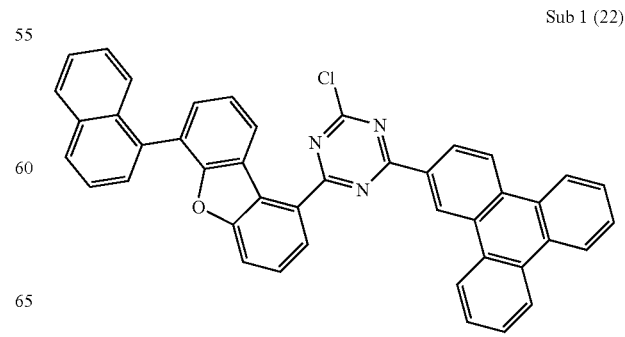

Sub 1 (23)
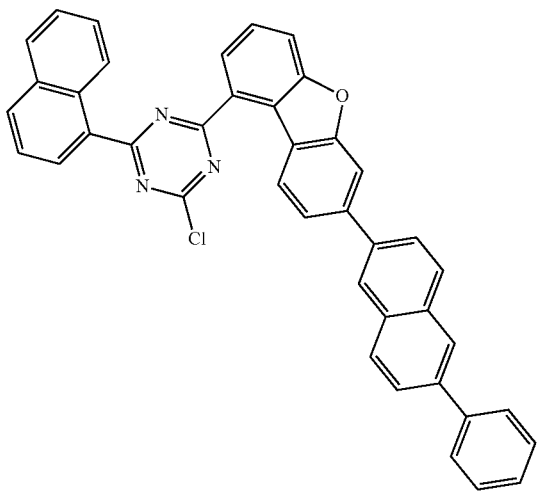
Sub 1 (24)
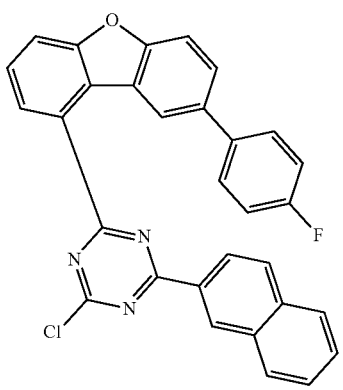
Sub 1 (25)
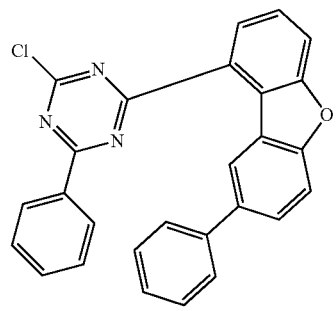
Sub 1 (26)
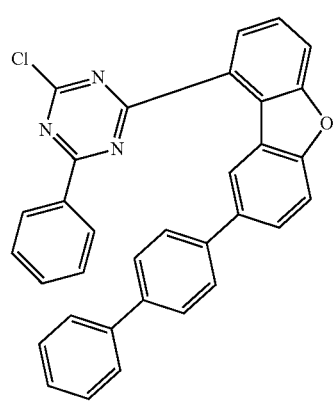
Sub 1 (27)
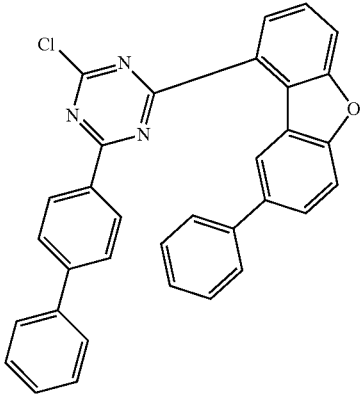
Sub 1 (28)
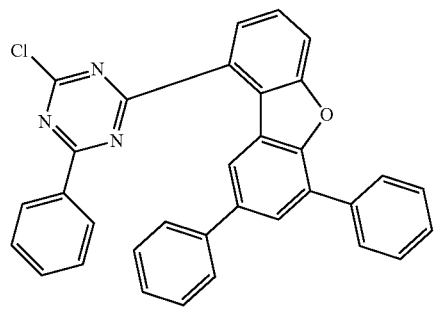
Sub 1 (29)
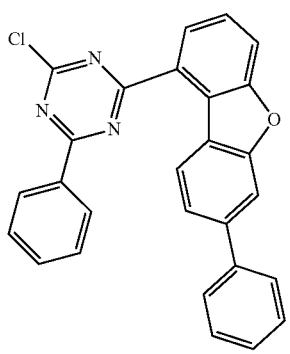
Sub 1 (30)
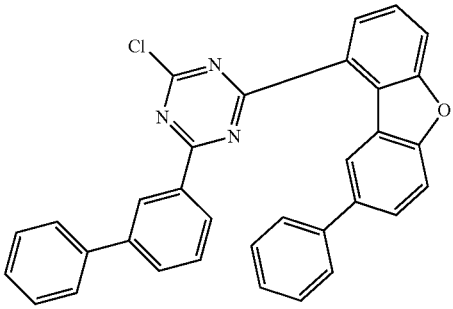

-continued
Sub 1 (31)
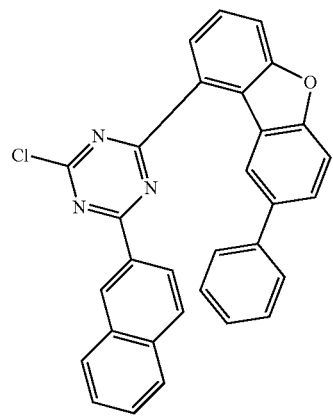
Sub 1 (32)
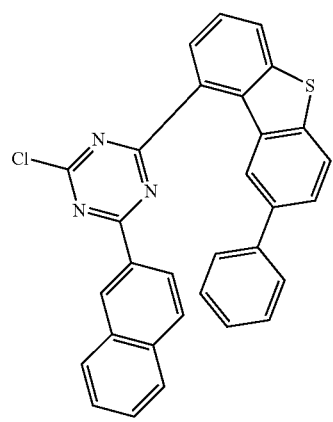
Sub 1 (33)
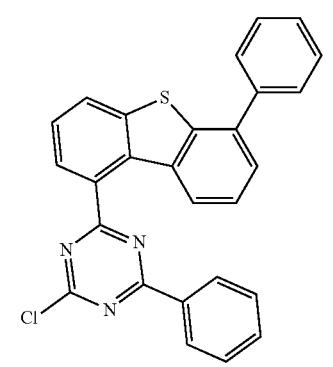
Sub 1 (34)
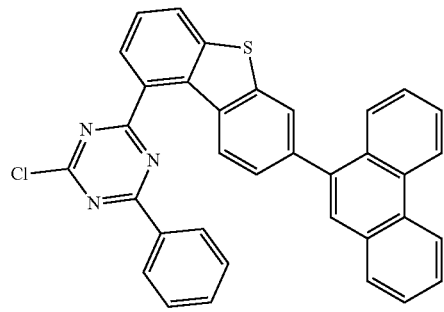
Sub 1 (35)
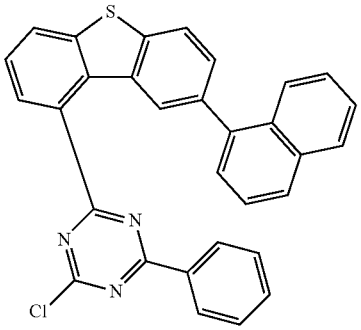
Sub 1 (36)
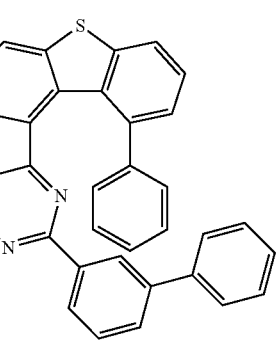
Sub 1 (33)
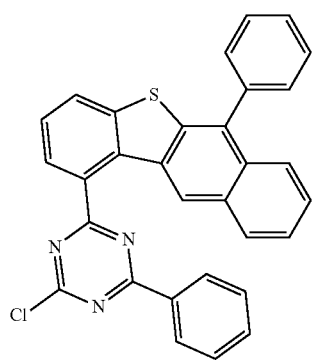

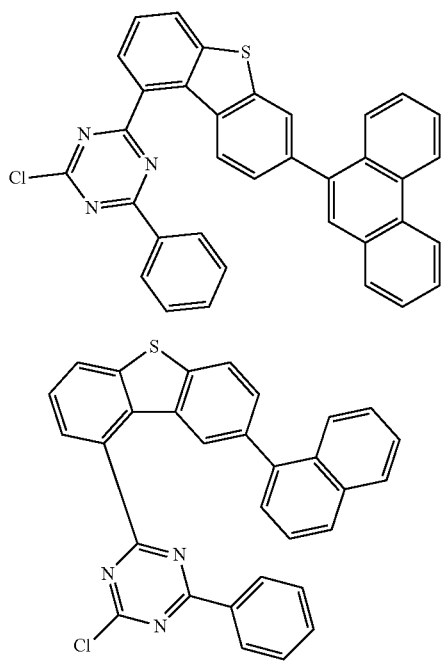

Sub 1 (34)

Sub 1 (35)

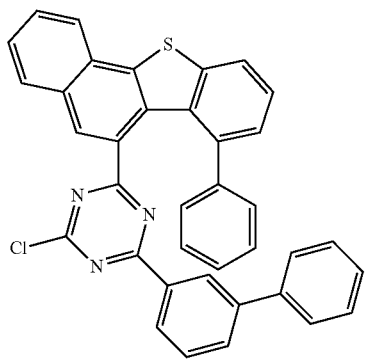

Sub 1 (36)

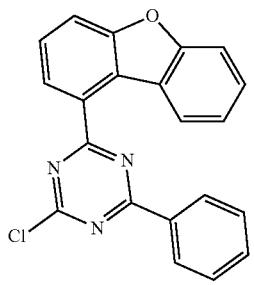

Sub 1 (37)

TABLE 1

| Compound | FD-MS | Compound | FD-MS |
|---|---|---|---|
| Sub 1(1) | m/z = 433.10($C_{27}H_{16}ClN_3O$ = 433.90) | Sub 1(2) | m/z = 483.11($C_{31}H_{18}ClN_3O$ = 483.96) |
| Sub 1(3) | m/z = 483.11($C_{31}H_{18}ClN_3O$ = 483.96) | Sub 1(4) | m/z = 509.13($C_{31}H_{20}ClN_3O$ = 509.99) |
| Sub 1(5) | m/z = 533.13($C_{35}H_{20}ClN_3O$ = 534.02) | Sub 1(6) | m/z = 557.13($C_{37}H_{20}ClN_3O$ = 558.04) |
| Sub 1(7) | m/z = 585.16($C_{39}H_{24}ClN_3O$ = 586.09) | Sub 1(8) | m/z = 447.11($C_{28}H_{18}ClN_3O$ = 447.92) |
| Sub 1(9) | m/z = 483.11($C_{31}H_{18}ClN_3O$ = 483.96) | Sub 1(10) | m/z = 483.11($C_{31}H_{18}ClN_3O$ = 483.96) |
| Sub 1(11) | m/z = 509.13($C_{33}H_{20}ClN_3O$ = 509.99) | Sub 1(12) | m/z = 533.13($C_{35}H_{20}ClN_3O$ = 534.02) |
| Sub 1(13) | m/z = 483.11($C_{31}H_{18}ClN_3O$ = 483.96) | Sub 1(14) | m/z = 483.11($C_{31}H_{18}ClN_3O$ = 483.96) |
| Sub 1(15) | m/z = 509.13($C_{33}H_{20}ClN_3O$ = 509.99) | Sub 1(16) | m/z = 585.16($C_{39}H_{24}ClN_3O$ = 586.09) |
| Sub 1(17) | m/z = 583.15($C_{39}H_{22}ClN_3O$ = 584.08) | Sub 1(18) | m/z = 533.13($C_{35}H_{20}ClN_3O$ = 534.02) |
| Sub 1(19) | m/z = 559.15($C_{37}H_{22}ClN_3O$ = 560.05) | Sub 1(20) | m/z = 585.16($C_{39}H_{24}ClN_3O$ = 586.09) |
| Sub 1(21) | m/z = 509.13($C_{33}H_{20}ClN_3O$ = 509.99) | Sub 1(22) | m/z = 633.16($C_{43}H_{24}ClN_3O$ = 634.14) |
| Sub 1(23) | m/z = 609.16($C_{41}H_{24}ClN_3O$ = 610.11) | Sub 1(24) | m/z = 501.10($C_{31}H_{17}ClFN_3O$ = 501.95) |
| Sub 1(25) | m/z = 433.10($C_{27}H_{16}ClN_3O$ = 433.90) | Sub 1(26) | m/z = 509.13($C_{33}H_{20}ClN_3O$ = 509.99) |
| Sub 1(27) | m/z = 509.13($C_{33}H_{20}ClN_3O$ = 509.99) | Sub 1(28) | m/z = 509.13($C_{33}H_{20}ClN_3O$ = 509.99) |
| Sub 1(29) | m/z = 433.10($C_{27}H_{16}ClN_3O$ = 433.90) | Sub 1(30) | m/z = 509.13($C_{33}H_{20}ClN_3O$ = 509.99) |
| Sub 1(31) | m/z = 483.11($C_{31}H_{18}ClN_3O$ = 483.96) | Sub 1(32) | m/z = 499.09($C_{31}H_{18}ClN_3S$ = 500.02) |
| Sub 1(33) | m/z = 499.09($C_{31}H_{18}ClN_3S$ = 500.02) | Sub 1(34) | m/z = 549.11($C_{35}H_{20}ClN_3S$ = 550.08) |
| Sub 1(35) | m/z = 499.09($C_{31}H_{18}ClN_3S$ = 500.02) | Sub 1(36) | m/z = 575.12($C_{37}H_{22}ClN_3S$ = 576.11) |
| Sub 1(37) | m/z = 357.07($C_{21}H_{12}ClN_3O$ = 357.80) | | |

Synthesis Example of Sub 2
Sub 2 of the Reaction Scheme 1 can be synthesized according to the reaction route of the following Reaction Scheme 3, but there is no limitation thereto.
<Reaction Scheme 3>
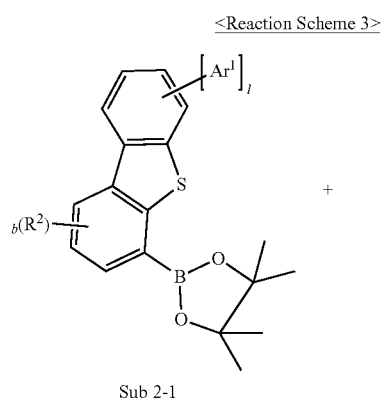
Sub 2-1
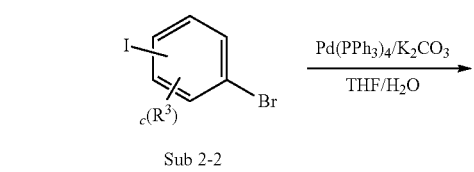
Sub 2-2
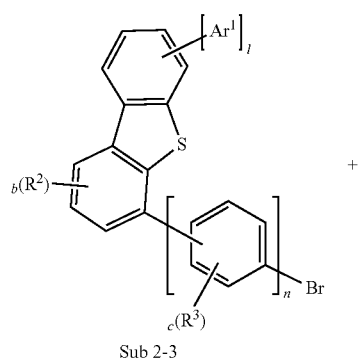
Sub 2-3
Sub 2-4
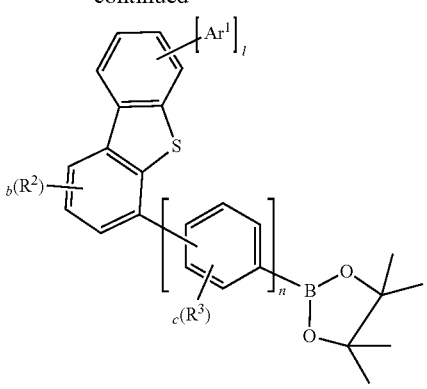
Sub 2
Synthesis Example of Sub 2(3)
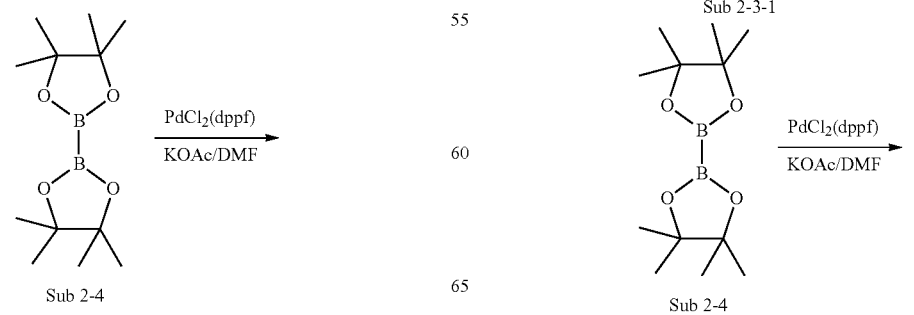

-continued

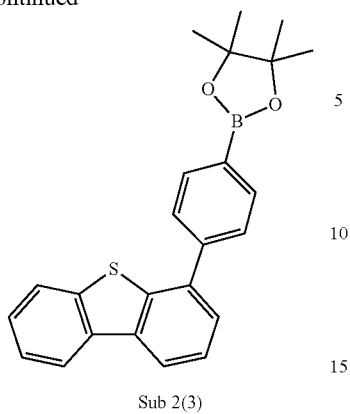

Sub 2(3)

Synthesis of Sub 2-3-1

Sub 2-1-1 (24.8 g, 80 mmol) and Sub 2-2-1 (22.5 g, 80 mmol) were reacted in the same manner as in the synthesis method of Sub 1(1), as a result, 20.6 g (yield: 76%) of the product was obtained.

Synthesis Example of Sub 2(3)

After dissolving Sub 2-3-1 (4.7 g, 14 mmol) in DMF (98 mL), bispinacolborate (3.6 g, 15 mmol), PdCl$_2$(dppf) catalyst (0.3 g, 0.4 mmol), KOAc (4.1 g, 42 mmol)) were added in order and the mixture was stirred for 24 hours. Thereafter, the mixed solution was passed through a silica gel column and recrystallized to obtain 3.9 g (yield: 72%) of the borate compound Sub 2 (3).

Synthesis Example of Sub 2(23)

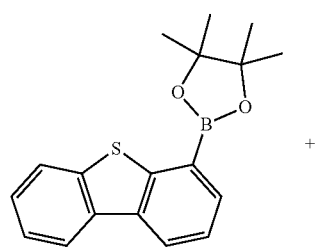

Sub 2-1-1

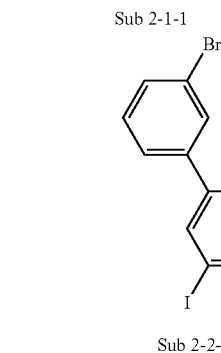

Sub 2-2-2

-continued

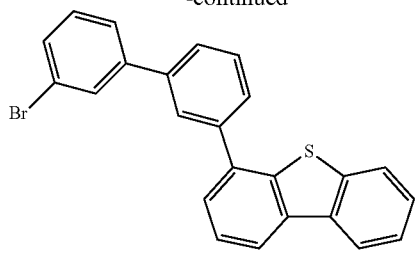

Sub 2-3-2

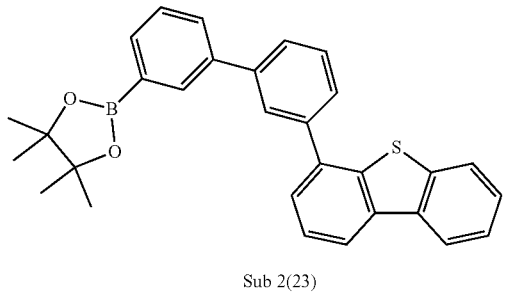

Sub 2-4

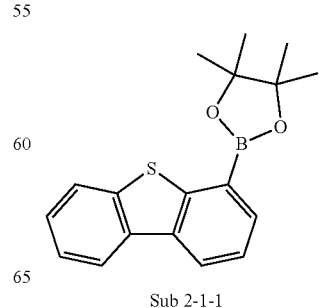

Sub 2(23)

Synthesis of Sub 2-3-2

Sub 2-1-1 (24.8 g, 80 mmol) and Sub 2-2-2 (28.7 g, 80 mmol) were reacted in the same manner as in the synthesis method of Sub 1(1), as a result, 25.3 g (76%) of the product was obtained.

Synthesis of Sub 2(23)

Sub 2-3-2 (5.8 g, 14 mmol) and bispinacolborate (3.6 g, 15 mmol) were reacted in the same manner as in the synthesis method of Sub 2(3), as a result, 4.6 g (71%) of the product Sub 2(23) was obtained.

Synthesis Example of Sub 2(28)

Sub 2-1-1

Synthesis of Sub 2(28)

Sub 2-3-3 (6.9 g, 14 mmol) and bispinacolborate (3.6 g, 15 mmol) were reacted in the same manner as in the synthesis method of Sub 2(3), as a result, 5.1 g (68%) of the product Sub 2(28) was obtained.

Synthesis Example of Sub 2(31)

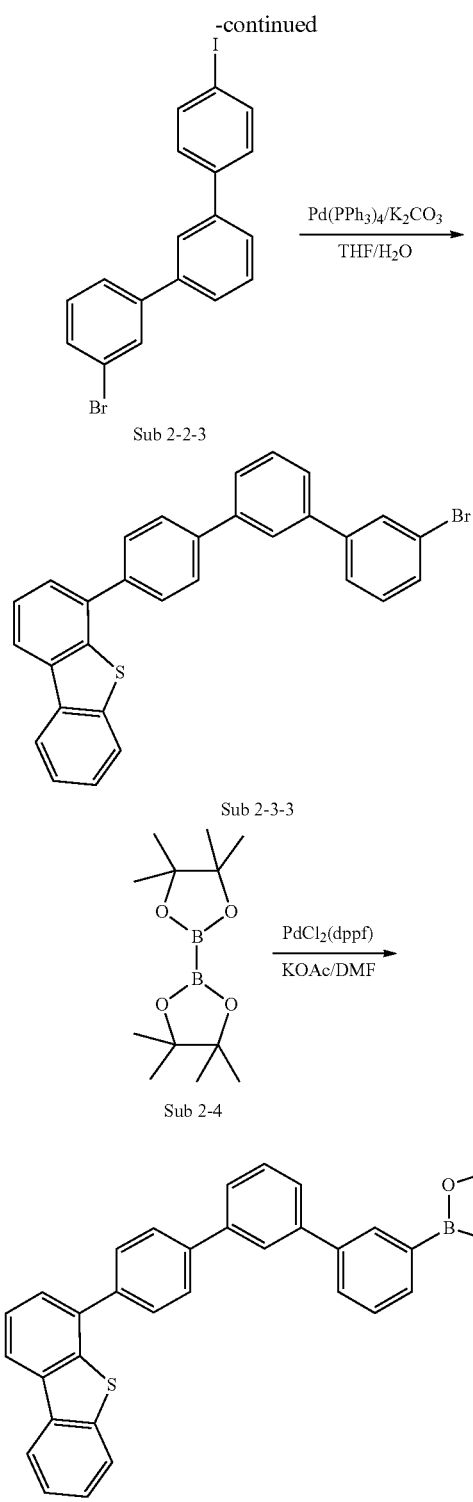

Sub 2-2-3

Sub 2-3-3

Sub 2-4

Sub 2(28)

Synthesis of Sub 2-3-3

Sub 2-1-1 (24.8 g, 80 mmol) and Sub 2-2-3 (34.8 g, 80 mmol) were reacted in the same manner as in the synthesis method of Sub 1(1), as a result, 29.1 g (74%) of the product was obtained.

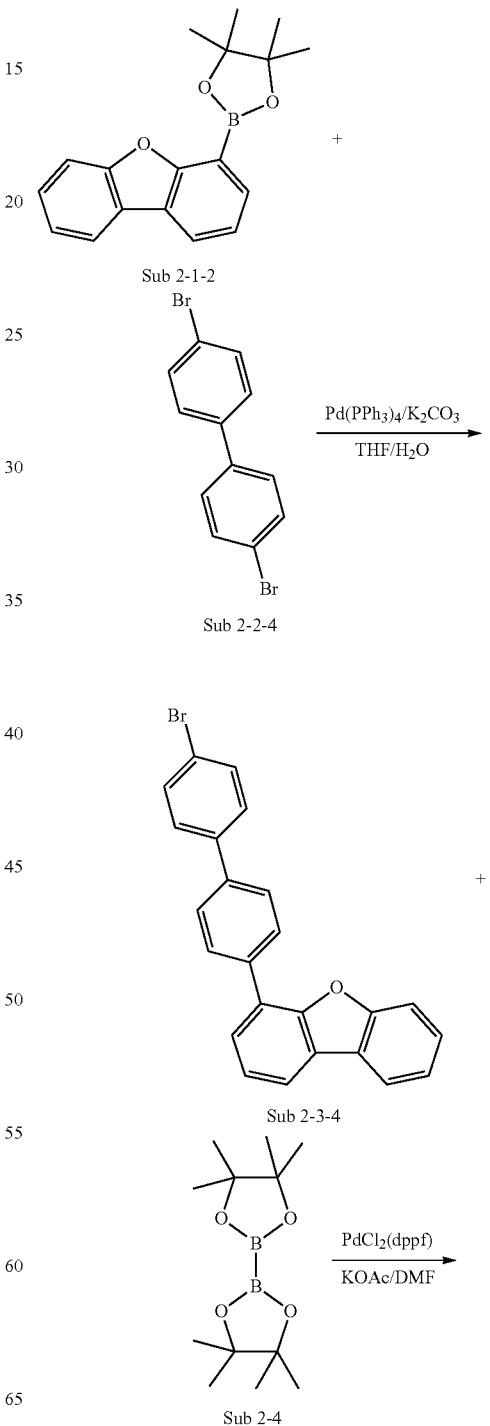

Sub 2-1-2

Sub 2-2-4

Sub 2-3-4

Sub 2-4

-continued

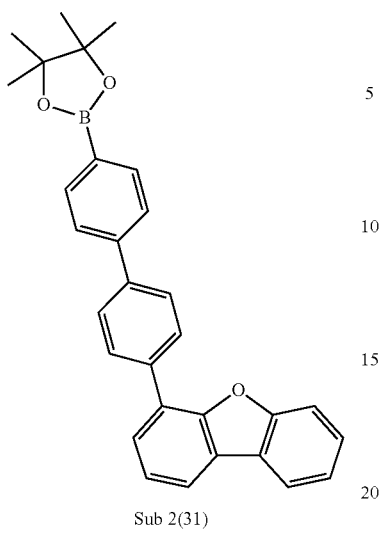
Sub 2(31)

Synthesis of Sub 2-3-4

Sub 2-1-2 (23.5 g, 80 mmol) and Sub 2-2-4 (25.0 g, 80 mmol) were reacted in the same manner as in the synthesis method of Sub 1(1), as a result, 22.7 g (71%) of the product was obtained.

Synthesis of Sub 2(31)

Sub 2-3-4 (5.6 g, 14 mmol) and bispinacolborate (3.6 g, 15 mmol) were reacted in the same manner as in the synthesis method of Sub 2(3), as a result, 4.4 g (70%) of the product Sub 2(31) was obtained.

The example of the compound belonging to Sub 2 may be, but not limited to, the following compounds, and Table 2 shows FD-MS values of the following compounds.

Sub 2(1)
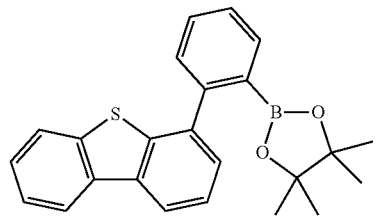

Sub 2(2)
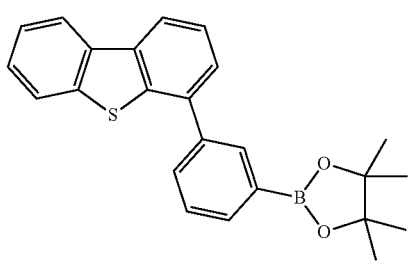

-continued

Sub 2(3)
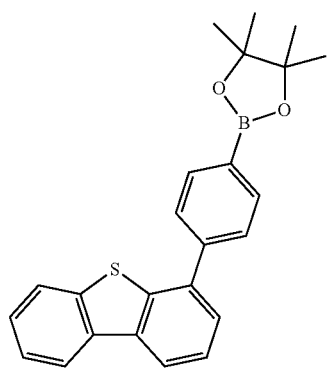

Sub 2(4)
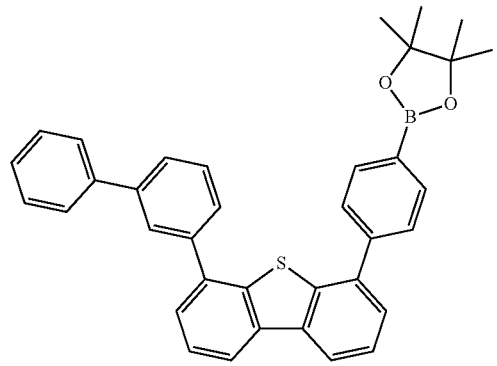

Sub 2(5)
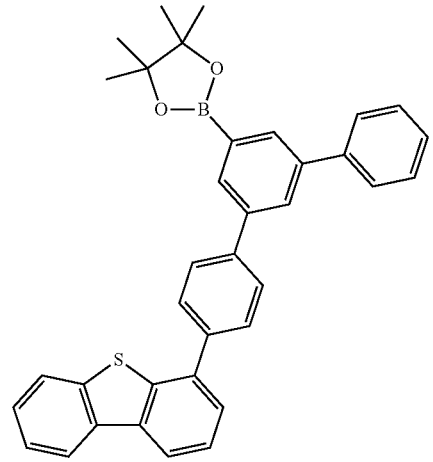

Sub 2(6)
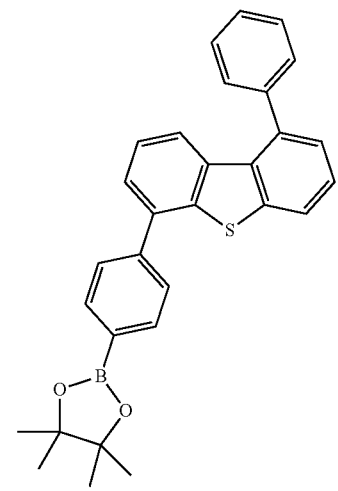
Sub 2(7)
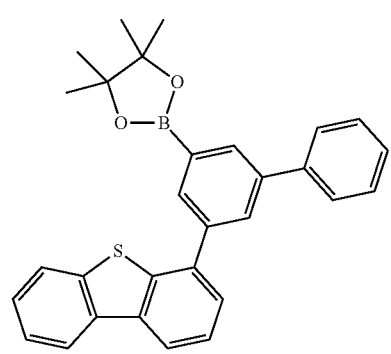
Sub 2(8)
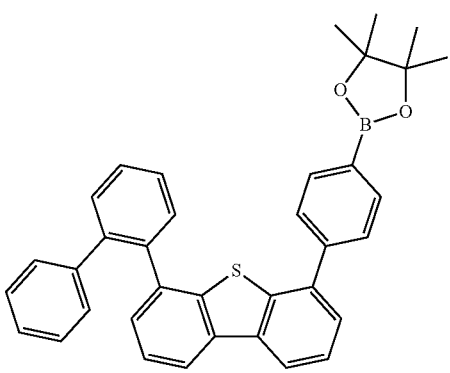
Sub 2(9)
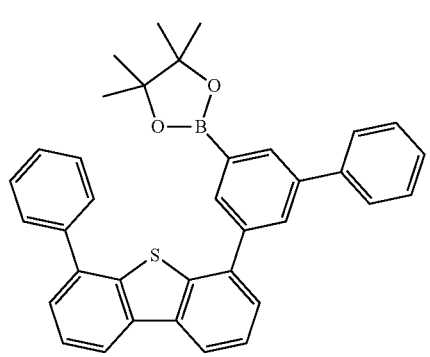
Sub 2(10)
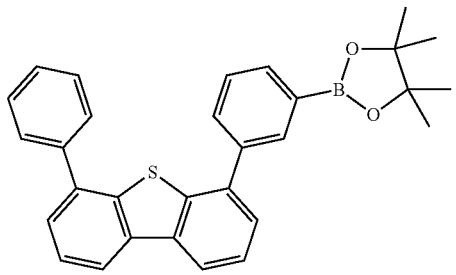
Sub 2(11)
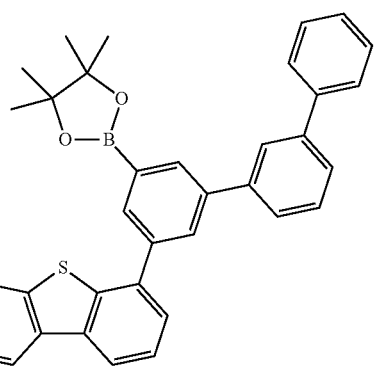
Sub 2(12)
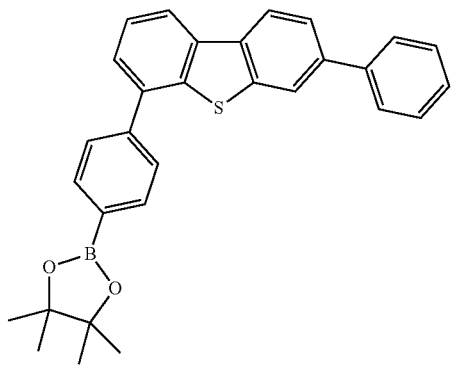
Sub 2(13)
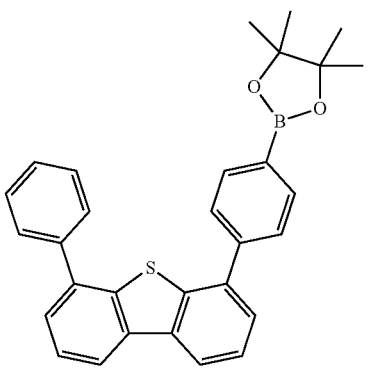

Sub 2(14)
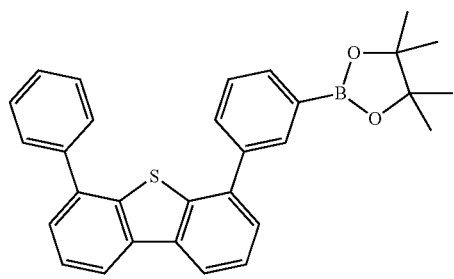
Sub 2(15)
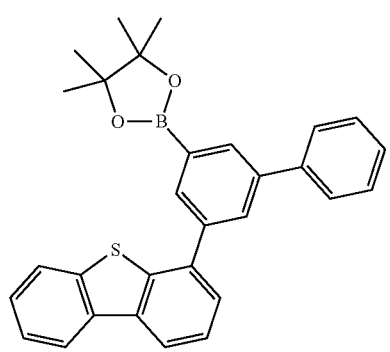
Sub 2(16)
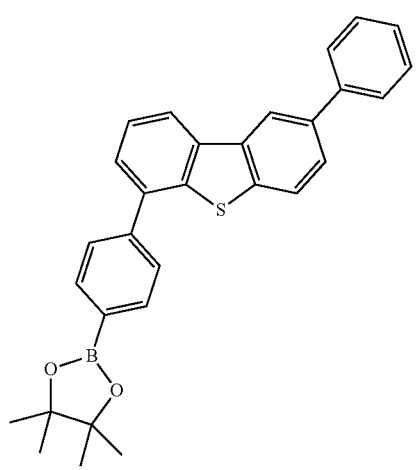
Sub 2(17)
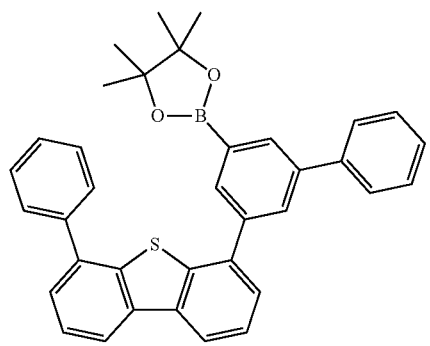
Sub 2(18)
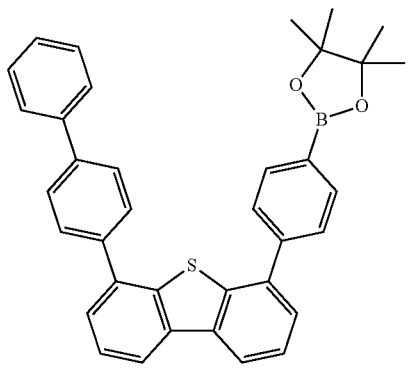
Sub 2(19)
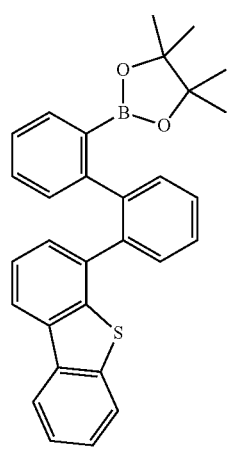
Sub 2(20)
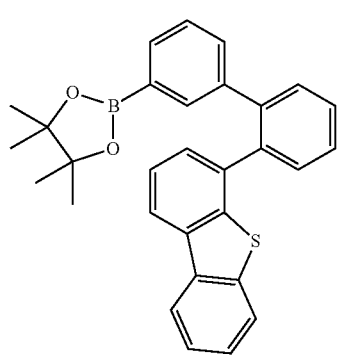
Sub 2(21)
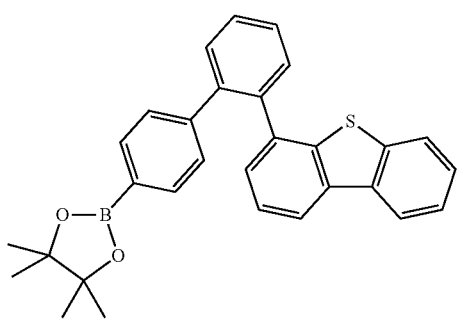

Sub 2(22)
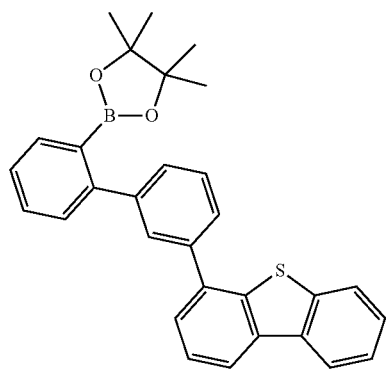
Sub 2(23)
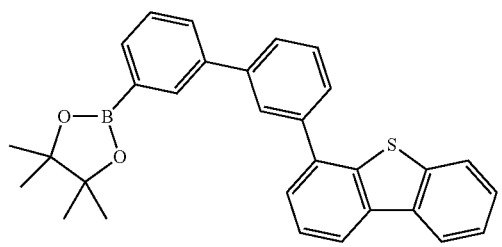
Sub 2(24)
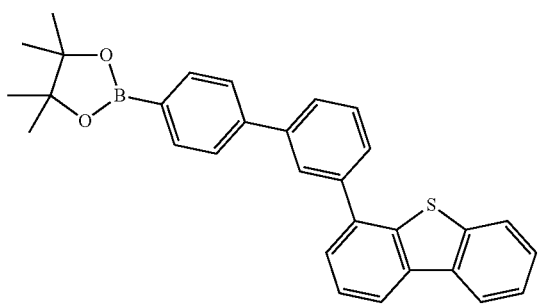
Sub 2(25)
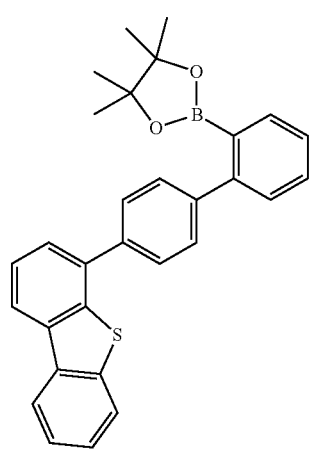
Sub 2(26)
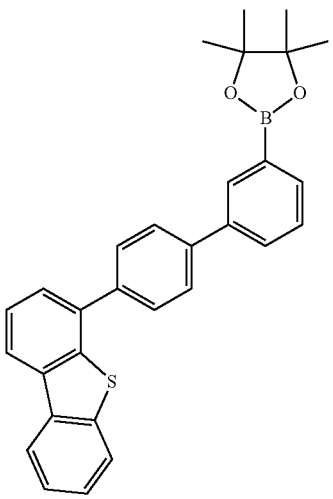
Sub 2(27)
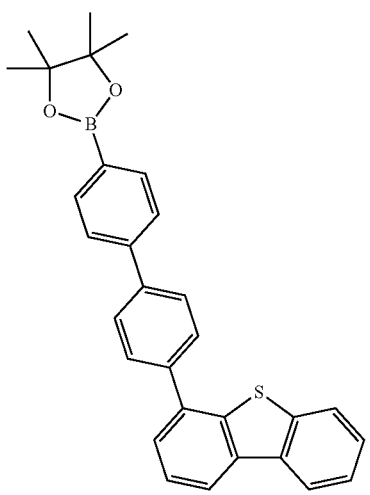
Sub 2(28)
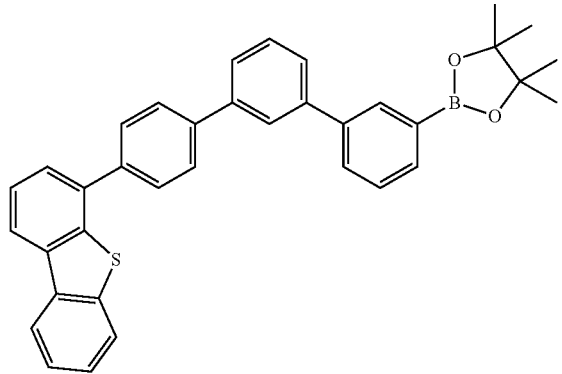

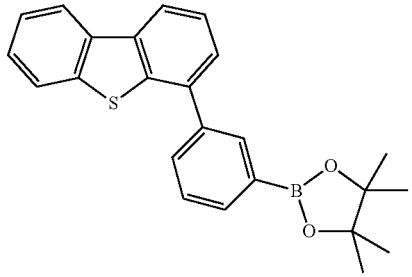
Sub 2(29)

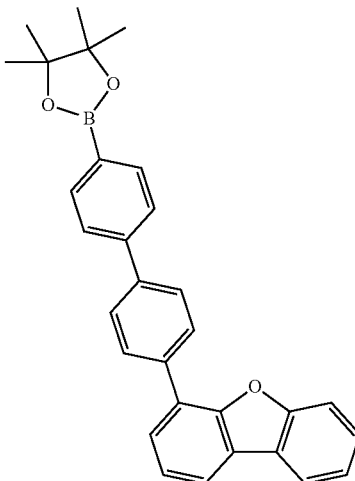
Sub 2(31)

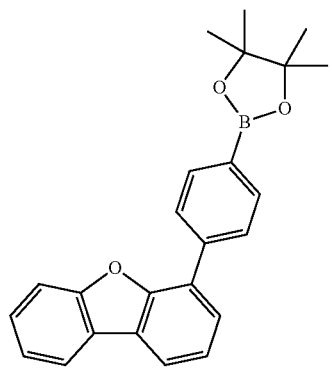
Sub 2(30)

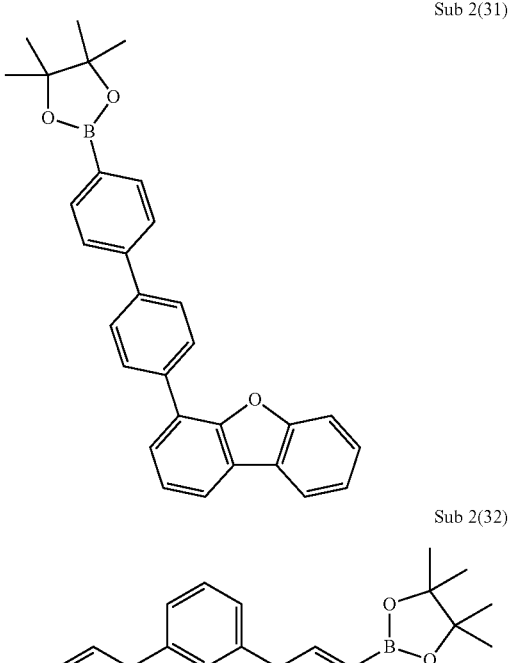
Sub 2(32)

TABLE 2

| Compound | FD-MS | Compound | FD-MS |
|---|---|---|---|
| Sub 2(1) | m/z = 386.15($C_{24}H_{23}BO_2S$ = 386.32) | Sub 2(2) | m/z = 386.15($C_{24}H_{23}BO_2S$ = 386.32) |
| Sub 2(3) | m/z = 386.15($C_{24}H_{23}BO_2S$ = 386.32) | Sub 2(4) | m/z = 538.21($C_{36}H_{31}BO_2S$ = 538.51) |
| Sub 2(5) | m/z = 538.21($C_{36}H_{31}BO_2S$ = 538.51) | Sub 2(6) | m/z = 462.18($C_{30}H_{27}BO_2S$ = 462.41) |
| Sub 2(7) | m/z = 462.18($C_{30}H_{27}BO_2S$ = 462.41) | Sub 2(8) | m/z = 538.21($C_{36}H_{31}BO_2S$ = 538.51) |
| Sub 2(9) | m/z = 538.21($C_{36}H_{31}BO_2S$ = 538.51) | Sub 2(10) | m/z = 462.18($C_{30}H_{27}BO_2S$ = 467.41) |
| Sub 2(11) | m/z = 538.21($C_{36}H_{31}BO_2S$ = 538.51) | Sub 2(12) | m/z = 462.18($C_{30}H_{27}BO_2S$ = 462.41) |
| Sub 2(13) | m/z = 462.18($C_{30}H_{27}BO_2S$ = 462.41) | Sub 2(14) | m/z = 462.18($C_{30}H_{27}BO_2S$ = 462.41) |
| Sub 2(15) | m/z = 462.18($C_{30}H_{27}BO_2S$ = 462.41) | Sub 2(16) | m/z = 462.18($C_{30}H_{27}BO_2S$ = 462.41) |
| Sub 2(17) | m/z = 538.21($C_{36}H_{31}BO_2S$ = 538.51) | Sub 2(18) | m/z = 538.21($C_{36}H_{31}BO_2S$ = 538.51) |
| Sub 2(19) | m/z = 462.18($C_{30}H_{27}BO_2S$ = 462.41) | Sub 2(20) | m/z = 462.18($C_{30}H_{27}BO_2S$ = 462.41) |
| Sub 2(21) | m/z = 462.18($C_{30}H_{27}BO_2S$ = 462.41) | Sub 2(22) | m/z = 462.18($C_{30}H_{27}BO_2S$ = 462.41) |
| Sub 2(23) | m/z = 462.18($C_{30}H_{27}BO_2S$ = 462.41) | Sub 2(24) | m/z = 462.18($C_{30}H_{27}BO_2S$ = 462.41) |
| Sub 2(25) | m/z = 462.18($C_{30}H_{27}BO_2S$ = 462.41) | Sub 2(26) | m/z = 462.18($C_{30}H_{27}BO_2S$ = 462.41) |
| Sub 2(27) | m/z = 462.18($C_{30}H_{27}BO_2S$ = 462.41) | Sub 2(28) | m/z = 538.21($C_{36}H_{31}BO_2S$ = 538.51) |
| Sub 2(29) | m/z = 370.17($C_{24}H_{23}BO_3$ = 370.26) | Sub 2(30) | m/z = 370.17($C_{24}H_{23}BO_3$ = 370.26) |
| Sub 2(31) | m/z = 446.21($C_{30}H_{27}BO_3$ = 446.35) | Sub 2(32) | m/z = 522.24($C_{36}H_{31}BO_3$ = 522.45) |

Synthesis Example of Final Product

Synthesis Example of 1-1

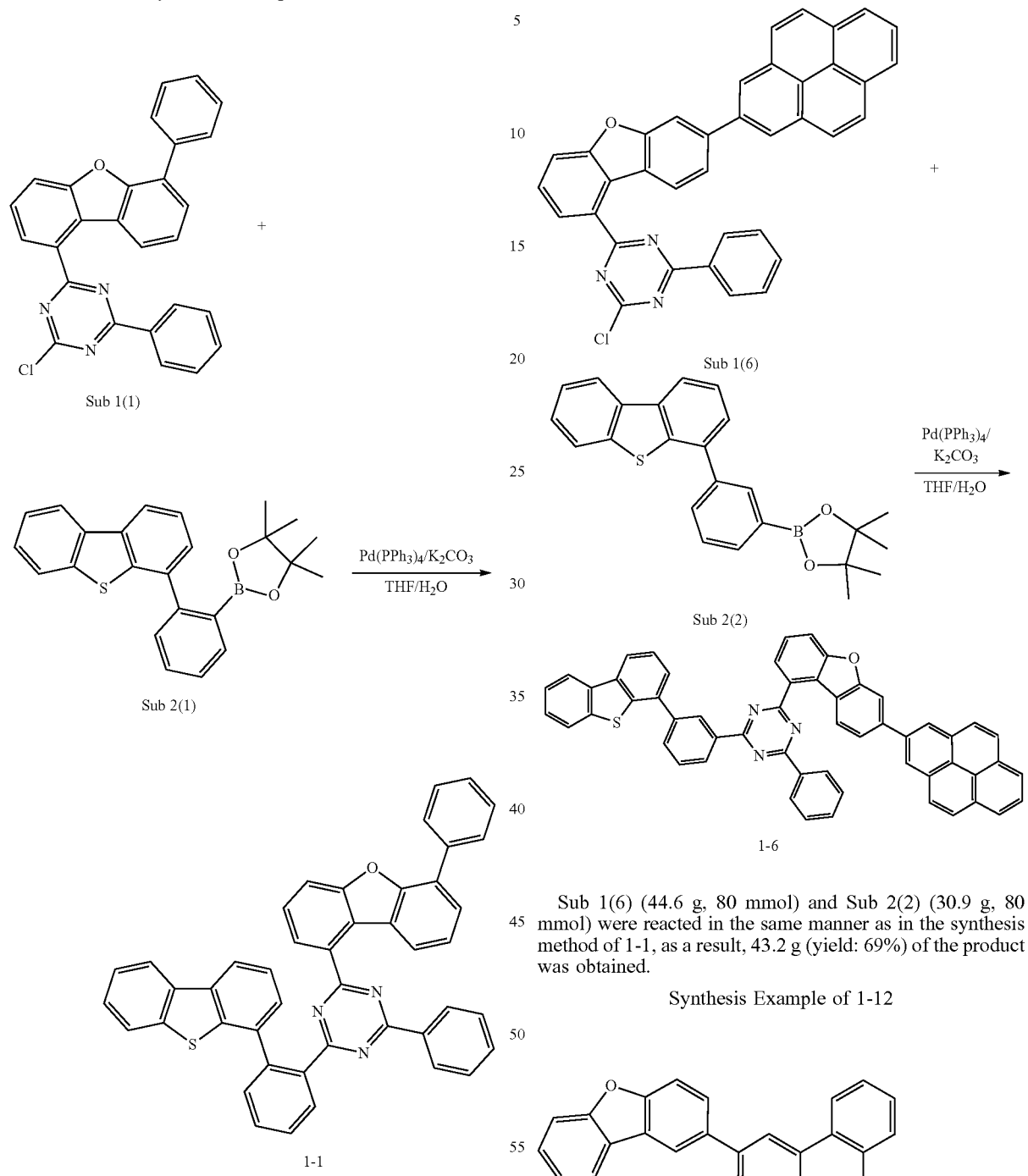

Sub 1(1) (34.7 g, 80 mmol), Sub 2(1) (30.9 g, 80 mmol) and $K_2CO_3$ (19.3 g, 140 mmol), $Pd(PPh_3)_4$ (2.8 g, 2.4 mmol) in a round bottom flask were dissolved in THF and water. The solution was refluxed at 80□ for 12 hours. When the reaction was completed, the reaction product was cooled to room temperature, extracted with $CH_2Cl_2$ and washed with water. The organic layer was dried with $MgSO_4$ and concentrated. Thereafter, the concentrate was applied to silica gel column to obtain 37.4 g (yield: 71%) of the product.

Synthesis Example of 1-6

Sub 1(6) (44.6 g, 80 mmol) and Sub 2(2) (30.9 g, 80 mmol) were reacted in the same manner as in the synthesis method of 1-1, as a result, 43.2 g (yield: 69%) of the product was obtained.

Synthesis Example of 1-12

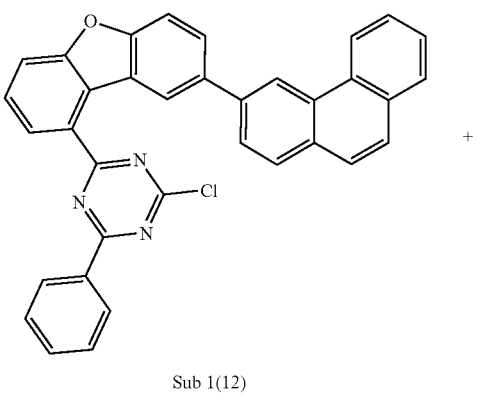

Synthesis Example of 1-33
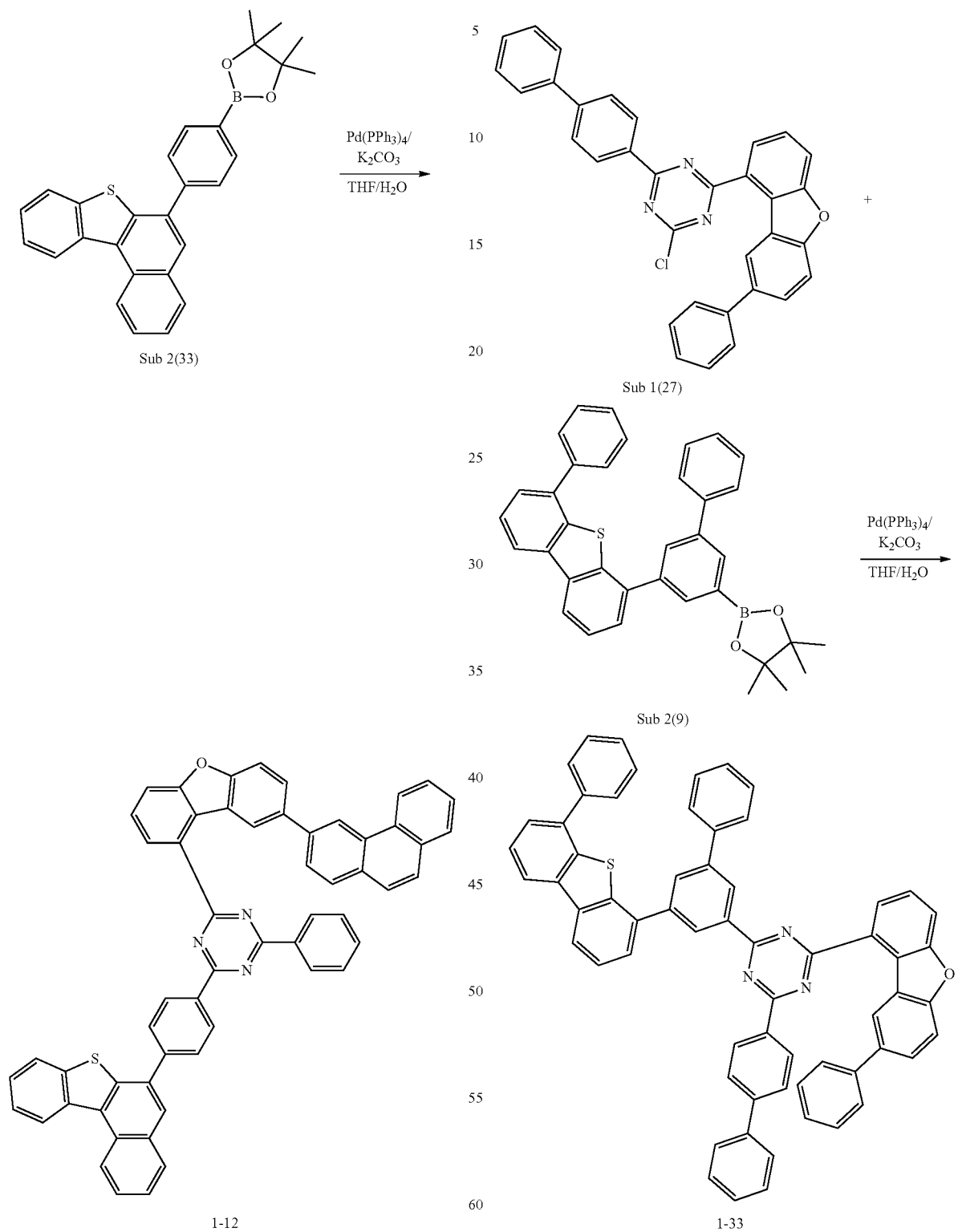
Sub 1(12) (42.7 g, 80 mmol) and Sub 2(33) (34.9 g, 80 mmol) were reacted in the same manner as in the synthesis method of 1-1, as a result, 42.7 g (yield: 66%) of the product was obtained.
Sub 1(27) (40.8 g, 80 mmol) and Sub 2(9) (43.1 g, 80 mmol) were reacted in the same manner as in the synthesis method of 1-1, as a result, 51.0 g (yield: 72%) of the product was obtained.

Synthesis Example of 1-44
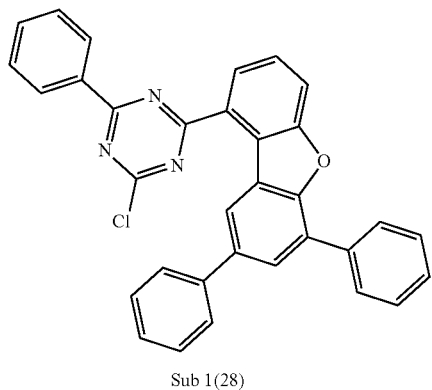
Sub 1(28)
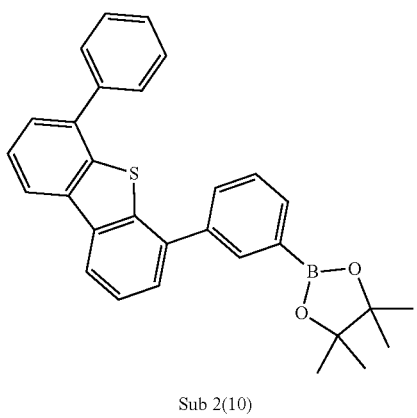
Sub 2(10)
Pd(PPh₃)₄/
K₂CO₃
THF/H₂O
→
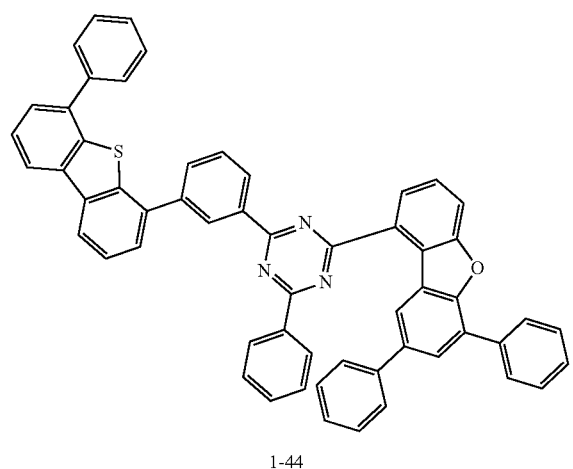
1-44
Sub 1(28) (40.8 g, 80 mmol) and Sub 2(10) (37.0 g, 80 mmol) were reacted in the same manner as in the synthesis method of 1-1, as a result, 45.4 g (yield: 70%) of the product was obtained.
Synthesis Example of 1-53
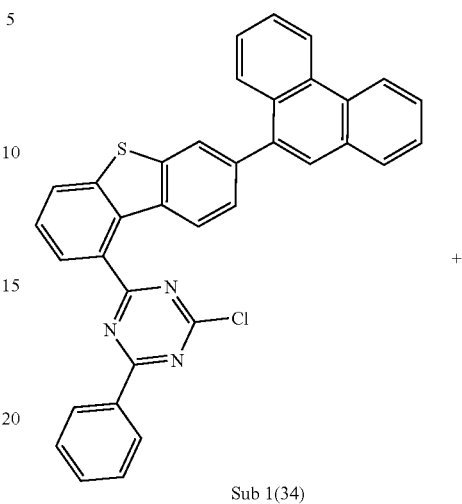
Sub 1(34) (44.0 g, 80 mmol) and Sub 2(29) (29.6 g, 80 mmol) were reacted in the same manner as in the synthesis method of 1-1, as a result, 41.2 g (yield: 68%) of the product was obtained.

Synthesis Example of 1-64
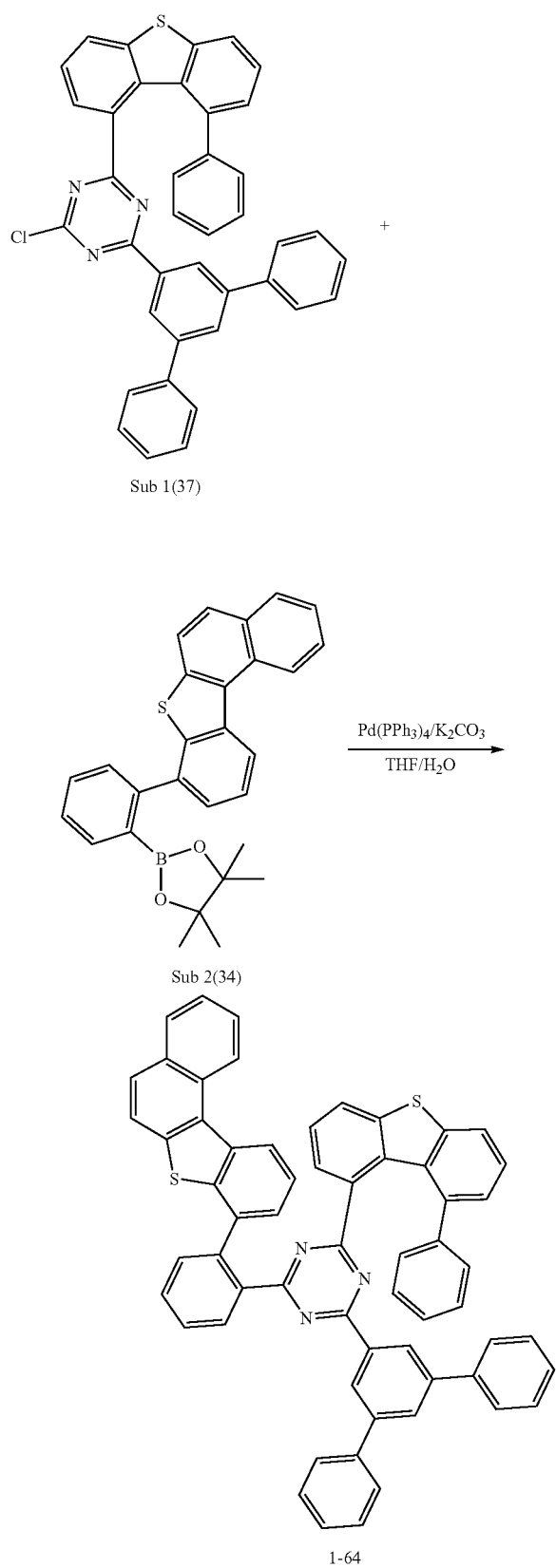
Sub 1(37)
Sub 2(34)
1-64
Sub 1(37) (48.2 g, 80 mmol) and Sub 2(34) (34.9 g, 80 mmol) were reacted in the same manner as in the synthesis method of 1-1, as a result, 45.6 g (yield: 71%) of the product was obtained.
Synthesis Example of 1-75
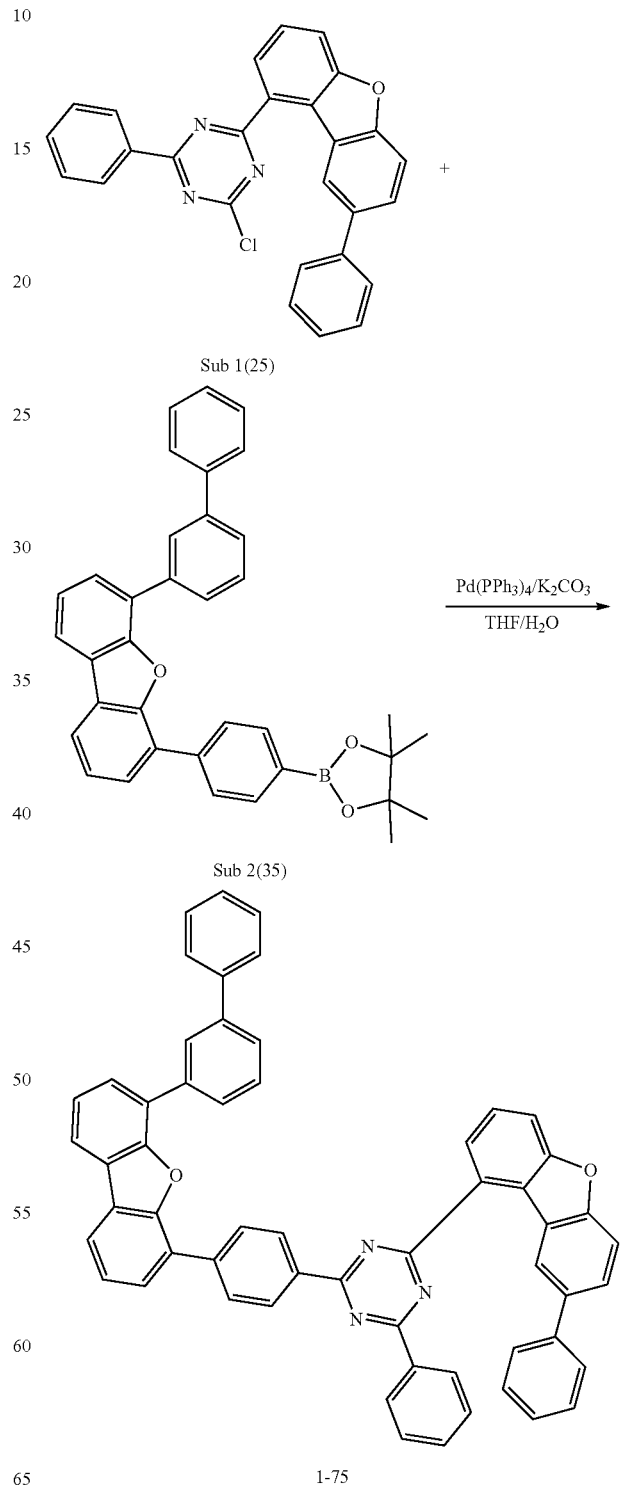
Sub 1(25)
Sub 2(35)
1-75

Sub 1(25) (34.7 g, 80 mmol) and Sub 2(35) (41.8 g, 80 mmol) were reacted in the same manner as in the synthesis method of 1-1, as a result, 46.4 g (yield: 73%) of the product was obtained.

Synthesis Example of 2-1

Synthesis Example of 2-22

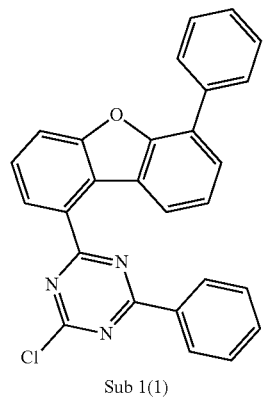
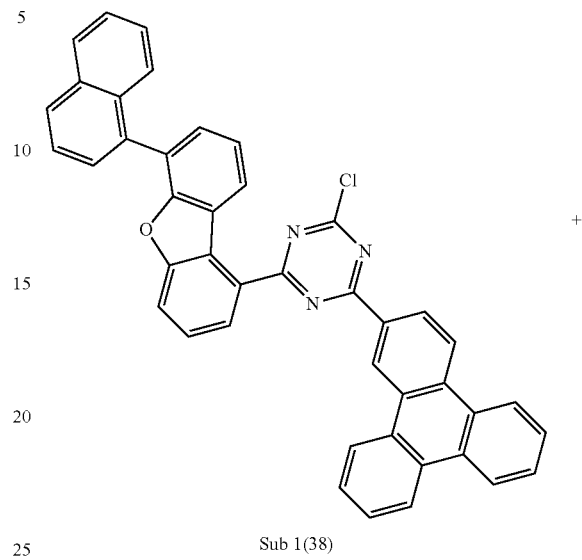
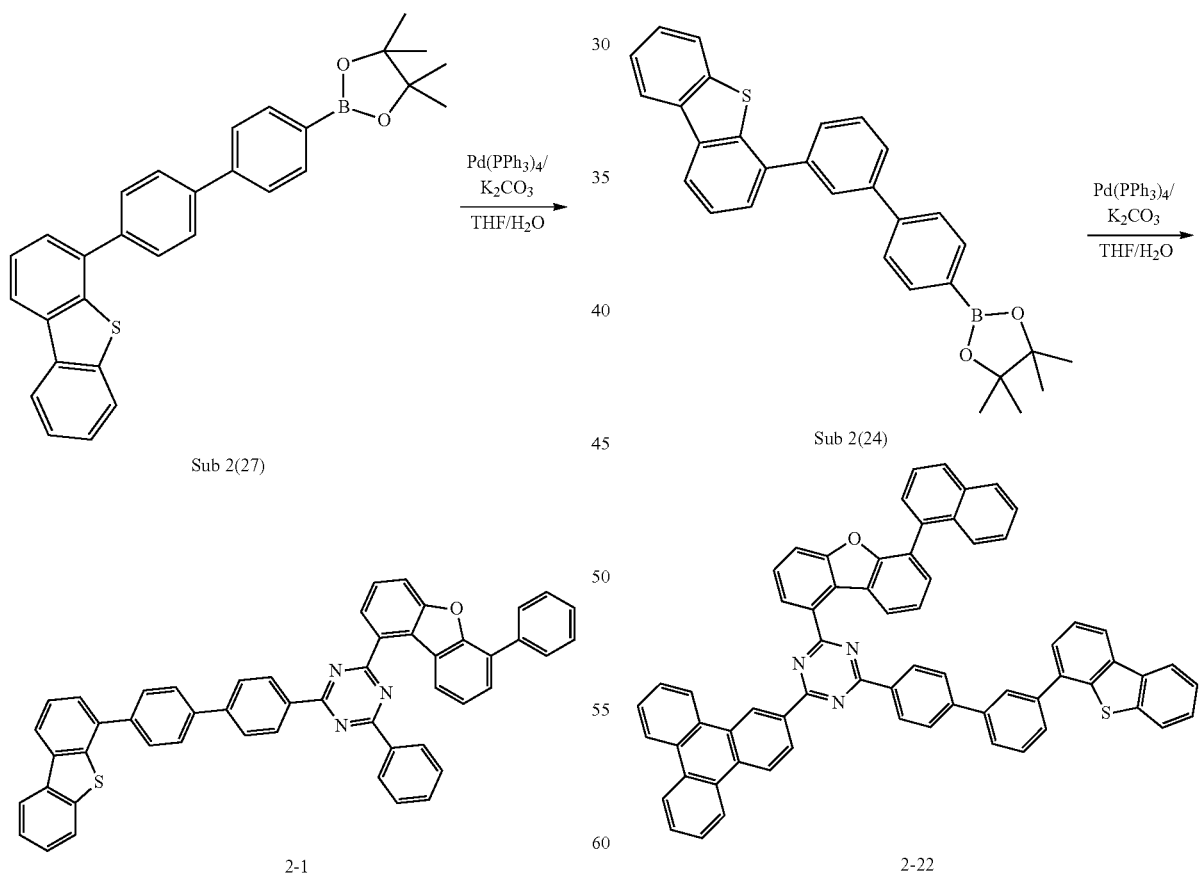

Sub 1(1) (34.7 g, 80 mmol) and Sub 2(27) (37.0 g, 80 mmol) were reacted in the same manner as in the synthesis method of 1-1, as a result, 42.3 g (yield: 72%) of the product was obtained.

Sub 1(38) (50.7 g, 80 mmol) and Sub 2(24) (37.0 g, 80 mmol) were reacted in the same manner as in the synthesis method of 1-1, as a result, 51.6 g (yield: 69%) of the product was obtained.

Synthesis Example of 2-33
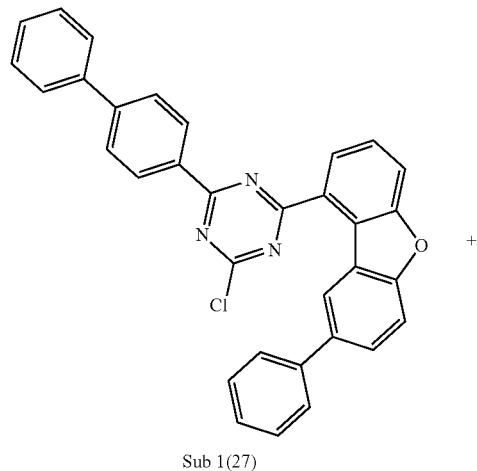
Sub 1(27)
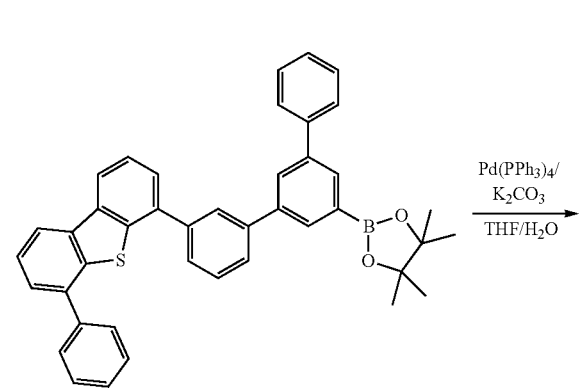
Sub 2(36)
2-33
Sub 1(27) (40.8 g, 80 mmol) and Sub 2(36) (49.2 g, 80 mmol) were reacted in the same manner as in the synthesis method of 1-1, as a result, 53.9 g (yield: 70%) of the product was obtained.
Synthesis Example of 2-40
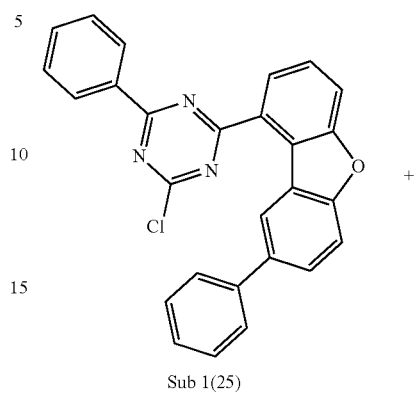
Sub 1(25)
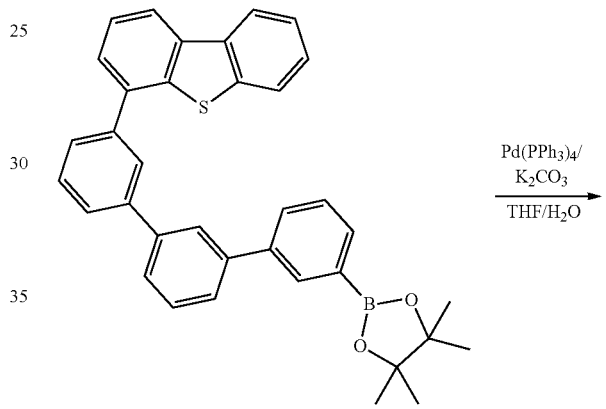
Sub 2(37)
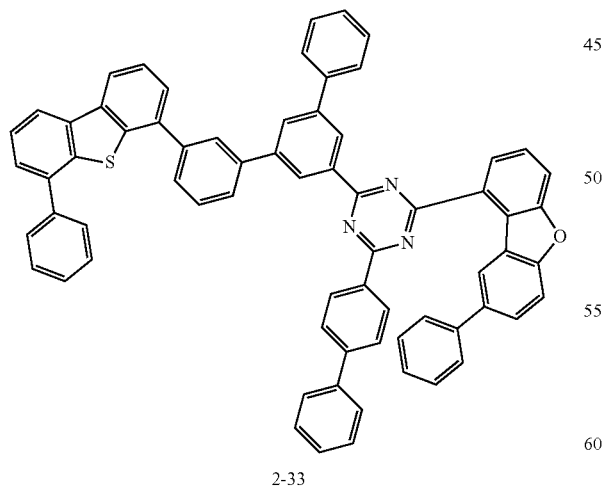
2-40
Sub 1(25) (34.7 g, 80 mmol) and Sub 2(37) (43.1 g, 80 mmol) were reacted in the same manner as in the synthesis method of 1-1, as a result, 44.7 g (yield: 69%) of the product was obtained.

Synthesis Example of 2-51
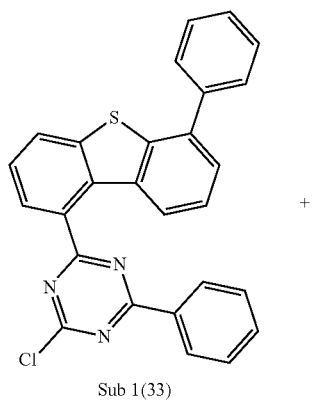
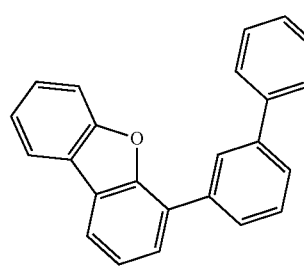
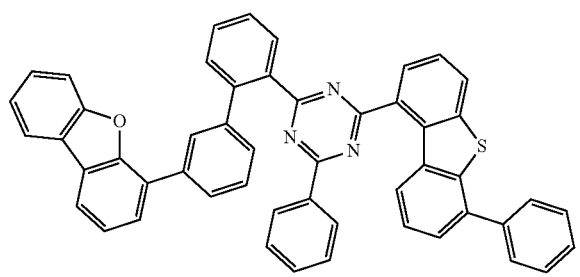
Sub 1(33) (36.0 g, 80 mmol) and Sub 2(38) (35.7 g, 80 mmol) were reacted in the same manner as in the synthesis method of 1-1, as a result, 41.1 g (yield: 70%) of the product was obtained.
Synthesis Example of 2-55
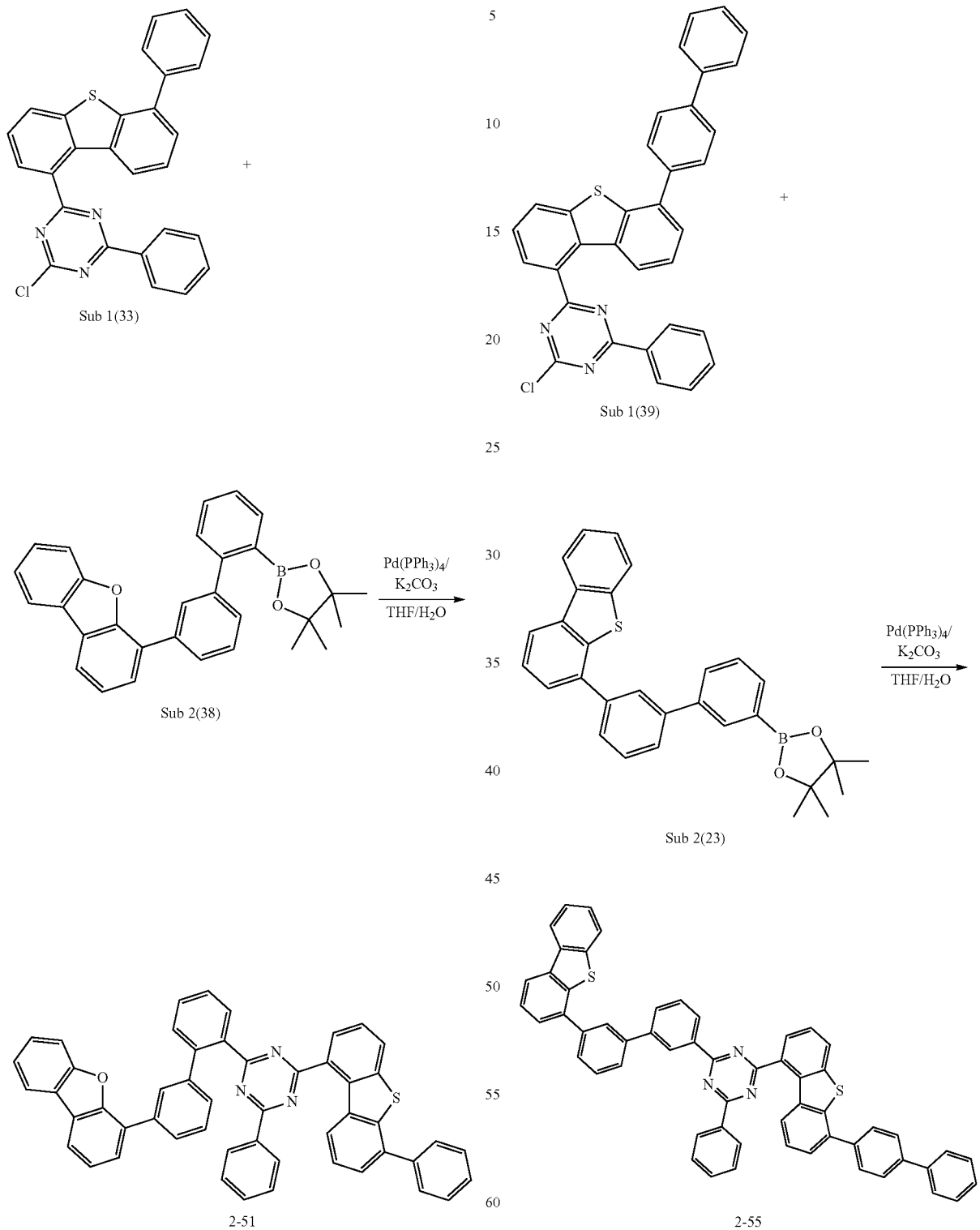
Sub 1(39) (42.1 g, 80 mmol) and Sub 2(23) (37.0 g, 80 mmol) were reacted in the same manner as in the synthesis method of 1-1, as a result, 44.9 g (yield: 68%) of the product was obtained.

Synthesis Example of 2-58

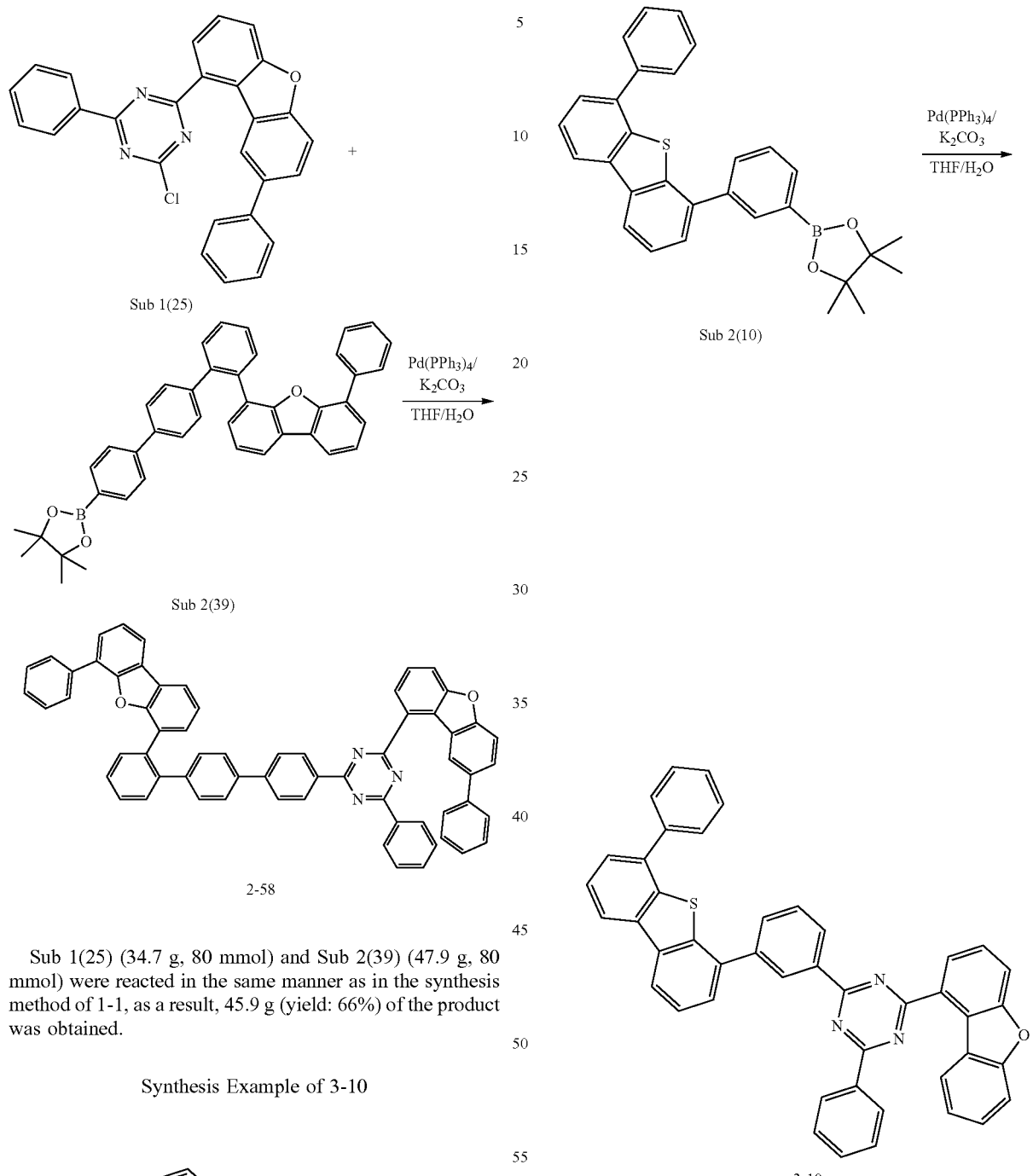

Sub 1(25) (34.7 g, 80 mmol) and Sub 2(39) (47.9 g, 80 mmol) were reacted in the same manner as in the synthesis method of 1-1, as a result, 45.9 g (yield: 66%) of the product was obtained.

Synthesis Example of 3-10

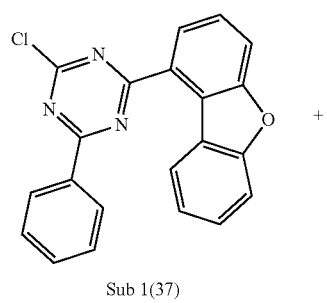

Sub 1(37) (28.6 g, 80 mmol) and Sub 2(10) (37.0 g, 80 mmol) were reacted in the same manner as in the synthesis method of 1-1, as a result, 38.9 g (yield: 74%) of the product was obtained.

The FD-MS values of the compounds 1-1 to 1-84, 2-60 to 2-60 and 3-1 to 3-36 of the present invention prepared according to the above synthesis examples are shown in Table 3 below.

TABLE 3

| Compound | FD-MS | Compound | FD-MS |
|---|---|---|---|
| H | m/z = 657.19($C_{45}H_{27}N_3OS$ = 657.79) | 1-2 | m/z = 707.20($C_{49}H_{29}N_3OS$ = 707.85) |
| 1-3 | m/z = 707.20($C_{49}H_{29}N_3OS$ = 707.85) | 1-4 | m/z = 783.23($C_{55}H_{33}N_3OS$ = 783.95) |
| 1-5 | m/z = 757.22($C_{53}H_{31}N_3OS$ = 757.91) | 1-6 | m/z = 781.22($C_{55}H_{31}N_3OS$ = 781.93) |
| 1-7 | m/z = 809.25($C_{57}H_{35}N_3OS$ = 809.99) | 1-8 | m/z = 721.22($C_{50}H_{31}N_3OS$ = 721.88) |
| 1-9 | m/z = 707.20($C_{49}H_{29}N_3OS$ = 707.85) | 1-10 | m/z = 707.20($C_{49}H_{29}N_3OS$ = 707.85) |
| 1-11 | m/z = 733.22($C_{51}H_{31}N_3OS$ = 733.89) | 1-12 | m/z = 807.23($C_{57}H_{33}N_3OS$ = 807.97) |
| 1-13 | m/z = 707.20($C_{49}H_{29}N_3OS$ = 707.85) | 1-14 | m/z = 707.20($C_{49}H_{29}N_3OS$ = 707.85) |
| 1-15 | m/z = 733.22($C_{51}H_{31}N_3OS$ = 733.89) | 1-16 | m/z = 859.27($C_{61}H_{37}N_3OS$ = 860.05) |
| 1-17 | m/z = 807.23($C_{57}H_{33}N_3OS$ = 807.97) | 1-18 | m/z = 757.22($C_{53}H_{31}N_3OS$ = 757.91) |
| 1-19 | m/z = 783.23($C_{55}H_{33}N_3OS$ = 783.95) | 1-20 | m/z = 859.27($C_{61}H_{37}N_3OS$ = 860.05) |
| 1-21 | m/z = 733.22($C_{51}H_{31}N_3OS$ = 733.89) | 1-22 | m/z = 857.25($C_{61}H_{35}N_3OS$ = 858.03) |
| 1-23 | m/z = 833.25($C_{59}H_{35}N_3OS$ = 834.01) | 1-24 | m/z = 825.23($C_{57}H_{32}FN_3OS$ = 825.96) |
| 1-25 | m/z = 657.19($C_{45}H_{27}N_3OS$ = 657.79) | 1-26 | m/z = 733.22($C_{51}H_{31}N_3OS$ = 733.89) |
| 1-27 | m/z = 809.25($C_{57}H_{35}N_3OS$ = 809.99) | 1-28 | m/z = 809.25($C_{57}H_{35}N_3OS$ = 809.99) |
| 1-29 | m/z = 732.22($C_{51}H_{31}N_3OS$ = 733.89) | 1-30 | m/z = 733.22($C_{51}H_{31}N_3OS$ = 733.89) |
| 1-31 | m/z = 657.19($C_{45}H_{27}N_3OS$ = 657.79) | 1-32 | m/z = 809.25($C_{57}H_{35}N_3OS$ = 809.99) |
| 1-33 | m/z = 885.28($C_{63}H_{39}N_3OS$ = 886.09) | 1-34 | m/z = 733.22($C_{51}H_{31}N_3OS$ = 733.89) |
| 1-35 | m/z = 733.22($C_{51}H_{31}N_3OS$ = 733.89) | 1-36 | m/z = 809.25($C_{57}H_{35}N_3OS$ = 809.99) |
| 1-37 | m/z = 733.22($C_{51}H_{31}N_3OS$ = 733.89) | 1-38 | m/z = 733.22($C_{51}H_{31}N_3OS$ = 733.89) |
| 1-39 | m/z = 809.25($C_{57}H_{35}N_3OS$ = 809.99) | 1-40 | m/z = 657.19($C_{45}H_{27}N_3OS$ = 657.79) |
| 1-41 | m/z = 783.23($C_{55}H_{33}N_3OS$ = 783.95) | 1-42 | m/z = 733.22($C_{51}H_{31}N_3OS$ = 733.89) |
| 1-43 | m/z = 733.22($C_{51}H_{31}N_3OS$ = 733.89) | 1-44 | m/z = 809.25($C_{57}H_{35}N_3OS$ = 809.99) |
| 1-45 | m/z = 809.25($C_{57}H_{35}N_3OS$ = 809.99) | 1-46 | m/z = 809.25($C_{57}H_{35}N_3OS$ = 809.99) |
| 1-47 | m/z = 885.28($C_{63}H_{39}N_3OS$ = 886.09) | 1-48 | m/z = 783.23($C_{55}H_{33}N_3OS$ = 783.95) |
| 1-49 | m/z = 657.19($C_{45}H_{27}N_3OS$ = 657.79) | 1-50 | m/z = 707.20($C_{49}H_{29}N_3OS$ = 707.85) |
| 1-51 | m/z = 707.20($C_{49}H_{29}N_3OS$ = 707.85) | 1-52 | m/z = 783.23($C_{55}H_{33}N_3OS$ = 783.95) |
| 1-53 | m/z = 757.22($C_{53}H_{31}N_3OS$ = 757.91) | 1-54 | m/z = 781.22($C_{55}H_{31}N_3OS$ = 781.93) |
| 1-55 | m/z = 809.25($C_{57}H_{35}N_3OS$ = 809.99) | 1-56 | m/z = 721.22($C_{50}H_{31}N_3OS$ = 721.88) |
| 1-57 | m/z = 707.20($C_{49}H_{29}N_3OS$ = 707.85) | 1-58 | m/z = 707.20($C_{49}H_{29}N_3OS$ = 707.85) |
| 1-59 | m/z = 733.22($C_{51}H_{31}N_3OS$ = 733.89) | 1-60 | m/z = 807.23($C_{57}H_{33}N_3OS$ = 807.97) |
| 1-61 | m/z = 723.18($C_{49}H_{29}N_3S_2$ = 723.91) | 1-62 | m/z = 723.18($C_{49}H_{29}N_3S_2$ = 723.91) |
| 1-63 | m/z = 749.20($C_{51}H_{31}N_3S_2$ = 749.95) | 1-64 | m/z = 875.24($C_{61}H_{37}N_3S_2$ = 876.11) |
| 1-65 | m/z = 823.21($C_{57}H_{33}N_3S_2$ = 824.03) | 1-66 | m/z = 773.20 ($C_{53}H_{31}N_3S_2$ = 773.9 7) |
| 1-67 | m/z = 799.21($C_{55}H_{33}N_3S_2$ = 800.01) | 1-68 | m/z = 875.24($C_{61}H_{37}N_3S_2$ = 876.11) |
| 1-69 | m/z = 749.20($C_{51}H_{31}N_3S_2$ = 749.95) | 1-70 | m/z = 873.23($C_{61}H_{35}N_3S_2$ = 874.09) |
| 1-71 | m/z = 849.23($C_{59}H_{35}N_3S_2$ = 850.07) | 1-72 | m/L = 791.19($C_{53}H_{30F}N_3S_2$ = 791.96) |
| 1-73 | m/z = 641.21($C_{45}H_{27}N_3O_2$ = 641.73) | 1-74 | m/z = 717.24($C_{51}H_{31}N_3O_2$ = 717.83) |
| 1-75 | m/z = 798.30($C_{57}H_{30}D_5N_3O_2$ = 799.0) | 1-76 | m/z = 843.29 ($C_{61}H_{37}N_3O_2$ = 843.99) |
| 1-77 | m/z = 717.24($C_{51}H_{31}N_3O_2$ = 717.83) | 1-78 | m/z = 717.24($C_{51}H_{31}N_3O_3$ = 717.83) |
| 1-79 | m/z = 641.21($C_{45}H_{27}N_3O_2$ = 641.73) | 1-80 | m/z = 793.27($C_{57}H_{35}N_3O_2$ = 793.93) |
| 1-81 | m/z = 869.30($C_{63}H_{39}N_3O_2$ = 870.02) | 1-82 | m/z = 717.24($C_{51}H_{31}N_3O_2$ = 717.83) |
| 1-83 | m/z = 722.27($C_{51}H_{26}D_5N_3O_2$ = 722.9) | 1-84 | m/z = 793.27($C_{57}H_{35}N_3O_2$ = 793.93) |
| 2-1 | m/z = 733.22($C_{51}H_{31}N_3OS$ = 733.89) | 2-2 | m/z = 783.23($C_{55}H_{33}N_3OS$ = 783.95) |
| 2-3 | m/z = 783.23($C_{55}H_{33}N_3OS$ = 783.95) | 2-4 | m/z = 859.27($C_{61}H_{37}N_3OS$ = 860.05) |
| 2-5 | m/z = 833.25($C_{59}H_{35}N_3OS$ = 834.01) | 2-6 | m/z = 857.25($C_{61}H_{35}N_3OS$ = 858.03) |
| 2-7 | m/z = 885.28($C_{63}H_{39}N_3OS$ = 886.09) | 2-8 | m/z = 79 7.25($C_{56}H_{35}N_3OS$ = 79 7.98) |
| 2-9 | m/z = 783.23($C_{55}H_{33}N_3OS$ = 783.95) | 2-10 | m/z = 783.23($C_{55}H_{33}N_3OS$ = 783.95) |
| 2-11 | m/z = 809.25($C_{57}H_{35}N_3OS$ = 809.99) | 2-12 | m/z = 883.27($C_{63}H_{37}N_3OS$ = 884.07) |
| 2-13 | m/z = 783.23($C_{55}H_{33}N_3OS$ = 783.95) | 2-14 | m/z = 783.23($C_{55}H_{33}NN_3OS$ = 783.95) |
| 2-15 | m/z = 809.25($C_{57}H_{35}N_3OS$ = 809.99) | 2-16 | m/z = 935.30($C_{67}H_{41}N_3OS$ = 936.15) |
| 2-17 | m/z = 883.27($C_{63}H_{37}N_3OS$ = 884.07) | 2-18 | m/z = 833.25($C_{59}H_{35}N_3OS$ = 834.01) |
| 2-19 | m/z = 885.28($C_{63}H_{39}N_3OS$ = 886.09) | 2-20 | m/z = 909.28($C_{65}H_{39}N_3OS$ = 910.11) |
| 2-21 | m/z = 809.25($C_{57}H_{35}N_3OS$ = 809.99) | 2-22 | m/z = 933.28($C_{67}H_{39}N_3OS$ = 934.13) |
| 2-23 | m/z = 909.28($C_{65}H_{39}N_3OS$ = 910.11) | 2-24 | m/z = 851.24 ($C_{59}H_{34}FN_3OS$ = 852.00) |
| 2-25 | m/z = 733.22($C_{51}H_{31}N_3OS$ = 733.89) | 2-26 | m/z = 809.25($C_{57}H_{35}N_3OS$ = 809.99) |
| 2-27 | m/z = 885.28($C_{63}H_{39}N_3OS$ = 886.09) | 2-28 | m/z = 935.30($C_{67}H_{41}N_3OS$ = 936.15) |
| 2-29 | m/z = 809.25($C_{57}H_{35}N_3OS$ = 809.99) | 2-30 | m/z = 809.25($C_{57}H_{35}N_3OS$ = 809.99) |
| 2-31 | m/z = 733.22($C_{51}H_{31}N_3OS$ = 733.89) | 2-32 | m/z = 885.28($C_{63}H_{39}N_3OS$ = 886.09) |
| 2-33 | m/z = 961.31($C_{69}H_{43}N_3OS$ = 962.18) | 2-34 | m/z = 809.25($C_{57}H_{35}N_3OS$ = 809.99) |
| 2-35 | m/z = 809.25($C_{57}H_{35}N_3OS$ = 809.99) | 2-36 | m/z = 885.28($C_{63}H_{39}N_3OS$ = 886.09) |
| 2-37 | m/z = 885.28($C_{63}H_{39}N_3OS$ = 886.09) | 2-38 | m/z = 885.28($C_{63}H_{39}N_3OS$ = 886.09) |
| 2-39 | m/z = 961.31($C_{69}H_{43}N_3OS$ = 962.18) | 2-40 | m/z = 809.25($C_{57}H_{35}N_3OS$ = 809.99) |
| 2-41 | m/z = 885.28($C_{63}H_{39}N_3OS$ = 886.09) | 2-42 | m/z = 885.28($C_{63}H_{39}N_3OS$ = 886.09) |
| 2-43 | m/z = 885.28($C_{63}H_{39}N_3OS$ = 886.09) | 2-44 | m/z = 1032.40($C_{74}H_{54}N_3OS$ = 1033.33) |
| 2-45 | m/z = 885.28($C_{63}H_{39}N_3OS$ = 886.09) | 2-46 | m/z = 885.28($C_{63}H_{39}N_3OS$ = 886.09) |
| 2-47 | m/z = 961.31($C_{69}H_{43}N_3OS$ = 962.18) | 2-48 | m/z = 859.27($C_{61}H_{37}N_3OS$ = 860.08) |
| 2-49 | m/z = 809.25($C_{57}H_{35}N_3OS$ = 809.99) | 2-50 | m/z = 809.25($C_{57}H_{35}N_3OS$ = 809.99) |
| 2-51 | m/z = 733.22($C_{52}H_{32}N_3OS$ = 733.89) | 2-52 | m/z = 885.28($C_{63}H_{39}N_3OS$ = 886.09) |
| 2-53 | m/z = 977.29($C_{69}H_{43}N_3S_2$ = 978.24) | 2-54 | m/z = 825.23($C_{57}H_{35}N_3S_2$ = 826.05) |
| 2-55 | m/z = 825.23($C_{57}H_{35}N_3S_2$ = 826.05) | 2-56 | m/z = 901.26($C_{63}H_{39}N_3S_2$ = 902.15) |
| 2-57 | m/z = 869.30($C_{63}H_{39}N_3O_2$ = 870.02) | 2-58 | m/z = 869.30($C_{63}H_{39}N_3O_2$ = 870.02) |
| 2-59 | m/z = 945.34($C_{69}H_{43}N_3O_2$ = 946.12) | 2-60 | m/z = 809.25($C_{57}H_{35}N_3OS$ = 809.99) |
| 3-1 | m/z = 581.16($C_{39}H_{23}N_3OS$ = 581.69) | 3-2 | m/z = 581.16($C_{39}H_{23}N_3OS$ = 581.69) |
| 3-3 | m/z = 581.16($C_{39}H_{23}N_3OS$ = 581.69) | 3-4 | m/z = 783.23($C_{55}H_{33}N_3OS$ = 783.95) |
| 3-5 | m/z = 631.17($C_{43}H_{25}N_3OS$ = 631.75) | 3-6 | m/z = 731.20($C_{52}H_{29}N_3OS$ = 731.87) |
| 3-7 | m/z = 581.16($C_{39}H_{23}N_3OS$ = 581.69) | 3-8 | m/z = 657.19($C_{45}H_{27}N_3OS$ = 657.79) |
| 3-9 | m/z = 581.16($C_{39}H_{23}N_3OS$ = 581.69) | 3-10 | m/z = 657.19($C_{45}H_{27}N_3OS$ = 657.79) |
| 3-11 | m/z = 657.19($C_{45}H_{27}N_3OS$ = 657.79) | 3-12 | m/z = 733.22($C_{52}H_{32}N_3OS$ = 733.89) |

TABLE 3-continued

| Compound | FD-MS | Compound | FD-MS |
|---|---|---|---|
| 3-13 | m/z = 631.17($C_{43}H_{25}N_3OS$ = 631.75) | 3-14 | m/z = 581.16($C_{39}H_{23}N_3OS$ = 581.69) |
| 3-15 | m/z = 581.16($C_{39}H_{23}N_3OS$ = 581.69) | 3-16 | m/z = 799.21($C_{55}H_{33}N_3S_2$ = 800.01) |
| 3-17 | m/z = 647.15($C_{43}H_{25}N_3S_2$ = 647.81) | 3-18 | m/z = 747.18($C_{51}H_{29}N_3S_2$ = 747.93) |
| 3-19 | m/z = 565.18($C_{39}H_{23}N_3O_2$ = 565.63) | 3-20 | m/z = 641.21($C_{45}H_{27}N_3O_2$ = 641.73) |
| 3-21 | m/z = 722.27($C_{51}H_{26}D_5N_3S_2$ = 722.86) | 3-22 | m/z = 657.19($C_{45}H_{27}N_3OS$ = 657.79) |
| 3-23 | m/z = 657.19($C_{45}H_{27}N_3OS$ = 657.79) | 3-24 | m/z = 707.20($C_{49}H_{29}N_3OS$ = 707.85) |
| 3-25 | m/z = 733.22($C_{52}H_{32}N_3OS$ = 733.89) | 3-26 | m/z = 707.20($C_{49}H_{29}N_3OS$ = 707.85) |
| 3-27 | m/z = 707.20($C_{49}H_{29}N_3OS$ = 707.85) | 3-28 | m/z = 859.27($C_{62}H_{37}N_3OS$ = 860.05) |
| 3-29 | m/z = 657.19($C_{45}H_{27}N_3OS$ = 657.79) | 3-30 | m/z = 733.22($C_{52}H_{32}N_3OS$ = 733.89) |
| 3-31 | m/z = 809.25($C_{57}H_{35}N_3OS$ = 809.99) | 3-32 | m/z = 809.25($C_{57}H_{35}N_3OS$ = 809.99) |
| 3-33 | m/z = 885.28($C_{63}H_{39}N_3OS$ = 886.09) | 3-34 | m/z = 809.25($C_{57}H_{35}N_3OS$ = 809.99) |
| 3-35 | m/z = 673.16($C_{45}H_{27}N_3S_2$ = 673.85) | 3-36 | m/z = 793.27($C_{57}H_{35}N_3O_2$ = 793.93) |

Synthesis Example of Formula 11

As shown in the reaction Scheme 4, the compound (final products) represented by Formula 11 according to the present invention can be synthesized by reacting Sub 3 with Sub 4, but there is no limitation thereto.

<Reaction Scheme 4>

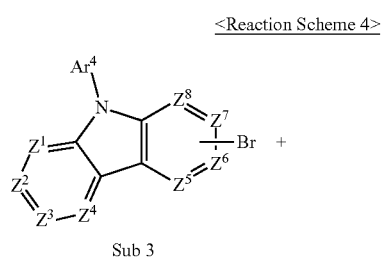

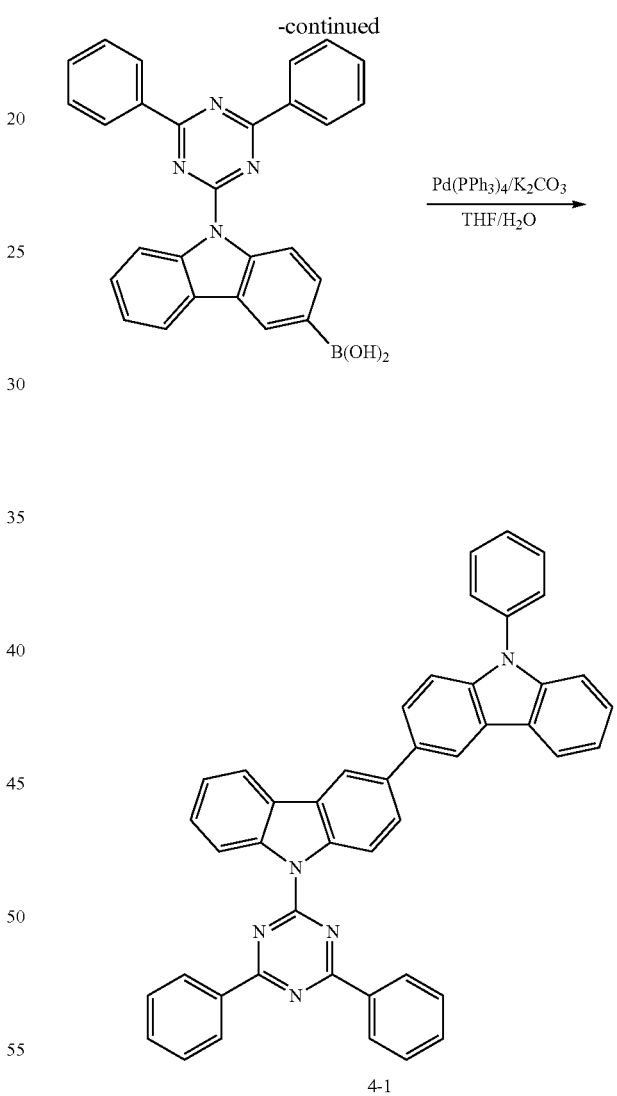

Synthesis Example of 4-1

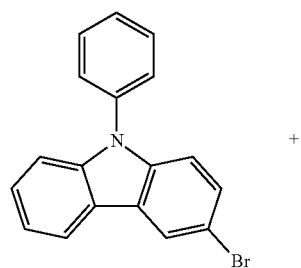

After 3-bromo-9-phenyl-9H-carbazole (6.4 g, 20 mmol) was dissolved in THF, (9-(4,6-diphenyl-1,3,5-triazin-2-yl)-9H-carbazol-3-yl)boronic acid (8.8 g, 20 mmol), Pd(PPh$_3$)$_4$ (0.03 eq,), K$_2$CO$_3$ (3 eq.) and water were added thereto and the solution was stirred under reflux. When the reaction was completed, the reaction product was extracted with ether and water. The organic layer was dried with MgSO$_4$ and concentrated. Thereafter, the concentrate was applied to silica gel column to obtain 9.2 g (yield: 72%) of the product.

Synthesis Example of Synthesis Example of 4-21

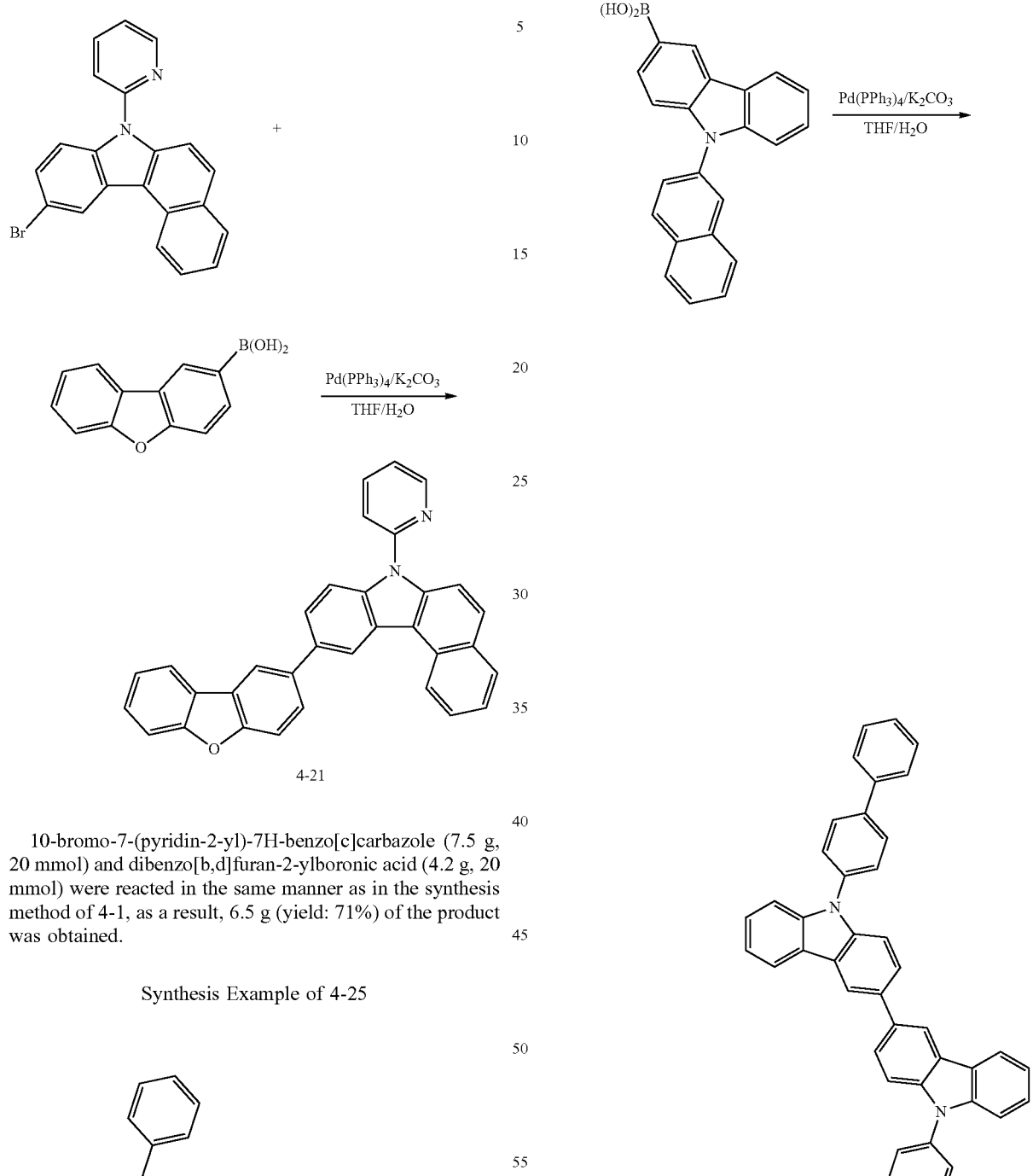

4-21

10-bromo-7-(pyridin-2-yl)-7H-benzo[c]carbazole (7.5 g, 20 mmol) and dibenzo[b,d]furan-2-ylboronic acid (4.2 g, 20 mmol) were reacted in the same manner as in the synthesis method of 4-1, as a result, 6.5 g (yield: 71%) of the product was obtained.

Synthesis Example of 4-25

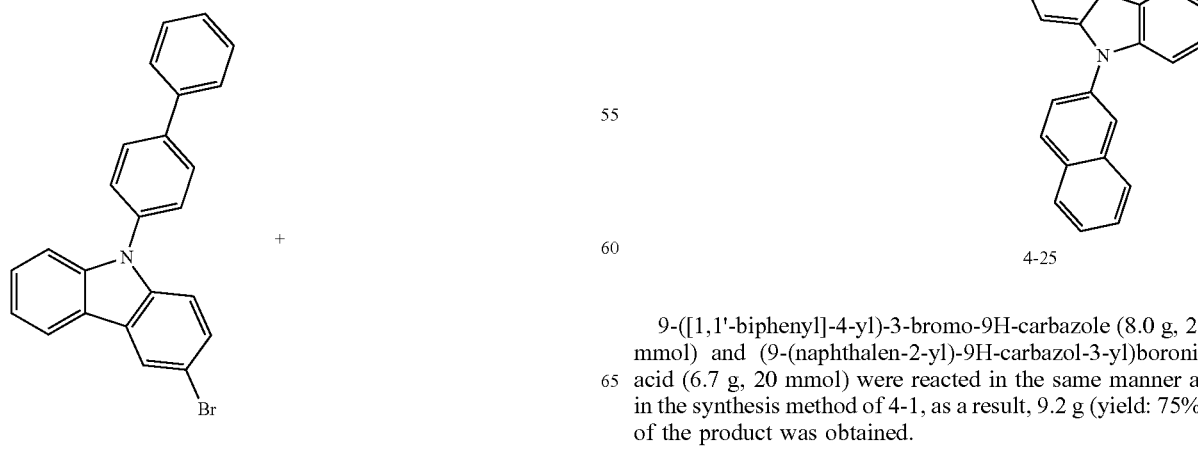

4-25

9-([1,1'-biphenyl]-4-yl)-3-bromo-9H-carbazole (8.0 g, 20 mmol) and (9-(naphthalen-2-yl)-9H-carbazol-3-yl)boronic acid (6.7 g, 20 mmol) were reacted in the same manner as in the synthesis method of 4-1, as a result, 9.2 g (yield: 75%) of the product was obtained.

Synthesis Example of 4-31
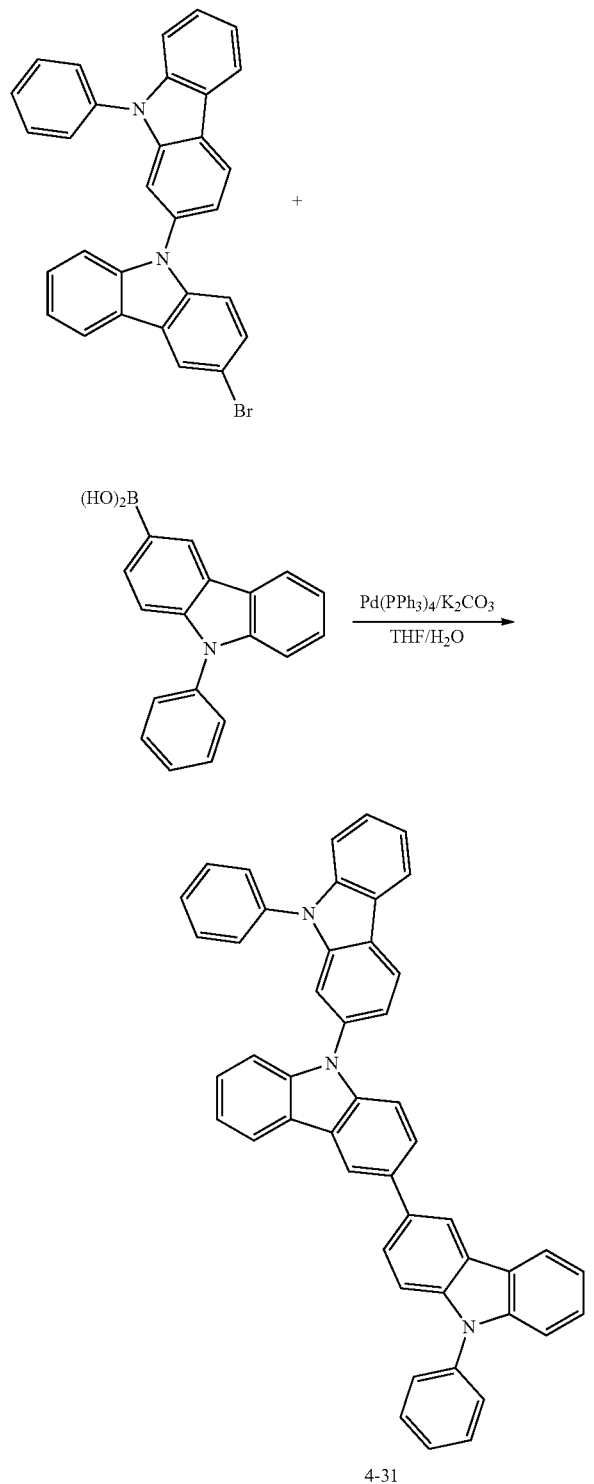
4-31
3'-bromo-9-phenyl-9H-2,9'-bicarbazole (9.7 g, 20 mmol) and (9-phenyl-9H-carbazol-3-yl)boronic acid (5.7 g, 20 mmol) were reacted in the same manner as in the synthesis method of 4-1, as a result, 9.5 g (yield: 73%) of the product was obtained.
Synthesis Example of 4-32
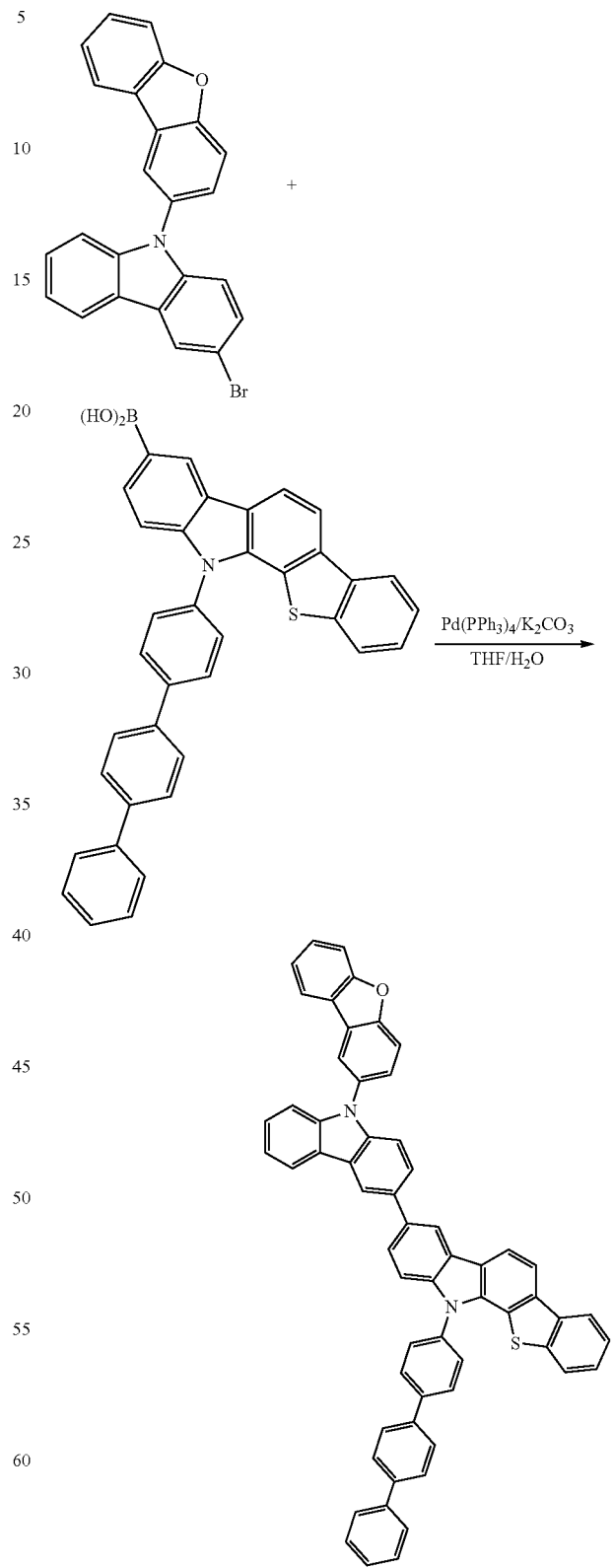
4-32

3-bromo-9-(dibenzo[b,d]furan-2-yl)-9H-carbazole (8.2 g, 20 mmol) and (12-([1,1':4',1''-terphenyl]-4-yl)-12H-benzo[4,5]thieno[2,3-a]carbazol-3-yl)boronic acid (10.9 g, 20 mmol) were reacted in the same manner as in the synthesis method of 4-1, as a result, 11.5 g (yield: 69%) of the product was obtained.

Synthesis Example of 4-34

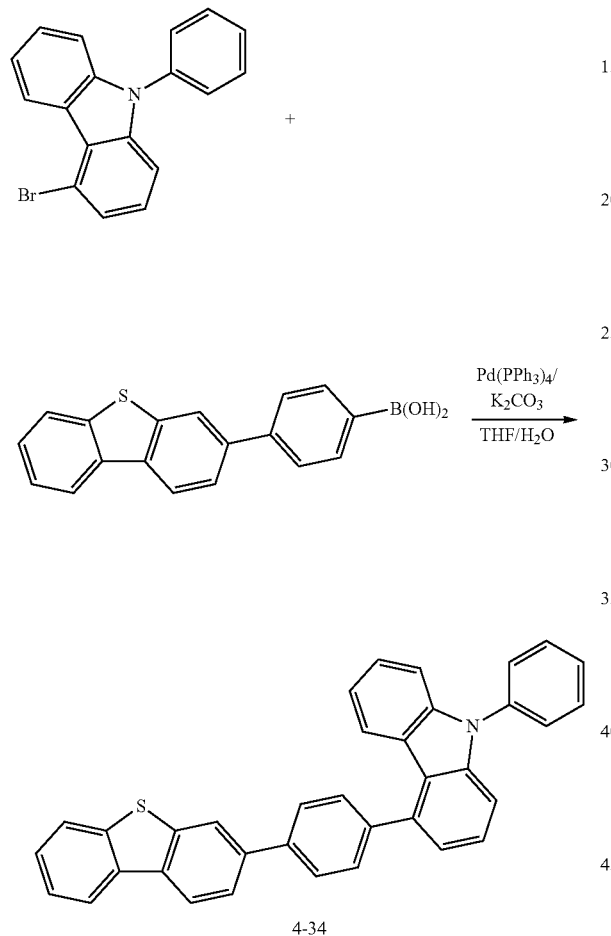

4-34

4-bromo-9-phenyl-9H-carbazole (6.4 g, 20 mmol) and (4-(dibenzo[b,d]thiophen-3-yl)phenyl)boronic acid (6.1 g, 20 mmol) were reacted in the same manner as in the synthesis method of 4-1, as a result, 6.7 g (yield: 67%) of the product was obtained.

Synthesis Example of 4-35

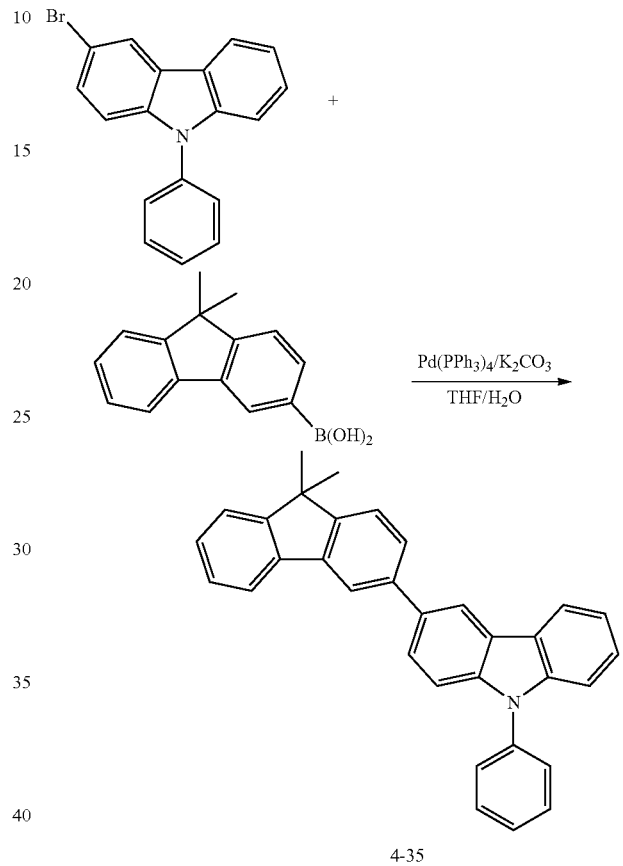

4-35

3-bromo-9-phenyl-9H-carbazole (6.4 g, 20 mmol) and 9(9,9-dimethyl-9H-fluoren-3-yl)boronic acid (4.8 g, 20 mmol) were reacted in the same manner as in the synthesis method of 4-1, as a result, 6.1 g (yield: 70%) of the product was obtained.

The FD-MS values of the compounds 4-1 to 4-52 of the present invention prepared according to the above synthesis examples are shown in Table 4 below.

TABLE 4

| Compound | FD-MS | Compound | FD-MS |
|---|---|---|---|
| 4-1 | m/z = 639.24($C_{45}H_{29}N_5$ = 639.75) | 4-2 | m/z = 715.27($C_{51}H_{33}N_5$ = 715.84) |
| 4-3 | m/z = 780.33($C_{57}H_{40}N_4$ = 780.95) | 4-4 | m/z = 639.24($C_{45}H_{29}N_5$ = 639.75) |
| 4-5 | m/z = 715.27($C_{51}H_{33}N_5$ = 715.84) | 4-6 | m/z = 780.33($C_{57}H_{40}N_4$ = 780.95) |
| 4-7 | m/z = 612.23($C_{44}H_{28}N_4$ = 612.72) | 4-8 | m/z = 612.23($C_{44}H_{28}N_4$ = 612.72) |
| 4-9 | m/z = 662.25($C_{48}H_{30}N_4$ = 662.78) | 4-10 | m/z = 484.19($C_{36}H_{24}N2$ = 484.59) |
| 4-11 | m/z = 639.24($C_{45}H_{29}N_5$ = 639.75) | 4-12 | m/z = 715.27($C_{51}H_{33}N_5$ = 715.84) |
| 4-13 | m/z = 715.27($C_{51}H_{33}N_5$ = 715.84) | 4-14 | m/z = 638.25($C_{46}H_{30}N_4$ = 638.76) |
| 4-15 | m/z = 579.18($C_{40}H_{25}N_3S$ = 579.71) | 4-16 | m/z = 410.14($C_{29}H_{18}N_2S$ = 410.47) |
| 4-17 | m/z = 486.17($C_{35}H_{22}N_2O$ = 486.56) | 4-18 | m/z = 486.17($C_{35}H_{22}N_2O$ = 486.56) |
| 4-19 | m/z = 486.17($C_{35}H_{22}N_2O$ = 486.56) | 4-20 | m/z = 563.20($C_{40}H_{25}N_3O$ = 563.65) |
| 4-21 | m/z = 460.16($C_{33}H_{20}N_2O$ = 460.52) | 4-22 | m/z = 536.19($C_{39}H_{24}N_2O$ = 536.62) |
| 4-23 | m/z = 689.26($C_{40}H_{31}N_5$ = 689.80) | 4-24 | m/z = 585.22($C_{43}H_{27}N_3$ = 585.69) |
| 4-25 | m/z = 610.24($C_{46}H_{30}N_2$ = 610.76) | 4-26 | m/z = 610.24($C_{46}H_{30}N_2$ = 610.76) |
| 4-27 | m/z = 636.26($C_{48}H_{32}N_2$ = 636.80) | 4-28 | m/z = 636.26($C_{48}H_{32}N_2$ = 636.80) |

TABLE 4-continued

| Compound | FD-MS | Compound | FD-MS |
|---|---|---|---|
| 4-29 | m/z = 610.24($C_{46}H_{30}N_2$ = 610.76) | 4-30 | m/z = 610.24($C_{46}H_{30}N_2$ = 610.76) |
| 4-31 | m/z = 649.25($C_{48}H_{31}N_3$ = 649.80) | 4-32 | m/z = 832.25($C_{60}H_{36}N_2OS$ = 833.02) |
| 4-33 | m/z = 560.23($C_{42}H_{28}N_2$ = 560.70) | 4-34 | m/z = 501.16($C_{36}H_{23}NS$ = 501.65) |
| 4-35 | m/z = 435.20($C_{33}H_{25}N$ = 435.57) | 4-36 | m/z = 725.28($C_{54}H_{35}N_3$ = 725.90) |
| 4-37 | m/z = 650.24($C_{40}H_{30}N_2O$ = 650.78) | 4-38 | m/z = 650.24($C_{48}H_{30}N_2O$ = 650.78) |
| 4-39 | m/z = 650.24($C_{48}H_{30}N_2O$ = 650.78) | 4-40 | m/z = 650.24($C_{48}H_{30}N_2O$ = 650.78) |
| 4-41 | m/z = 666.21($C_{48}H_{30}N_2S$ = 666.84) | 4-42 | m/z = 666.21($C_{48}H_{30}N_2S$ = 666.84) |
| 4-43 | m/z = 666.21($C_{48}H_{30}N_2S$ = 666.84) | 4-44 | m/z = 666.21($C_{48}H_{30}N_2S$ = 666.84) |
| 4-45 | m/z = 650.24($C_{40}H_{30}N_2O$ = 650.78) | 4-46 | m/z = 650.24($C_{48}H_{30}N_2O$ = 650.78) |
| 4-47 | m/z = 650.24($C_{48}H_{30}N_2O$ = 650.78) | 4-48 | m/z = 650.24($C_{48}H_{30}N_2O$ = 650.78) |
| 4-49 | m/z = 666.21($C_{48}H_{30}N_2S$ = 666.84) | 4-50 | m/z = 666.21($C_{48}H_{30}N_2S$ = 666.84) |
| 4-51 | m/z = 666.21($C_{48}H_{30}N_2S$ = 666.84) | 4-52 | m/z = 666.21($C_{48}H_{30}N_2S$ = 666.84) |

Fabrication and Evaluation of Organic Electronic Element

[Example 1] Green OLED (a Phosphorescent Host)

Organic light emitting diodes (OLEDs) were fabricated according to a conventional method by using a compound of the present invention as luminous host material of the light emitting layer. First, an ITO layer (anode) was formed on a glass substrate, and then 4,4',4"-tris[2-naphthyl(phenyl) amino]triphenylamine (hereinafter, "2-TNATA") was vacuum-deposited on the ITO layer to form a hole injection layer with a thickness of 60 nm. And 4,4'-bis[N-(1-naphthyl)-N-phenylamino]biphenyl (hereinafter, "NPD") was vacuum-deposited on the hole injection layer to form a hole transport layer with a thickness of 60 nm.

Subsequently, a light emitting layer with a thickness of 30 nm was vacuum-deposited on the hole transport layer by using compound 1-1 of the present invention as a host material and tris(2-phenylpyridine)-iridium (hereinafter, "Ir(ppy)$_3$") as a dopant material in a weight ratio of 95:5.

Subsequently, (1,1'-biphenyl-4-olato)bis(2-methyl-8-quinolinolato)aluminum (hereinafter, "BAlq") was vacuum-deposited with a thickness of 10 nm on the light emitting layer to form a hole blocking layer, and tris-(8-hydroxyquinoline)aluminum (hereinafter, "Alq$_3$") was vacuum-deposited with a thickness of 40 nm on the hole blocking layer to form an electron transport layer.

Next, LiF was deposited with a thickness of 0.2 nm on the electron transport layer to form an electron injection layer, and then Al was deposited with a thickness of 150 nm on the electron injection layer to form a cathode.

[Example 2] to [Example 40] Green OLED

The OLEDs were fabricated in the same manner as described in Example 1 except that compounds of the present invention described in Table 5 instead of the compound 1-1 of the present invention were used as host material of a light emitting layer, respectively.

[Comparative Example 1 to [Comparative Example 5]

The OLEDs were fabricated in the same manner as described in Example 1 except that one of the comparative compounds A to E of the present invention instead of the compound 1-1 of the present invention was used as host material of a light emitting layer.

<Comp.compd A>

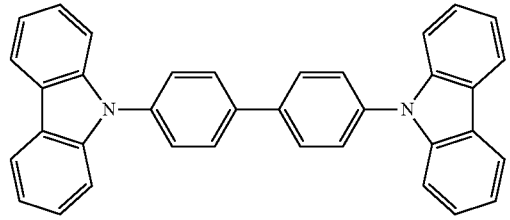

<Comp.compd B>

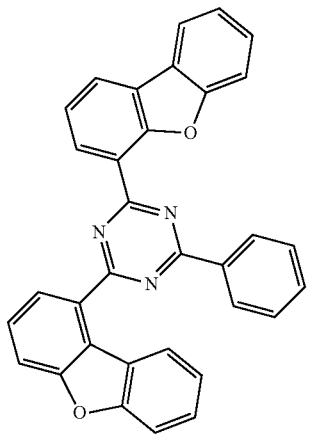

<Comp.compd C>

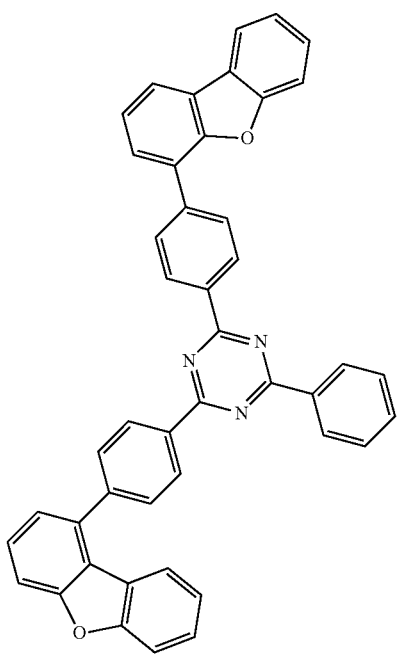

<Comp.compd D>

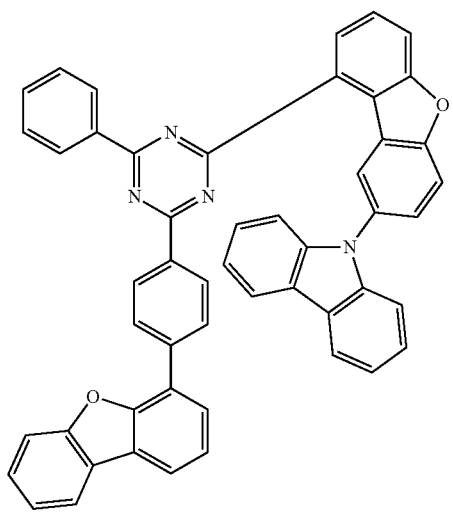

<Comp. compd E>

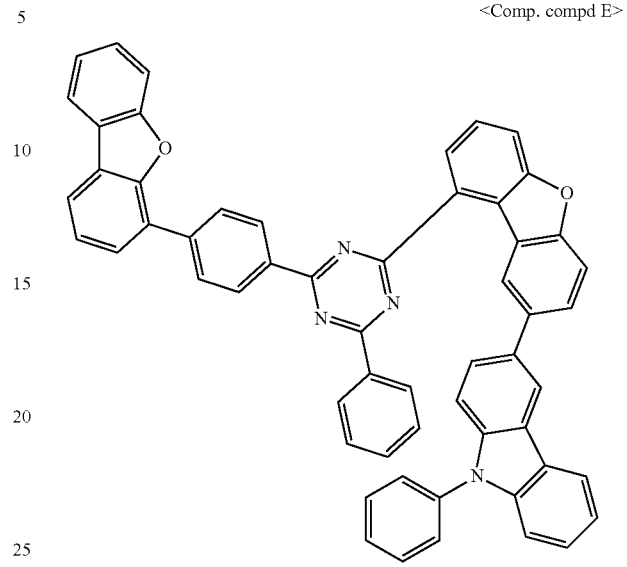

Electroluminescence (EL) characteristics were measured with a PR-650 (Photoresearch) by applying a forward bias DC voltage to the OLEDs prepared in Examples 1 to 40 of the present invention and Comparative Examples 1 to 5. And, the T95 life time was measured using a life time measuring apparatus manufactured by Mac science Inc. at reference brightness of 5000 cd/m². The measurement results are shown in Tables 5 below.

TABLE 5

|  | Compound | Voltage (V) | Current Density (mA/cm²) | Brightness (cd/m²) | Efficiency (cd/A) | Lifetime T (95) | CIE x | CIE y |
|---|---|---|---|---|---|---|---|---|
| comp. Ex (1) | comp. Com A | 5.9 | 21.2 | 5000.0 | 23.6 | 56.1 | 0.31 | 0.60 |
| comp. Ex (2) | comp. Com B | 5.5 | 18.0 | 5000.0 | 27.8 | 76.6 | 0.32 | 0.63 |
| comp. Ex (3) | comp. Com C | 5.7 | 17.4 | 5000.0 | 28.7 | 72.1 | 0.30 | 0.62 |
| comp. Ex (4) | comp. Com D | 5.3 | 15.6 | 5000.0 | 32.1 | 84.8 | 0.31 | 0.61 |
| comp. Ex (5) | comp. Com E | 5.1 | 13.9 | 5000.0 | 35.9 | 83.7 | 0.33 | 0.62 |
| Ex. (1) | 1-1 | 4.2 | 10.6 | 5000.0 | 47.2 | 105.0 | 0.34 | 0.63 |
| Ex. (2) | 1-7 | 4.3 | 10.3 | 5000.0 | 48.8 | 103.3 | 0.34 | 0.64 |
| Ex. (3) | 1-9 | 4.2 | 10.3 | 5000.0 | 48.5 | 108.3 | 0.34 | 0.64 |
| Ex. (4) | 1-14 | 4.2 | 10.2 | 5000.0 | 48.8 | 102.0 | 0.34 | 0.63 |
| Ex. (5) | 1-20 | 4.1 | 10.2 | 5000.0 | 48.9 | 104.1 | 0.33 | 0.65 |
| Ex. (6) | 1-21 | 4.2 | 10.6 | 5000.0 | 47.3 | 101.6 | 0.34 | 0.63 |
| Ex. (7) | 1-25 | 4.0 | 10.1 | 5000.0 | 49.7 | 107.2 | 0.31 | 0.61 |
| Ex. (8) | 1-26 | 4.0 | 10.6 | 5000.0 | 47.1 | 100.6 | 0.33 | 0.63 |
| Ex. (9) | 1-27 | 4.0 | 10.6 | 5000.0 | 47.1 | 104.1 | 0.31 | 0.62 |

TABLE 5-continued

| | Compound | Voltage (V) | Current Density (mA/cm$^2$) | Brightness (cd/m$^2$) | Efficiency (cd/A) | Lifetime T (95) | CIE x | CIE y |
|---|---|---|---|---|---|---|---|---|
| Ex. (10) | 1-28 | 4.2 | 10.7 | 5000.0 | 46.7 | 102.5 | 0.35 | 0.63 |
| Ex. (11) | 1-33 | 4.2 | 10.0 | 5000.0 | 49.8 | 109.1 | 0.30 | 0.60 |
| Ex. (12) | 1-34 | 4.0 | 10.1 | 5000.0 | 49.4 | 105.9 | 0.35 | 0.61 |
| Ex. (13) | 1-35 | 4.2 | 10.8 | 5000.0 | 46.3 | 103.8 | 0.33 | 0.65 |
| Ex. (14) | 1-36 | 4.2 | 10.7 | 5000.0 | 46.7 | 103.5 | 0.32 | 0.64 |
| Ex. (15) | 1-51 | 4.5 | 10.9 | 5000.0 | 45.9 | 109.7 | 0.30 | 0.64 |
| Ex. (16) | 1-56 | 4.5 | 10.9 | 5000.0 | 45.8 | 105.7 | 0.31 | 0.62 |
| Ex. (17) | 1-57 | 4.3 | 11.3 | 5000.0 | 44.1 | 105.2 | 0.31 | 0.64 |
| Ex. (18) | 1-62 | 4.5 | 11.9 | 5000.0 | 42.2 | 100.2 | 0.33 | 0.64 |
| Ex. (19) | 1-67 | 4.6 | 11.9 | 5000.0 | 42.1 | 102.1 | 0.32 | 0.63 |
| Ex. (20) | 1-72 | 4.6 | 11.6 | 5000.0 | 43.0 | 106.1 | 0.32 | 0.63 |
| Ex. (21) | 1-73 | 4.6 | 11.8 | 5000.0 | 42.2 | 105.8 | 0.33 | 0.64 |
| Ex. (22) | 1-75 | 4.6 | 11.8 | 5000.0 | 42.3 | 105.6 | 0.31 | 0.64 |
| Ex. (23) | 1-77 | 4.6 | 11.9 | 5000.0 | 42.1 | 104.1 | 0.31 | 0.64 |
| Ex. (24) | 2-1 | 4.5 | 11.1 | 5000.0 | 45.0 | 105.3 | 0.34 | 0.62 |
| Ex. (25) | 2-6 | 4.5 | 11.2 | 5000.0 | 44.7 | 105.8 | 0.32 | 0.61 |
| Ex. (26) | 2-11 | 4.4 | 11.2 | 5000.0 | 44.6 | 100.1 | 0.32 | 0.65 |
| Ex. (27) | 2-16 | 4.4 | 10.9 | 5000.0 | 45.7 | 102.3 | 0.31 | 0.63 |
| Ex. (28) | 2-20 | 4.5 | 11.0 | 5000.0 | 45.4 | 101.2 | 0.34 | 0.62 |
| Ex. (29) | 2-23 | 4.5 | 10.9 | 5000.0 | 46.0 | 109.1 | 0.35 | 0.60 |
| Ex. (30) | 2-26 | 4.4 | 11.1 | 5000.0 | 45.1 | 106.6 | 0.35 | 0.63 |
| Ex. (31) | 2-29 | 4.4 | 11.2 | 5000.0 | 44.8 | 101.2 | 0.35 | 0.64 |
| Ex. (32) | 2-34 | 4.5 | 10.9 | 5000.0 | 45.8 | 105.4 | 0.34 | 0.61 |
| Ex. (33) | 2-39 | 4.5 | 11.0 | 5000.0 | 45.5 | 101.1 | 0.32 | 0.62 |
| Ex. (34) | 2-44 | 4.5 | 11.3 | 5000.0 | 44.1 | 103.6 | 0.35 | 0.60 |
| Ex. (35) | 2-45 | 4.4 | 11.3 | 5000.0 | 44.2 | 106.8 | 0.34 | 0.64 |
| Ex. (36) | 2-51 | 4.6 | 11.4 | 5000.0 | 43.9 | 102.2 | 0.31 | 0.60 |
| Ex. (37) | 2-55 | 4.8 | 12.0 | 5000.0 | 41.5 | 105.9 | 0.34 | 0.63 |
| Ex. (38) | 2-60 | 4.8 | 12.3 | 5000.0 | 40.6 | 103.1 | 0.32 | 0.61 |
| Ex. (39) | 3-10 | 4.3 | 10.4 | 5000.0 | 48.3 | 109.4 | 0.35 | 0.60 |
| Ex. (40) | 3-2 | 4.9 | 12.9 | 5000.0 | 38.9 | 98.9 | 0.33 | 0.65 |

From Table 5, it can be seen that when using the compound according to an embodiment of the present invention as a phosphorescent host material of the light-emitting layer, compared with the case of using one of Comparative Compound A to Comparative Compound E, the driving voltage, the luminous efficiency and lifetime are significantly improved that are the electrical characteristics of the organic electroluminescent device. Comparative Compound A is CBP generally used as a host material, and Comparative Compounds B to E contain triazine and have a skeleton similar to that of the compounds of the present invention.

Comparing Comparative Examples 1 to 5, Comparative Examples 2 to 5 have better electrical characteristics of the organic electroluminescent device than Comparative Example 1, wherein CBP generally used as a host material is used as a phosphorescent host material of a light emitting layer in Comparative Example 1, and Comparative Compounds B to E contain triazine and have a skeleton similar to that of the compounds of the present invention in Comparative Examples 2 to 5.

On the other hand, comparing the Examples of the present invention and Comparative Examples 2 to 5, it can be seen that the driving voltage of the organic electric device manufactured according to the embodiment of the present invention is lower, and the luminous efficiency and lifespan are significantly improved. This seems to be due to the difference in physical properties between the compounds of the present invention and Comparative Compounds B to E used as phosphorescent host materials.

The compounds of the present invention and Comparative Compounds B to E are all similar in that they contain triazine and heterocycles are attached to both sides of the triazine.

However, in the compound of the present invention, 1-dibenzofuran or 1-dibenzothiophene substituted with an aryl group (corresponding to Ar$^3$ in Formula 1) is directly bonded to one side of the triazine (one of the carbons of the triazine ring), and 4-dibenzofuran or 4-dibenzothiophene is bonded to the other side (another carbon of the triazine ring) via an arylene group such as phenyl or biphenyl. On the other hand, in the case of Comparative Compound B, 1-dibenzofuran and 4-dibenzofuran are both directly connected to the carbon of the triazine, in the case of Comparative Compound C, 1-dibenzofuran and 4-dibenzofuran are both bonded to the triazine through a linking group such as phenyl, in Comparative Compounds D and E, 1-dibenzofuran is connected to the triazine via a phenyl linkage group. The comparative compounds are similar to the compound of the present invention in that 4-dibenzofuran is directly connected to the triazine, but the portion corresponding to Ar$^3$ is different in that the present invention is substituted with an aryl group, while the comparative compounds are substituted with a heteroaryl group.

Due to such a difference in the structure of the compound, when using each of these compounds as a phosphorescent host material, the characteristics of the device are different, and the device properties of Comparative Examples 4 and 5 were better than those of Comparative Examples 2 and 3.

Therefore, it can be seen that the device characteristics are further improved in compound in which 1-dibenzofuran is bonded to triazine through a linkage group such as phenyl, and 4-dibenzofuran is directly bonded to triazine than in compound in which 1-dibenzofuran and 4-dibenzofuran are directly bonded to triazine or they are bonded via phenyl.

In addition, compared to Comparative Example 4 and Comparative Example 5, the driving voltage of the organic electroluminescent device manufactured according to the embodiment of the present invention was significantly lowered, and the luminous efficiency and lifespan were significantly improved. From this, it can be seen that the device characteristics are further improved in case of using compound of the present invention in which the substituent substituted on the benzene ring of 4-dibenzofuran (or 4-dibenzothiophene) is hydrogen or an aryl group, compared to case of using compound having a heterocycle as a substituent.

Figure 2:
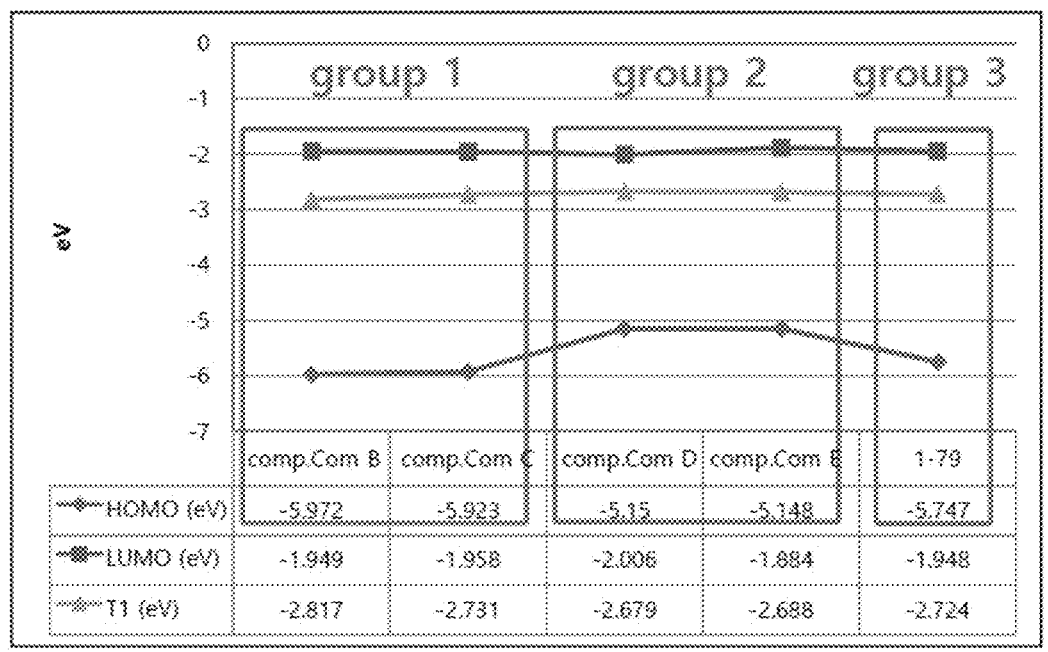
FIG. 2 shows a comparison of the energy levels of the comparative example compounds and the inventive example compounds.
Figure 3:
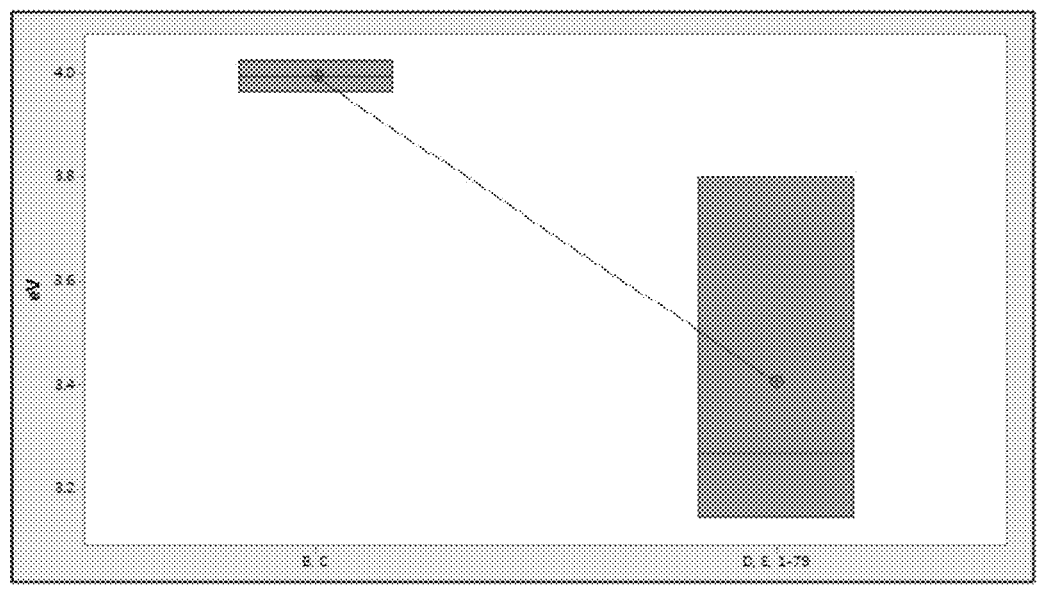
FIG. 3 shows a band gap of the comparative example compound and the inventive example compound.

To determine the cause of this result, the energy levels of Comparative Compounds B to E and Compounds 1-79 of the present invention were compared as shown in FIGS. 2 and 3.

FIG. 2 is a diagram comparing the energy levels of the comparative example compound and the example compound of the present invention.

Referring to FIG. 2, Comparative Compound B and C are classified into Group 1, Comparative Compound D and E are classified into Group 2, and Compound 1-79 of the present invention is classified into Group 3.

Group 1 is a group of compounds in which a substituent other than hydrogen is not bonded to dibenzofuran directly or indirectly attached to triazine, Group 2 is a group of compounds in which a heterocyclic group such as carbazole is substituted in the benzene ring of dibenzofuran which dibenzofuran is indirectly bound to a triazine through a linking group, and Group 3 is a group of compounds in which an aryl group such as phenyl is bonded to a benzene ring of dibenzofuran which is indirectly linked via a linking group to a triazine.

Referring to FIG. 2, the LUMO values and the T1 values of Groups 1 to 3 do not show significant differences in all three groups, while the HOMO values show great differences. It can be seen that the HOMO value of the compound of Group 3 in which dibenzofuran is substituted with an aryl is larger than that of Group 1 in which dibenzofuran is substituted with hydrogen only.

Therefore, from these results, the HOMO energy level of the compound can be significantly changed according to the type of the substituent attached to the benzene ring of dibenzofuran, and the difference in physical properties of these compounds affects device performance in depositing the compound during device fabrication and it suggests that since it acts as a main factor (for example, energy balance, charge balance, etc.), device characteristics such as driving voltage, luminous efficiency, and lifetime may vary.

On the other hand, FIG. 3 is a view comparing the band gap (band gap) of the comparative example compound and the compound of the present invention.

In FIG. 3, the band gap values are divided into two groups according to the characteristics of each compound, and the first group to which Comparative Compound B and C belong and the second group to which Comparative Compounds D, E and Compound 1-79 of the present invention belong are divided.

In the compound belonging to the first group, all dibenzofurans are directly connected to the triazine or both are indirectly connected through a phenylene linking group, while in the compound belonging to the second group, dibenzofuran is directly connected to one side of the triazine and indirectly to the other side through a linking group such as phenylene.

Referring to FIG. 3, Group 1 has a band gap of approximately 4.0 eV, while Group 2 has a band gap of approximately 3.4 eV, and the two groups have significant differences in band gap.

Therefore, it can be seen that the energy level (band gab) of the compound may vary depending on the form of the combination of triazine and dibenzofuran, and the difference in physical properties affects device performance when depositing the compound during device manufacturing. It can be seen that different device characteristics can be derived by changing the main factors (eg, energy balance or charge balance).

In conclusion, referring to FIGS. 2 and 3, it can be seen that the compounds of the present invention differ from the comparative compounds in HOMO value and band gap, wherein the inventive compound has 1-dibenzofuran (or 1-dibenzothiophene) on one side of a triazine via a linking group such as an arylene group and 4-dibenzofuran (or 4-dibenzothiophene) substituted with an aryl group on the other side of a triazin. Due to this difference, the characteristics of the device are significantly improved when the compound of the present invention is used as a phosphorescent host material.

[Example 41] to [Example 96] Green OLED (Phosphorescent Host Mixture)

The OLEDs were fabricated in the same manner as described in Example 1 except that a mixture of two kinds of compounds of the present invention in a weight ratio of 6:4 was used as host material of a light emitting layer as shown in Table 6 below, instead of using compound 1-1 of the present invention alone.

[Example 6] to [Example 9] Green OLED (Phosphorescent Host Mixture)

The OLEDs were fabricated in the same manner as described in Example 1 except that a mixture of one of Comparative Compounds B to Comparative Compound E and Compound 4-27 of the present invention in a weight ratio of 6:4 was used as host material of a light emitting layer as shown in Table 6 below, instead of using compound 1-1 of the present invention alone.

Electroluminescence (EL) characteristics were measured with a PR-650 (Photoresearch) by applying a forward bias DC voltage to the OLEDs prepared in Examples 41 to 96 of the present invention and Comparative Examples 6 to 9. And, the T95 life time was measured using a life time measuring apparatus manufactured by Mac science Inc. at reference brightness of 5000 cd/m$^2$. The measurement results are shown in Tables 6 below.

TABLE 6

| Host 1 | Host 2 | Voltage (V) | Current Density (mA/cm$^2$) | Brightness (cd/m$^2$) | Efficiency (cd/A) | Lifetime T (95) |
|---|---|---|---|---|---|---|
| comp. Ex (6) | comp. Com B | 4-27 | 5.4 | 17.8 | 5000.0 | 28.1 | 110.8 |
| comp. Ex (7) | comp. Com C | | 5.6 | 17.1 | 5000.0 | 29.3 | 113.9 |
| comp. Ex (8) | comp. Com D | | 5.0 | 14.5 | 5000.0 | 34.5 | 113.0 |

TABLE 6-continued

| | Host 1 | Host 2 | Voltage (V) | Current Density (mA/cm$^2$) | Brightness (cd/m$^2$) | Efficiency (cd/A) | Lifetime T (95) |
|---|---|---|---|---|---|---|---|
| comp. Ex (9) | comp. Com E | | 4.9 | 13.4 | 5000.0 | 37.3 | 115.0 |
| Ex. (41) | 1-1 | 4-27 | 3.6 | 10.0 | 5000.0 | 49.9 | 117.5 |
| Ex. (42) | 1-7 | | 3.7 | 10.1 | 5000.0 | 49.4 | 116.1 |
| Ex. (43) | 1-9 | | 3.6 | 10.1 | 5000.0 | 49.5 | 119.2 |
| Ex. (44) | 1-21 | | 3.7 | 10.0 | 5000.0 | 49.8 | 115.4 |
| Ex. (45) | 1-28 | | 3.6 | 10.1 | 5000.0 | 49.4 | 117.7 |
| Ex. (46) | 1-35 | | 3.7 | 10.1 | 5000.0 | 49.3 | 116.3 |
| Ex. (47) | 1-48 | | 3.6 | 10.2 | 5000.0 | 49.2 | 115.1 |
| Ex. (48) | 1-1 | 4-25 | 3.6 | 10.0 | 5000.0 | 49.9 | 117.6 |
| Ex. (49) | 1-7 | | 3.7 | 10.2 | 5000.0 | 49.2 | 116.8 |
| Ex. (50) | 1-9 | | 3.7 | 10.1 | 5000.0 | 49.5 | 117.1 |
| Ex. (51) | 1-21 | | 3.7 | 10.1 | 5000.0 | 49.5 | 118.0 |
| Ex. (52) | 1-28 | | 3.7 | 10.1 | 5000.0 | 49.3 | 115.1 |
| Ex. (53) | 1-35 | | 3.7 | 10.0 | 5000.0 | 49.9 | 115.9 |
| Ex. (54) | 1-48 | | 3.7 | 10.0 | 5000.0 | 49.9 | 117.4 |
| Ex. (55) | 1-1 | 4-30 | 3.7 | 10.0 | 5000.0 | 49.9 | 116.1 |
| Ex. (56) | 1-7 | | 3.7 | 10.1 | 5000.0 | 49.3 | 116.8 |
| Ex. (57) | 1-9 | | 3.6 | 10.2 | 5000.0 | 49.2 | 118.9 |
| Ex. (58) | 1-21 | | 3.6 | 10.1 | 5000.0 | 49.6 | 119.9 |
| Ex. (59) | 1-28 | | 3.7 | 10.2 | 5000.0 | 49.2 | 117.8 |
| Ex. (60) | 1-35 | | 3.7 | 10.1 | 5000.0 | 49.5 | 119.9 |
| Ex. (61) | 1-48 | | 3.6 | 10.1 | 5000.0 | 49.5 | 119.6 |
| Ex. (62) | 1-1 | 4-31 | 3.5 | 9.9 | 5000.0 | 50.5 | 124.1 |
| Ex. (63) | 1-7 | | 3.5 | 9.9 | 5000.0 | 50.4 | 120.7 |
| Ex. (64) | 1-9 | | 3.5 | 10.0 | 5000.0 | 50.1 | 120.3 |
| Ex. (65) | 1-21 | | 3.5 | 9.9 | 5000.0 | 50.7 | 120.9 |
| Ex. (66) | 1-28 | | 3.4 | 9.9 | 5000.0 | 50.3 | 121.9 |
| Ex. (67) | 1-35 | | 3.5 | 9.9 | 5000.0 | 50.7 | 121.3 |
| Ex. (68) | 1-48 | | 3.4 | 9.9 | 5000.0 | 50.3 | 123.4 |
| Ex. (69) | 1-1 | 4-37 | 3.8 | 10.3 | 5000.0 | 48.4 | 111.2 |
| Ex. (70) | 1-7 | | 3.7 | 10.3 | 5000.0 | 48.6 | 110.5 |
| Ex. (71) | 1-9 | | 3.8 | 10.4 | 5000.0 | 48.0 | 113.7 |
| Ex. (72) | 1-21 | | 3.8 | 10.3 | 5000.0 | 48.4 | 113.4 |
| Ex. (73) | 1-28 | | 3.7 | 10.3 | 5000.0 | 48.5 | 110.5 |
| Ex. (74) | 1-35 | | 3.7 | 10.4 | 5000.0 | 48.3 | 113.2 |
| Ex. (75) | 1-48 | | 3.8 | 10.4 | 5000.0 | 48.2 | 113.3 |
| Ex. (76) | 1-1 | 4-42 | 3.8 | 10.4 | 5000.0 | 48.1 | 114.2 |
| Ex. (77) | 1-7 | | 3.7 | 10.3 | 5000.0 | 48.6 | 113.1 |
| Ex. (78) | 1-9 | | 3.8 | 10.3 | 5000.0 | 48.6 | 111.6 |
| Ex. (79) | 1-21 | | 3.8 | 10.2 | 5000.0 | 48.9 | 113.9 |
| Ex. (80) | 1-28 | | 3.8 | 10.3 | 5000.0 | 48.8 | 112.8 |
| Ex. (81) | 1-35 | | 3.7 | 10.2 | 5000.0 | 48.9 | 110.2 |
| Ex. (82) | 1-48 | | 3.7 | 10.3 | 5000.0 | 48.7 | 113.2 |
| Ex. (83) | 1-1 | 4-47 | 3.8 | 10.3 | 5000.0 | 48.4 | 110.0 |
| Ex. (84) | 1-7 | | 3.8 | 10.2 | 5000.0 | 48.9 | 115.0 |
| Ex. (85) | 1-9 | | 3.7 | 10.3 | 5000.0 | 48.5 | 113.0 |
| Ex. (86) | 1-21 | | 3.8 | 10.4 | 5000.0 | 48.1 | 112.2 |
| Ex. (87) | 1-28 | | 3.8 | 10.3 | 5000.0 | 48.5 | 114.6 |
| Ex. (88) | 1-35 | | 3.7 | 10.4 | 5000.0 | 48.1 | 110.5 |
| Ex. (89) | 1-48 | | 3.8 | 10.3 | 5000.0 | 48.7 | 113.2 |
| Ex. (90) | 1-1 | 4-52 | 3.7 | 10.2 | 5000.0 | 48.8 | 110.4 |
| Ex. (91) | 1-7 | | 3.7 | 10.4 | 5000.0 | 48.1 | 113.2 |
| Ex. (92) | 1-9 | | 3.7 | 10.3 | 5000.0 | 48.4 | 113.3 |
| Ex. (93) | 1-21 | | 3.8 | 10.4 | 5000.0 | 48.1 | 113.1 |
| Ex. (94) | 1-28 | | 3.8 | 10.3 | 5000.0 | 48.4 | 113.1 |
| Ex. (95) | 1-35 | | 3.8 | 10.3 | 5000.0 | 48.4 | 110.8 |
| Ex. (96) | 1-48 | | 3.8 | 10.3 | 5000.0 | 48.5 | 111.1 |

From Table 6, it can be seen that the driving voltage and the luminous efficiency of the organic electroluminescent device manufactured according to the embodiment of the present invention are significantly improved and the lifetime is also improved as compared to the comparative example. That is, when a mixture of a compound represented by Formula 1 of the present invention as a first host component and a compound represented by Formula 11 of the present invention as a second host component is used as host material, compared to a mixture using one of Comparative Compounds B to E as a first host component and a compound represented by Formula 11 of the present invention as a second host component, device characteristics of the organic electroluminescent device are significantly improved.

From these results, it can be seen that as in the case where the compound represented by Formula 1 of the present invention is used alone as a host material, even when a mixture of the compound represented by the formula 1 of the present invention and the compound represented by the formula 11 of the present invention is used as a host material, the driving voltage, luminous efficiency and lifetime of the device are significantly improved.

Although exemplary embodiments of the present invention have been described for illustrative purposes, those skilled in the art will appreciate that various modifications

The invention claimed is:
1. A compound of Formula 1:

<Formula 1>

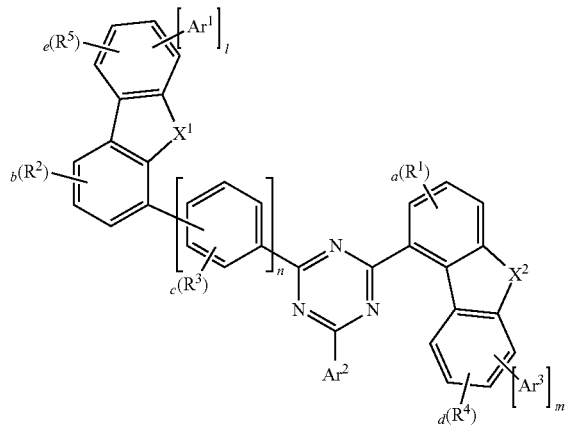

wherein:
$X^1$ and $X^2$ are each independently O or S,
$Ar^1$ to $Ar^3$ are each independently a $C_6$-$C_{60}$ aryl group,
$R^1$ $R^2$, $R^4$ and $R^5$ are each independently selected from the group consisting of hydrogen, deuterium, halogen, a $C_6$-$C_{60}$ aryl group, a fluorenyl group, a $C_2$-$C_{60}$ heterocyclic group containing at least one heteroatom selected from the group consisting of O, N, S, Si, and P, a $C_3$-$C_{60}$ aliphatic ring, a fused ring group formed by a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -L'-N($R_a$)($R_b$), and adjacent groups may be optionally linked to each other to form a ring, wherein the ring is selected from the group consisting of a $C_6$-$C_{60}$ aromatic ring, a $C_2$-$C_{60}$ heterocyclic group, a $C_3$-$C_{60}$ aliphatic ring, and a fused ring group formed by a $C_3$-$C_{60}$ aliphatic ring with a $C_6$-$C_{60}$ aromatic ring, and wherein the ring formed by adjacent groups of $R^2$ or adjacent groups of $R^5$ is a benzene ring in the case where $X^1$ is O,
$R^3$ is selected from the group consisting of deuterium, halogen, a $C_6$-$C_{60}$ aryl group, a fluorenyl group, a $C_2$-$C_{60}$ heterocyclic group containing at least one heteroatom selected from the group consisting of O, N, S, Si, and P, a $C_3$-$C_{60}$ aliphatic ring, a fused ring group formed by a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -L'-N($R_a$)($R_b$), and adjacent groups may be optionally linked to each other to form a ring, wherein the ring is selected from the group consisting of a $C_6$-$C_{60}$ aromatic ring, a $C_2$-$C_{60}$ heterocyclic group, a $C_3$-$C_{60}$ aliphatic ring, and a fused ring group formed by a $C_3$-$C_{60}$ aliphatic ring with a $C_6$-$C_{60}$ aromatic ring,
a and b are each an integer of 0 to 3, c, d, e, and l are each an integer of 0 to 4 with the proviso that c+l is an integer of 1 or more, m is an integer of 1 to 4, and n is an integer of 1 to 5,
L' is selected from the group consisting of a single bond, a $C_6$-$C_{60}$ arylene group, a fluorenylene group, a $C_2$-$C_{60}$ heterocyclic group containing at least one heteroatom selected from the group consisting of O, N, S, Si, and P, a $C_3$-$C_{60}$ aliphatic ring and a fused ring group formed by a $C_3$-$C_{60}$ aliphatic ring with a $C_6$-$C_{60}$ aromatic ring, and
$R_a$ and $R_b$ are each independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a $C_3$-$C_{60}$ aliphatic ring and a fused ring group formed by a $C_3$-$C_{60}$ aliphatic ring with a $C_6$-$C_{60}$ aromatic ring,
wherein $Ar^1$ to $Ar^3$, $R^1$ to $R^5$, L', $R_a$, $R_b$, and a ring formed by the adjacent groups of $R^1$ to $R^5$ may be each further substituted with one or more substituents selected from the group consisting of deuterium, halogen, a silane group unsubstituted or substituted with a $C_1$-$C_{20}$ alkyl group or a $C_6$-$C_{20}$ aryl group, a siloxane group, a boron group, a germanium group, a cyano group, a nitro group, a phosphine oxide group unsubstituted or substituted with a $C_1$-$C_{20}$ alkyl group or a $C_6$-$C_{20}$ aryl group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a fused ring group formed by a $C_3$-$C_{60}$ aliphatic ring with a $C_6$-$C_{60}$ aromatic ring, a $C_7$-$C_{20}$ arylalkyl group, and a $C_8$-$C_{20}$ arylalkenyl group.

2. A compound represented by one of Formula 2 to Formula 5:

<Formula 2>

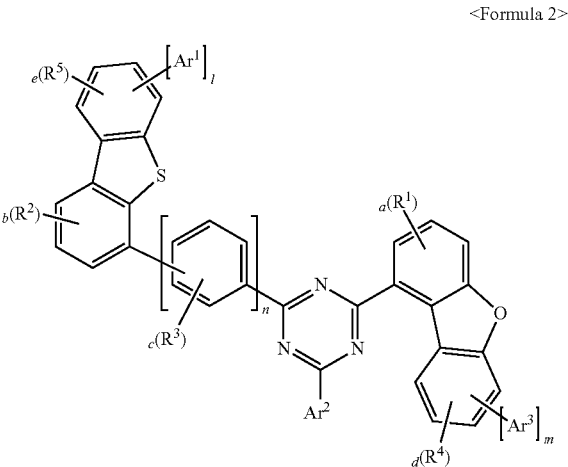

-continued

<Formula 3>

<Formula 4>

<Formula 5>

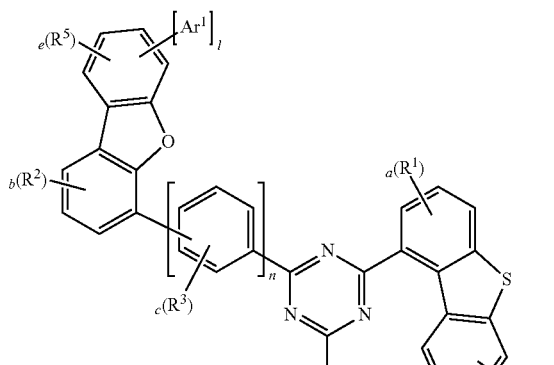

wherein:
$Ar^1$ to $Ar^3$ are each independently a $C_6$-$C_{60}$ aryl group,
$R^1$ to $R^5$ are each independently selected from the group consisting of hydrogen, deuterium, halogen, a $C_6$-$C_{60}$ aryl group, a fluorenyl group, a $C_2$-$C_{60}$ heterocyclic group containing at least one heteroatom selected from the group consisting of O, N, S, Si, and P, a $C_3$-$C_{60}$ aliphatic ring, a fused ring group formed by a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -L'-N($R_a$)($R_b$), and adjacent groups of $R^1$ to $R^5$ may be linked to each other to form a ring selected from the group consisting of a $C_6$-$C_{60}$ aromatic ring, a $C_2$-$C_{60}$ heterocyclic group, a $C_3$-$C_{60}$ aliphatic ring, and a fused ring group formed by a $C_3$-$C_{60}$ aliphatic ring with a $C_6$-$C_{60}$ aromatic ring, with the proviso that b+e is an integer of 3 or more and adjacent groups of $R^2$ or adjacent groups of $R^5$ are linked to each other to form a benzene ring,
a and b are each an integer of 0 to 3; c, d, e, l and m are each an integer of 0 to 4, and n is an integer of 1 to 5,
L' is selected from the group consisting of a single bond, a $C_6$-$C_{60}$ arylene group, a fluorenylene group, a $C_2$-$C_{60}$ heterocyclic group containing at least one heteroatom selected from the group consisting of O, N, S, Si, and P, a $C_3$-$C_{60}$ aliphatic ring and a fused ring group formed by a $C_3$-$C_{60}$ aliphatic ring with a $C_6$-$C_{60}$ aromatic ring, and
$R_a$ and $R_b$ are each independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a $C_3$-$C_{60}$ aliphatic ring and a fused ring group formed by a $C_3$-$C_{60}$ aliphatic ring with a $C_6$-$C_{60}$ aromatic ring,
wherein $Ar^1$ to $Ar^3$, $R^1$ to $R^5$, L', $R_a$, $R_b$, and a ring formed by the adjacent groups of $R^1$ to $R^5$ may be each further substituted with one or more substituents selected from the group consisting of deuterium, halogen, a silane group unsubstituted or substituted with a $C_1$-$C_{20}$ alkyl group or a $C_6$-$C_{20}$ aryl group, a siloxane group, a boron group, a germanium group, a cyano group, a nitro group, a phosphine oxide group unsubstituted or substituted with a $C_1$-$C_{20}$ alkyl group or a $C_6$-$C_{20}$ aryl group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a fused ring group formed by a $C_3$-$C_{60}$ aliphatic ring with a $C_6$-$C_{60}$ aromatic ring, a $C_7$-$C_{20}$ arylalkyl group, and a $C_8$-$C_{20}$ arylalkenyl group.

3. The compound of claim 1, wherein Formula 1 is represented by one of Formula 6 to Formula 8:

<Formula 6>

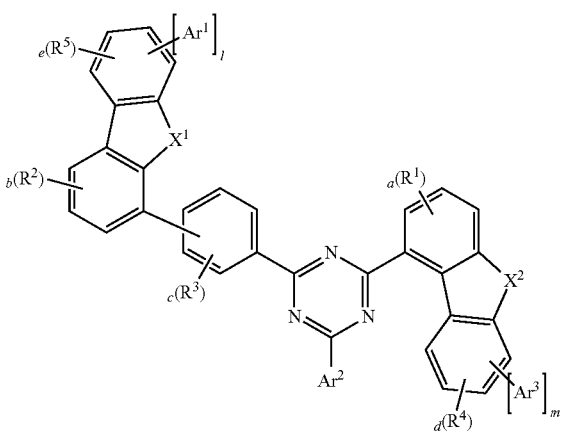

-continued
<Formula 7>
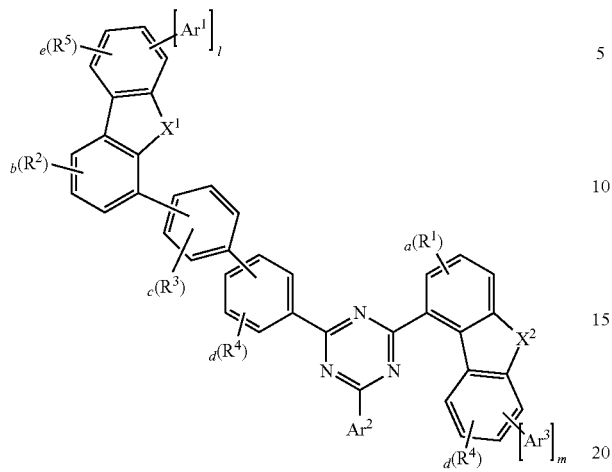
<Formula 8>
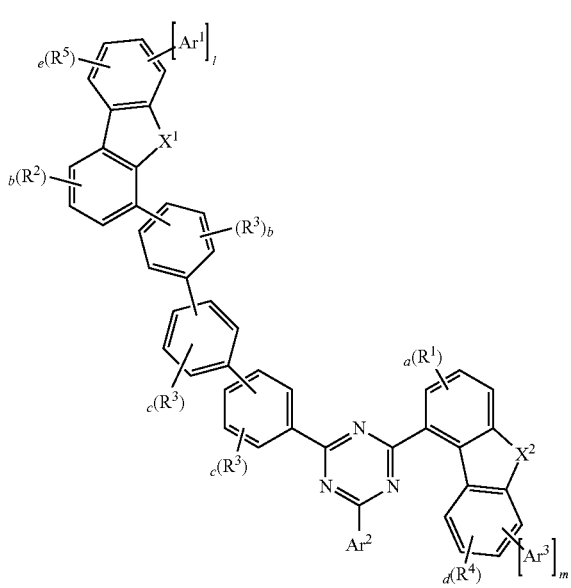
wherein $X^1$, $X^2$, $Ar^1$ to $Ar^3$, $R^1$ to $R^5$, a, b, c, d, e, l and m are the same as defined in claim 1.
4. The compound of claim 1, wherein Formula 1 is represented Formula 9 or Formula 10:
<Formula 9>
<Formula 10>
wherein $X^1$, $X^2$, $Ar^1$ to $Ar^3$, $R^1$ to $R^5$, a, b, c, d, e, m and n are the same as defined in claim 1.
5. A compound represented by one of Formula 11 to Formula 13:
<Formula 11>
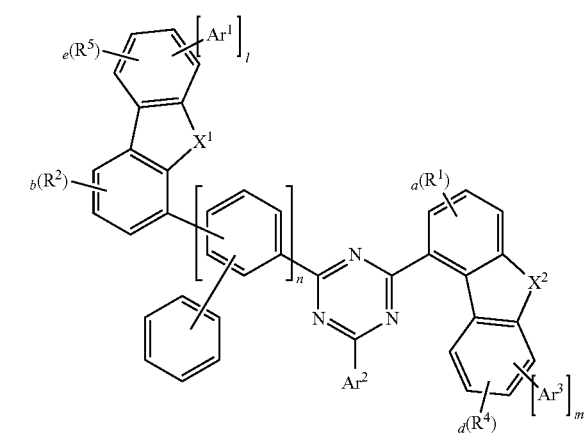

<Formula 12>

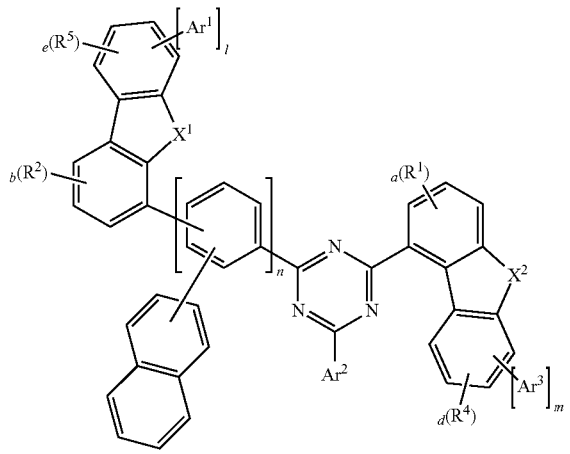

<Formula 13> wherein:
X¹ and X² are each independently O or S,
Ar¹ to Ar³ are each independently a $C_6$-$C_{60}$ aryl group,
$R^1$, $R^2$, $R^4$ and $R^5$ are each independently selected from the group consisting of hydrogen, deuterium, halogen, a $C_6$-$C_{60}$ aryl group, a fluorenyl group, a $C_2$-$C_{60}$ heterocyclic group containing at least one heteroatom selected from the group consisting of O, N, S, Si, and P, a $C_3$-$C_{60}$ aliphatic ring, a fused ring group formed by a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -L'-N($R_a$)($R_b$), and adjacent groups may be optionally linked to each other to form a ring, wherein the ring is selected from the group consisting of a $C_6$-$C_{60}$ aromatic ring, a $C_2$-$C_{60}$ heterocyclic group, a $C_3$-$C_{60}$ aliphatic ring, and a fused ring group formed by a $C_3$-$C_{60}$ aliphatic ring with a $C_6$-$C_{60}$ aromatic ring, and wherein the ring formed by adjacent groups of $R^2$ or adjacent groups of $R^5$ is a benzene ring in the case where X¹ is O,
a and b are each an integer of 0 to 3; -d, e, l and m are each an integer of 0 to 4, and n is an integer of 1 to 5, L' is selected from the group consisting of a single bond, a $C_6$-$C_{60}$ arylene group, a fluorenylene group, a $C_2$-$C_{60}$ heterocyclic group containing at least one heteroatom selected from the group consisting of O, N, S, Si, and P, a $C_3$-$C_{60}$ aliphatic ring and a fused ring group formed by a $C_3$-$C_{60}$ aliphatic ring with a $C_6$-$C_{60}$ aromatic ring, and $R_a$ and $R_b$ are each independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a $C_3$-$C_{60}$ aliphatic ring and a fused ring group formed by a $C_3$-$C_{60}$ aliphatic ring with a $C_6$-$C_{60}$ aromatic ring, wherein Ar¹ to Ar³, $R^1$, $R^2$, $R^4$ and $R^5$, L', $R_a$, $R_b$, and a ring formed by the adjacent groups of $R^1$, $R^2$, $R^4$ and $R^5$ may be each further substituted with one or more substituents selected from the group consisting of deuterium, halogen, a silane group unsubstituted or substituted with a $C_1$-$C_{20}$ alkyl group or a $C_6$-$C_{20}$ aryl group, a siloxane group, a boron group, a germanium group, a cyano group, a nitro group, a phosphine oxide group unsubstituted or substituted with a $C_1$-$C_{20}$ alkyl group or a $C_6$-$C_{20}$ aryl group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a fused ring group formed by a $C_3$-$C_{60}$ aliphatic ring with a $C_6$-$C_{60}$ aromatic ring, a $C_7$-$C_{20}$ arylalkyl group, and a $C_8$-$C_{20}$ arylalkenyl group.

6. The compound of claim 1, wherein Formula 1 is represented by Formula 14:

<Formula 14>

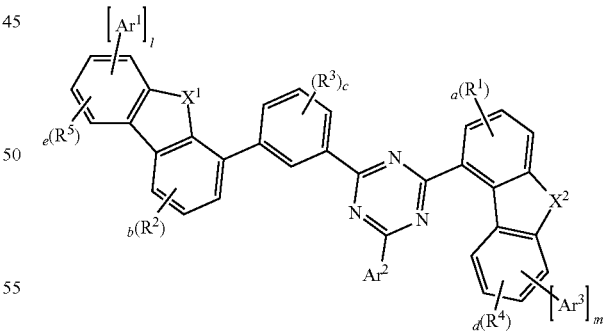

wherein, X¹, X², Ar¹ to Ar³, $R^1$ to $R^5$, a, b, c, d, e, l and m are the same as defined in claim 1.

7. The compound of claim 1, wherein at least one of Ar¹, Ar³ and $R^3$ is a $C_6$-$C_{24}$ aryl group.

8. The compound of claim 1, wherein Ar¹ or Ar³ is a $C_6$-$C_{24}$ aryl group.

9. The compound of claim 1, wherein $R^3$ is a $C_6$-$C_{24}$ aryl group.

10. A compound selected from the group consisting of the following compounds:
1-4
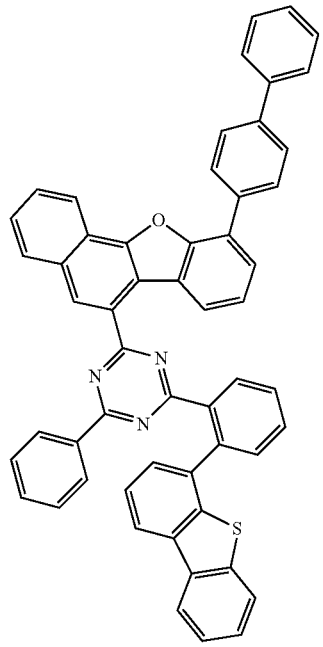
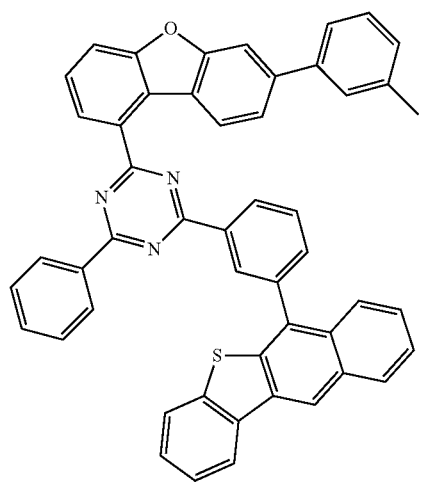

213 214
-continued
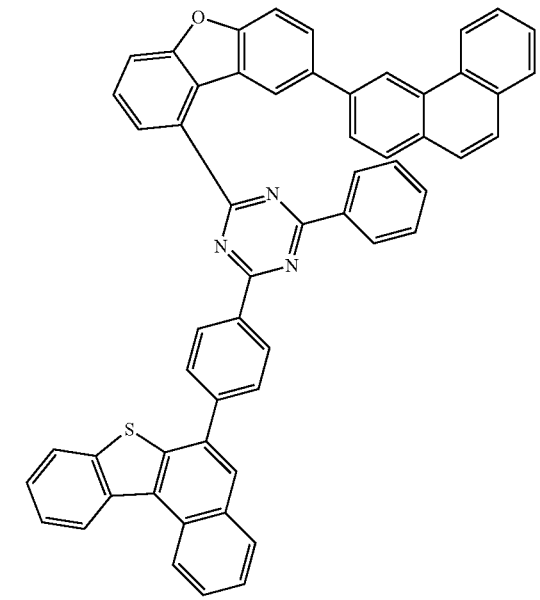
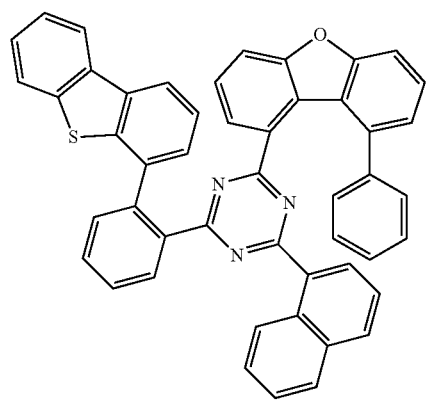
1-13
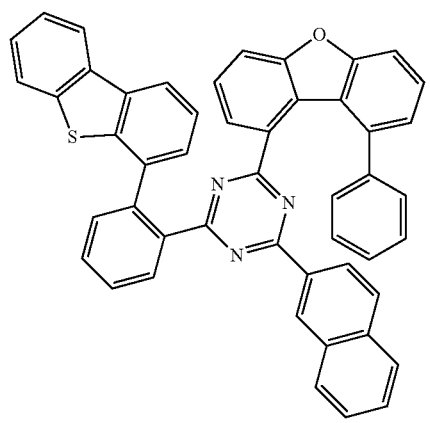
1-14
1-16
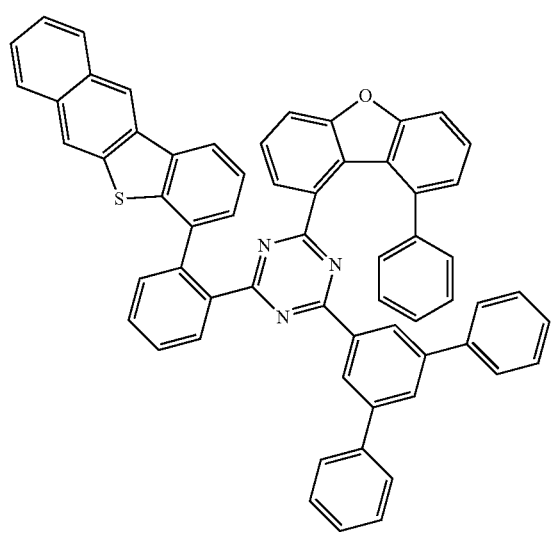

1-17
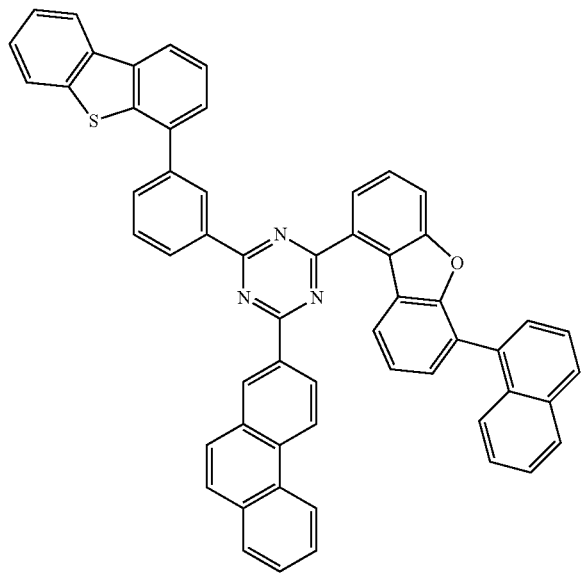
1-18
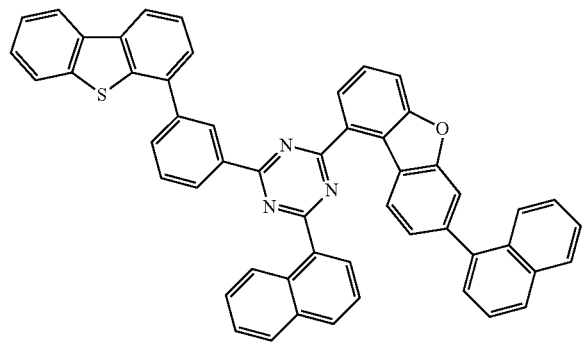
1-19
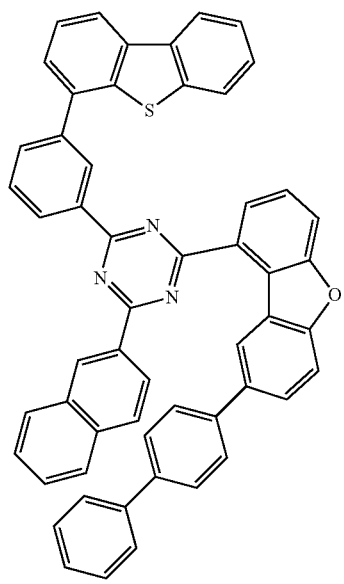
1-20
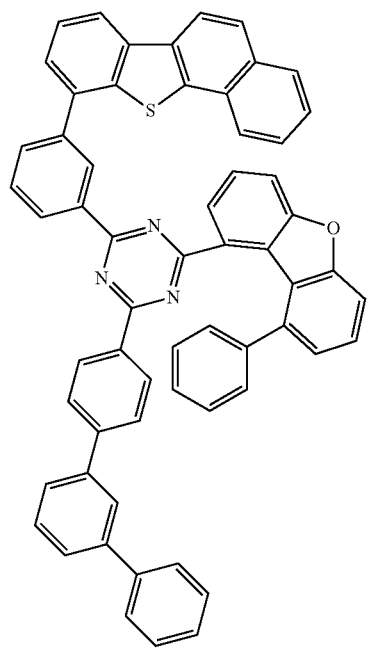

1-22
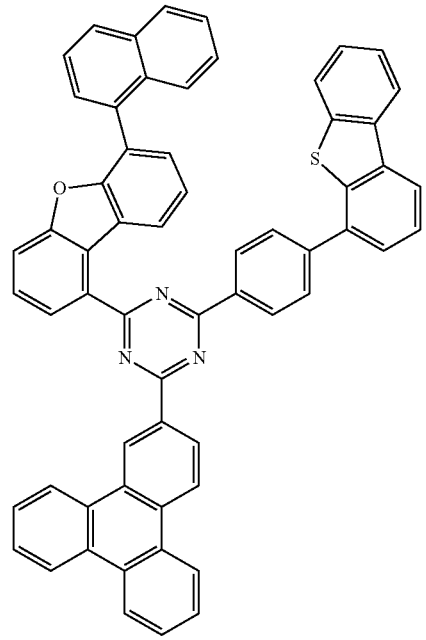
1-23
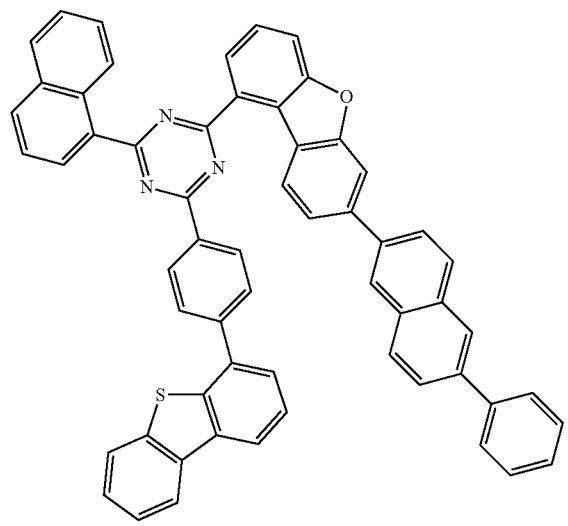
1-24
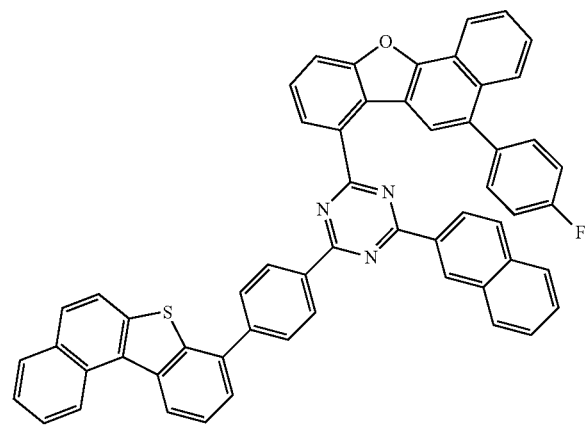

1-27
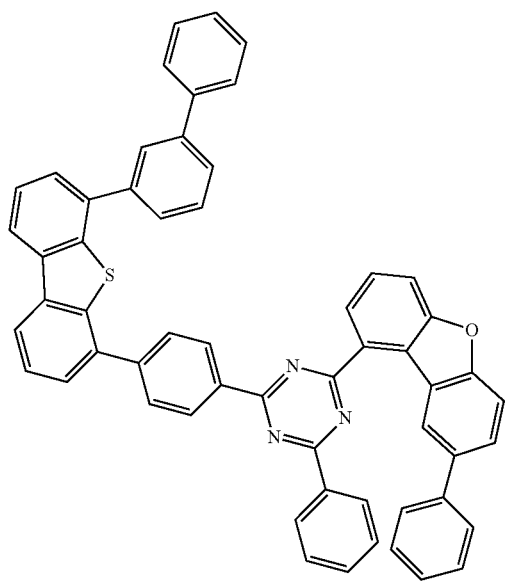
1-28
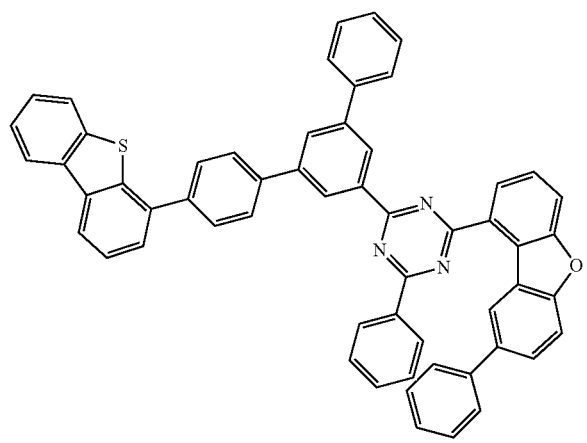
1-29
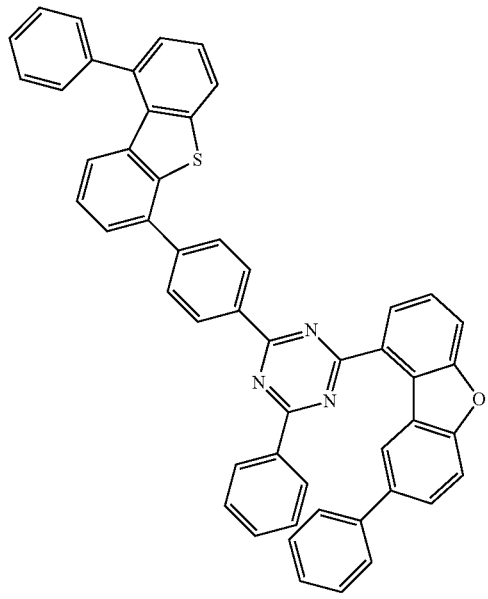
1-30
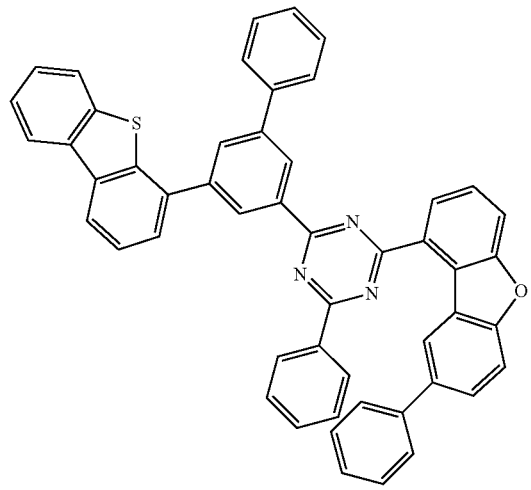

-continued
1-32
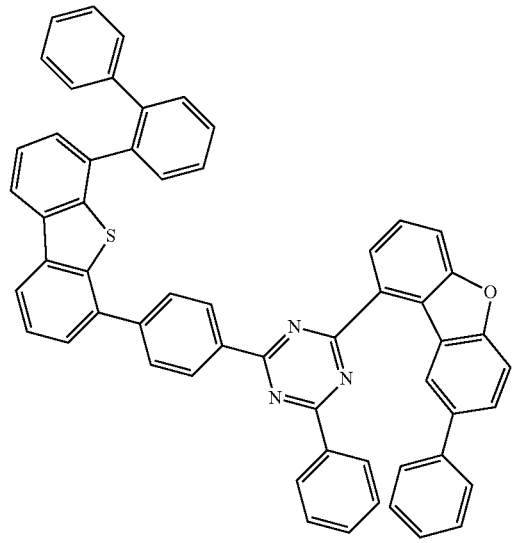
1-33
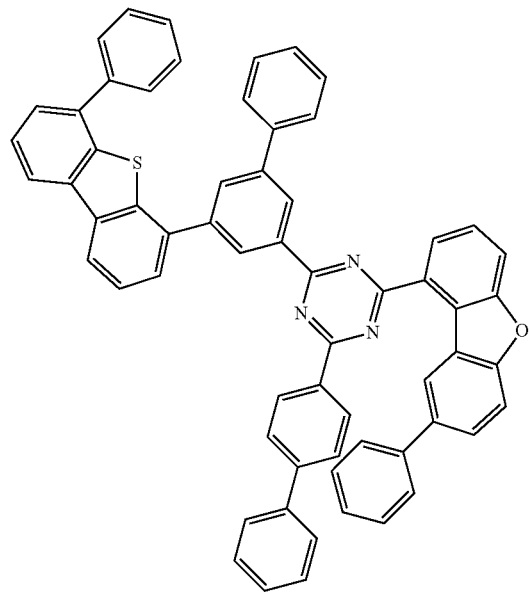
1-34
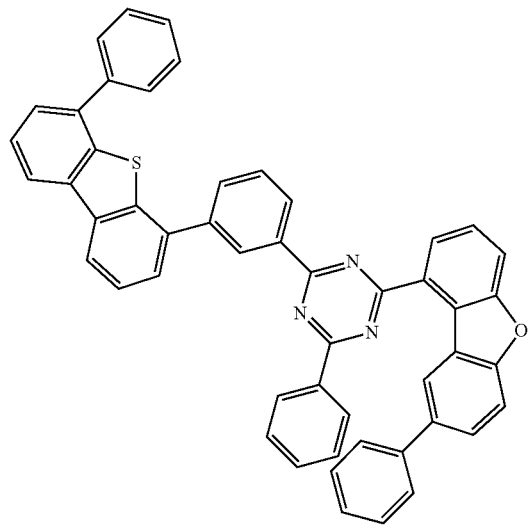
1-36
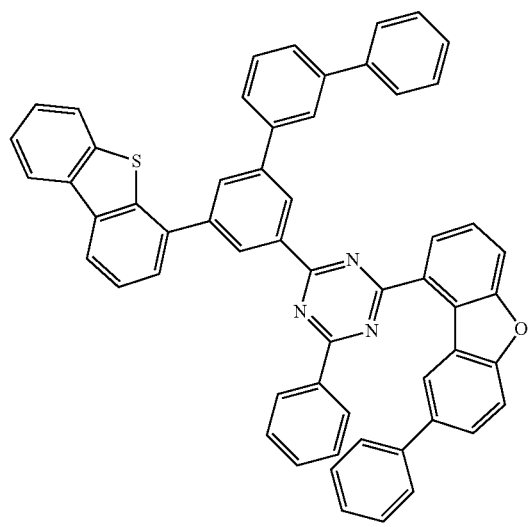

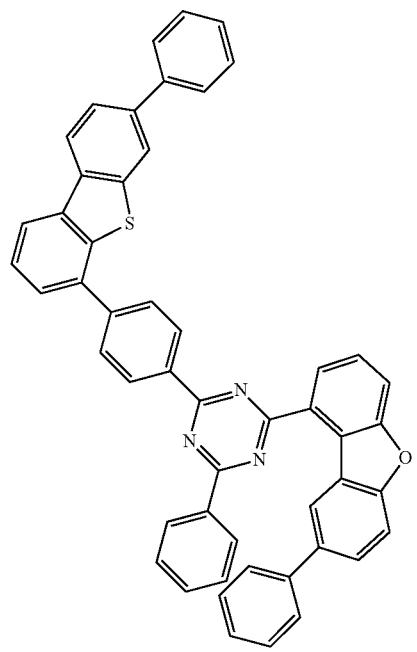
1-37
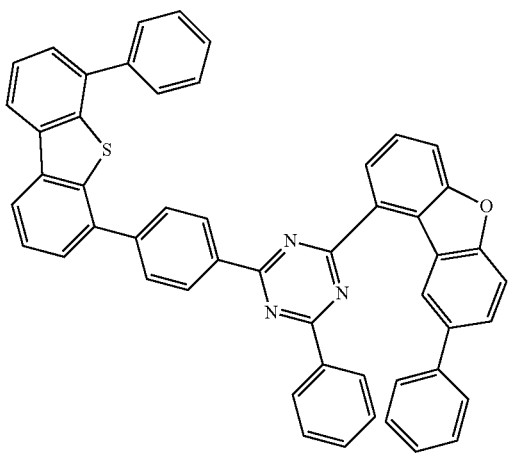
1-38
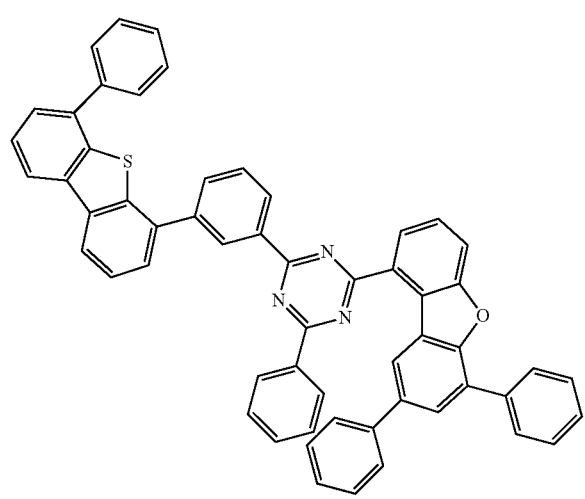
1-39

1-41
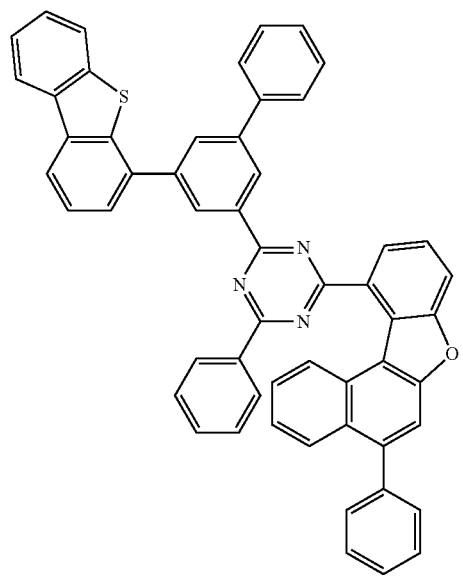
1-42
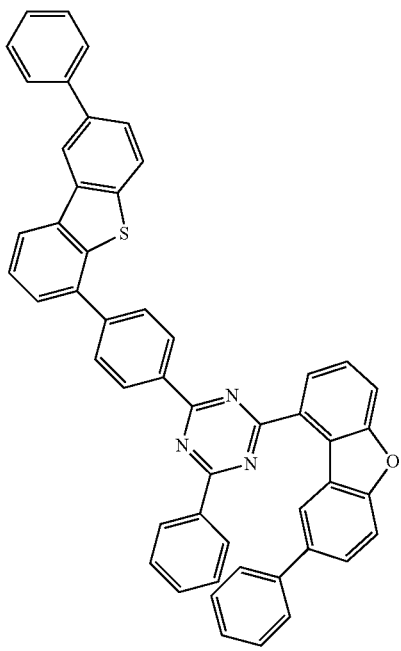
1-43
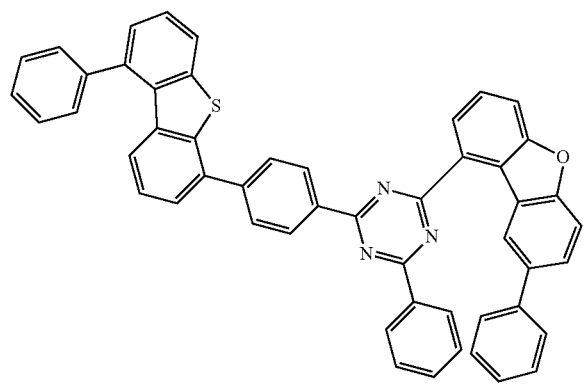
1-44
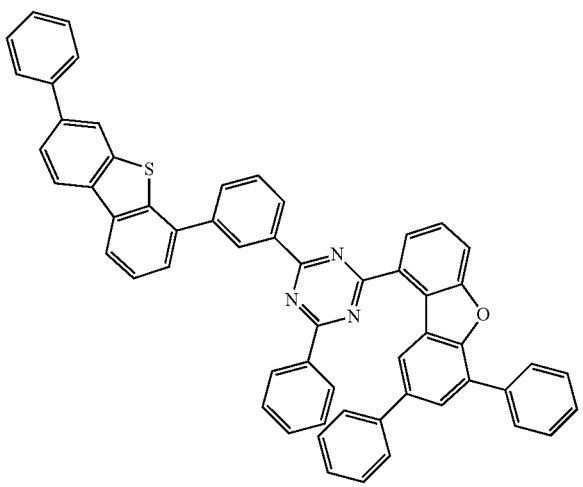
1-45
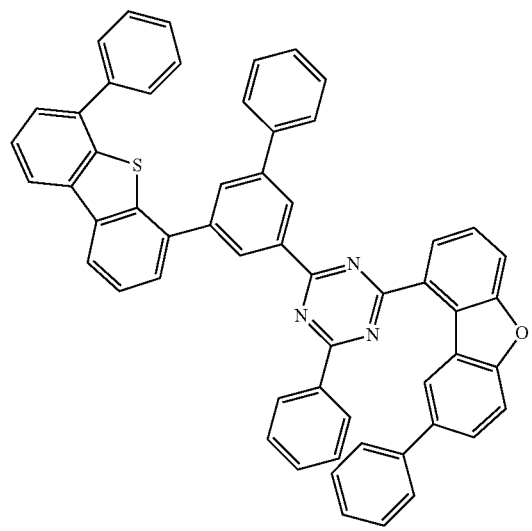
1-46
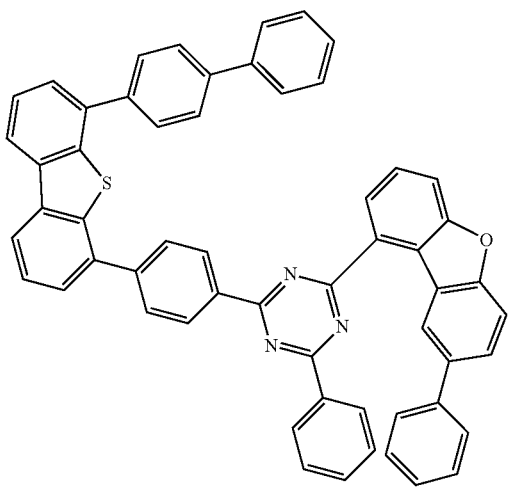

1-47
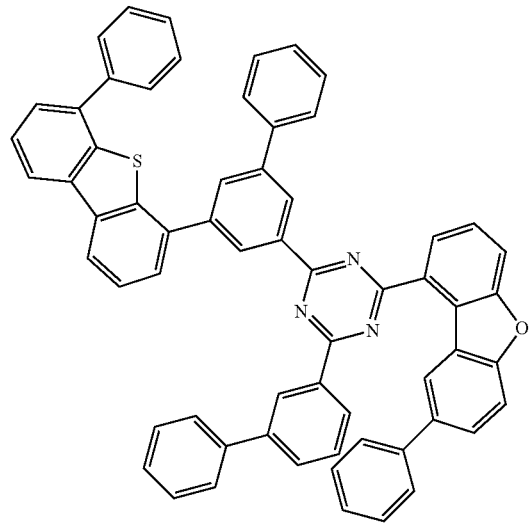
1-48
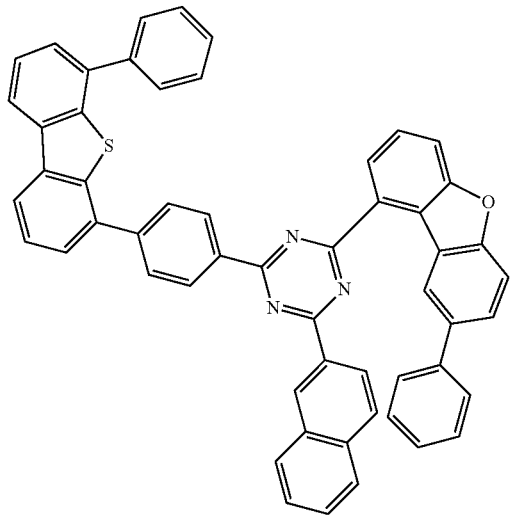
1-49
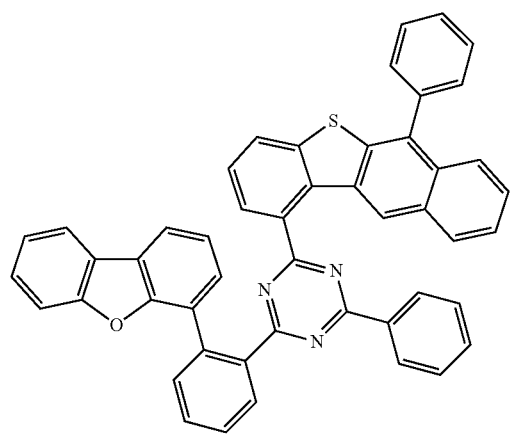
1-50
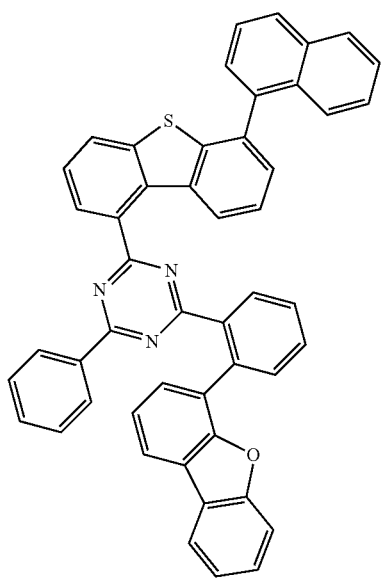

-continued
1-51
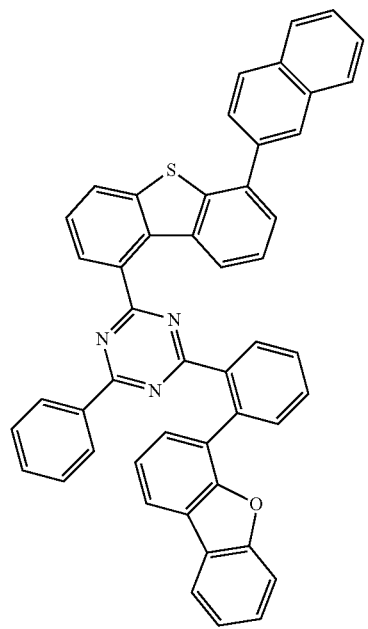
1-52
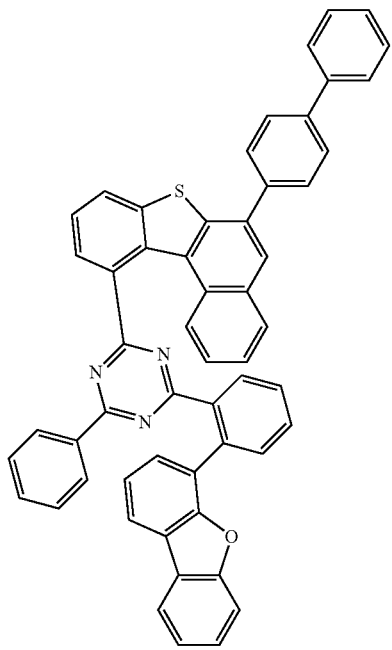
1-53
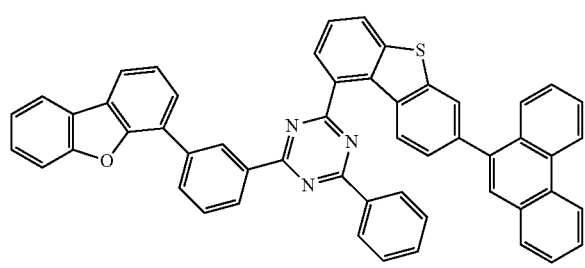
1-54
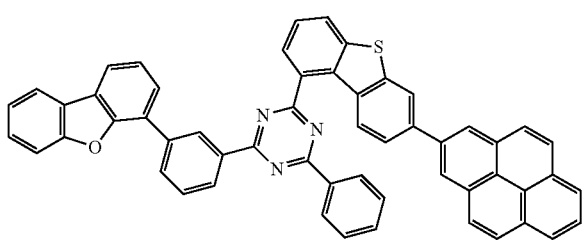
1-55
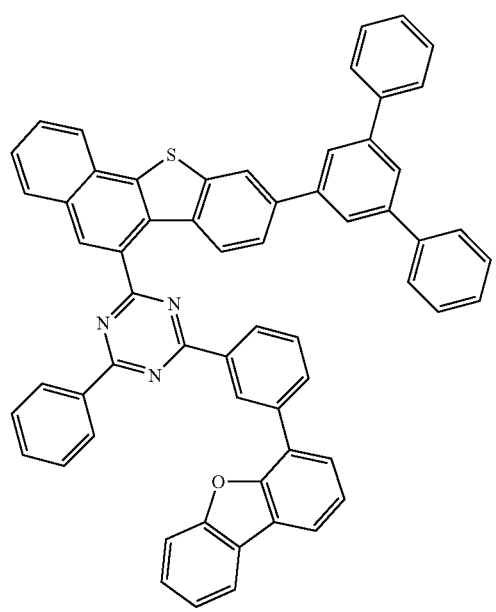

-continued
1-57
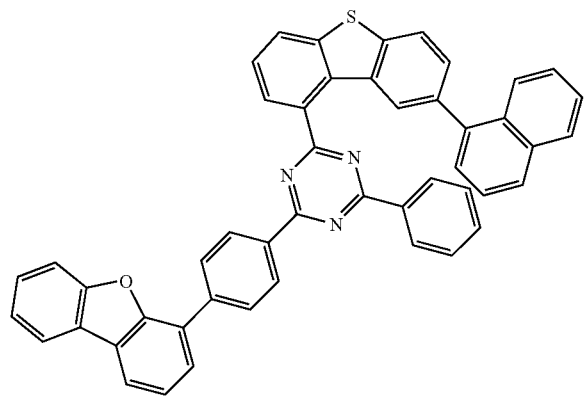
1-58
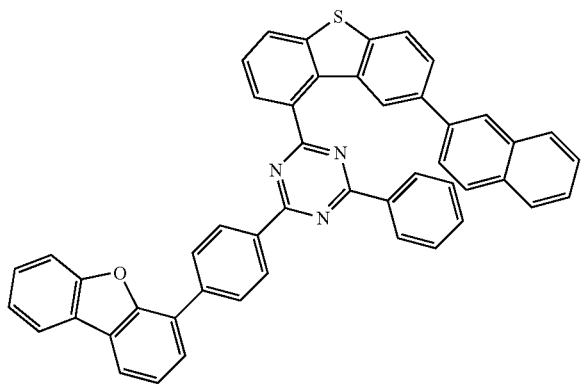
1-60
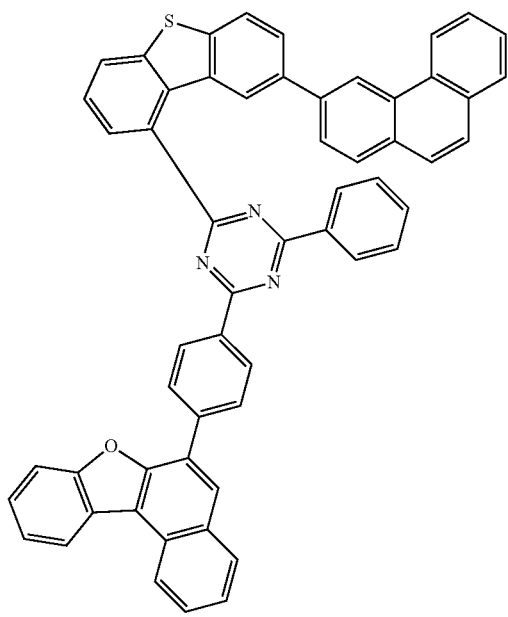
1-61
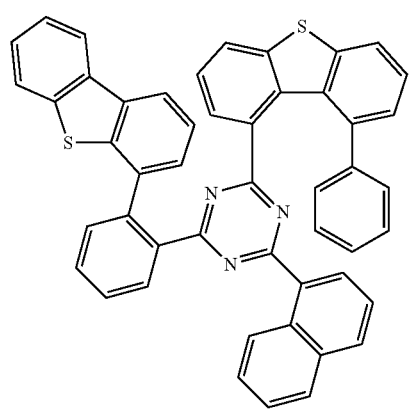
1-62
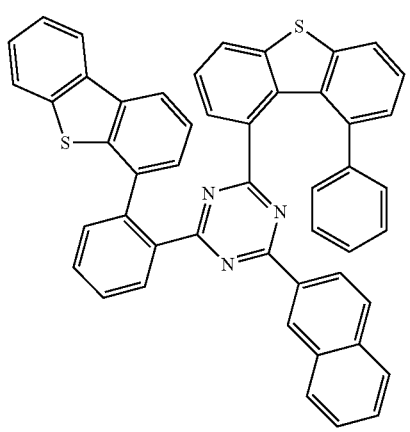

1-64
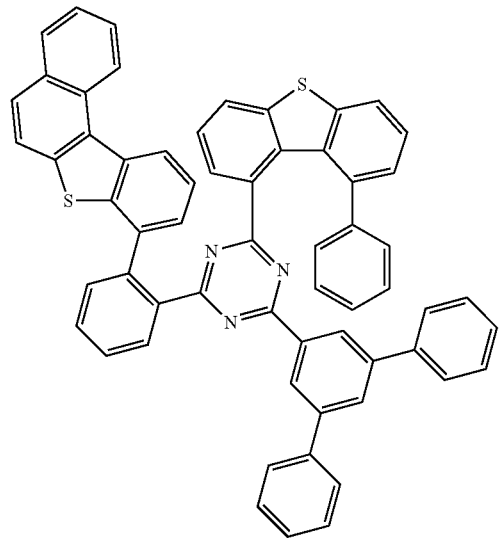
1-65
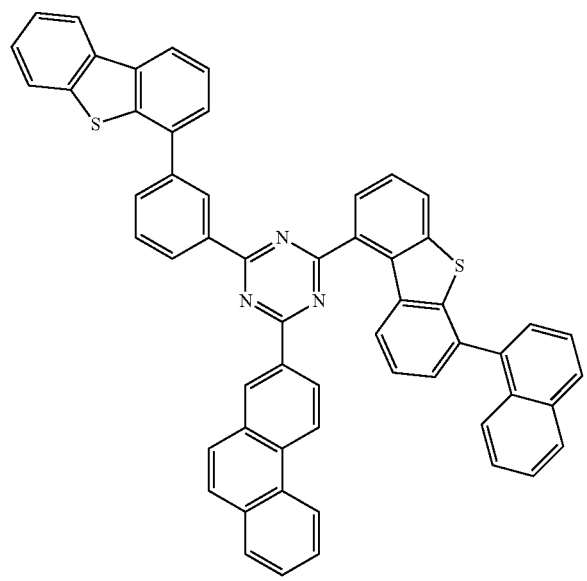
1-66
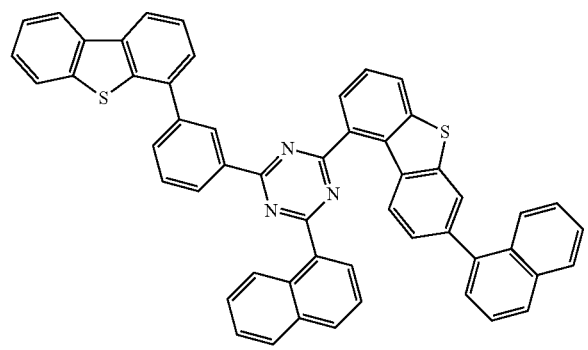

-continued
1-67
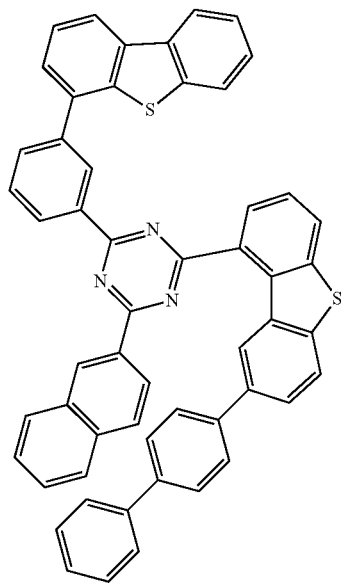
1-68
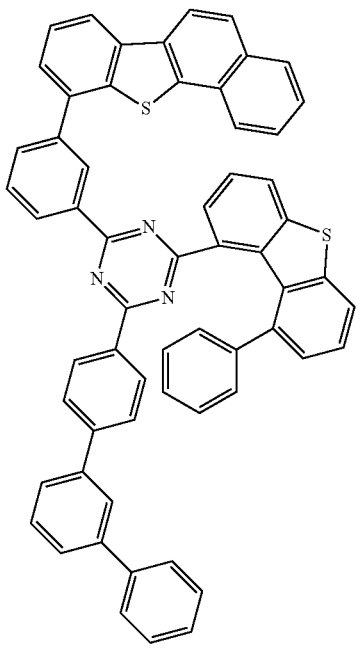
1-70
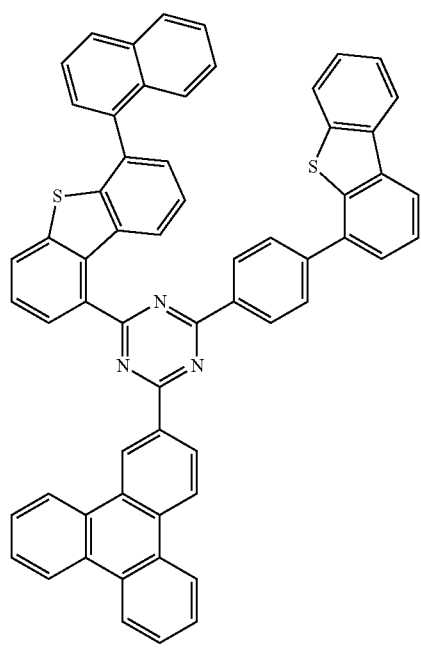

1-71
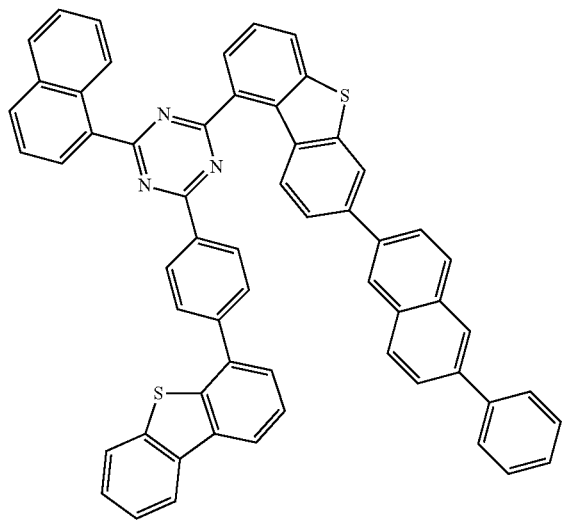
1-72
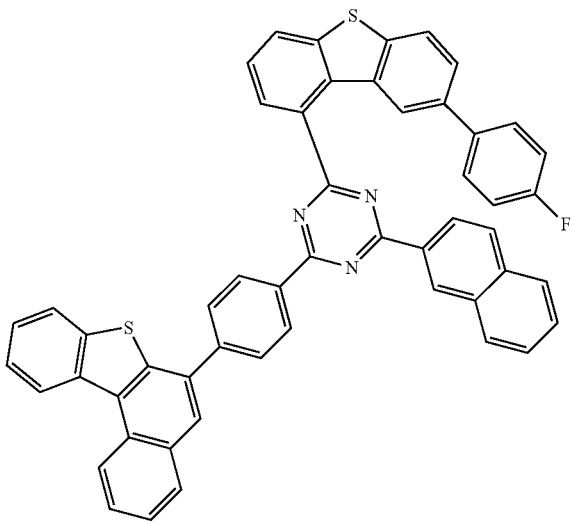
1-75
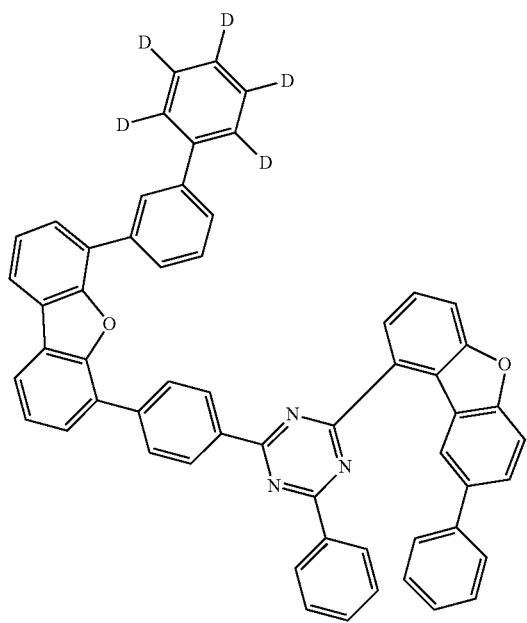
1-76
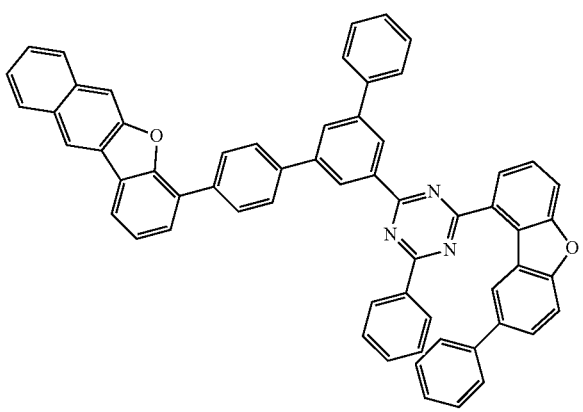

1-77
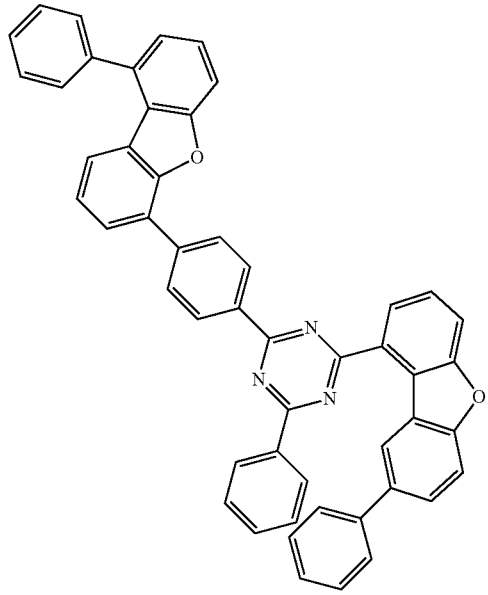
1-78
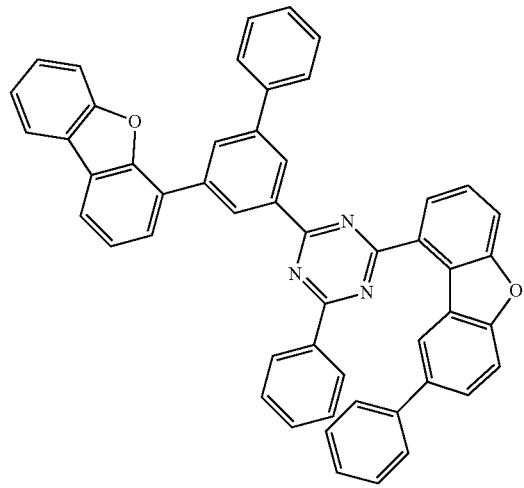
1-80
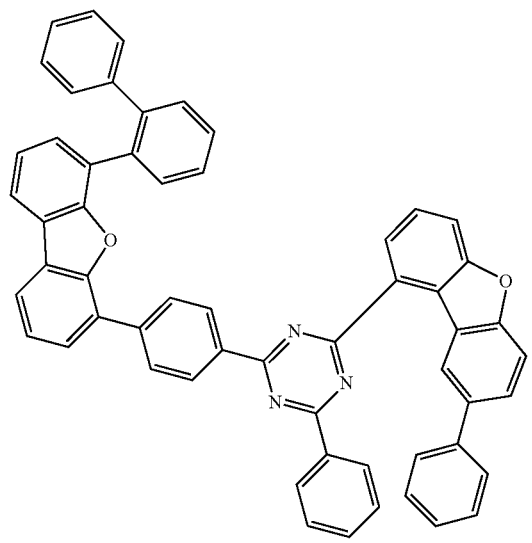

-continued
1-81
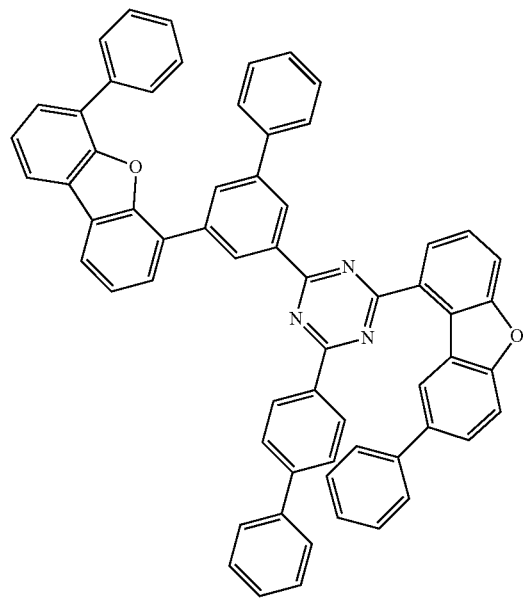
1-82
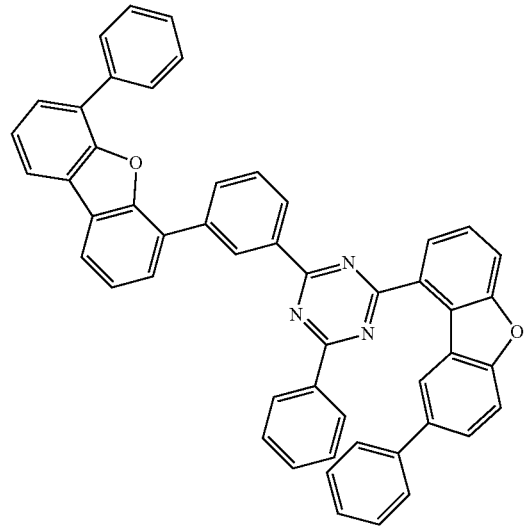
1-84
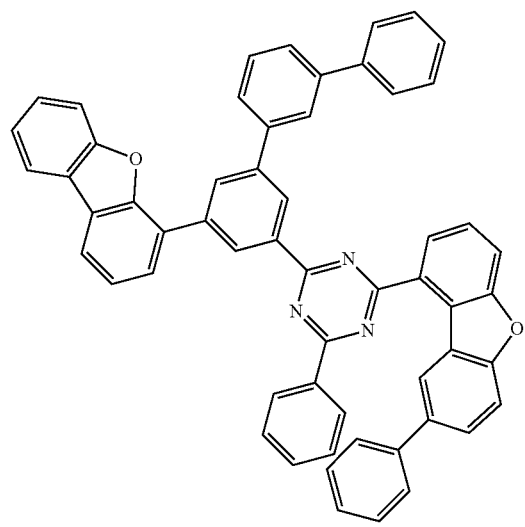
2-2
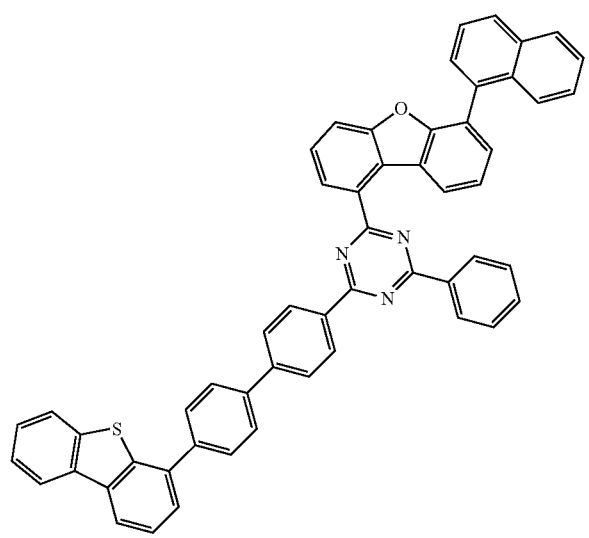

2-3
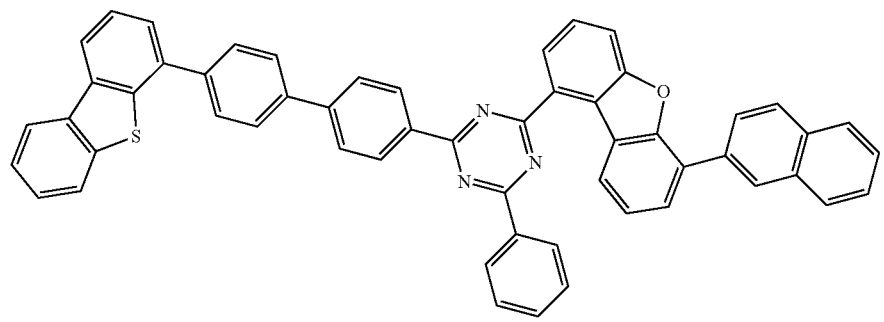
2-4
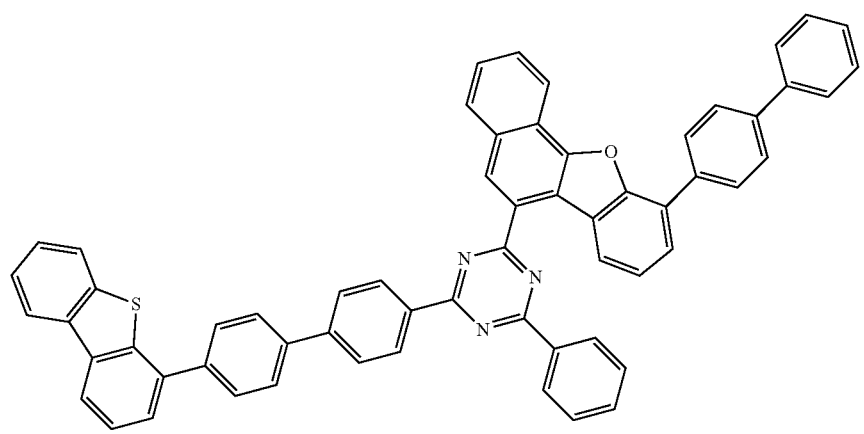
2-5
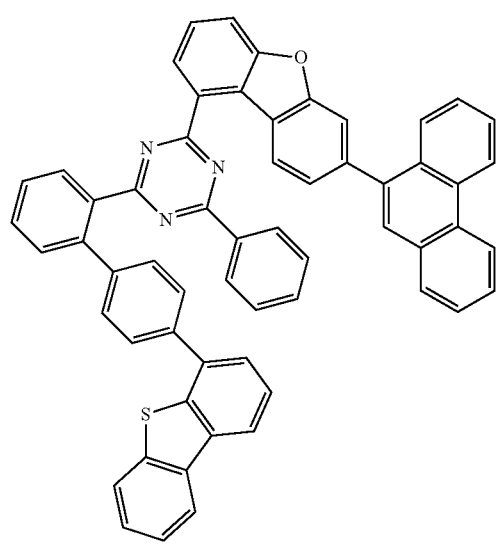
2-6
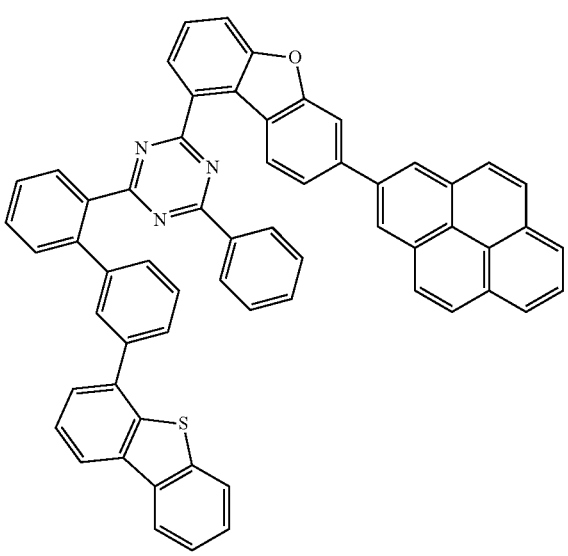

2-7
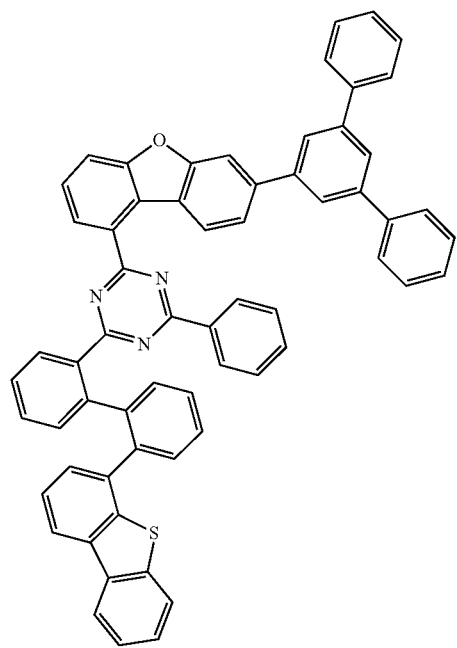
2-8
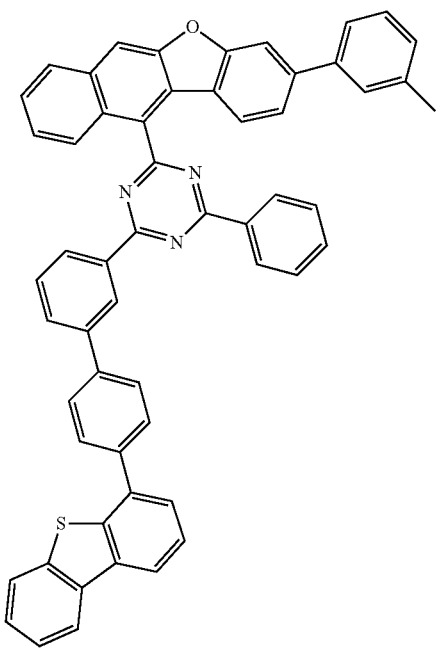
2-9
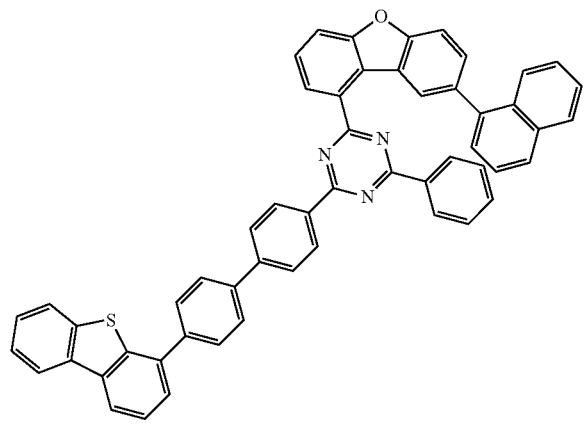
2-10
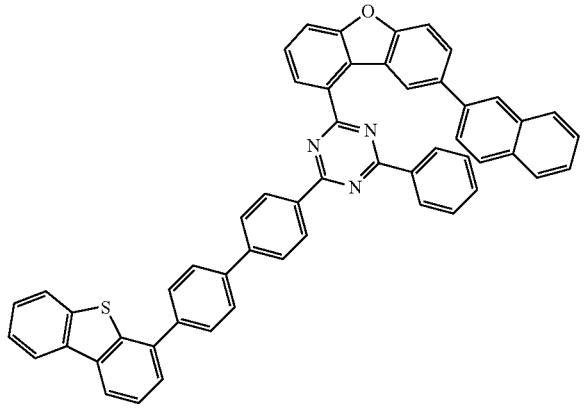
2-12
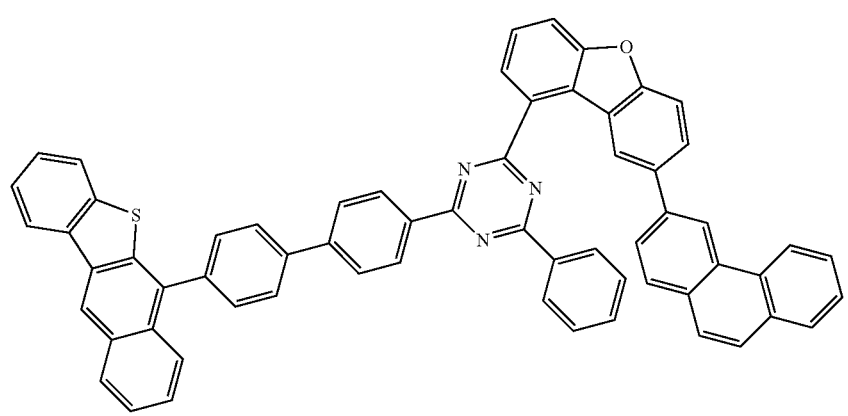

-continued
247
2-13
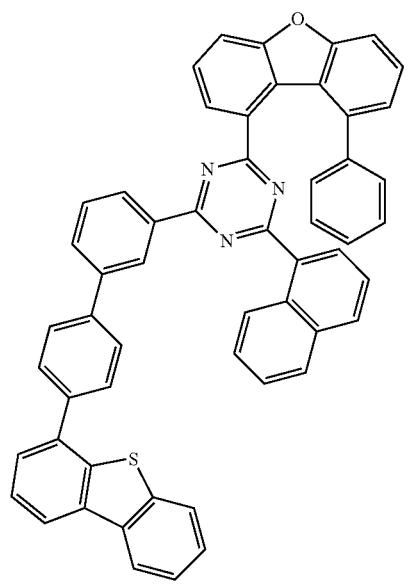
248
2-14
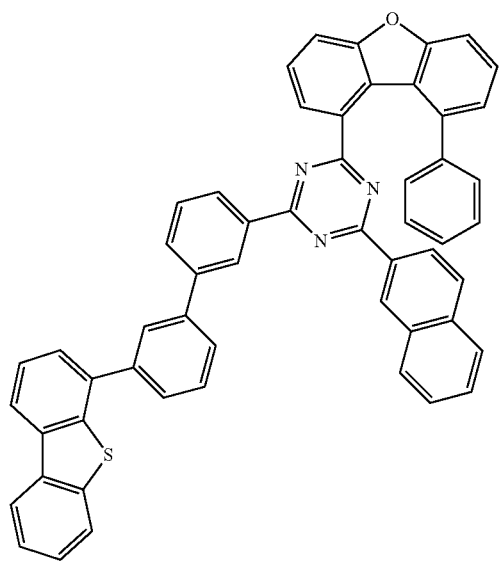
2-16
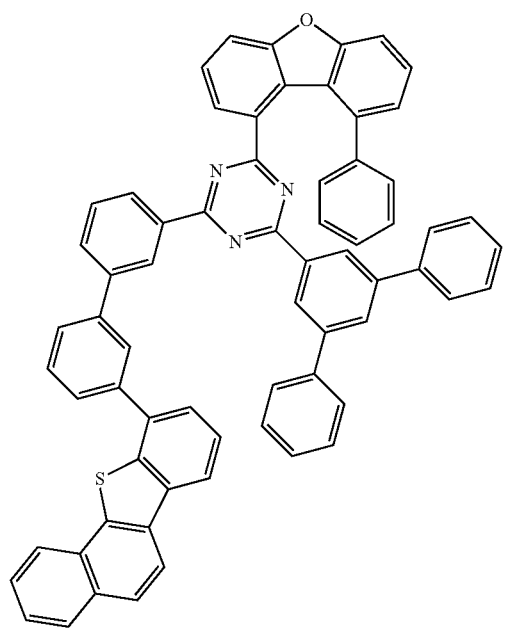
2-17
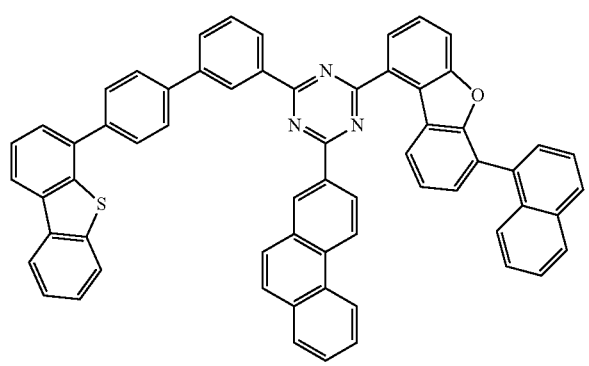
2-18
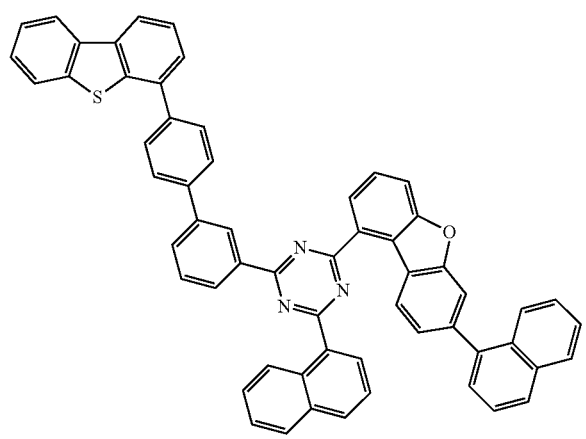

-continued
2-20
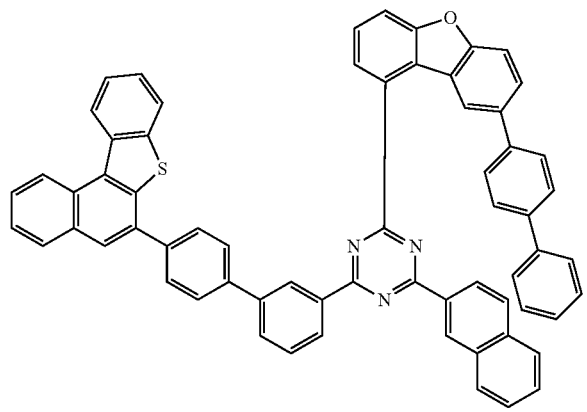
2-22
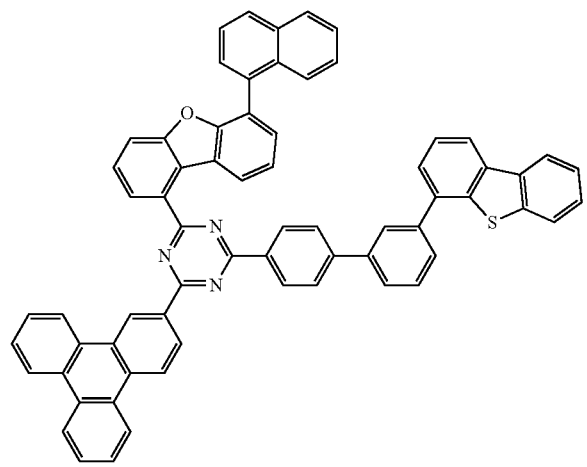
2-23
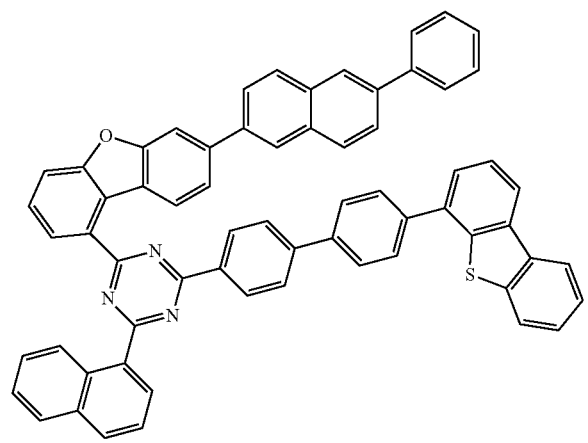
2-24
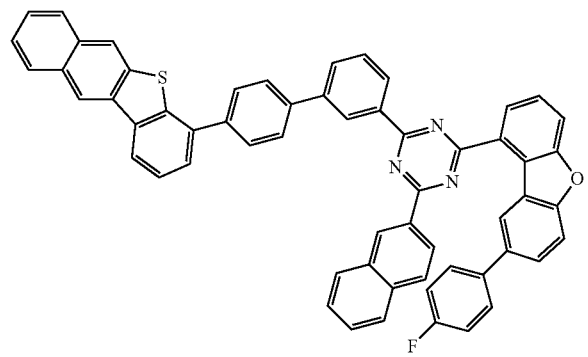

2-27
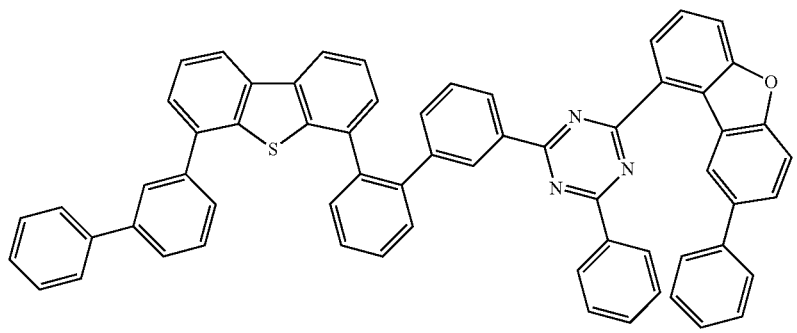
2-28
2-29
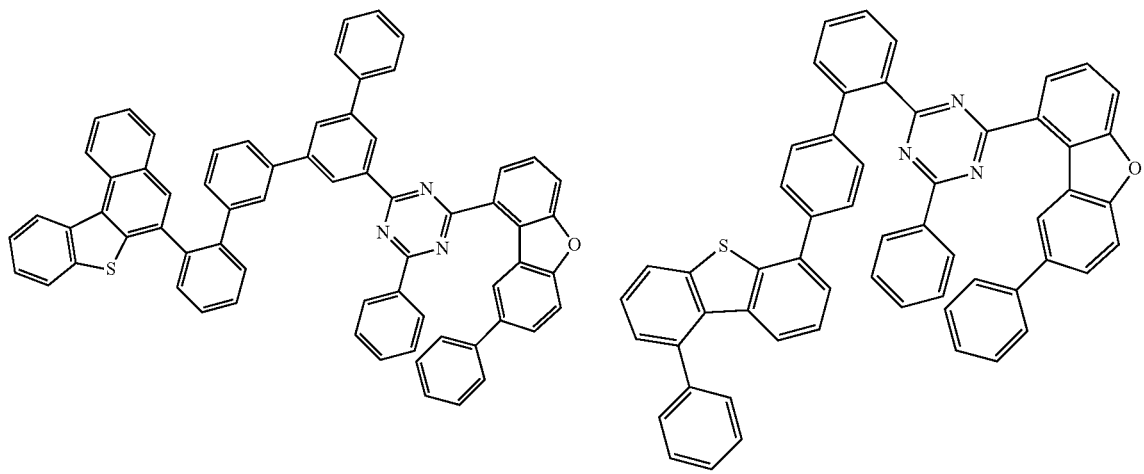
2-30
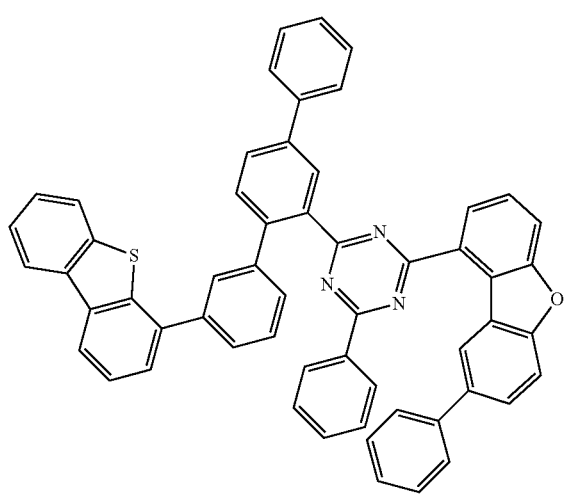

-continued
2-32
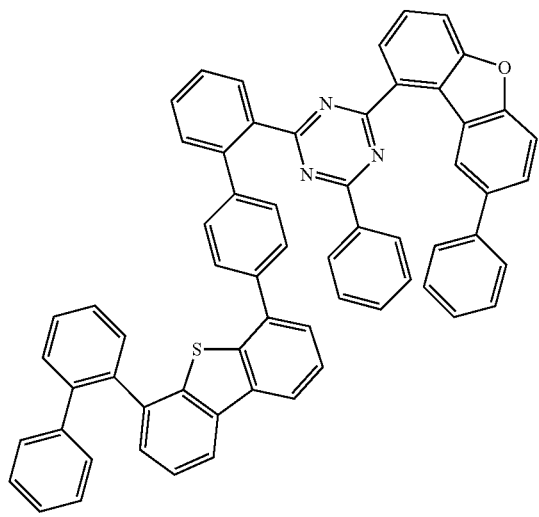
2-33
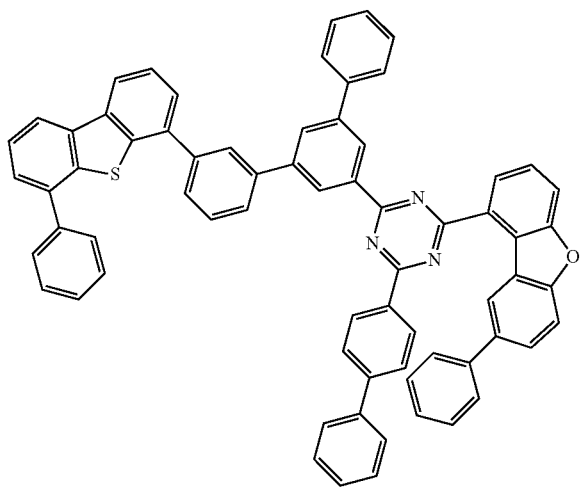
2-34
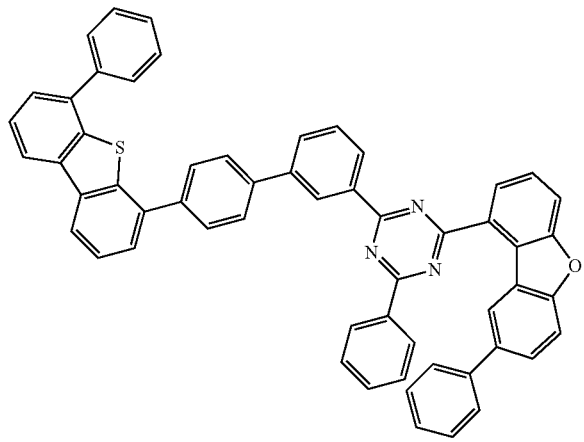
2-36
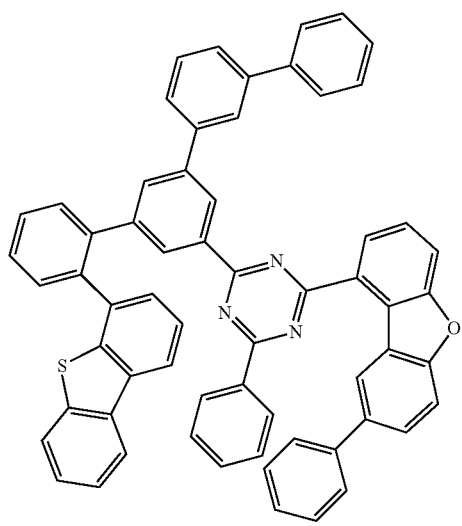

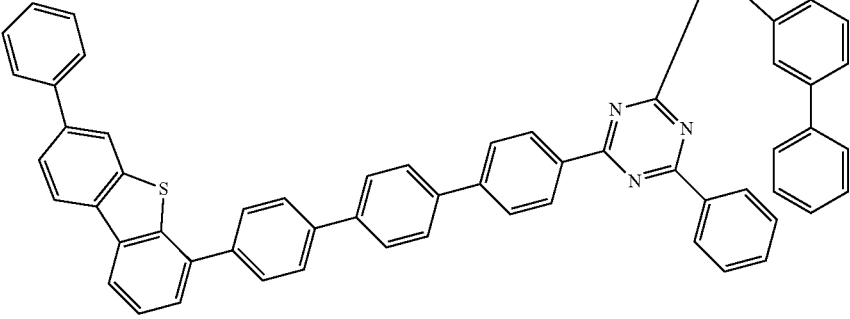
2-37
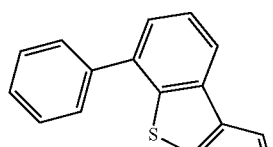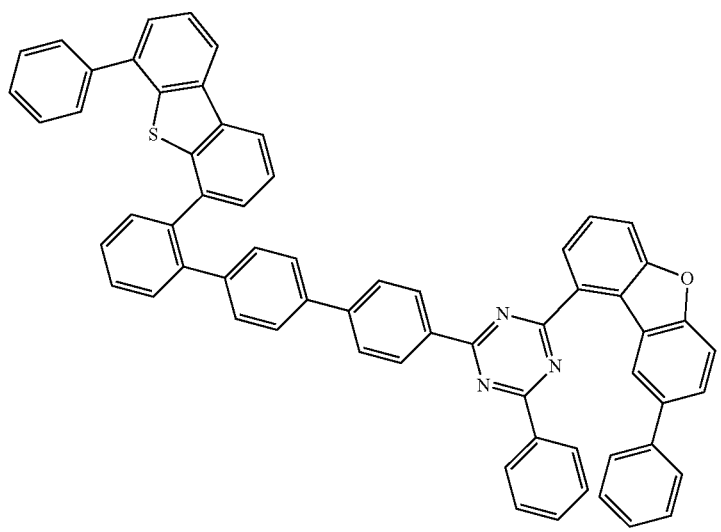
2-38
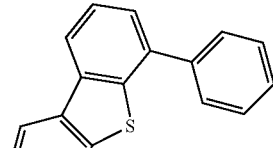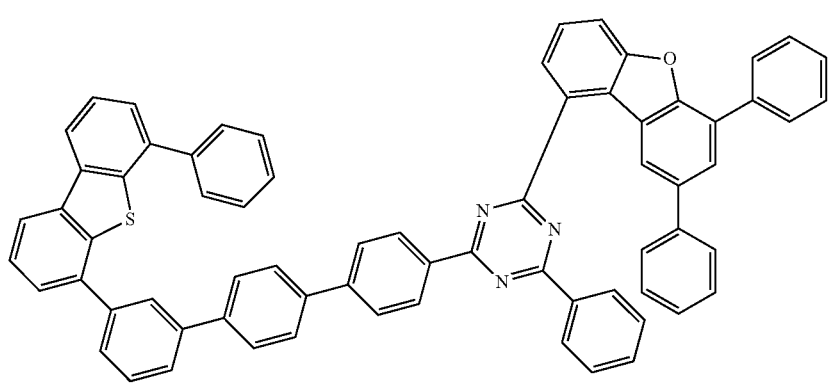
2-39

2-40

2-41

2-42

2-43
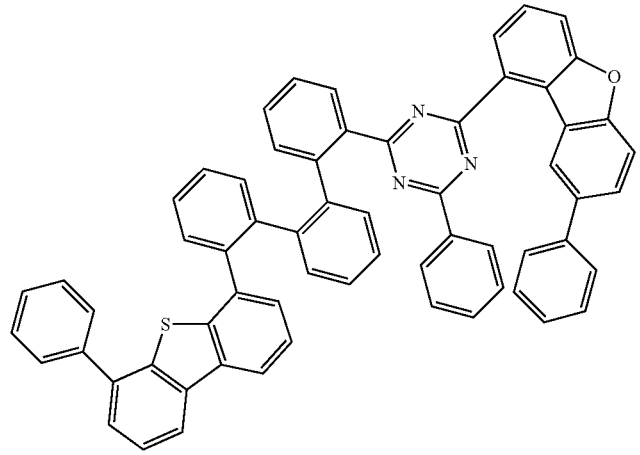
2-44
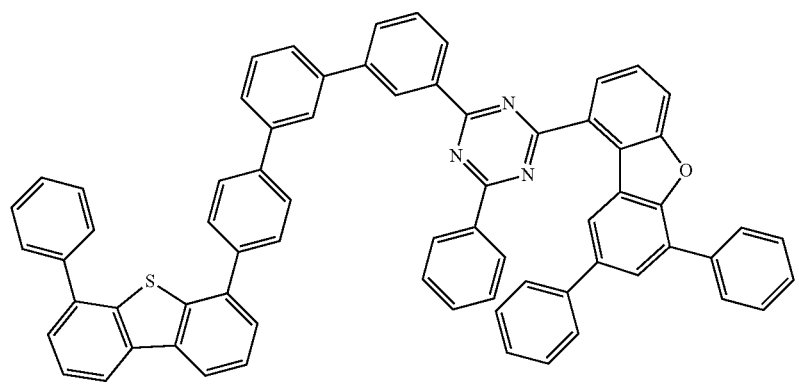
2-45 2-46
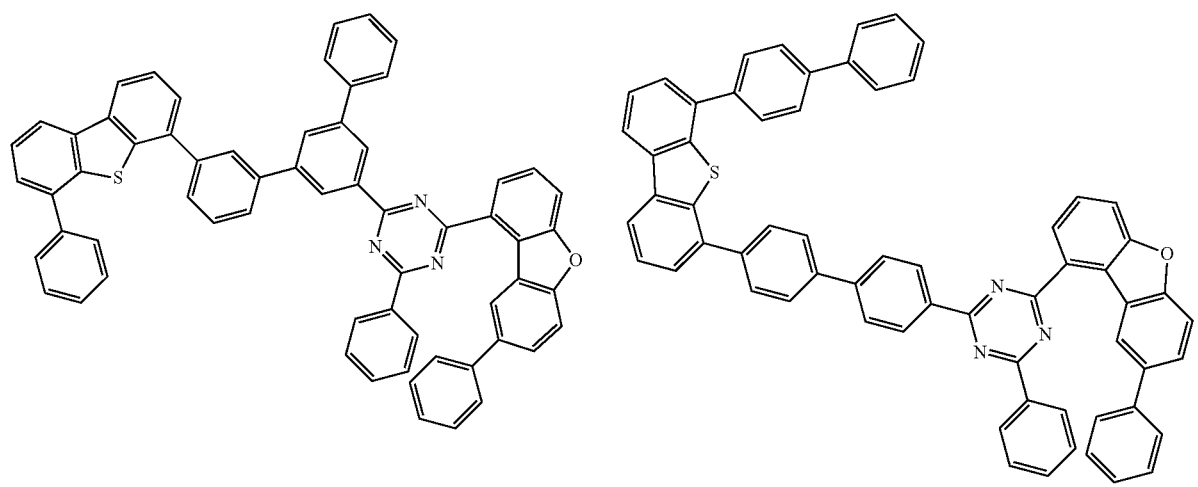

-continued
2-47
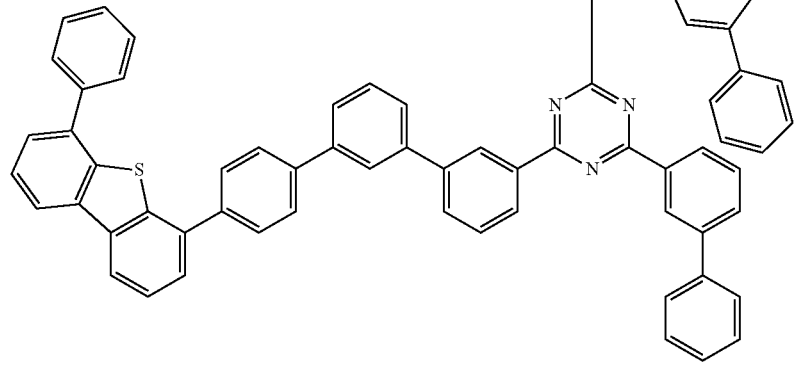
2-48
2-49
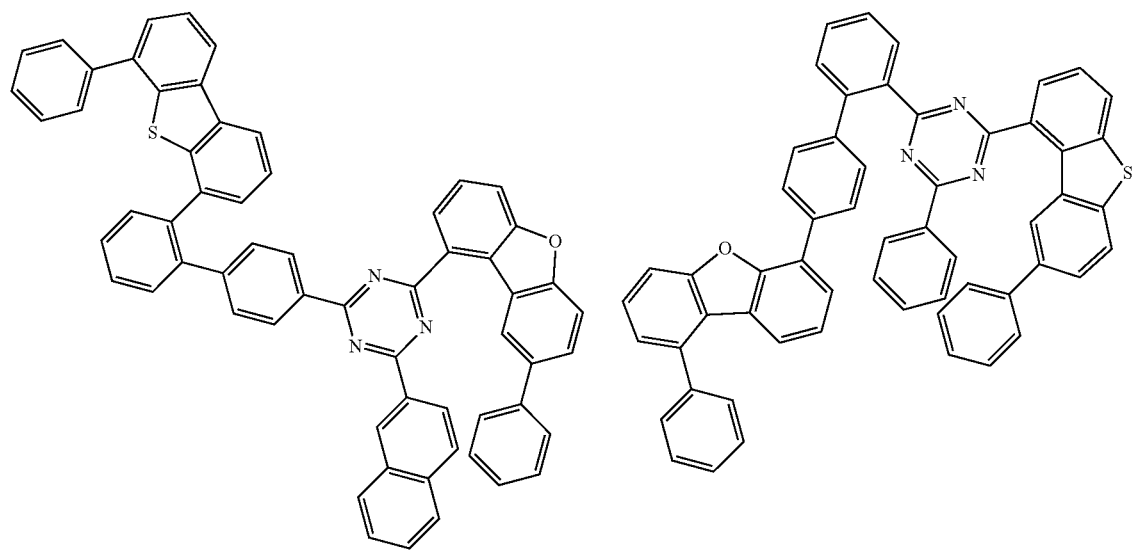
2-50
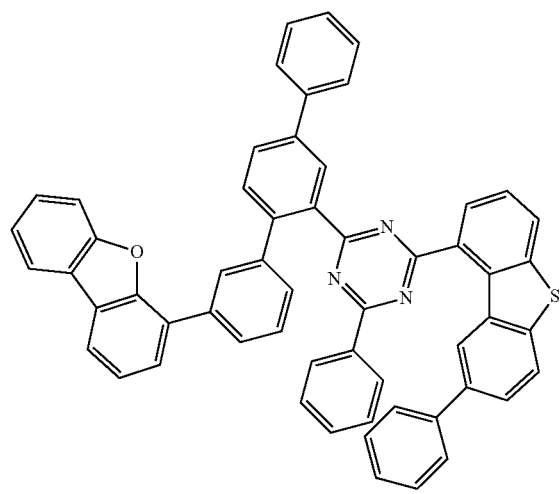

2-52
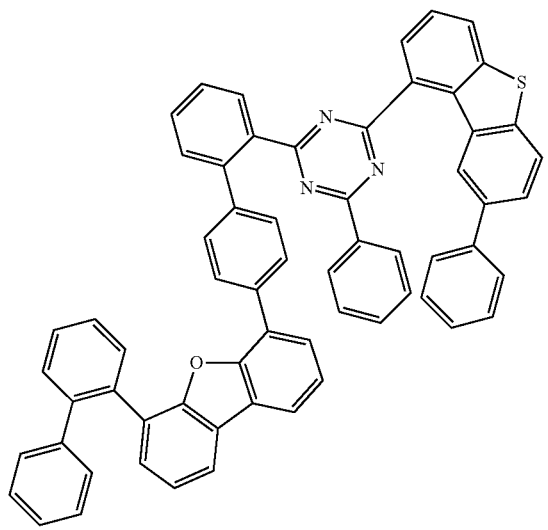
2-53
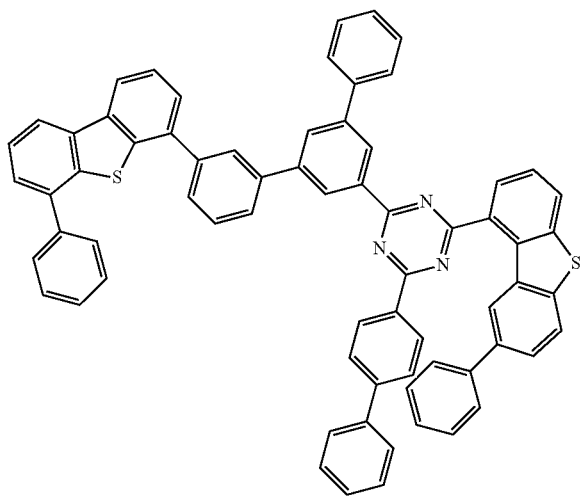
2-54
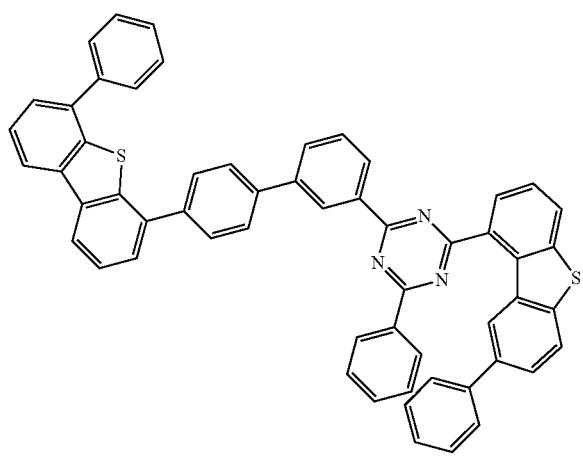
2-56
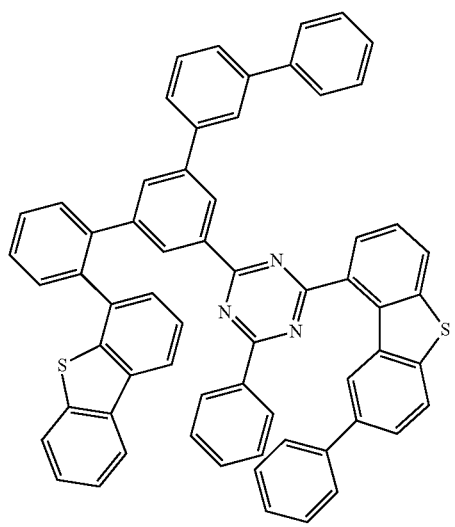

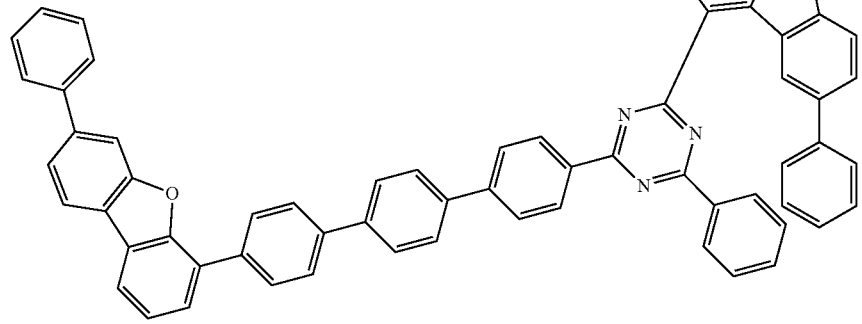
2-57
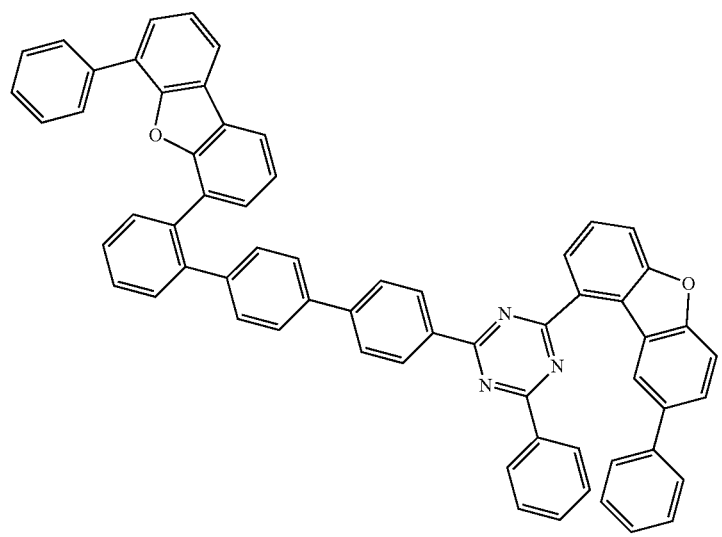
2-58
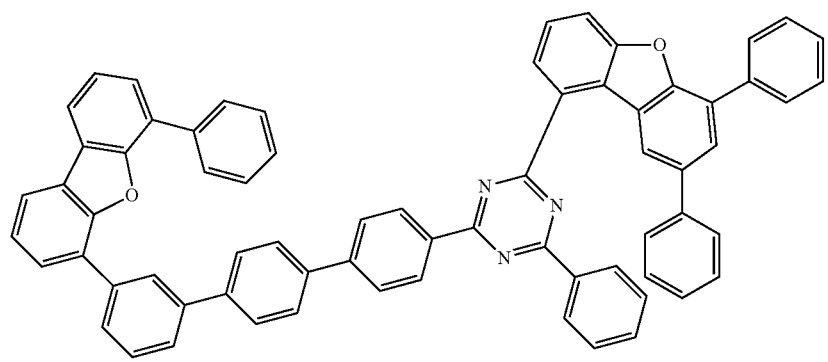
2-59

-continued
2-60
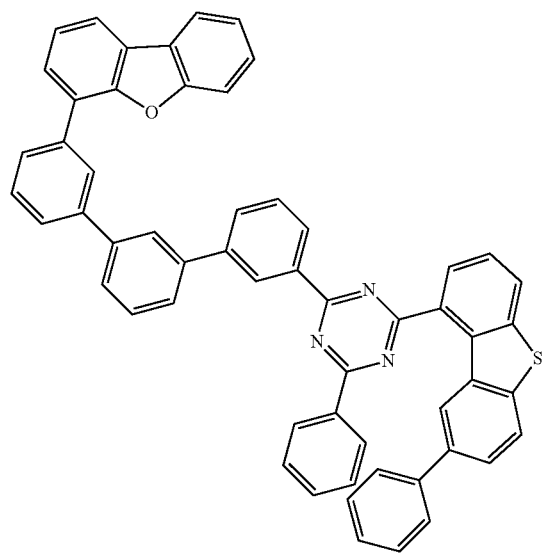
3-1
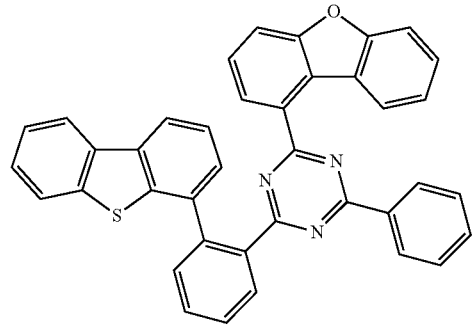
3-2
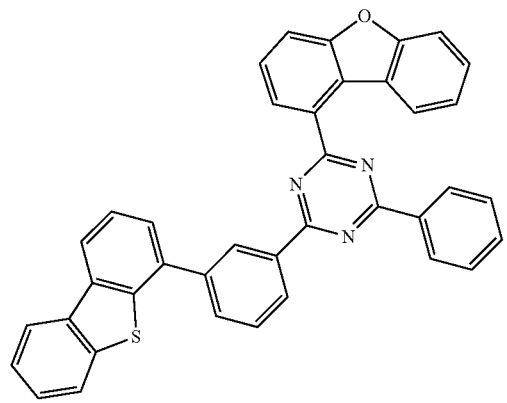
3-3
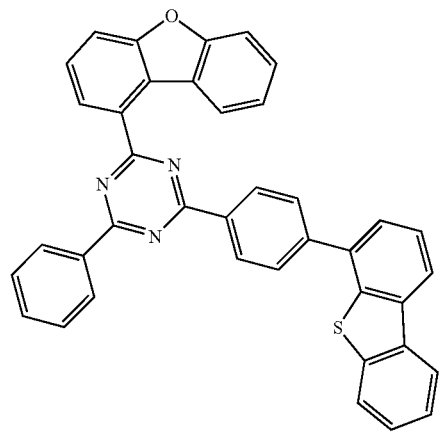
3-4
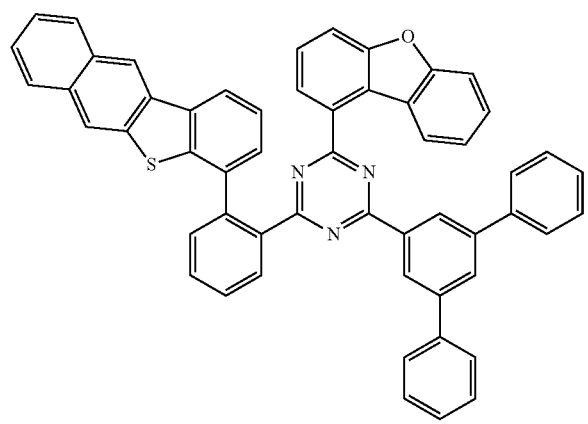
3-5
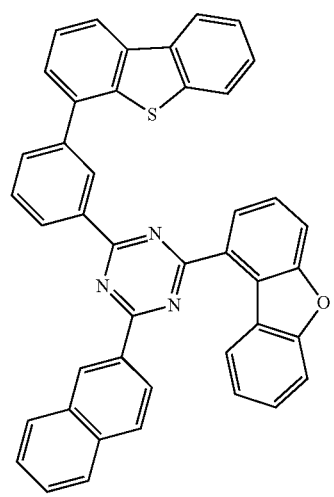

-continued
3-6
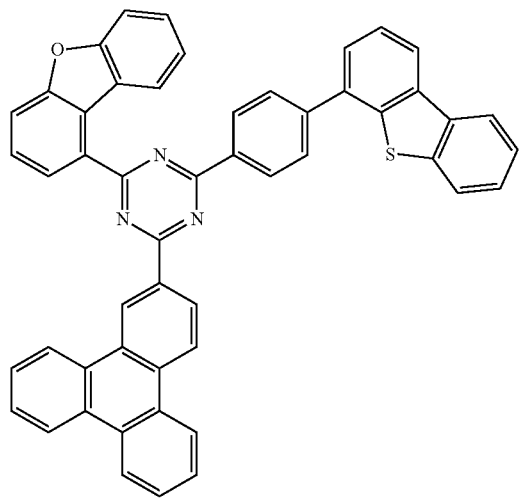
3-7
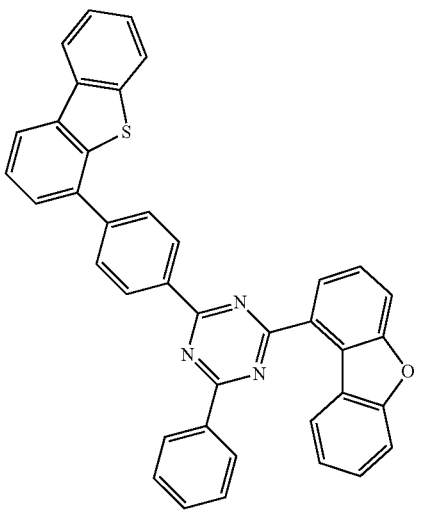
3-8
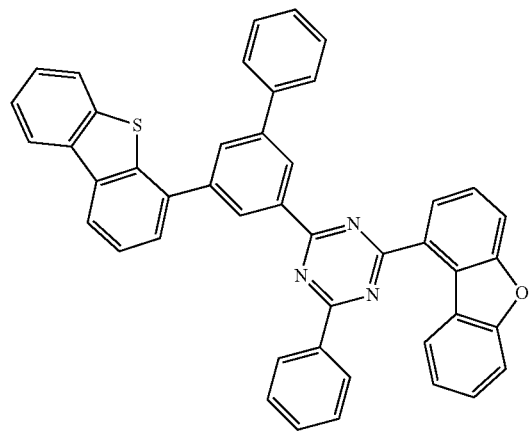
3-9
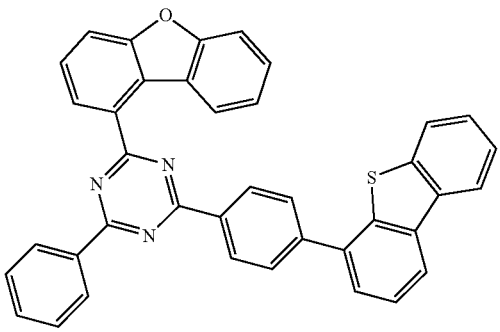
3-10
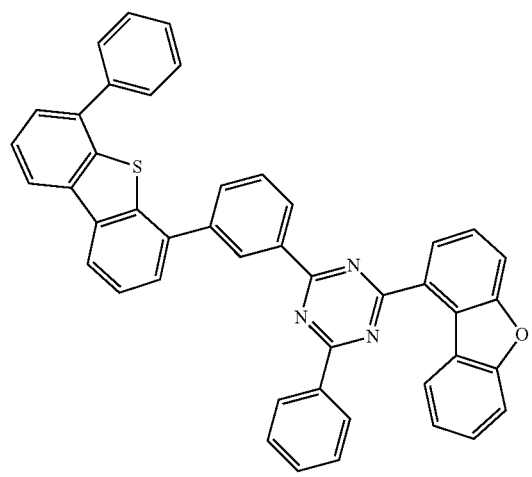
3-11
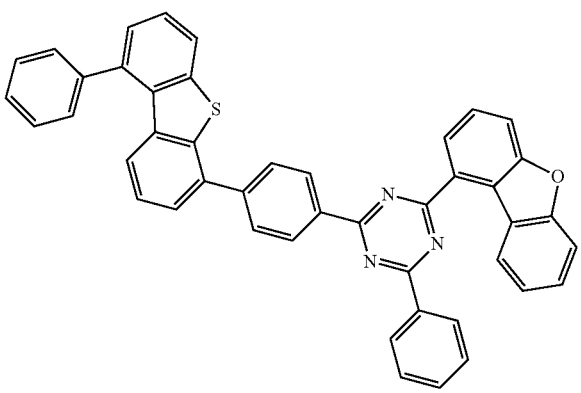

-continued
3-12
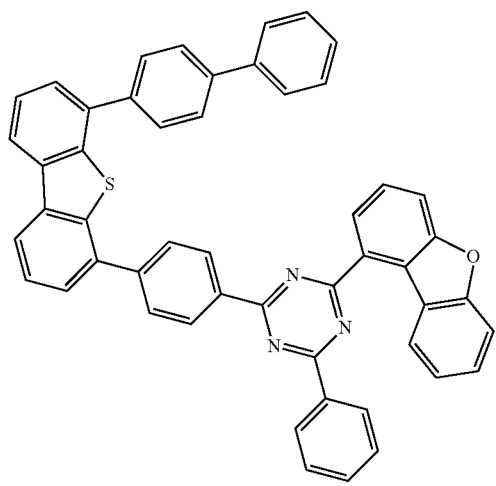
3-13
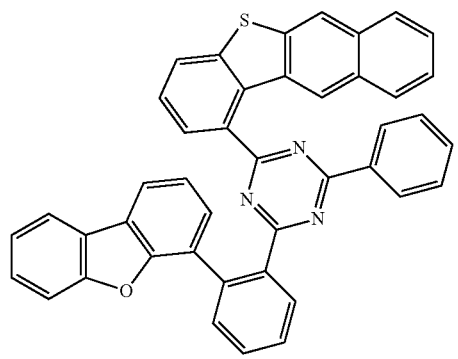
3-14
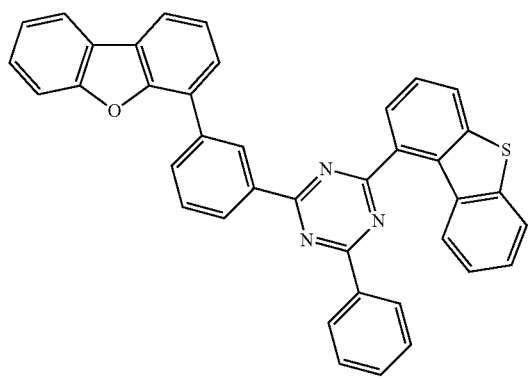
3-15
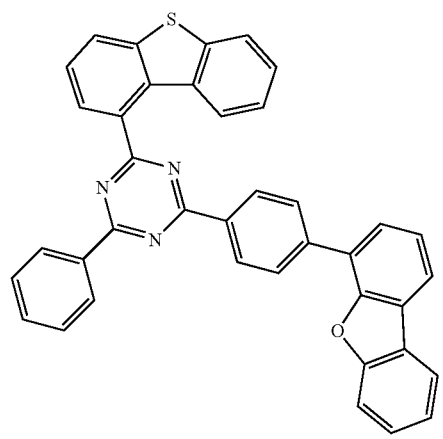
3-16
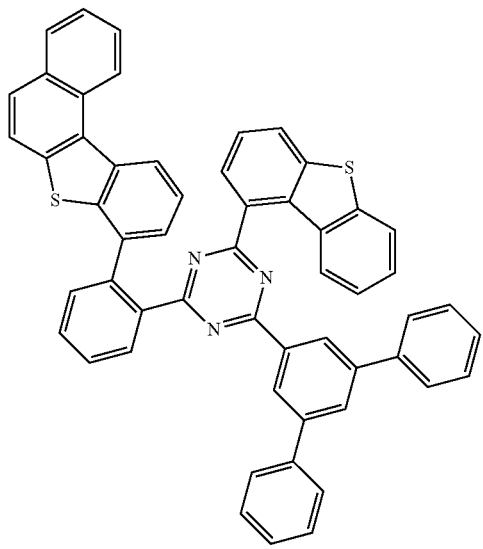
3-17
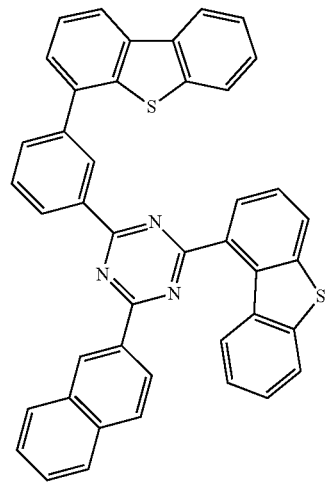

-continued
3-18
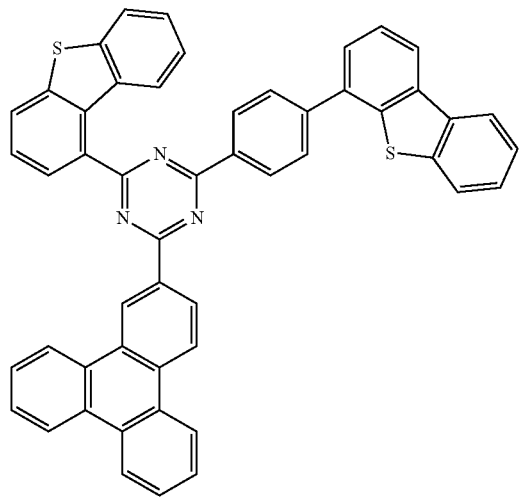
3-19
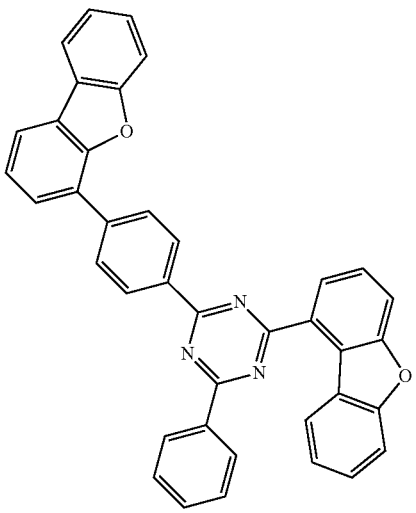
3-20
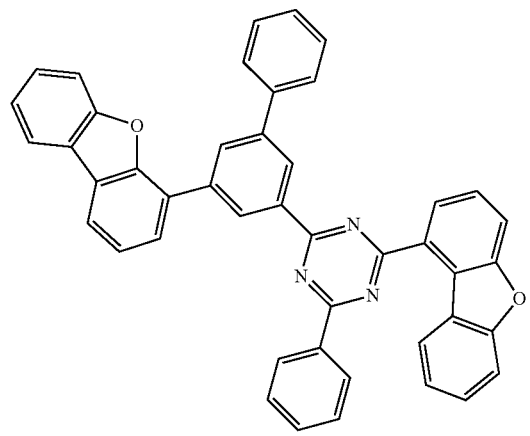
3-21
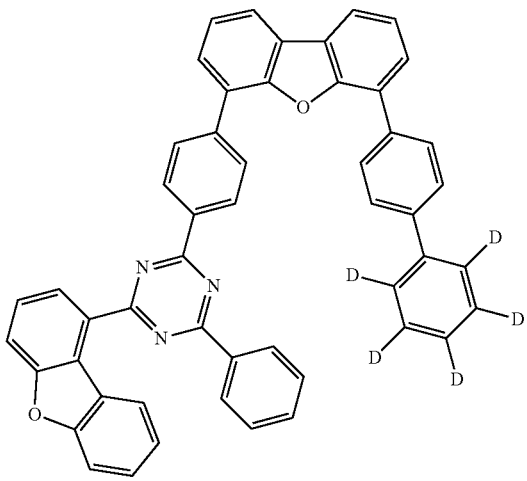
3-22
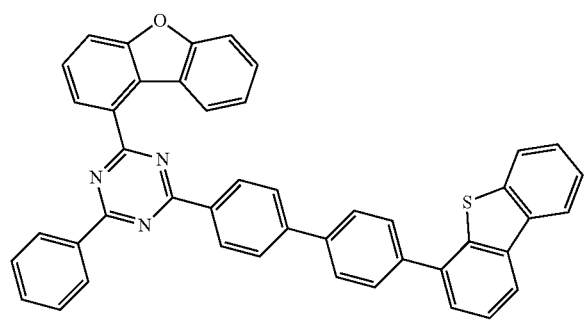
3-23
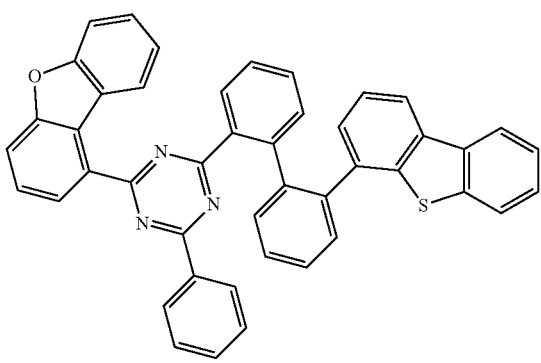

-continued
3-24
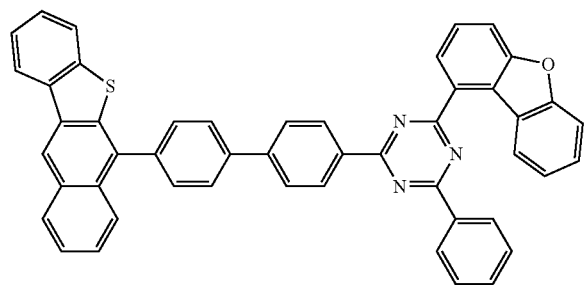
3-25
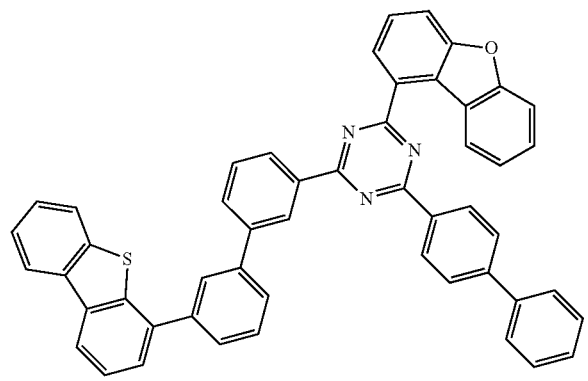
3-26
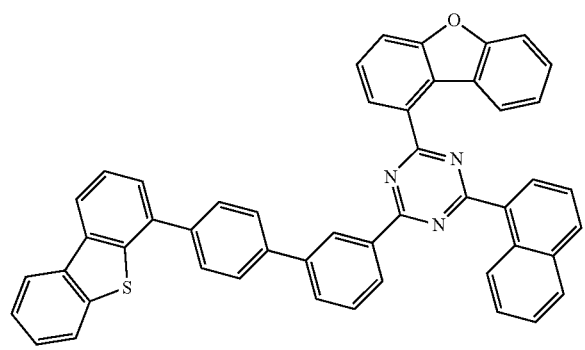
3-27
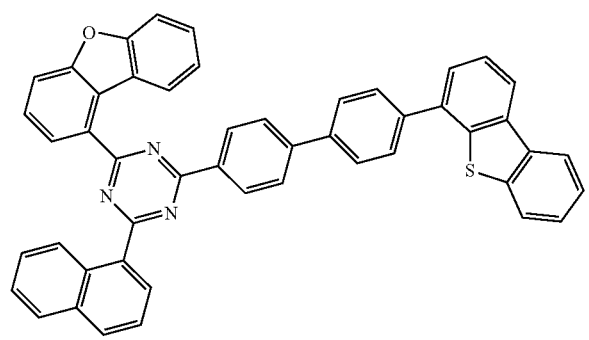
3-28
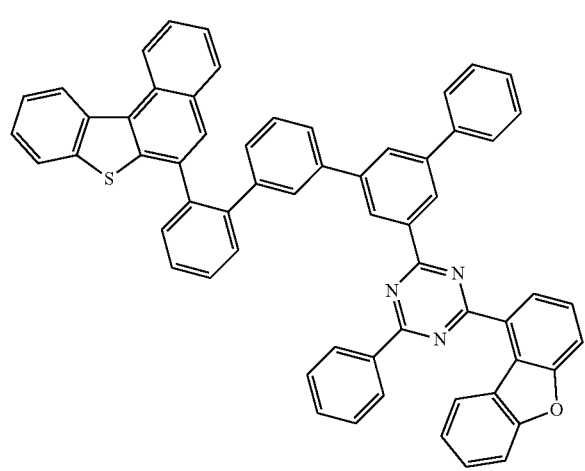
3-29
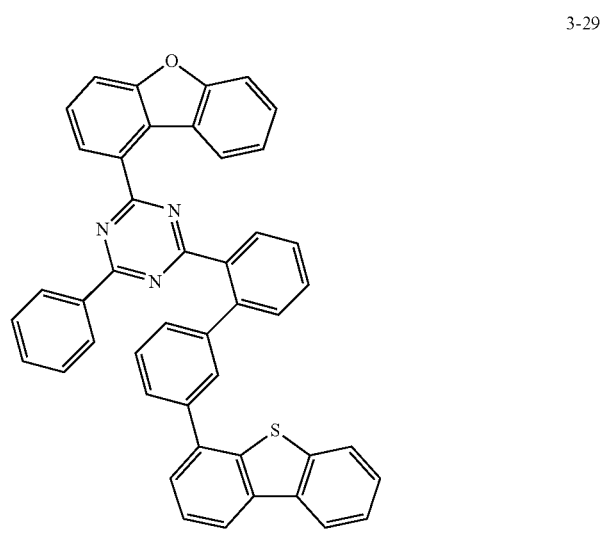

3-30
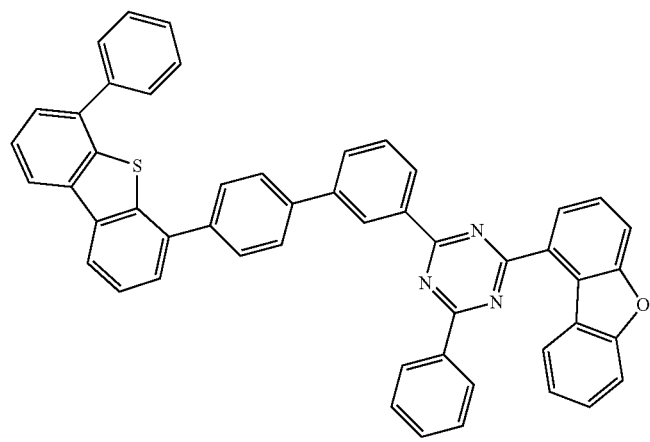
3-31
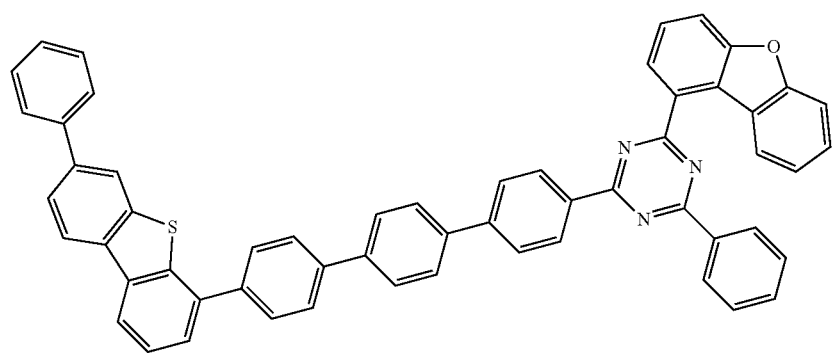
3-32
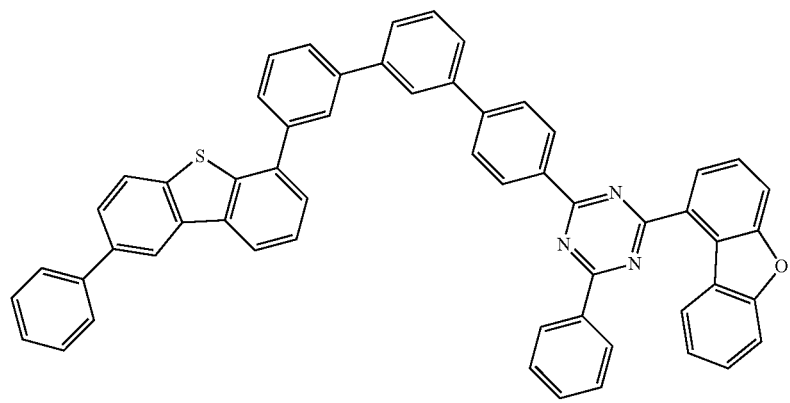

3-33
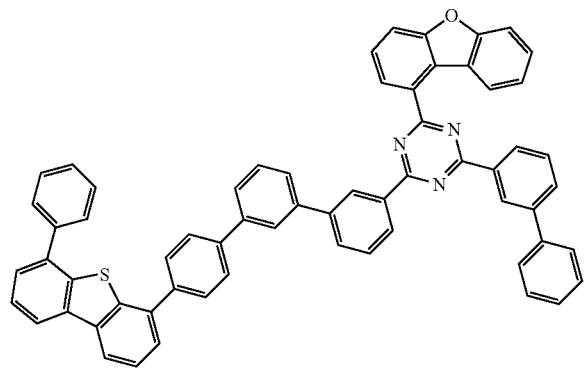
3-34
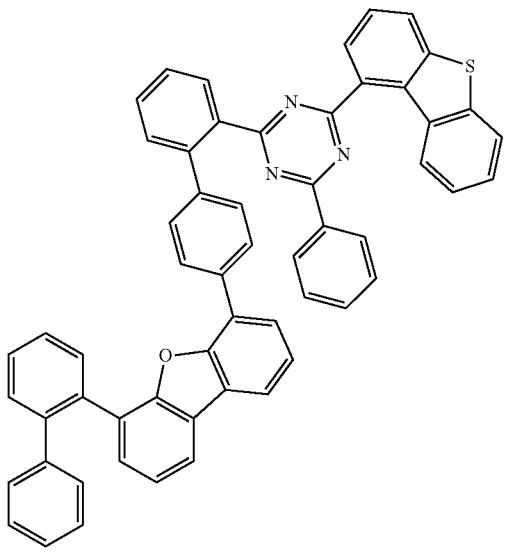
3-35
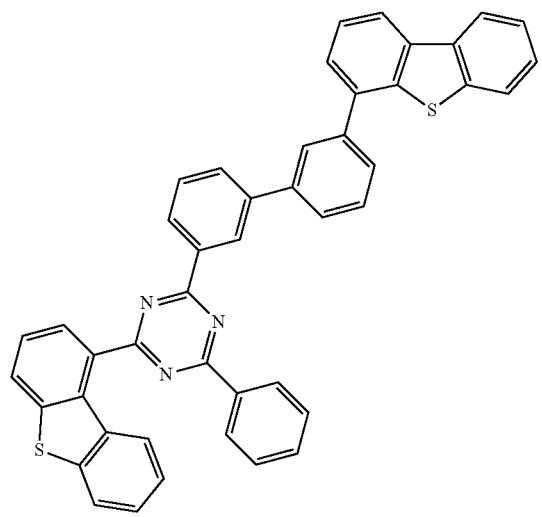
3-36
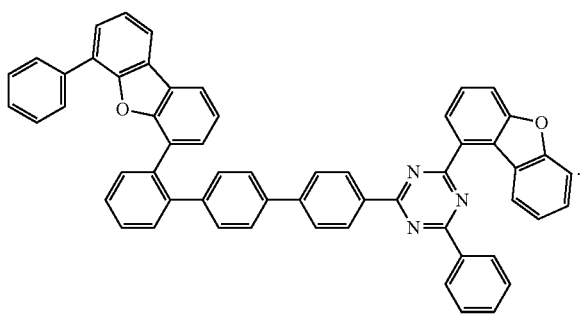

11. An organic electric element comprising a first electrode, a second electrode, and an organic material layer formed between the first electrode and the second electrode, wherein the organic material layer comprises a single compound or two or more compounds represented by the Formula 1 of claim 1.

12. The organic electric element of claim 11, wherein the organic material layer comprises at least one layer of a hole injection layer, a hole transport layer, an emission-auxiliary layer, a light emitting layer, an electron transport auxiliary layer, an electron transport layer and an electron injection layer.

13. The organic electric element of claim 12, wherein the compound is comprised in the light emitting layer.

14. An organic electric element comprising a first electrode, a second electrode, and an organic material layer formed between the first electrode and the second electrode, wherein the organic material layer comprises a light emitting layer, and the light emitting layer comprise a compound represented by Formula 1 and a compound represented by Formula 15:

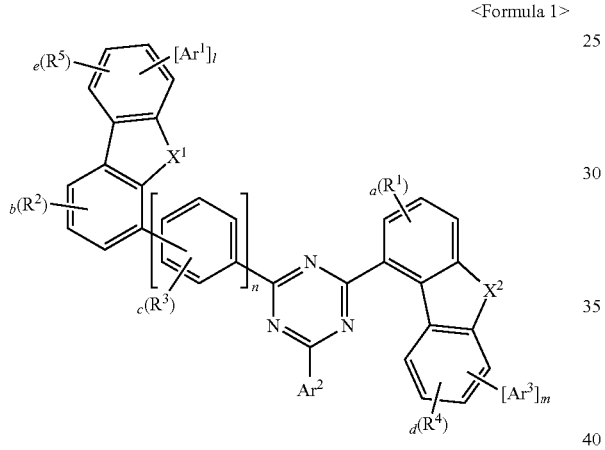

<Formula 1> wherein:
$X^1$ and $X^2$ are each independently O or S,
$Ar^1$ to $Ar^3$ are each independently a $C_6$-$C_{60}$ aryl group,
$R^1$ to $R^5$ are each independently selected from the group consisting of hydrogen, deuterium, halogen, a $C_6$-$C_{60}$ aryl group, a fluorenyl group, a $C_2$-$C_{60}$ heterocyclic group containing at least one heteroatom selected from the group consisting of O, N, S, Si, and P, a $C_3$-$C_{60}$ aliphatic ring, a fused ring group formed by a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -L'-N($R_a$)($R_b$), and adjacent groups may be optionally linked to each other to form a ring, wherein the ring is selected from the group consisting of a $C_6$-$C_{60}$ aromatic ring, a $C_2$-$C_{60}$ heterocyclic group, a $C_3$-$C_{60}$ aliphatic ring, and a fused ring group formed by a $C_3$-$C_{60}$ aliphatic ring with a $C_6$-$C_{60}$ aromatic ring, and wherein the ring formed by adjacent groups of $R^2$ or adjacent groups of $R^5$ is a benzene ring in the case where $X^1$ is O,
a and b are each an integer of 0 to 3; c, d, e, l and m are each an integer of 0 to 4, and n is an integer of 1 to 5,
L' is selected from the group consisting of a single bond, a $C_6$-$C_{60}$ arylene group, a fluorenylene group, a $C_2$-$C_{60}$ heterocyclic group containing at least one heteroatom selected from the group consisting of O, N, S, Si, and P, a $C_3$-$C_{60}$ aliphatic ring and a fused ring group formed by a $C_3$-$C_{60}$ aliphatic ring with a $C_6$-$C_{60}$ aromatic ring, and $R_a$ and $R_b$ are each independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a $C_3$-$C_{60}$ aliphatic ring and a fused ring group formed by a $C_3$-$C_{60}$ aliphatic ring with a $C_6$-$C_{60}$ aromatic ring, wherein $Ar^1$ to $Ar^3$, $R^1$ to $R^5$, L', $R_a$, $R_b$, and a ring formed by the adjacent groups of $R^1$ to $R^5$ may be each further substituted with one or more substituents selected from the group consisting of deuterium, halogen, a silane group unsubstituted or substituted with a $C_1$-$C_{20}$ alkyl group or a $C_6$-$C_{20}$ aryl group, a siloxane group, a boron group, a germanium group, a cyano group, a nitro group, a phosphine oxide group unsubstituted or substituted with a $C_1$-$C_{20}$ alkyl group or a $C_6$-$C_{20}$ aryl group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a fused ring group formed by a $C_3$-$C_{60}$ aliphatic ring with a $C_6$-$C_{60}$ aromatic ring, a $C_7$-$C_{20}$ arylalkyl group, and a $C_8$-$C_{20}$ arylalkenyl group;

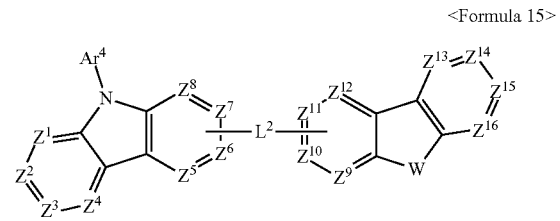

<Formula 15> wherein:
$Z^1$ to $Z^4$, $Z^{13}$ to $Z^{16}$ are independently C(R) or N,
$Z^5$ to $Z^{12}$ are independently C, C(R) or N,
$L^2$ is selected from the group consisting of a single bond, a $C_6$-$C_{60}$ arylene group, a fluorenylene group, a $C_2$-$C_{60}$ heterocyclic group containing at least one heteroatom selected from the group consisting of O, N, S, Si, and P, a $C_3$-$C_{60}$ aliphatic ring and a fused ring group formed by a $C_3$-$C_{60}$ aliphatic ring with a $C_6$-$C_{60}$ aromatic ring,
W is N($Ar^5$), O, S or C(R')(R"),
$Ar^4$ and $Ar^5$ are each independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a $C_3$-$C_{60}$ aliphatic ring, a fused ring group formed by a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group, -L'-N($R_a$)($R_b$) and a combination thereof,
R, R' and R" are each independently selected from the group consisting of hydrogen, deuterium, halogen, a $C_6$-$C_{60}$ aryl group, a fluorenyl group, a $C_2$-$C_{60}$ heterocyclic group containing at least one heteroatom selected from the group consisting of O, N, S, Si, and P, a $C_3$-$C_{60}$ aliphatic ring, a fused ring group formed by a $C_3$-$C_{60}$ aliphatic ring with a $C_6$-$C_{60}$ aromatic ring, a $C_1$-$O_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -L'-N($R_a$)($R_b$), adjacent R groups may be optionally linked to each other to form a ring, and R' and R" may be optionally linked to each other to form a ring, wherein the ring is selected from the group consisting of a $C_6$-$C_{60}$ aromatic ring, a $C_2$-$C_{60}$ heterocyclic group, a $C_3$-$C_{60}$ aliphatic ring, and a fused ring group formed by a $C_3$-$C_{60}$ aliphatic ring with a $C_6$-$C_{60}$ aromatic ring, L', $R_a$ and $R_b$ are the same as defined above in Formula 1, $Z^1$ to $Z^{16}$, $L^2$, $Ar^4$, $Ar^5$, R, R', R", a ring formed by adjacent R groups, and a ring formed by R' and R" may be each further substituted with one or more substituents selected from the group consisting of deuterium, halogen, a silane group unsubstituted or substituted with a $C_1$-$C_{20}$ alkyl group or a $C_6$-$C_{20}$ aryl group, a siloxane group, a boron group, a germanium group, a cyano group, a nitro group, a phosphine oxide group unsubstituted or substituted with a $C_1$-$C_{20}$ alkyl group or a $C_6$-$C_{20}$ aryl group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a fused ring group formed by a $C_3$-$C_{60}$ aliphatic ring with a $C_6$-$C_{60}$ aromatic ring, a $C_7$-$C_{20}$ arylalkyl group, and a $C_8$-$C_{20}$ arylalkenyl group.

15. The organic electric element of claim 14, wherein Formula 15 is represented by one of Formulas 16 to 19:

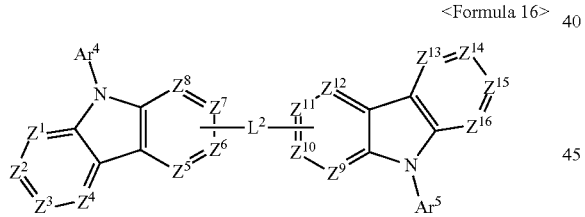

<Formula 16>

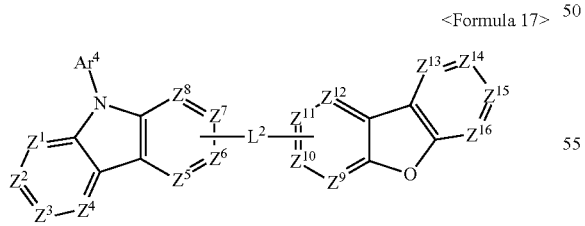

<Formula 17>

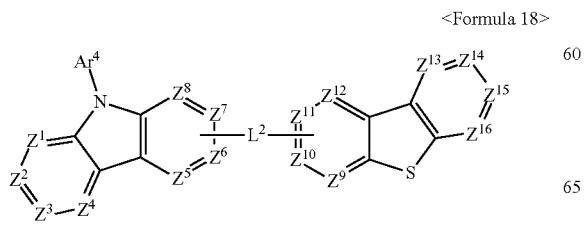

<Formula 18>

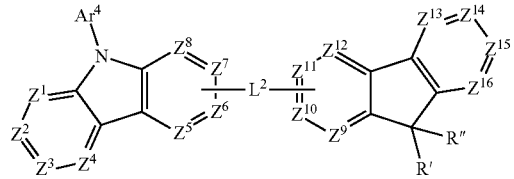

<Formula 19> wherein, $Ar^4$, $Ar^5$, $Z^1$ to $Z^{16}$, $L^2$, R' and R" are the same as defined in claim 14.

16. The organic electric element of claim 14, wherein both $Ar^4$ and $Ar^5$ are a $C_6$-$C_{30}$ aryl group.

17. The organic electric element of claim 14, wherein Formula 15 is represented by Formula 20:

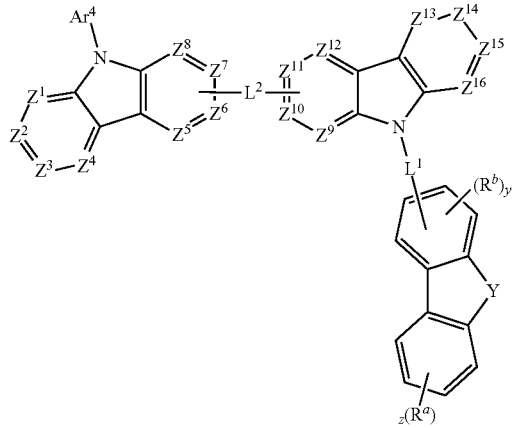

<Formula 20> wherein, $Ar^4$, $Z^1$ to $Z^{16}$, and $L^2$ are the same as defined in claim 14, Y is O, S or N($R^c$), $L^1$ is selected from the group consisting of a single bond, a $C_6$-$C_{60}$ arylene group, a fluorenylene group, a $C_2$-$C_{60}$ heterocyclic group containing at least one heteroatom selected from the group consisting of O, N, S, Si, and P, a $C_3$-$C_{60}$ aliphatic ring and a fused ring group formed by a $C_3$-$C_{60}$ aliphatic ring with a $C_6$-$C_{60}$ aromatic ring, $R^a$ and $R_b$ are each independently selected from the group consisting of hydrogen, deuterium, halogen, a $C_6$-$C_{20}$ aryl group, a fluorenyl group, a $C_6$-$C_{20}$ aryl group substituted with deuterium, a $C_2$-$C_{20}$ heterocyclic group containing at least one heteroatom selected from the group consisting of O, N, S, Si, and P, a $C_3$-$C_{20}$ cycloalkyl group, a fused ring group formed by a $C_3$-$C_{60}$ aliphatic ring with a $C_6$-$C_{60}$ aromatic ring, a $C_7$-$C_{20}$ arylalkyl group and a $C_8$-$C_{20}$ arylalkenyl group, and adjacent groups may be optionally linked to each other to form a ring, wherein the ring is selected from the group consisting of a $C_6$-$C_{60}$ aromatic ring, a $C_2$-$C_{60}$ heterocyclic group, a $C_3$-$C_{60}$ aliphatic ring, and a fused ring group formed by a $C_3$-$C_{60}$ aliphatic ring with a $C_6$-$C_{60}$ aromatic ring, $R^c$ is selected from the group consisting of a $C_6$-$C_{20}$ aryl group, a fluorenyl group, a $C_6$-$C_{20}$ aryl group substituted with deuterium, a $C_2$-$C_{20}$ heterocyclic group containing at least one heteroatom selected from the group consisting of O, N, S, Si, and P, a $C_3$-$C_{20}$ cycloalkyl group, a fused ring group formed by a C$_3$-C$_{60}$ aliphatic ring with a C$_6$-C$_{60}$ aromatic ring and a combination thereof, y is an integer of 0 to 3, z is an integer of 0 to 4, where each of these is an integer of 2 or more, each of R$^a$s, each of R$^b$s is the same or different from each other.

18. The organic electric element of claim 14, wherein the compound represented by Formula 15 is one of the following compounds:

4-1
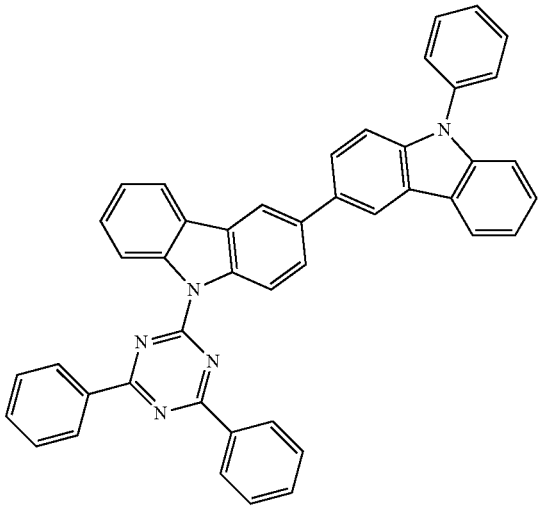

4-2
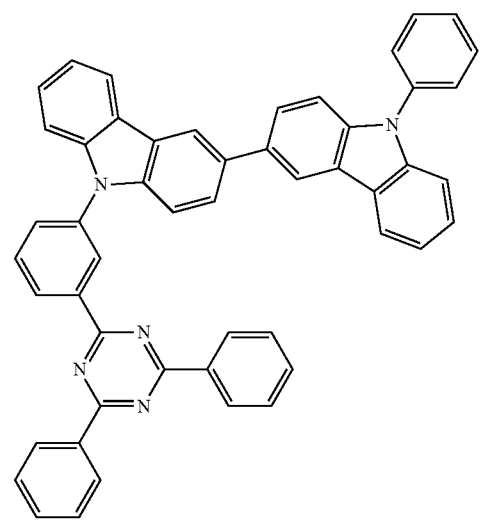

4-3
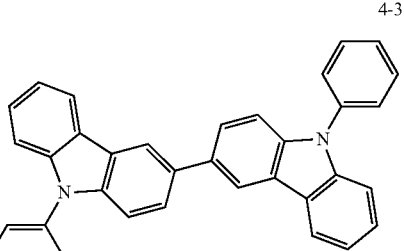
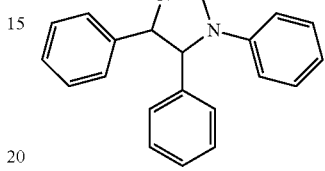

4-4
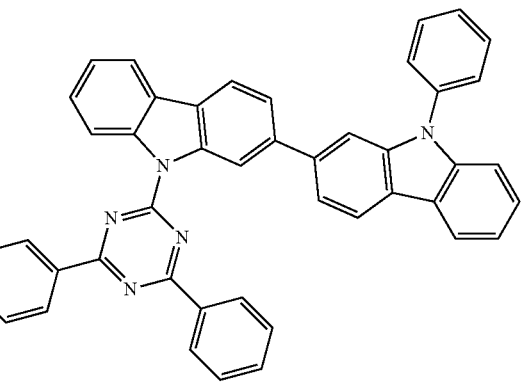

4-5
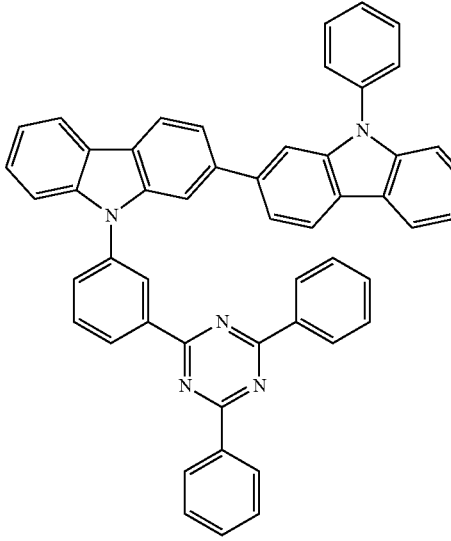

287
-continued
4-6
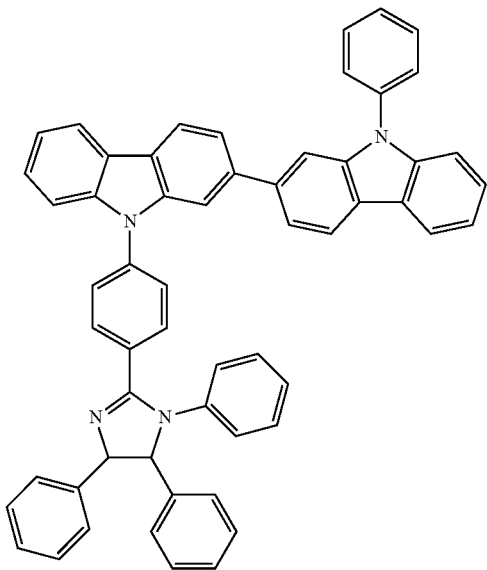
4-7
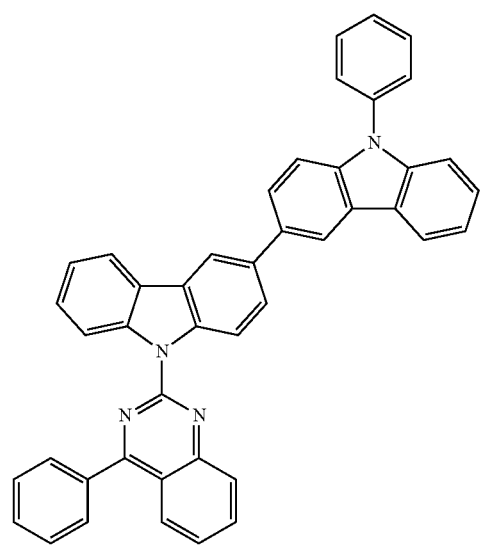
4-8
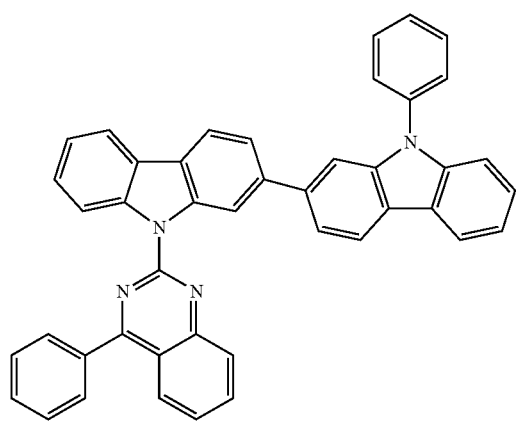
288
-continued
4-9
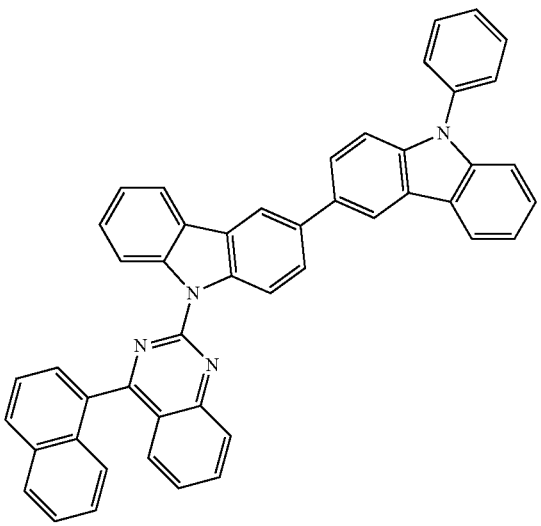
4-10
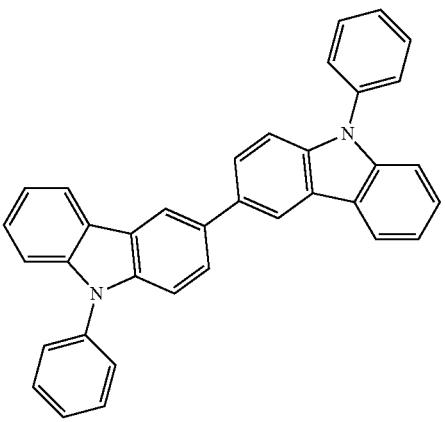
4-11
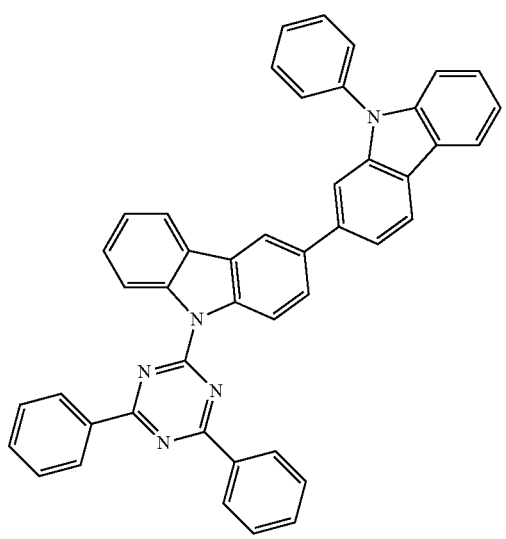

-continued
4-12
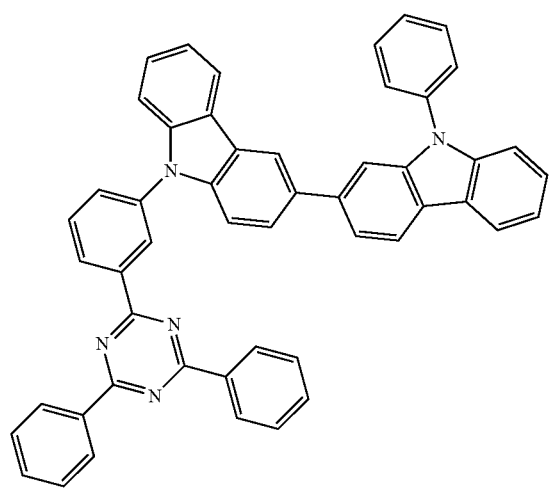
4-13
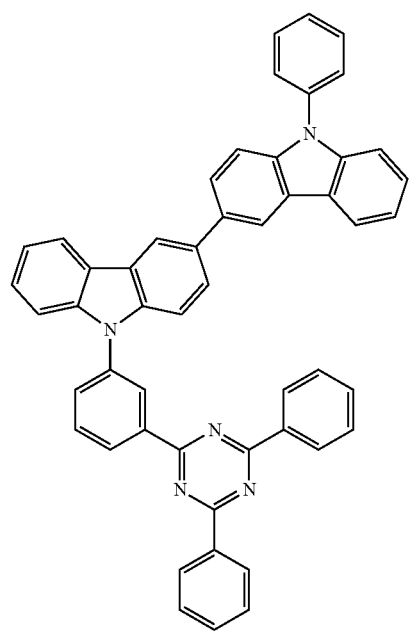
4-14
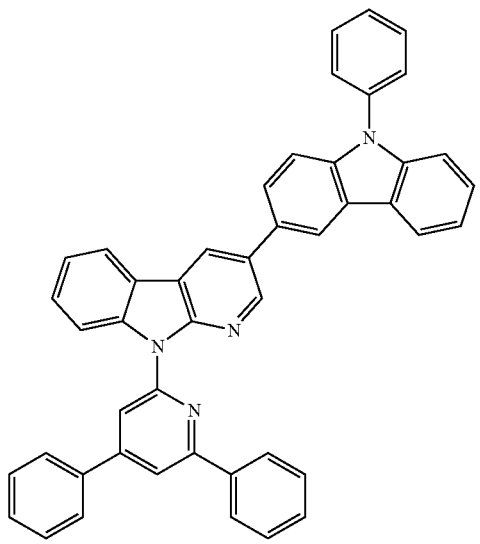
-continued
4-15
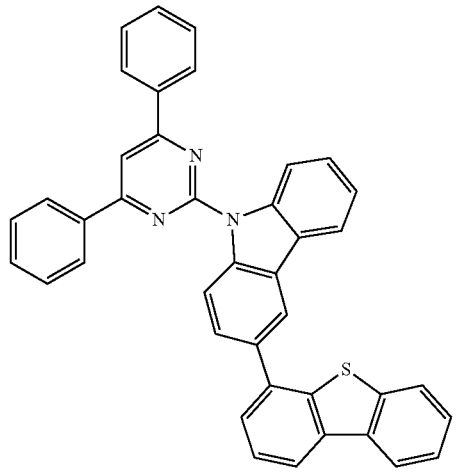
4-16
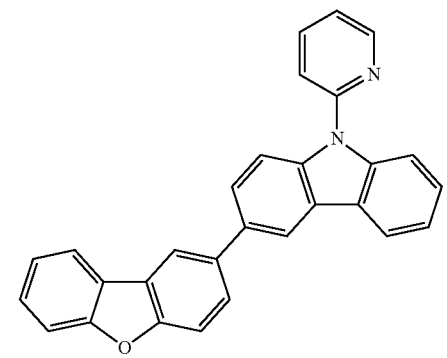
4-17
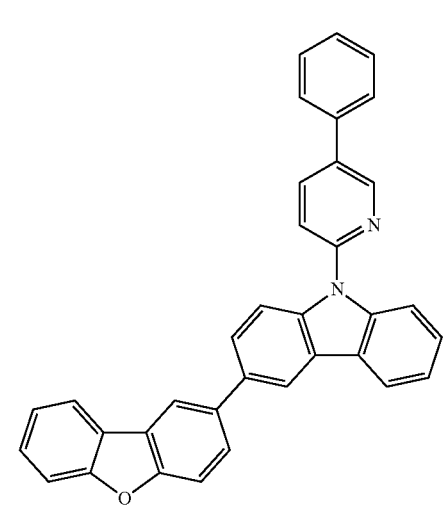

4-18
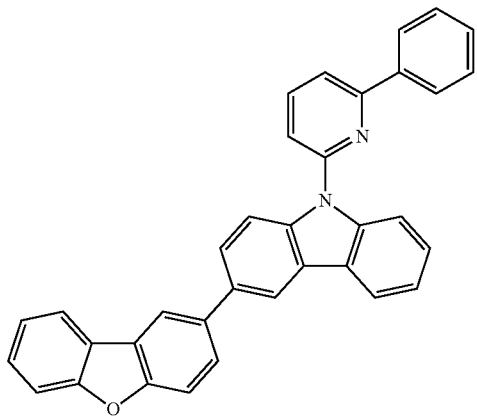
4-19
4-20
4-21
4-22
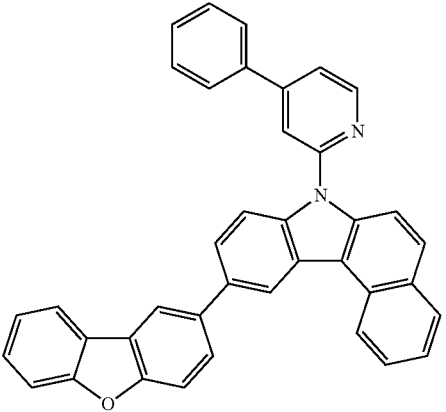
4-23
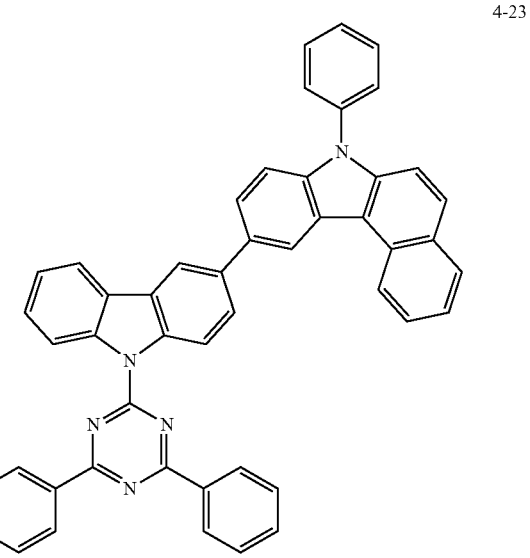
4-24
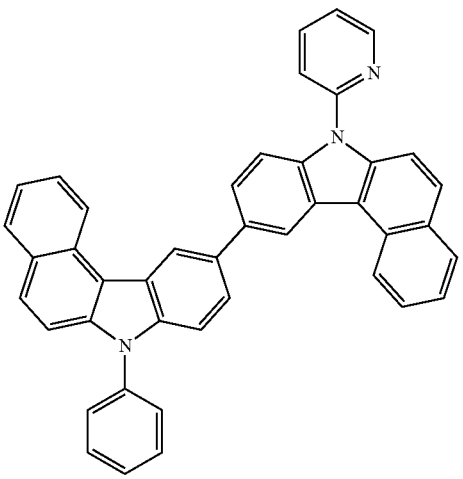

293
-continued
4-25
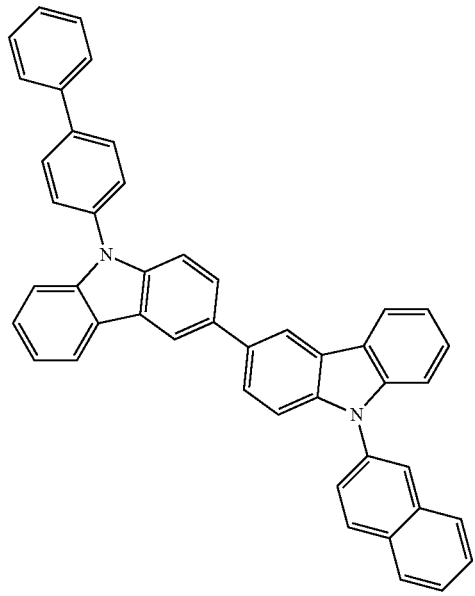
4-26
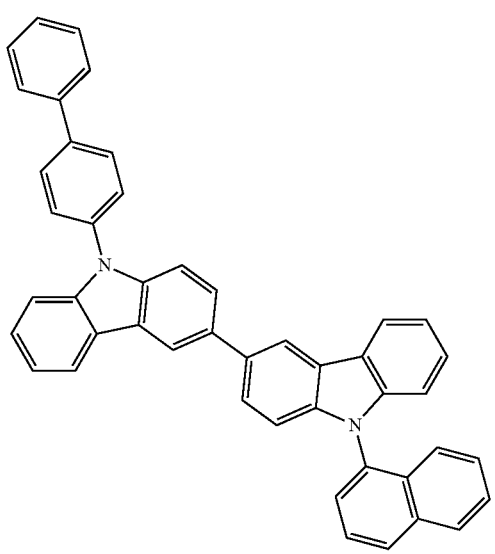
294
-continued
4-27
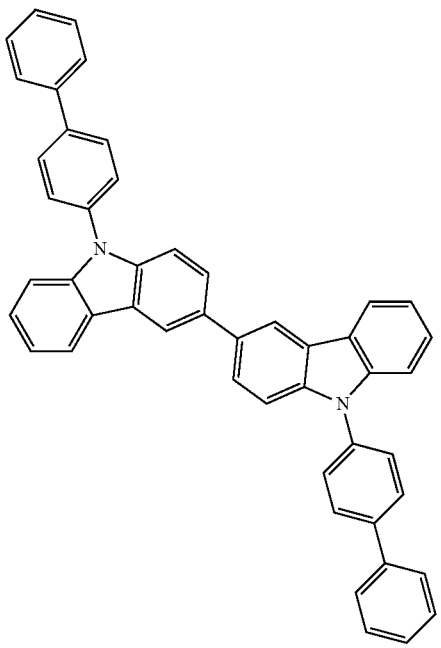
4-28
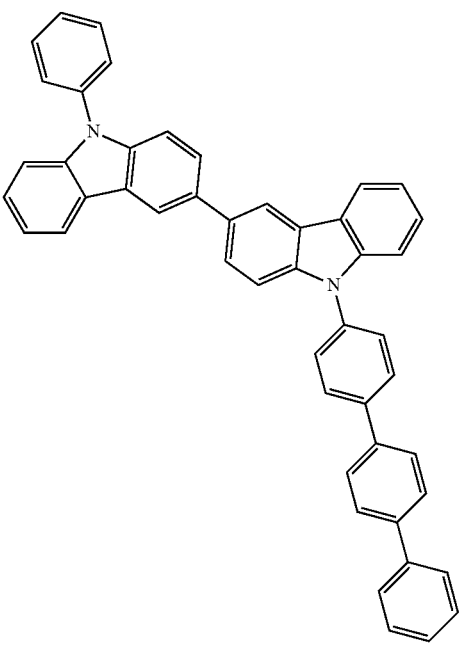

4-29
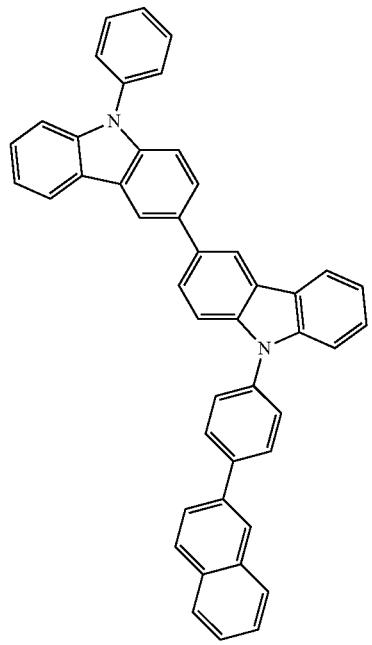
4-30
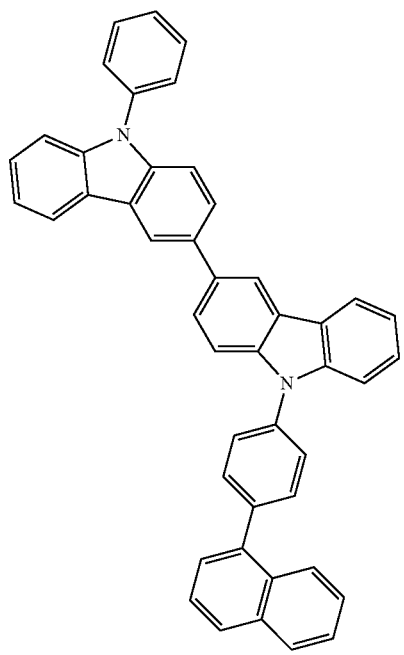
4-31
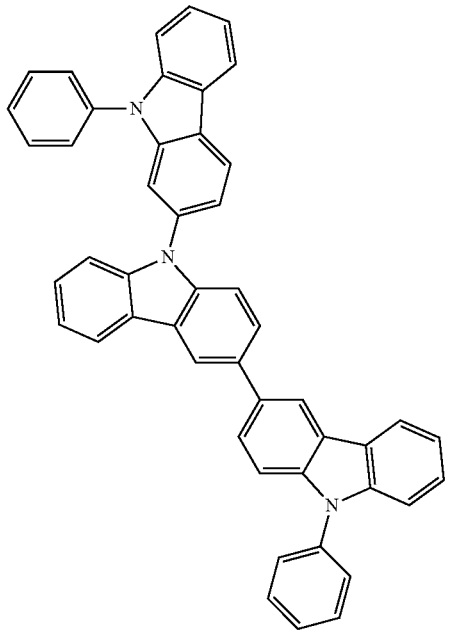
4-32
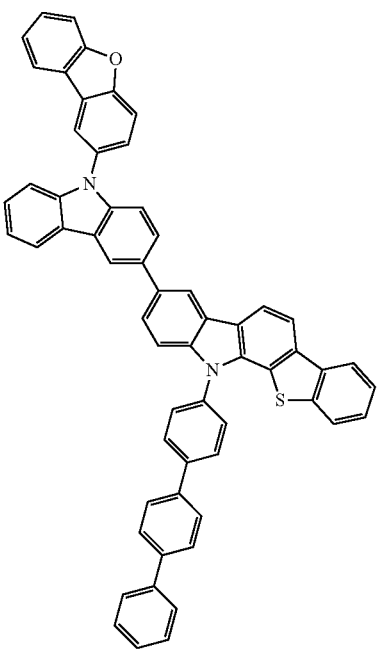
4-33
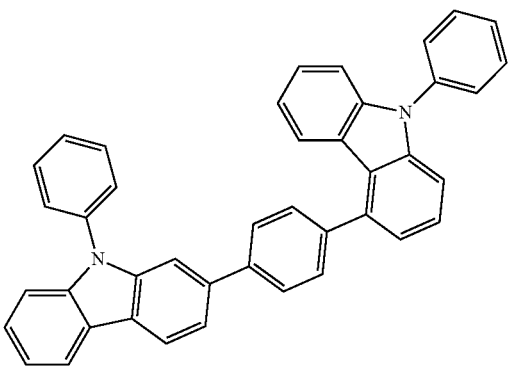

4-34
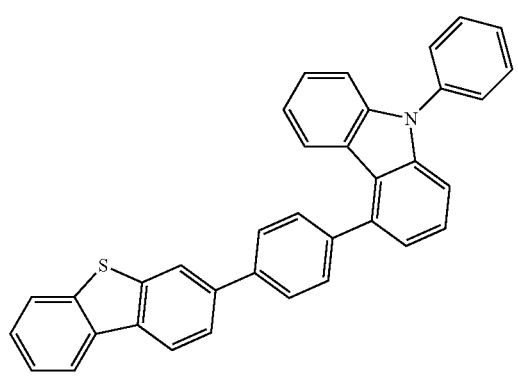
4-35
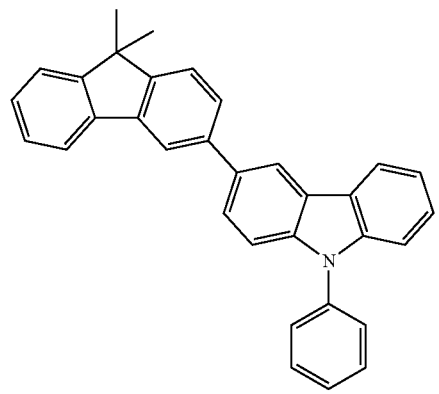
4-36
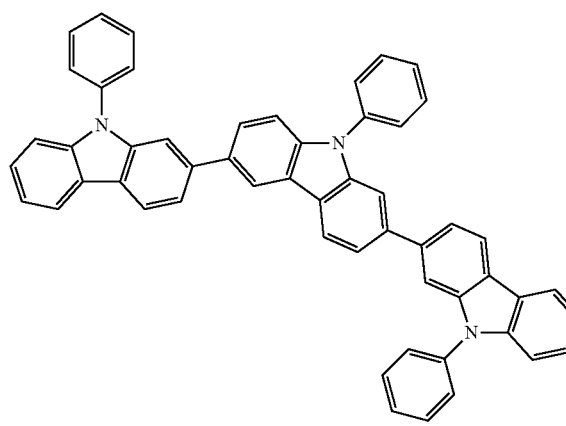
4-37
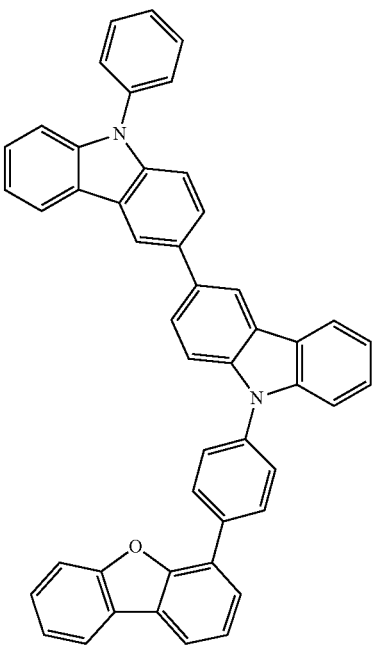
4-38
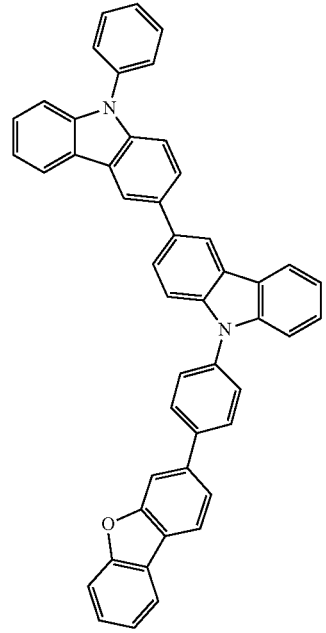

4-39
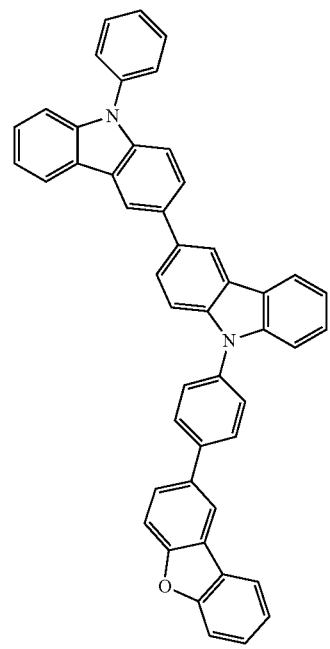
4-40
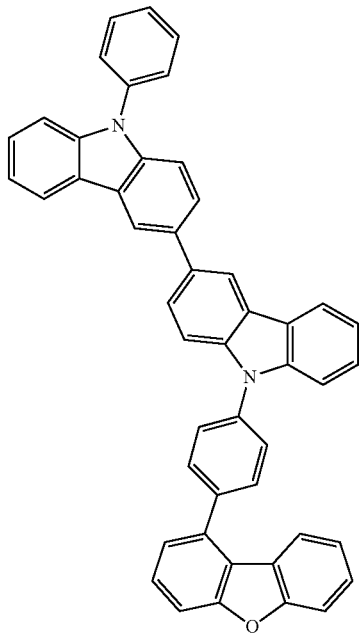
4-41
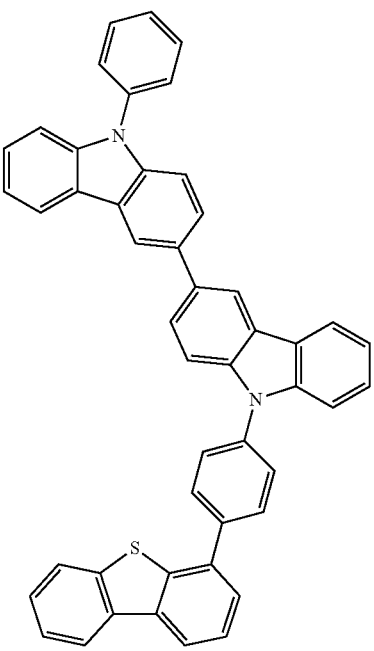
4-42
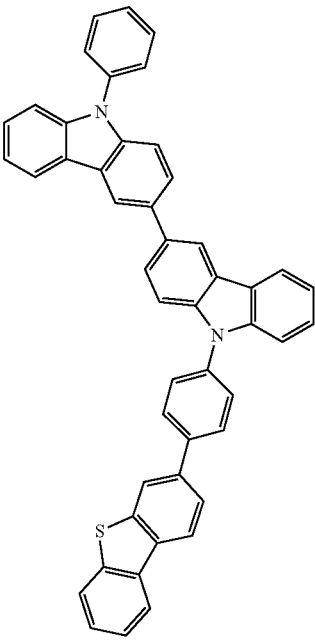

4-43
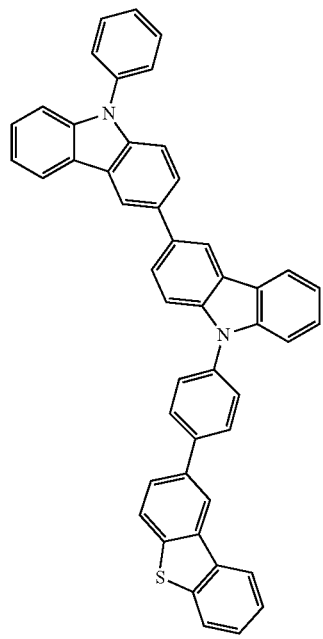
4-45
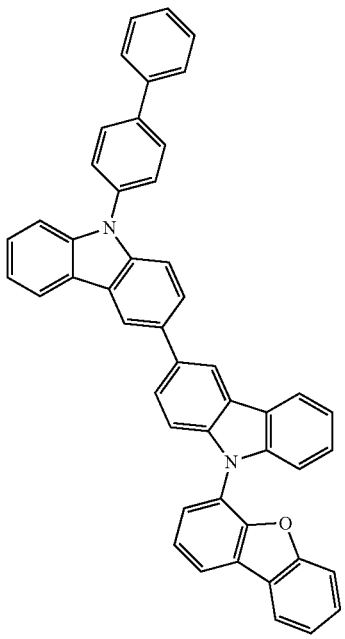
4-44
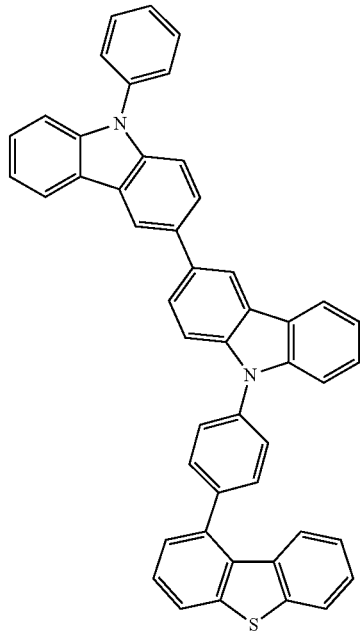
4-46
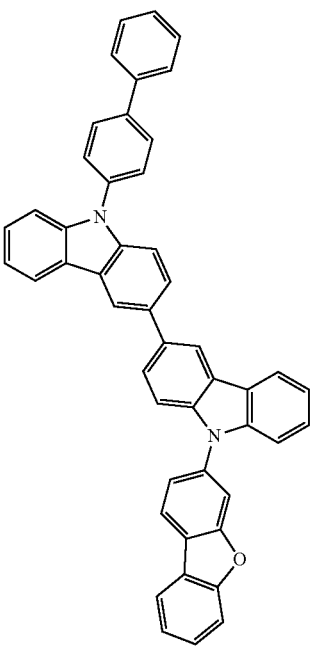

4-47
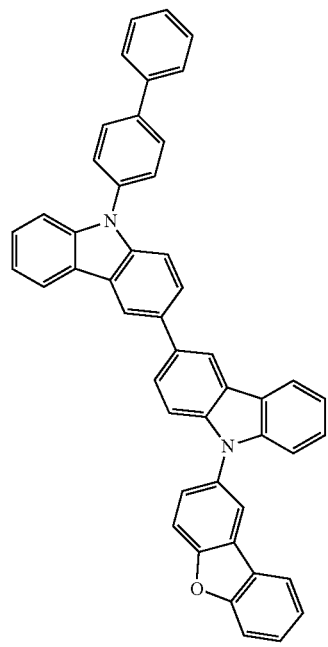
4-48
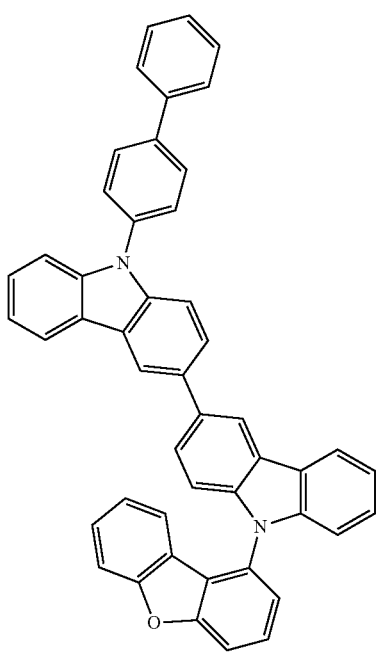
4-49
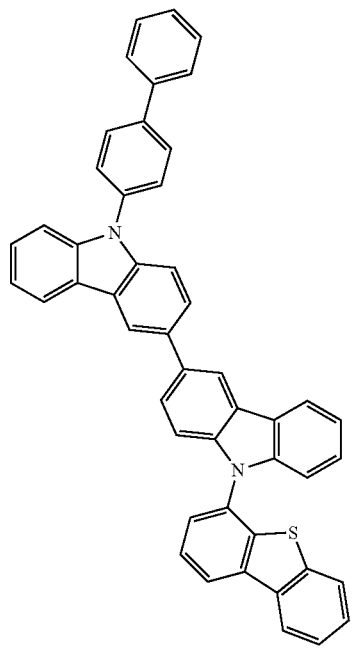
4-50
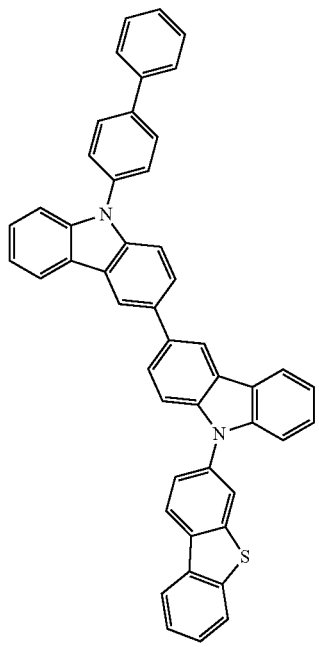

4-51 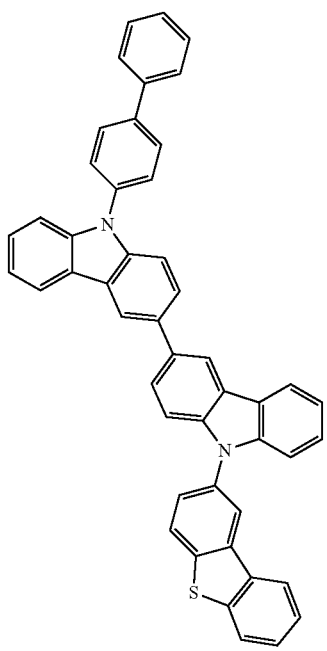

4-52 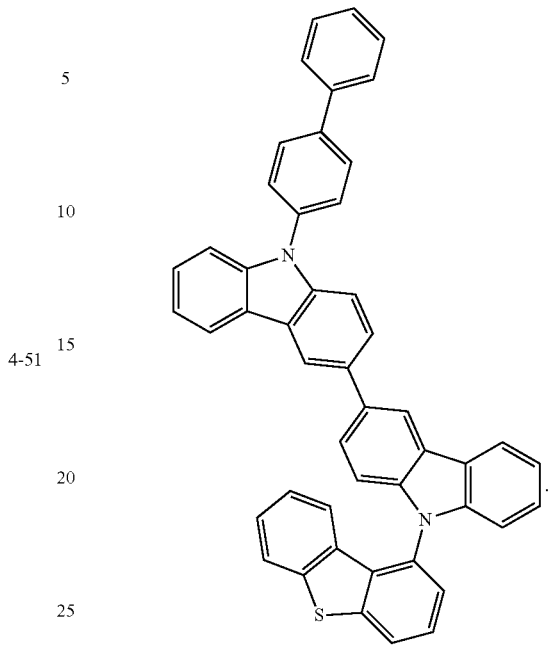

19. An electronic device comprising a display device and a control unit for driving the display device, wherein the display device comprises the organic electric element of claim 11.

20. An organic electric element comprising a first electrode, a second electrode, and an organic material layer formed between the first electrode and the second electrode, wherein the organic material layer comprises a compound represented by any of Formulas 2 to 5 of claim 2.

21. An organic electric element comprising a first electrode, a second electrode, and an organic material layer formed between the first electrode and the second electrode, wherein the organic material layer comprises a compound represented by any of Formulas 11 to 13 of claim 5.

* * * * *

UNITED STATES PATENT AND TRADEMARK OFFICE
CERTIFICATE OF CORRECTION

| | | |
|---|---|---|
| PATENT NO. | : 11,691,966 B2 | Page 1 of 5 |
| APPLICATION NO. | : 16/652369 | |
| DATED | : July 4, 2023 | |
| INVENTOR(S) | : Chae et al. | |

It is certified that error appears in the above-identified patent and that said Letters Patent is hereby corrected as shown below:

In the Specification

Column 10, Formula 7:

Please delete " 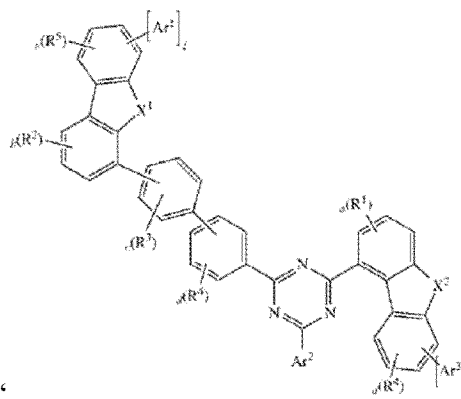 " and replace with

-- 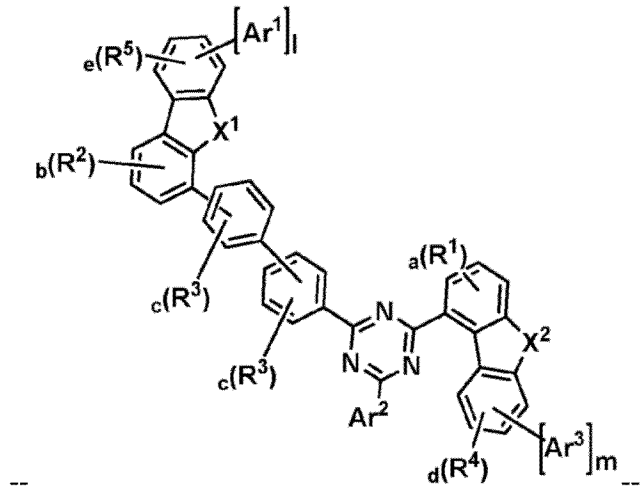 --

Signed and Sealed this
Twentieth Day of February, 2024

Katherine Kelly Vidal
*Director of the United States Patent and Trademark Office*

Column 10, Formula 8:
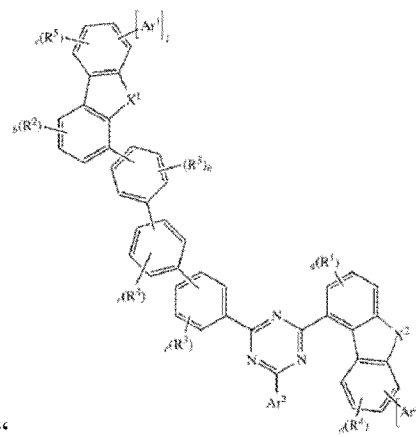
Please delete " 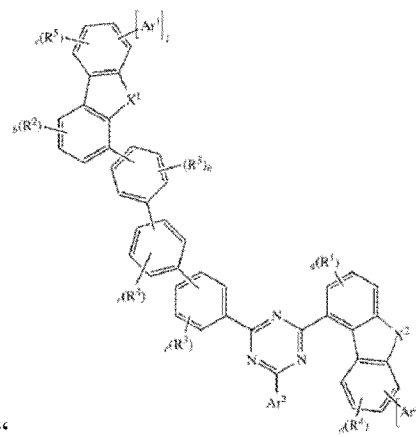 " and replace with
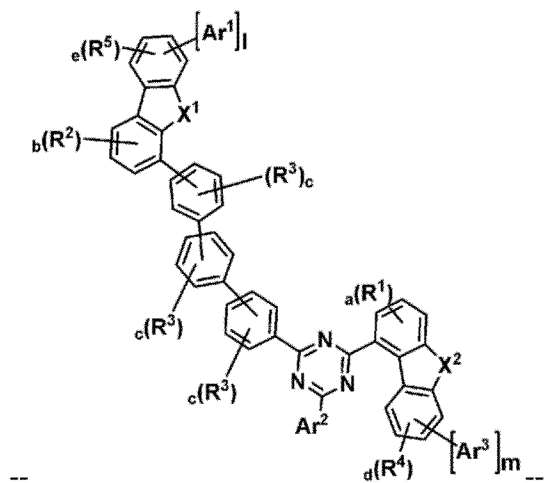
--
In the Claims
Column 204, Claim 1, Line 5:
Please delete "0 to 3, c, d, e, and I are" and replace with -- 0 to 3, c, d, e, and l are --
Column 207, Claim 3, Formula 7:
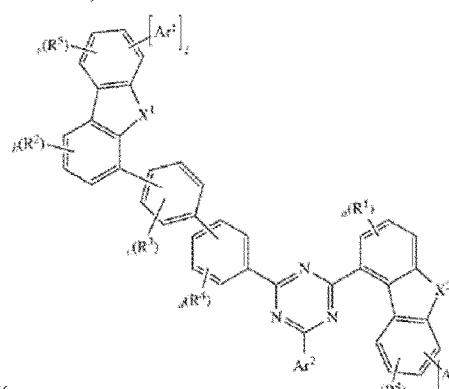
Please delete " 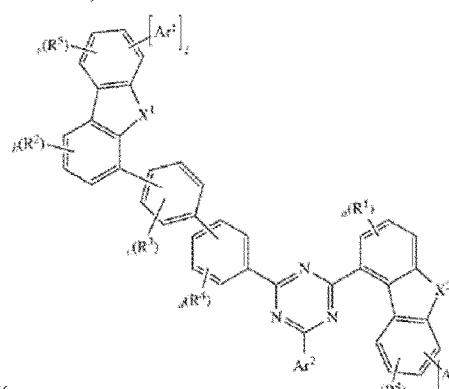 " and replace with

CERTIFICATE OF CORRECTION (continued)
U.S. Pat. No. 11,691,966 B2

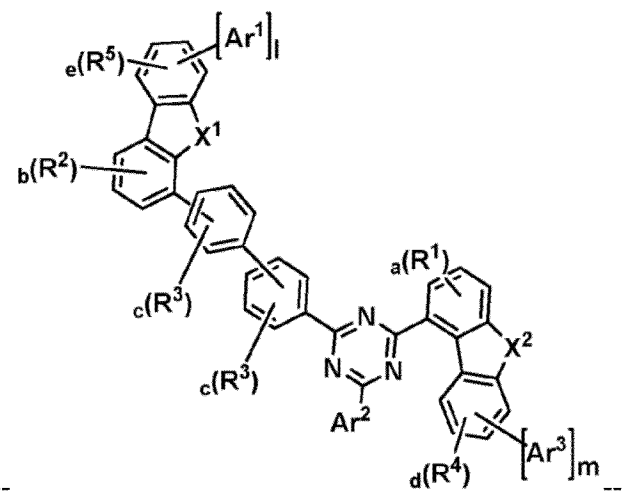

Column 207, Claim 3, Formula 8:

Please delete " 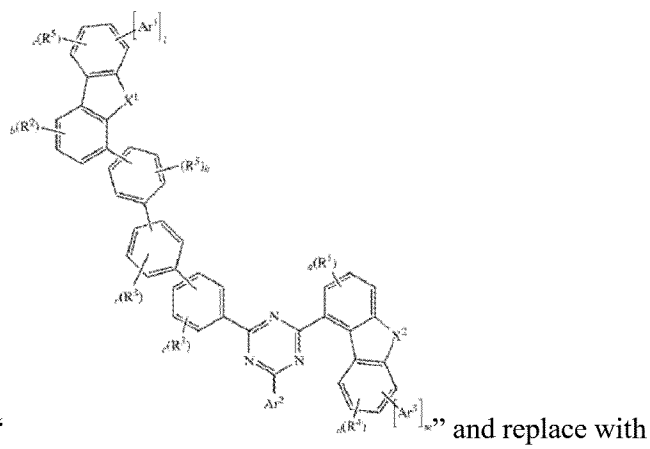 " and replace with

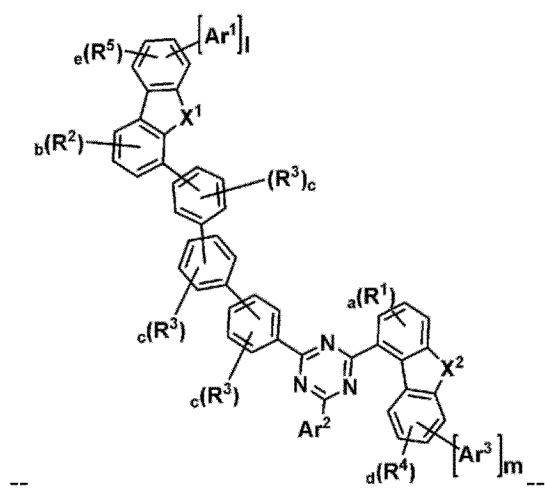

CERTIFICATE OF CORRECTION (continued)
U.S. Pat. No. 11,691,966 B2

Column 212, Claim 10, Please label Formula 1-8:

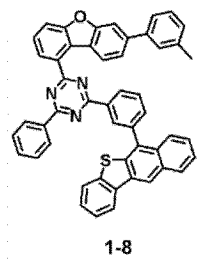

Column 214, Claim 10, Please label Formula 1-12:

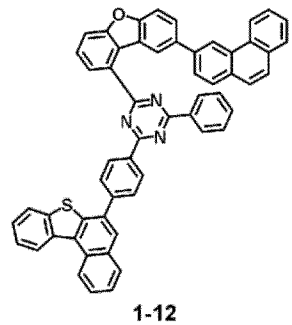

Column 237, Claim 10, Formula 1-75:

Please delete " " and replace with -- -- 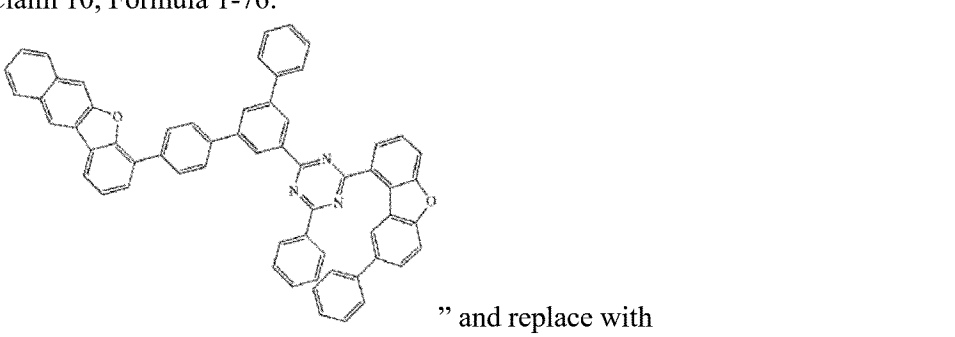

Column 238, Claim 10, Formula 1-76:

Please delete " " and replace with

CERTIFICATE OF CORRECTION (continued)
U.S. Pat. No. 11,691,966 B2

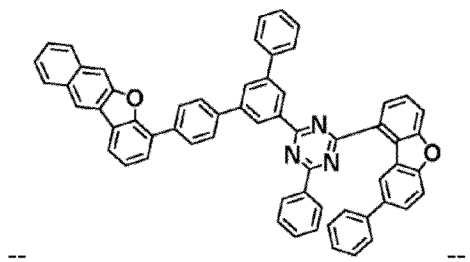

-- --

Column 283, Claim 14, Line 3:
Please delete "$C_1$-C050" and replace with -- $C_1$-$C_{50}$ --

Column 284, Claim 17, Line 41:
Please delete "Y is 0," and replace with -- Y is O, --